(12) United States Patent
Clinch et al.

(10) Patent No.: US 8,853,224 B2
(45) Date of Patent: Oct. 7, 2014

(54) ACYCLIC AMINE INHIBITORS OF NUCLEOSIDE PHOSPHORYLASES AND HYDROLASES

(75) Inventors: Keith Clinch, Lower Hutt (NZ); Gary Brian Evans, Lower Hutt (NZ); Richard Hubert Furneaux, Wellington (NZ); Shivali Ashwin Gulab, Wellington (NZ); Peter Michael Kelly, Wellington (NZ); Vern L. Schramm, New Rochelle, NY (US); Peter Charles Tyler, Wellington (NZ); Anthony David Woolhouse, Wellington (NZ)

(73) Assignees: Industrial Research Limited, Lower Hutt (NZ); Albert Einstein College of Medicine of Yeshiva University, Bronx, NY (US)

( * ) Notice: Subject to any disclaimer, the term of this patent is extended or adjusted under 35 U.S.C. 154(b) by 569 days.

(21) Appl. No.: 12/310,708

(22) PCT Filed: Sep. 7, 2007

(86) PCT No.: PCT/NZ2007/000261
§ 371 (c)(1),
(2), (4) Date: Sep. 29, 2009

(87) PCT Pub. No.: WO2008/030119
PCT Pub. Date: Mar. 13, 2008

(65) Prior Publication Data
US 2011/0130412 A1    Jun. 2, 2011

Related U.S. Application Data

(60) Provisional application No. 60/842,867, filed on Sep. 7, 2006.

(51) Int. Cl.
*C07D 487/00* (2006.01)
*A61K 31/519* (2006.01)
*C07D 487/04* (2006.01)

(52) U.S. Cl.
CPC .................... *C07D 487/04* (2013.01)
USPC ...... 514/265.1; 544/262; 544/280; 514/262.1

(58) Field of Classification Search
None
See application file for complete search history.

(56) References Cited

U.S. PATENT DOCUMENTS

| | | | |
|---|---|---|---|
| 5,985,848 A | 11/1999 | Furneaux et al. | |
| 6,066,722 A | 5/2000 | Furneaux et al. | |
| 6,228,847 B1 | 5/2001 | Furneaux et al. | |
| 6,379,911 B2 | 4/2002 | Schramm et al. | |
| 6,458,799 B1 | 10/2002 | Montgomery et al. | |
| 6,492,347 B2 | 12/2002 | Furneaux et al. | |
| 6,693,193 B1 | 2/2004 | Furneaux et al. | |
| 6,764,829 B2 | 7/2004 | Schramm et al. | |
| 6,803,455 B2 | 10/2004 | Furneaux et al. | |
| 7,022,852 B2 | 4/2006 | Furneaux et al. | |
| 7,098,334 B2 | 8/2006 | Furneaux et al. | |
| 7,109,331 B2 | 9/2006 | Furneaux et al. | |
| 7,211,653 B2 | 5/2007 | Furneaux et al. | |
| 7,211,677 B2 | 5/2007 | Furneaux et al. | |
| 7,390,890 B2 | 6/2008 | Furneaux et al. | |
| 7,405,297 B2 | 7/2008 | Furneaux et al. | |
| 7,528,140 B2 | 5/2009 | Kataoka et al. | |
| 7,553,839 B2 | 6/2009 | Evans et al. | |
| 7,655,795 B2 | 2/2010 | Evans et al. | |
| 2004/0110772 A1 | 6/2004 | Furneaux | |
| 2006/0160765 A1 | 7/2006 | Evans et al. | |
| 2006/0217551 A1 | 9/2006 | Evans et al. | |
| 2008/0280334 A1 | 11/2008 | Lenz et al. | |
| 2009/0192138 A1 | 7/2009 | Baeschlin et al. | |
| 2009/0233948 A1 | 9/2009 | Evans et al. | |
| 2009/0239885 A1 | 9/2009 | Evans et al. | |
| 2009/0325986 A1 | 12/2009 | Furneaux et al. | |
| 2010/0062995 A1 | 3/2010 | Schramm | |
| 2010/0094003 A1 | 4/2010 | Evans et al. | |
| 2010/0168141 A1 | 7/2010 | Evans et al. | |
| 2010/0222370 A1 | 9/2010 | Schramm et al. | |
| 2011/0046167 A1 | 2/2011 | Clinch et al. | |

FOREIGN PATENT DOCUMENTS

| | | |
|---|---|---|
| EP | 1477489 A1 | 11/2004 |
| JP | 09020777 A2 | 1/1997 |
| WO | WO 00/061783 | 10/2000 |
| WO | WO 02/18371 | 3/2002 |
| WO | WO 03/080620 A1 | 10/2003 |
| WO | WO 2004/018496 A1 | 3/2004 |
| WO | 2004065389 A1 | 8/2004 |
| WO | WO 2005/118532 | 12/2005 |
| WO | WO 2006/014913 A2 | 2/2006 |
| WO | WO 2006/123953 A1 | 11/2006 |
| WO | 2007016291 A2 | 2/2007 |

(Continued)

OTHER PUBLICATIONS

Communication from European Patent Office dated Jul. 30, 2009 in connection with European Patent Application No. 07834863.8, 6 pages.

(Continued)

*Primary Examiner* — Sreeni Padmanabhan
*Assistant Examiner* — Jody Karol
(74) *Attorney, Agent, or Firm* — Amster, Rothstein & Ebenstein LLP

(57) ABSTRACT

The invention relates to compounds of the general formula (I) which are inhibitors of purine nucleoside phosphorylases (PNPs) and/or nucleoside hydrolases (NHs). The invention also relates to the use of these compounds in the treatment of diseases and infections including cancer, bacterial infections, protozoal infections, and T-cell mediated disease and to pharmaceutical compositions containing the compounds.

12 Claims, 1 Drawing Sheet

(56) References Cited

FOREIGN PATENT DOCUMENTS

| WO | 2007717738 A1 | 6/2007 |
| WO | WO 2007/069923 A1 | 6/2007 |
| WO | WO 2007/097647 A1 | 8/2007 |
| WO | WO 2007/097648 A1 | 8/2007 |
| WO | WO 2008/030118 A1 | 3/2008 |
| WO | 2009082247 A1 | 7/2009 |
| WO | 2010033236 A2 | 2/2010 |
| WO | 2011008110 A1 | 1/2011 |

OTHER PUBLICATIONS

Taylor E A et al., entitled "Acyclic Ribooxacarbenium Ion Mimics as Transition State Analogues of Human and Malarial Purine Nucleoside Phosphorylases," J. Am. Chem Soc., 2007, 129, 6984-6985, and Supplemental Information, 9 pgs.

Ektova et al, "Synthesis and properties of an acyclic analog of 9-deazainosine and related compounds," Bioorganicheskaya Khimiya, 1985, vol. 11(8), pp. 1105-1109.

Sizova et al., "Synthesis and biological activity of 4, 6-diazatryptophan and 4,6-diazaheteroauxin derivatives," Khimiko-Farmatsevticheskii Zhurnal, 1985, vol. 19(6), pp. 689-691.

Modnikova et al., "Pyrrolo[3,2-d]pyrimidine derivatives. III. 7-Aminomethyl-substituted pyrrolo[3,2-d]pyrimidines," Khimiko-Farmatsevticheskii Zhurnal, 1982, vol. 16(5), pp. 548-552.

Semeraro et al., "Simplified analogues of immucillin-G retain potent human purine nucleoside phosphorylase inhibitory activity," Journal of Medicinal Chemistry, 2006, vol. 49, pp. 6037-6045.

Lewandowicz et al., "Energetic mapping of transition state analogue interactions with human and *Plasmodium falciparum* purine nucleoside phosphorylases," Journal of Biological Chemistry, 2005, vol. 280(34), pp. 30320-30328.

Sizova O S et al., entitled "Synthesis and biological activity of derivatives of 4, 6-diazatryptophan and 4, 6-diazaheterchauxin," Pharmaceutical Chemistry Journal, 19(6):401-403, 1965.

PCT Notification Concerning Transmittal of International Preliminary Report on Patenetability dated Mar. 19, 2009 in connection with PCT International Patent Application No. PCT/NZ2007/00261, 2 pages.

Written Opinion of the International Searching Authority dated Dec. 7, 2007 in connection with PCT International Patent Application No. PCT/NZ2007000261, 4 pages.

Notice of Reasons for Rejection dated Nov. 27, 2012 in connection with Japanese Patent Application No. P2009-527314, 6 pages.

Bzowska A et al., entitled "Acyclonucleoside Analogue Inhibitors of Mammalian Purine Nucleoside Phosphorylase," Biochemical Pharmacology, vol. 41, No. 12, pp. 1791-1803, 1991.

Bzowska A et al., entitled "Purine Nucleoside Phosphorylase: Inhibition by Purine N(7)-and N(9)-Acyclonucleosides; and Substrate Properties of 7-β-D-Ribofuranosylguanine and 7-β-D-Ribofuranosylhypoxanthine," Biochemical Pharmacology, vol. 48, No. 5, pp. 937-947, 1994.

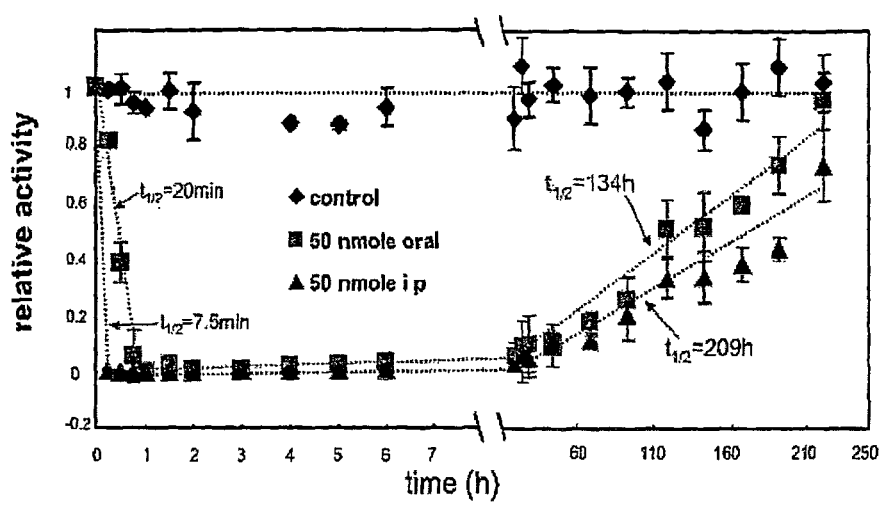

ACYCLIC AMINE INHIBITORS OF NUCLEOSIDE PHOSPHORYLASES AND HYDROLASES

CROSS-REFERENCE TO RELATED APPLICATIONS

This application is a national stage entry under 35 U.S.C. §371 of PCT International Patent Application No. PCT/NZ2007/000261, filed Sep. 7, 2007, and claims priority to U.S. Provisional Patent Application No. 60/842,867, filed Sep. 7, 2006, the contents of which are incorporated herein by reference in their entirety.

STATEMENT OF GOVERNMENT SUPPORT

The invention disclosed herein was made with U.S. Government support under grant number GM41916 from the National Institutes of Health, U.S. Department of Health and Human Services. Accordingly, the U.S. Government has certain rights in this invention.

TECHNICAL FIELD

This invention relates generally to certain nucleoside analogues, the use of these compounds as pharmaceuticals, pharmaceutical compositions containing the compounds, processes for preparing the compounds, and methods of treating diseases or conditions in which it is desirable to inhibit purine nucleoside phosphorylases and nucleoside hydrolases.

BACKGROUND

U.S. Pat. No. 5,985,848, U.S. Pat. No. 6,066,722 and U.S. Pat. No. 6,228,741 describe nucleoside analogues that are inhibitors of purine nucleoside phosphorylases (PNPs) and purine phosphoribosyl-transferases (PRTs). The analogues are useful in treating parasitic infections, T-cell malignancies, autoimmune diseases and inflammatory disorders. The analogues are also useful for immunosuppression in organ transplantation.

U.S. Pat. No. 6,693,193 describes a process for preparing certain PNP inhibitor compounds. This application recognises the compounds as PNP inhibitors and addresses a need for simpler methods of preparing them. U.S. Ser. No. 10/363,424 discloses further nucleoside analogues that are inhibitors of PNPs and PRTs.

PNPs catalyse the phosphorolytic cleavage of ribo- and deoxyribonucleosides, for example those of guanine and hypoxanthine, to give the corresponding sugar-1-phosphate and guanine, hypoxanthine or other purine bases.

Humans deficient in PNP suffer a specific T-cell immunodeficiency due to an accumulation of dGTP which prevents proliferation of stimulated T lymphocytes. Inhibitors of PNP are therefore immunosuppressive, and are active against T-cell malignancies and T-cell proliferative disorders.

Nucleoside hydrolases (NHs) catalyse the hydrolysis of nucleosides. These enzymes are not found in mammals but are required for nucleoside salvage in some protozoan parasites. Some protozoan parasites use nucleoside phosphorylases either instead of or in addition to nucleoside hydrolases for this purpose. Inhibitors of nucleoside hydrolases and phosphorylases can be expected to interfere with the metabolism of the parasite and can therefore be usefully employed against protozoan parasites.

The imino sugar part of the compounds described in the patent specifications referred to above has the nitrogen atom located between C-1 and C-4 so as to form 1,4-dideoxy-1,4-imino-D-ribitol compounds. The location of the nitrogen atom in the ribitol ring may be critical for binding to PNP and NH enzymes. In addition, the location of the link between the sugar moiety and the nucleoside base analogue may be critical for enzyme inhibitory activity. The compounds described above have that link at C-1 of the sugar ring.

The applicants have also developed other nucleoside phosphorylase, phosphoribosyltransferase, and hydrolase inhibitors, where the location of the nitrogen atom in the sugar ring is varied and, additionally, where two nitrogen atoms form part of the sugar ring. Alternative modes of linking the sugar part and the base analogue have also been investigated, resulting in a class of inhibitors where the sugar moiety is linked to the nucleoside base analogue via a methylene bridge. These other inhibitors are described in U.S. Ser. No. 10/395,636.

It has been considered to date that the three dimensional structure of the imino sugar ring of the above compounds is critical for effective binding to PNPs and NHs, and therefore inhibition of these enzymes. The ring structure constrains the spatial locations that important functional groups, such as the imino nitrogen and various hydroxyl groups, can adopt when interacting with the enzymes. These steric constraints have previously been considered to be necessary for binding of the compounds in the active site of the enzymes. In the absence of such steric constraints, compounds would not be expected to be proficient binders to the enzyme active sites and consequently would not be effective inhibitors of the enzymes.

The view that the imino sugar ring is important for effective enzyme inhibition is reinforced in *J. Biol. Chem.*, 2005, 280, 30320-30328, which describes an investigation of transition state analogue interactions with human and *Plasmodium falciparum* PNPs. Inhibition activities against these PNPs for various nucleoside analogues are described. The structure of the great majority of the analogues contains an imino sugar ring. Two compounds are described where that ring is, in effect, opened to give hydroxyethyl and hydroxypropyl substituents on the amino nitrogen.

*J. Med. Chem.*, 2006, 49, 6037-6045 also describes a number of PNP inhibitor compounds, some of which comprise an imino sugar ring moiety and some of which have an acyclic N-hydroxyethyl amino group. Those compounds that do exhibit PNP inhibition activity are considered to have only moderate potency (inhibition constants at the micromolar or nanomolar level).

While there is some understanding of the structural features of compounds needed for binding to PNP enzymes and inhibition activity, it remains difficult to predict with certainty whether a compound will be a weak or potent inhibitor, or even an inhibitor at all, until the compound is synthesised and tested in the appropriate assays. The imino sugar ring-opened compounds disclosed in above mentioned *J. Biol. Chem* and *J. Med. Chem* publications are too few and structurally disparate to serve as predictors for a general class of acyclic amine inhibitors of PNP.

The applicants have now surprisingly found that certain compounds analogous to the compounds described above, having an acyclic amine group rather than an imino ring, are effective inhibitors of human and *Plasmodium falciparum* PNPs.

It is therefore an object of the present invention to provide acyclic amine compounds that are inhibitors of PNPs or NHs, or to at least provide a useful choice.

STATEMENTS OF INVENTION

Accordingly, in a first aspect, the present invention provides a compound of the formula (I):

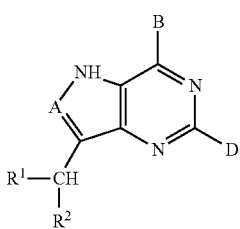

where:
- $R^1$ is H or $NR^3R^4$;
- $R^2$ is H or is an alkyl, alkenyl, alkynyl, aralkyl, aralkenyl, aralkynyl, or aryl group each of which is optionally substituted with one or more hydroxy, alkoxy, thiol, alkylthio, arylthio, aralkylthio, halogen, carboxylic acid, carboxylate alkyl ester, nitro, or $NR^3R^4$ groups, where each alkylthio, arylthio and aralkylthio group is optionally substituted with one or more alkyl, halogen, amino, hydroxy, or alkoxy groups;
  provided that when $R^1$ is H, $R^2$ is an alkyl, alkenyl, alkynyl, aralkyl, aralkenyl, aralkynyl, or aryl group which is substituted with at least one $NR^3R^4$ group;
- $R^3$ and $R^4$, independently of each other, is H or is an alkyl, alkenyl, alkynyl, aralkyl, aralkenyl, aralkynyl, or aryl group each of which is optionally substituted with one or more hydroxy, alkoxy, thiol, alkylthio, arylthio, aralkylthio, halogen, carboxylic acid, carboxylate alkyl ester, nitro, or $NR^3R^4$ groups, where each alkylthio, arylthio and aralkylthio group is optionally substituted with one or more alkyl, halogen, amino, hydroxy, or alkoxy groups;
- A is N or CH;
- B is OH or alkoxy; and
- D is H, OH, $NH_2$, or $SCH_3$;
  provided that when $R^1$ is $NR^3R^4$, $R^2$ is H, A is CH, B is OH, and D is H, then $R^3$ is not hydroxyethyl or hydroxypropyl when $R^4$ is hydroxyethyl; and
  provided that when $R^1$ is $NR^3R^4$, $R^2$ is H, A is CH, B is OH, and D is $NH_2$, then $R^3$ is not hydroxyethyl when $R^4$ is H, methyl, ethyl, or hydroxyethyl, and $R^4$ is not hydroxyethyl when $R^3$ is H, methyl, ethyl, or hydroxyethyl;

or a tautomer thereof, or a pharmaceutically acceptable salt thereof, or an ester prodrug form thereof.

When $R^1$ is H then $R^2$ is preferably alkyl substituted with at least one $NR^3R^4$ group.

When $R^3$ or $R^4$ is optionally substituted alkyl, the alkyl group is preferably substituted by one or more hydroxy groups. For example, $R^3$ or $R^4$ may be hydroxymethyl, hydroxyethyl, hydroxypropyl, dihydroxypropyl, hydroxybutyl, dihydroxybutyl, trihyroxybutyl, hydroxypentyl, dihydroxypentyl, or trihydroxpentyl.

$R^3$ or $R^4$ may also preferably be alkyl substituted by one or more hydroxy groups and/or one or more optionally substituted thiol, alkylthio, arylthio, or aralkylthio groups. For example, $R^3$ or $R^4$ may be methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

When $R^1$ is $NR^3R^4$, and $R^3$ and $R^4$ are H, $R^2$ is preferably an optionally substituted alkyl, more preferably an optionally substituted $C_1$-$C_5$ alkyl, for example, hydroxymethyl, hydroxyethyl, hydroxypropyl, dihydroxypropyl, hydroxybutyl, dihydroxybutyl, trihyroxybutyl, hydroxypentyl, dihydroxypentyl, trihydroxpentyl, methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

When $R^1$ is $NR^3R^4$, and $R^3$ is H and $R^4$ is an optionally substituted alkyl, $R^2$ is preferably H.

When $R^1$ is $NR^3R^4$, and $R^3$ is H and $R^4$ is an optionally substituted alkyl, $R^2$ is preferably an optionally substituted alkyl, more preferably an optionally substituted $C_1$-$C_5$ alkyl.

When $R^1$ is $NR^3R^4$, and $R^3$ and $R^4$ are each an optionally substituted alkyl, $R^2$ is preferably H.

Preferably A is CH. Alternatively, A may be N.

It is also preferred that B is OH.

It is further preferred that D is H or $NH_2$. Alternatively, D may preferably be OH or $SCH_3$.

Preferred compounds of the invention include:
- rac-(2R,3S)-3-((4-hydroxy-5H-pyrrolo[3,2-d]pyrimidin-7-yl)methylamino)butane-1,2,4-triol;
- 7-(((2,4-dihydroxybutyl)(methyl)amino)methyl)-3H-pyrrolo[3,2-d]pyrimidin-4(5H)-one;
- (R) 3-((4-hydroxy-5H-pyrrolo[3,2-d]pyrimidin-7-yl)methylamino)-propane-1,2-diol hydrochloride;
- (2R,3R)-3-((4-hydroxy-5H-pyrrolo[3,2-d]pyrimidin-7-yl) methylamino)butane-1,2,4-triol hydrochloride;
- 2-amino-7-(2,3-dihydroxy-1-(2-hydroxyethylamino)propyl)-3H-pyrrolo[3,2-d]pyrimidin-4(5H)-one;
- 7-(2,3-dihydroxy-1-(2-hydroxyethylamino)propyl)-3H-pyrrolo[3,2-d]pyrimidin-4(5H)-one;
- 2-amino-7-(1-amino-2,3,5-trihydroxypentyl)-3H-pyrrolo[3,2-d]pyrimidin-4(5H)-one;
- 7-(1-amino-2,3,5-trihydroxypentyl)-3H-pyrrolo[3,2-d]pyrimidin-4(5H)-one;
- 2-amino-7-(4-amino-2,3,5-trihydroxypentyl)-3H-pyrrolo[3,2-d]pyrimidin-4(5H)-one;
- 7-(4-amino-2,3,5-trihydroxypentyl)-3H-pyrrolo[3,2-d]pyrimidin-4(5H)-one;
- 2-amino-7-(1-(1,3-dihydroxypropan-2-ylamino)-2-hydroxyethyl)-3H-pyrrolo[3,2-d]pyrimidin-4(5H)-one;
- 7-(1-(1,3-dihydroxypropan-2-ylamino)-2-hydroxyethyl)-3H-pyrrolo[3,2-d]pyrimidin-4(5H)-one;
- 2-amino-7-(((2,4-dihydroxybutyl)(methyl)amino)methyl)-3H-pyrrolo[3,2-d]pyrimidin-4(5H)-one;
- 2-amino-7-((2,4-dihydroxybutylamino)methyl)-3H-pyrrolo[3,2-d]pyrimidin-4(5H)-one;
- 7-((2,4-dihydroxybutylamino)methyl)-3H-pyrrolo[3,2-d]pyrimidin-4(5H)-one;
- 2-amino-7-((3,4-dihydroxy-2-(hydroxymethyl)butylamino)methyl)-3H-pyrrolo[3,2-d]pyrimidin-4(5H)-one;
- 7-((3,4-dihydroxy-2-(hydroxymethyl)butylamino)methyl)-3H-pyrrolo[3,2-d]pyrimidin-4(5H)-one;
- 2-amino-7-((3-hydroxy-2-(hydroxymethyl)propylamino) methyl)-3H-pyrrolo[3,2-d]pyrimidin-4(5H)-one;
- 7-((3-hydroxy-2-(hydroxymethyl)propylamino)methyl)-3H-pyrrolo[3,2-d]pyrimidin-4(5H)-one;
- 2-amino-7-((3-hydroxy-2-(hydroxymethyl)propyl)(methyl) amino)methyl)-3H-pyrrolo[3,2-d]pyrimidin-4(5H)-one;
- 7-(((3-hydroxy-2-(hydroxymethyl)propyl)(methyl)amino) methyl)-3H-pyrrolo[3,2-d]pyrimidin-4(5H)-one;
- 2-amino-7-(3,4-dihydroxy-5-(methylthiomethyl)pyrrolidin-2-yl)-3H-pyrrolo[3,2-d]pyrimidin-4(5H)-one;

7-(3,4-dihydroxy-5-(methylthiomethyl)pyrrolidin-2-yl)-3H-pyrrolo[3,2-d]pyrimidin-4(5H)-one;

2-amino-7-(2,3-dihydroxy-1-(2-(methylthio)ethylamino)propyl)-3H-pyrrolo[3,2-d]pyrimidin-4(5H)-one;

7-(2,3-dihydroxy-1-(2-(methylthio)ethylamino)propyl)-3H-pyrrolo[3,2-d]pyrimidin-4(5H)-one;

2-amino-7-(1-amino-2,3-dihydroxy-5-(methylthio)pentyl)-3H-pyrrolo[3,2-d]pyrimidin-4(5H)-one;

7-(1-amino-2,3-dihydroxy-5-(methylthio)pentyl)-3H-pyrrolo[3,2-d]pyrimidin-4(5H)-one;

2-amino-7-(2-hydroxy-1-(1-hydroxy-3-(methylthio)propan-2-ylamino)ethyl)-3H-pyrrolo[3,2-d]pyrimidin-4(5H)-one;

7-(2-hydroxy-1-(1-hydroxy-3-(methylthio)propan-2-ylamino)ethyl)-3H-pyrrolo[3,2-d]pyrimidin-4(5H)-one;

2-amino-7-((3,4-dihydroxy-1-(methylthio)butan-2-ylamino)methyl)-3H-pyrrolo[3,2-d]pyrimidin-4(5H)-one;

7-((3,4-dihydroxy-1-(methylthio)butan-2-ylamino)methyl)-3H-pyrrolo[3,2-d]pyrimidin-4(5H)-one;

2-amino-7-(((2-hydroxy-4-(methylthio)butyl)(methyl)amino)methyl)-3H-pyrrolo[3,2-d]pyrimidin-4(5H)-one;

7-(((2-hydroxy-4-(methylthio)butyl)(methyl)amino)methyl)-3H-pyrrolo[3,2-d]pyrimidin-4(5H)-one;

2-amino-7-((2-hydroxy-4-(methylthio)butylamino)methyl)-3H-pyrrolo[3,2-d]pyrimidin-4(5H)-one;

7-((2-hydroxy-4-(methylthio)butylamino)methyl)-3H-pyrrolo[3,2-d]pyrimidin-4(5H)-one;

2-amino-7-((3,4-dihydroxy-2-(methylthiomethyl)butylamino)methyl)-3H-pyrrolo[3,2-d]pyrimidin-4(5H)-one;

7-((3,4-dihydroxy-2-(methylthiomethyl)butylamino)methyl)-3H-pyrrolo[3,2-d]pyrimidin-4(5H)-one;

2-amino-7-((3-hydroxy-2-(methylthiomethyl)propylamino)methyl)-3H-pyrrolo[3,2-d]pyrimidin-4(5H)-one;

7-((3-hydroxy-2-(methylthiomethyl)propylamino)methyl)-3H-pyrrolo[3,2-d]pyrimidin-4(5H)-one;

7-(((3-hydroxy-2-(methylthiomethyl)propyl)(methyl)amino)methyl)-3H-pyrrolo[3,2-d]pyrimidin-4(5H)-one;

2-amino-7-(((3-hydroxy-2-(methylthiomethyl)propyl)(methyl)amino)methyl)-3H-pyrrolo[3,2-d]pyrimidin-4(5H)-one;

7-(((2R,3R)-1,3,4-trihydroxybutan-2-ylamino)methyl)-3H-pyrrolo[3,2-d]pyrimidin-4(5H)-one;

7-(((2S,3S)-1,3,4-trihydroxybutan-2-ylamino)methyl)-3H-pyrrolo[3,2-d]pyrimidin-4(5H)-one;

7-(((2R,3S)-1,3,4-trihydroxybutan-2-ylamino)methyl)-3H-pyrrolo[3,2-d]pyrimidin-4(5H)-one;

7-(((2S,3R)-1,3,4-trihydroxybutan-2-ylamino)methyl)-3H-pyrrolo[3,2-d]pyrimidin-4(5H)-one;

2-amino-7-(((2R,3R)-1,3,4-trihydroxybutan-2-ylamino)methyl)-3H-pyrrolo[3,2-d]pyrimidin-4(5H)-one;

2-amino-7-(((2S,3S)-1,3,4-trihydroxybutan-2-ylamino)methyl)-3H-pyrrolo[3,2-d]pyrimidin-4(5H)-one;

2-amino-7-(((2R,3S)-1,3,4-trihydroxybutan-2-ylamino)methyl)-3H-pyrrolo[3,2-d]pyrimidin-4(5H)-one;

2-amino-7-(((2S,3R)-1,3,4-trihydroxybutan-2-ylamino)methyl)-3H-pyrrolo[3,2-d]pyrimidin-4(5H)-one;

5-amino-3-(((2R,3R)-1,3,4-trihydroxybutan-2-ylamino)methyl)-1H-pyrazolo[4,3-d]pyrimidin-7(6H)-one;

5-amino-3-(((2S,3S)-1,3,4-trihydroxybutan-2-ylamino)methyl)-1H-pyrazolo[4,3-d]pyrimidin-7(6H)-one;

5-amino-3-4(2R,3S)-1,3,4-trihydroxybutan-2-ylamino)methyl)-1H-pyrazolo[4,3-d]pyrimidin-7(6H)-one;

5-amino-3-(((2S,3R)-1,3,4-trihydroxybutan-2-ylamino)methyl)-1H-pyrazolo[4,3-d]pyrimidin-7(6H)-one;

7-((1,3-dihydroxy-2-(hydroxymethyl)propan-2-ylamino)methyl)-3H-pyrrolo[3,2-d]pyrimidin-4(5H)-one;

2-amino-7-((1,3-dihydroxy-2-(hydroxymethyl)propan-2-ylamino)methyl)-3H-pyrrolo[3,2-d]pyrimidin-4(5H)-one;

3-((1,3-dihydroxy-2-(hydroxymethyl)propan-2-ylamino)methyl)-1H-pyrazolo[4,3-d]pyrimidin-7(6H)-one;

7-((4-hydroxybutylamino)methyl)-3H-pyrrolo[3,2-d]pyrimidin-4(5H)-one;

2-amino-7-((4-hydroxybutylamino)methyl)-3H-pyrrolo[3,2-d]pyrimidin-4(5H)-one;

3-((4-hydroxybutylamino)methyl)-1H-pyrazolo[4,3-d]pyrimidin-7(6H)-one;

7-((2-hydroxyethylamino)methyl)-3H-pyrrolo[3,2-d]pyrimidin-4(5H)-one;

2-amino-7-((2-hydroxyethylamino)methyl)-3H-pyrrolo[3,2-d]pyrimidin-4(5H)-one;

3-((2-hydroxyethylamino)methyl)-1H-pyrazolo[4,3-d]pyrimidin-7(6H)-one;

7-((3-hydroxy-2-(hydroxymethyl)propylamino)methyl)-3H-pyrrolo[3,2-d]pyrimidin-4(5H)-one;

2-amino-7-((3-hydroxy-2-(hydroxymethyl)propylamino)methyl)-3H-pyrrolo[3,2-d]pyrimidin-4(5H)-one;

3-((3-hydroxy-2-(hydroxymethyl)propylamino)methyl)-1H-pyrazolo[4,3-d]pyrimidin-7(6H)-one;

7-(((3-hydroxy-2-(hydroxymethyl)propyl)(methyl)-amino)methyl)-3H-pyrrolo[3,2-d]pyrimidin-4(5H)-one;

2-amino-7-(((3-hydroxy-2-(hydroxymethyl)propyl)(methyl)-amino)methyl)-3H-pyrrolo[3,2-d]pyrimidin-4(5H)-one;

3-(((1,3-dihydroxypropan-2-yl)(methyl)amino)methyl)-1H-pyrazolo[4,3-d]pyrimidin-7(6H)-one;

7-((3-hydroxy-2-(hydroxymethyl)propylamino)methyl)-3H-pyrrolo[3,2-d]pyrimidin-4(5H)-one;

2-amino-7-((3-hydroxy-2-(hydroxymethyl)propylamino)methyl)-3H-pyrrolo[3,2-d]pyrimidin-4(5H)-one;

3-((1,3-dihydroxypropan-2-ylamino)methyl)-1H-pyrazolo[4,3-d]pyrimidin-7(6H)-one;

7-(((3-hydroxy-2-(hydroxymethyl)propyl)(methyl)-amino)methyl)-3H-pyrrolo[3,2-d]pyrimidin-4(5H)-one;

2-amino-7-(((3-hydroxy-2-(hydroxymethyl)propyl)(methyl)-amino)methyl)-3H-pyrrolo[3,2-d]pyrimidin-4(5H)-one;

3-(((1,3-dihydroxypropan-2-yl)(methyl)amino)methyl)-1H-pyrazolo[4,3-d]pyrimidin-7(6H)-one;

7-(((3-hydroxy-2-(hydroxymethyl)propyl)(hydroxymethyl)amino)methyl)-3H-pyrrolo[3,2-d]pyrimidin-4(5H)-one;

2-amino-7-(((3-hydroxy-2-(hydroxymethyl)propyl)(hydroxymethyl)amino)methyl)-3H-pyrrolo[3,2-d]pyrimidin-4(5H)-one;

5-amino-3-(((3-hydroxy-2-(hydroxymethyl)propyl)(hydroxymethyl)amino)methyl)-1H-pyrazolo[4,3-d]pyrimidin-7(6H)-one;

7-((1,3-dihydroxy-2-(methylthiomethyl)propan-2-ylamino)methyl)-3H-pyrrolo[3,2-d]pyrimidin-4(5H)-one;

2-amino-7-((1,3-dihydroxy-2-(methylthiomethyl)propan-2-ylamino)methyl)-3H-pyrrolo[3,2-d]pyrimidin-4(5H)-one;

5-amino-3-((1,3-dihydroxy-2-(methylthiomethyl)propan-2-ylamino)methyl)-1H-pyrazolo[4,3-d]pyrimidin-7(6H)-one;

7-(((2R,3R)-2,3,4-trihydroxybutylamino)methyl)-3H-pyrrolo[3,2-d]pyrimidin-4(5H)-one;

7-(((2S,3S)-2,3,4-trihydroxybutylamino)methyl)-3H-pyrrolo[3,2-d]pyrimidin-4(5H)-one;

7-(((2R,3S)-2,3,4-trihydroxybutylamino)methyl)-3H-pyrrolo[3,2-d]pyrimidin-4(5H)-one;

7-(((2S,3R)-2,3,4-trihydroxybutylamino)methyl)-3H-pyrrolo[3,2-d]pyrimidin-4(5H)-one;

2-amino-7-(((2R,3R)-2,3,4-trihydroxybutylamino)methyl)-3H-pyrrolo[3,2-d]pyrimidin-4(5H)-one;

2-amino-7-(((2S,3S)-2,3,4-trihydroxybutylamino)methyl)-3H-pyrrolo[3,2-d]pyrimidin-4(5H)-one;
2-amino-7-(((2R,3S)-2,3,4-trihydroxybutylamino)methyl)-3H-pyrrolo[3,2-d]pyrimidin-4(5H)-one;
2-amino-7-(((2S,3R)-2,3,4-trihydroxybutylamino)methyl)-3H-pyrrolo[3,2-d]pyrimidin-4(5H)-one;
5-amino-3-(((2R,3R)-2,3,4-trihydroxybutylamino)methyl)-1H-pyrazolo[4,3-d]pyrimidin-7(6H)-one;
5-amino-3-(((2S,3S)-2,3,4-trihydroxybutylamino)methyl)-1H-pyrazolo[4,3-d]pyrimidin-7(6H)-one;
5-amino-3-(((2R,3S)-2,3,4-trihydroxybutylamino)methyl)-1H-pyrazolo[4,3-d]pyrimidin-7(6H)-one;
5-amino-3-(((2S,3R)-2,3,4-trihydroxybutylamino)methyl)-1H-pyrazolo[4,3-d]pyrimidin-7(6H)-one;
7-((benzyl((2R,3R)-3,4-dihydroxy-2-(methylthiomethyl)butyl)amino)methyl)-3H-pyrrolo[3,2-d]pyrimidin-4(5H)-one;
7-((benzyl((2S,3S)-3,4-dihydroxy-2-(methylthiomethyl)butyl)amino)methyl)-3H-pyrrolo[3,2-d]pyrimidin-4(5H)-one;
7-((benzyl((2R,3S)-3,4-dihydroxy-2-(methylthiomethyl)butyl)amino)methyl)-3H-pyrrolo[3,2-d]pyrimidin-4(5H)-one;
7-((benzyl((2S,3R)-3,4-dihydroxy-2-(methylthiomethyl)butyl)amino)methyl)-3H-pyrrolo[3,2-d]pyrimidin-4(5H)-one;
2-amino-7-((benzyl((2R,3R)-3,4-dihydroxy-2-(methylthiomethyl)butyl)amino)methyl)-3H-pyrrolo[3,2-d]pyrimidin-4(5H)-one;
2-amino-7-((benzyl((2S,3S)-3,4-dihydroxy-2-(methylthiomethyl)butyl)amino)methyl)-3H-pyrrolo[3,2-d]-pyrimidin-4(5H)-one;
2-amino-7-((benzyl((2R,3S)-3,4-dihydroxy-2-(methylthiomethyl)butyl)amino)methyl)-3H-pyrrolo[3,2-d]pyrimidin-4(5H)-one;
2-amino-7-((benzyl((2S,3R)-3,4-dihydroxy-2-(methylthiomethyl)butyl)amino)methyl)-3H-pyrrolo[3,2-d]pyrimidin-4(5H)-one;
(S)-7-(1-(1,3-dihydroxypropan-2-ylamino)-2-hydroxyethyl)-3H-pyrrolo[3,2-d]pyrimidin-4(5H)-one;
(R)-7-(1-(1,3-dihydroxypropan-2-ylamino)-2-hydroxyethyl)-3H-pyrrolo[3,2-d]pyrimidin-4(5H)-one;
(S)-2-amino-7-(1-(1,3-dihydroxypropan-2-ylamino)-2-hydroxyethyl)-3H-pyrrolo[3,2-d]pyrimidin-4(5H)-one;
(R)-2-amino-7-(1-(1,3-dihydroxypropan-2-ylamino)-2-hydroxyethyl)-3H-pyrrolo[3,2-d]pyrimidin-4(5H)-one;
(S)-3-(1-(1,3-dihydroxypropan-2-ylamino)-2-hydroxyethyl)-1H-pyrazolo[4,3-d]pyrimidin-7(6H)-one;
(R)-3-(1-(1,3-dihydroxypropan-2-ylamino)-2-hydroxyethyl)-1H-pyrazolo[4,3-d]pyrimidin-7(6H)-one;
7-(((2R,3R)-2,3-dihydroxy-4-(methylthio)butylamino)methyl)-3H-pyrrolo[3,2-d]pyrimidin-4(5H)-one;
7-(((2S,3S)-2,3-dihydroxy-4-(methylthio)butylamino)methyl)-3H-pyrrolo[3,2-d]pyrimidin-4(5H)-one;
7-(((2R,3S)-2,3-dihydroxy-4-(methylthio)butylamino)methyl)-3H-pyrrolo[3,2-d]pyrimidin-4(5H)-one;
7-(((2S,3R)-2,3-dihydroxy-4-(methylthio)butylamino)methyl)-3H-pyrrolo[3,2-d]pyrimidin-4(5H)-one;
2-amino-7-(((2R,3R)-2,3-dihydroxy-4-(methylthio)butylamino)methyl)-3H-pyrrolo[3,2-d]pyrimidin-4(5H)-one;
2-amino-7-(((2S,3S)-2,3-dihydroxy-4-(methylthio)butylamino)methyl)-3H-pyrrolo[3,2-d]pyrimidin-4(5H)-one;
2-amino-7-(((2R,3S)-2,3-dihydroxy-4-(methylthio)butylamino)methyl)-3H-pyrrolo[3,2-d]pyrimidin-4(5H)-one;
2-amino-7-(((2S,3R)-2,3-dihydroxy-4-(methylthio)butylamino)methyl)-3H-pyrrolo[3,2-d]pyrimidin-4(5H)-one;
(R)-7-((benzyl(2,3-dihydroxypropyl)amino)methyl)-3H-pyrrolo[3,2-d]pyrimidin-4(5H)-one;
(S)-7-((benzyl(2,3-dihydroxypropyl)amino)methyl)-3H-pyrrolo[3,2-d]pyrimidin-4(5H)-one;
(R)-2-amino-7-((benzyl(2,3-dihydroxypropyl)amino)methyl)-3H-pyrrolo[3,2-d]pyrimidin-4(5H)-one;
(S)-2-amino-7-((benzyl(2,3-dihydroxypropyl)amino)methyl)-3H-pyrrolo[3,2-d]pyrimidin-4(5H)-one;
(R)-3-((2,3-dihydroxypropylamino)methyl)-1H-pyrazolo[4,3-d]pyrimidin-7(6H)-one;
(S)-3-((2,3-dihydroxypropylamino)methyl)-1H-pyrazolo[4,3-d]pyrimidin-7(6H)-one;
(R)-7-(((2,3-dihydroxypropyl)(2-hydroxyethyl)amino)methyl)-3H-pyrrolo[3,2-d]pyrimidin-4(5H)-one;
(S)-7-(((2,3-dihydroxypropyl)(2-hydroxyethyl)amino)methyl)-3H-pyrrolo[3,2-d]pyrimidin-4(5H)-one;
(R)-2-amino-7-(((2,3-dihydroxypropyl)(2-hydroxyethyl)amino)methyl)-3H-pyrrolo[3,2-d]pyrimidin-4(5H)-one;
(S)-2-amino-7-(((2,3-dihydroxypropyl)(2-hydroxyethyl)amino)methyl)-3H-pyrrolo[3,2-d]pyrimidin-4(5H)-one;
(R)-3-(((2,3-dihydroxypropyl)(2-hydroxyethyl)amino)methyl)-1H-pyrazolo[4,3-d]pyrimidin-7(6H)-one;
(S)-3-(((2,3-dihydroxypropyl)(2-hydroxyethyl)amino)methyl)-1H-pyrazolo[4,3-d]pyrimidin-7(6H)-one;
(2R,3R)-7-((3,4-dihydroxy-2-(hydroxymethyl)butylamino)methyl)-3H-pyrrolo[3,2-d]pyrimidin-4(5H)-one;
(2S,3S)-7-((3,4-dihydroxy-2-(hydroxymethyl)butylamino)methyl)-3H-pyrrolo[3,2-d]pyrimidin-4(5H)-one;
(2R,3S)-7-((3,4-dihydroxy-2-(hydroxymethyl)butylamino)methyl)-3H-pyrrolo[3,2-d]pyrimidin-4(5H)-one;
(2S,3R)-7-((3,4-dihydroxy-2-(hydroxymethyl)butylamino)methyl)-3H-pyrrolo[3,2-d]pyrimidin-4(5H)-one;
(2R,3R)-2-amino-7-((3,4-dihydroxy-2-(hydroxymethyl)butylamino)methyl)-3H-pyrrolo[3,2-d]pyrimidin-4(5H)-one;
(2S,3S)-2-amino-7-((3,4-dihydroxy-2-(hydroxymethyl)butylamino)methyl)-3H-pyrrolo[3,2-d]pyrimidin-4(5H)-one;
(2R,3S)-2-amino-7-((3,4-dihydroxy-2-(hydroxymethyl)butylamino)methyl)-3H-pyrrolo[3,2-d]pyrimidin-4(5H)-one;
(2S,3R)-2-amino-7-((3,4-dihydroxy-2-(hydroxymethyl)butylamino)methyl)-3H-pyrrolo[3,2-d]pyrimidin-4(5H)-one;
(2R,3R)-5-amino-3-((3,4-dihydroxy-2-(hydroxymethyl)butylamino)methyl)-1H-pyrazolo[4,3-d]pyrimidin-7(6H)-one;
(2S,3S)-5-amino-3-((3,4-dihydroxy-2-(hydroxymethyl)butylamino)methyl)-1H-pyrazolo[4,3-d]pyrimidin-7(6H)-one;
(2R,3S)-5-amino-3-((3,4-dihydroxy-2-(hydroxymethyl)butylamino)methyl)-1H-pyrazolo[4,3-d]pyrimidin-7(6H)-one;
(2S,3R)-5-amino-3-((3,4-dihydroxy-2-(hydroxymethyl)butylamino)methyl)-1H-pyrazolo[4,3-d]pyrimidin-7(6H)-one;
7-(((2R,3R)-3,4-dihydroxy-1-(methylthio)butan-2-ylamino)methyl)-3H-pyrrolo[3,2-d]pyrimidin-4(5H)-one;
7-(((2S,3S)-3,4-dihydroxy-1-(methylthio)butan-2-ylamino)methyl)-3H-pyrrolo[3,2-d]pyrimidin-4(5H)-one;
7-(((2R,3S)-3,4-dihydroxy-1-(methylthio)butan-2-ylamino)methyl)-3H-pyrrolo[3,2-d]pyrimidin-4(5H)-one;
7-(((2S,3R)-3,4-dihydroxy-1-(methylthio)butan-2-ylamino)methyl)-3H-pyrrolo[3,2-d]pyrimidin-4(5H)-one;
2-amino-7-(((2R,3R)-3,4-dihydroxy-1-(methylthio)butan-2-ylamino)methyl)-3H-pyrrolo[3,2-d]pyrimidin-4(5H)-one;

2-amino-7-(((2S,3S)-3,4-dihydroxy-1-(methylthio)butan-2-ylamino)methyl)-3H-pyrrolo[3,2-d]pyrimidin-4(5H)-one;
2-amino-7-(((2R,3S)-3,4-dihydroxy-1-(methylthio)butan-2-ylamino)methyl)-3H-pyrrolo[3,2-d]pyrimidin-4(5H)-one;
2-amino-7-(((2S,3R)-3,4-dihydroxy-1-(methylthio)butan-2-ylamino)methyl)-3H-pyrrolo[3,2-d]pyrimidin-4(5H)-one;
3-(((2R,3R)-3,4-dihydroxy-1-(methylthio)butan-2-ylamino)methyl)-1H-pyrazolo[4,3-d]pyrimidin-7(6H)-one;
3-(((2S,3S)-3,4-dihydroxy-1-(methylthio)butan-2-ylamino)methyl)-1H-pyrazolo[4,3-d]pyrimidin-7(6H)-one;
3-(((2R,3S)-3,4-dihydroxy-1-(methylthio)butan-2-ylamino)methyl)-1H-pyrazolo[4,3-d]pyrimidin-7(6H)-one;
3-(((2S,3R)-3,4-dihydroxy-1-(methylthio)butan-2-ylamino)methyl)-1H-pyrazolo[4,3-d]pyrimidin-7(6H)-one;
3-(((2R,3R)-3,4-dihydroxy-2-(methylthiomethyl)butylamino)methyl)-1H-pyrazolo[4,3-d]pyrimidin-7(6H)-one;
3-(((2S,3S)-3,4-dihydroxy-2-(methylthiomethyl)butylamino)methyl)-1H-pyrazolo[4,3-d]pyrimidin-7(6H)-one;
3-(((2R,3S)-3,4-dihydroxy-2-(methylthiomethyl)butylamino)methyl)-1H-pyrazolo[4,3-d]pyrimidin-7(6H)-one;
3-(((2S,3R)-3,4-dihydroxy-2-(methylthiomethyl)butylamino)methyl)-1H-pyrazolo[4,3-d]pyrimidin-7(6H)-one;
2-amino-7-(((2R,3R)-3,4-dihydroxy-2-(methylthiomethyl)butylamino)methyl)-3H-pyrrolo[3,2-d]pyrimidin-4(5H)-one;
2-amino-7-(((2S,3S)-3,4-dihydroxy-2-(methylthiomethyl)butylamino)methyl)-3H-pyrrolo[3,2-d]pyrimidin-4(5H)-one;
2-amino-7-(((2R,3S)-3,4-dihydroxy-2-(methylthiomethyl)butylamino)methyl)-3H-pyrrolo[3,2-d]pyrimidin-4(5H)-one;
2-amino-7-(((2S,3R)-3,4-dihydroxy-2-(methylthiomethyl)butylamino)methyl)-3H-pyrrolo[3,2-d]pyrimidin-4(5H)-one;
7-(((2R,3R)-3,4-dihydroxy-2-(methylthiomethyl)butylamino)methyl)-3H-pyrrolo[3,2-d]pyrimidin-4(5H)-one;
7-(((2S,3S)-3,4-dihydroxy-2-(methylthiomethyl)butylamino)methyl)-3H-pyrrolo[3,2-d]pyrimidin-4(5H)-one;
7-(((2R,3S)-3,4-dihydroxy-2-(methylthiomethyl)butylamino)methyl)-3H-pyrrolo[3,2-d]pyrimidin-4(5H)-one; and
7-(((2S,3R)-3,4-dihydroxy-2-(methylthiomethyl)butylamino)methyl)-3H-pyrrolo[3,2-d]pyrimidin-4(5H)-one.

Preferred compounds of the invention also include each one of the above identified compounds wherein the 4-hydroxy-5H-pyrrolo[3,2-d]pyrimidin-7-yl moiety (9-deazahypoxanthin-9-yl) is replaced by either a 2-amino-7-3H-pyrrolo[3,2-d]pyrimidin-4(5H)-one-7-yl (9-deazaguanine-9-yl) moiety or an (8-aza-9-deazahypoxanthin-9-yl) moiety.

In a second aspect of the invention there is provided a pharmaceutical composition comprising a pharmaceutically effective amount of a compound of formula (I).

In another aspect of the invention there is provided a method of treatment of a disease or condition in which it is desirable to inhibit a purine nucleoside phosphorylase or a nucleoside hydrolase comprising administering a pharmaceutically effective amount of a compound of formula (I) to a patient requiring treatment.

The diseases or conditions include cancer, bacterial and protozoal infections, and T-cell mediated diseases or conditions such as psoriasis, arthritis and transplant rejection.

The purine nucleoside phosphorylase is preferably human purine nucleoside phosphorylase (Hs PNP), but may be any other purine nucleoside phosphorylase including the purine nucleoside phosphorylase from the protozoan parasite *Plasmodium falciparum* (Pf PNP).

In a further aspect of the invention there is provided the use of a compound of formula (I) in the manufacture of a medicament for the treatment of one or more of these diseases or conditions.

DETAILED DESCRIPTION

Definitions

The term "alkyl" means any saturated hydrocarbon radical having up to 30 carbon atoms and includes any $C_1$-$C_{25}$, $C_1$-$C_{20}$, $C_1$-$C_{15}$, $C_1$-$C_{10}$, or $C_1$-$C_6$ alkyl group, and is intended to include both straight- and branched-chain alkyl groups. The same terminology applies to the non-aromatic moiety of an aralkyl radical. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group.

The term "alkenyl" means any hydrocarbon radical having at least one double bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkenyl group, and is intended to include both straight- and branched-chain alkenyl groups. The same terminology applies to the non-aromatic moiety of an aralkenyl radical. Examples of alkenyl groups include: ethenyl group, n-propenyl group, iso-propenyl group, n-butenyl group, iso-butenyl group, sec-butenyl group, t-butenyl group, n-pentenyl group, 1,1-dimethylpropenyl group, 1,2-dimethylpropenyl group, 2,2-dimethylpropenyl group, 1-ethylpropenyl group, 2-ethylpropenyl group, n-hexenyl group and 1-methyl-2-ethylpropenyl group.

The term "alkynyl" means any hydrocarbon radical having at least one triple bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkynyl group, and is intended to include both straight- and branched-chain alkynyl groups. The same terminology applies to the non-aromatic moiety of an aralkynyl radical. Examples of alkynyl groups include: ethynyl group, n-propynyl group, iso-propynyl group, n-butynyl group, iso-butynyl group, sec-butynyl group, t-butynyl group, n-pentynyl group, 1,1-dimethylpropynyl group, 1,2-dimethylpropynyl group, 2,2-dimethylpropynyl group, 1-ethylpropynyl group, 2-ethylpropynyl group, n-hexynyl group and 1-methyl-2-ethylpropynyl group.

The term "aryl" means an aromatic radical having 4 to 18 carbon atoms and includes heteroaromatic radicals. Examples include monocyclic groups, as well as fused groups such as bicyclic groups and tricyclic groups. Some examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "aralkyl" means an alkyl radical having an aryl substituent.

The term "alkoxy" means an hydroxy group with the hydrogen replaced by an alkyl group.

The term "halogen" includes fluorine, chlorine, bromine and iodine.

The term "optionally substituted" means, in reference to the optionally substituted group, the group may have one or more substituents chosen from the group comprising hydroxy, alkyl, alkoxy, thiol, optionally substituted alkylthio, optionally substituted arylthio, optionally substituted aralkylthio, halogen, amino, carboxylic acid, and carboxylate alkyl ester.

The term "prodrug" as used herein means a pharmacologically acceptable derivative of the compound of formula (I), such that an in vivo biotransformation of the derivative gives the compound as defined in formula (I). Prodrugs of compounds of formula (I) may be prepared by modifying functional groups present in the compounds in such a way that the modifications are cleaved in vivo to give the parent compound.

The term "pharmaceutically acceptable salts" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

The term "patient" includes human and non-human animals.

Description of Inhibitor Compounds

The acyclic amine compounds of the invention are surprisingly potent inhibitors of PNP. Based on their particular knowledge of the PNP enzyme, and the enzyme inhibitory activities of the imino ring compounds, the applicants would not have predicted that acyclic amine compounds would be potent PNP inhibitors. It was previously considered that a sterically unconstrained acyclic amine, rather than an imino ring, would have rendered the compounds much less potent. However, the compounds of the invention prove to be surprisingly potent inhibitors of human PNP. Indeed, one compound of the invention (Compound 17.3) has a $K_i^*$ for human PNP of 8.5±0.6 pM, a potency sufficient to have therapeutic potential, is orally available. This most potent "third generation" inhibitor, like the parent DADMe-Immucillin-H and Immucillin-H compounds, have Kd values in the picomolar range for binding to HsPNP. A common structural element of the picomolar inhibitors for HsPNP is a secondary N and three hydroxyl groups. It is expected that the geometric flexibility of the acyclic, singly bonded amino alcohol groups permits positioning of these three hydroxyl groups in the catalytic site to match those found for DADMe-Immucillin-H and Immucillin-H.

Synthesis of Inhibitor Compounds

The compounds of the invention may be prepared by a variety of different methods. The following are representative non-limiting examples.

Compounds where $R^1$ is $NR^3R^4$ may be prepared by reacting an amine $NHR^5R^6$ (where $R^5$ and $R^6$ may be the same as $R^3$ and $R^4$ or protected versions thereof) with an aldehyde (e.g. formaldehyde) and a 9-deazapurine (e.g. 9-deazahypoxanthine) in a Mannich reaction as shown in Scheme 1. The Mannich reaction is followed by deprotection, if necessary.

Scheme 1

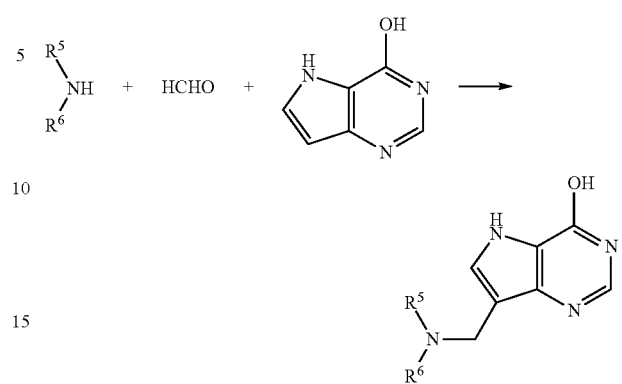

Alternatively reductive amination of an aldehyde with the amine $NHR^5R^6$ (as shown in Scheme 2) can be effected using reagents such as, but not limited to, $NaBH_3CN$ or $NaAcO_3BH$. Suitable deprotection steps follow. Suitable protected aldehydes are known (e.g. J. Org. Chem. 2004, 69, 2217-2220).

Scheme 2

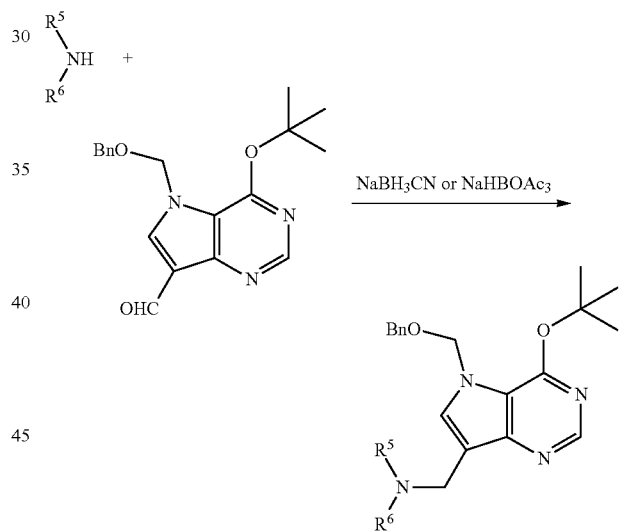

Another example is shown in Scheme 3. A carbonyl compound, where $R^7$ is an optionally substituted alkyl or protected version thereof and $R^8$ is H or an optionally substituted alkyl or protected version thereof, may be treated with a lithiated purine derivative (some examples of which may be found in J. Org. Chem. 2004, 69, 2217-2220). A standard deoxygenation step follows.

Scheme 3

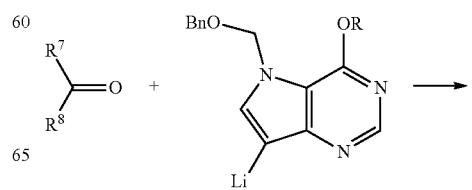

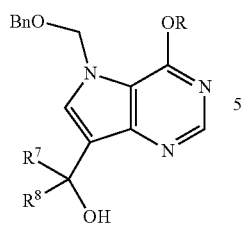

The amines NHR⁵R⁶ described above may be prepared by a number of methods. The following are representative non-limiting examples.

Cycloaddition of but-2-ene-1,4-diol with a nitrone derived from N-benzylhydroxylamine and formaldehyde (Scheme 4) followed by zinc reduction to give an amine that may be further functionalized to provide compounds of the invention.

Scheme 4

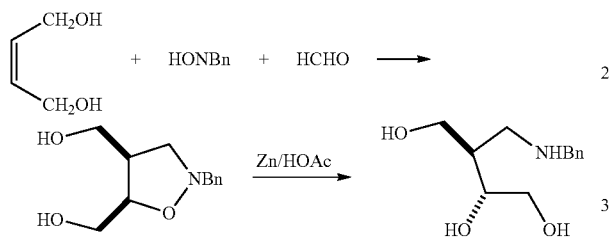

Conversion of butane 1,2,4-triol into either the 2,4-O-benzylidene or the 1,2-O-isopropylidene derivatives (Scheme 5). These compounds may then be converted into amines that can be further functionalized into compounds of the invention by activation of the primary hydroxy group, and displacement and appropriate manipulation of protecting groups.

Compounds such as (R)- or (S)-(2,2-dimethyl-1,3-dioxolan-4-yl)methanol may be converted into amines using the chemistry described in Scheme 5, and the amines then converted into compounds of the invention.

But-2-ene 1,4-diol may be protected, epoxidized and ring opened as shown in Scheme 6 to give precursors to amines that may then be converted into compounds of the invention.

Scheme 6

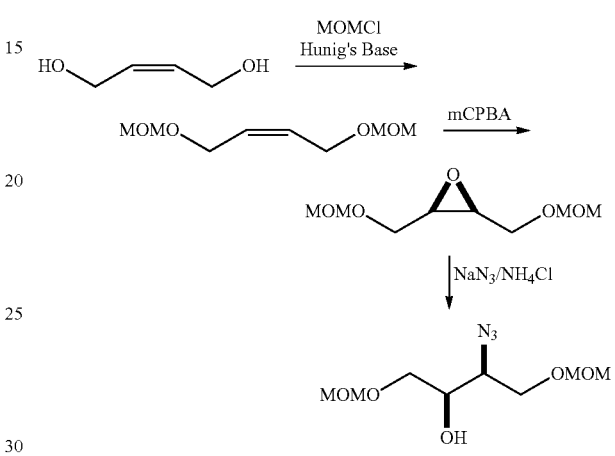

D- and L-Diethyl tartrate can be converted into chiral amines as shown in Scheme 7 (A. Breuning, R. Vicik and T. Schirmeister, *Tetrahedron Asymm.*, 2003, 14, 3301 and Z. Tang, Z.-H. Yang, X.-H. Chen, L.-F. Cun, A.-Q. Mi, Y.-Z. Jiang and L.-Z. Gong, *J. Am. Chem. Soc.*, 2005, 127, 9285) from which other useful amines may be derived.

Scheme 5

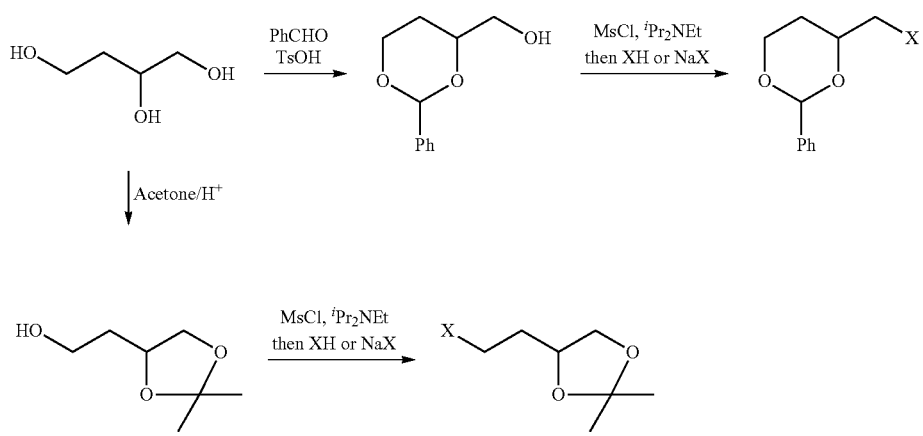

X = N₃, NH₂, NHBn, NHMe etc

Scheme 7

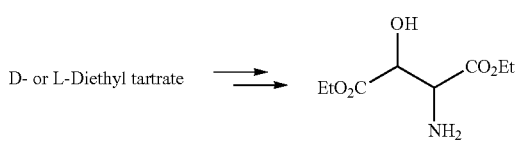

Reaction of 4,4-dimethyl-3,5,8-trioxabicyclo[5.1.0]octane with either enantiomer of α-methylbenzylamine (J. Org. Chem. 1998, 63, 7582-7583) affords diastereomeric mixtures of amino alcohols (Scheme 8). Crystallisation of the desired diastereomer followed by hydrogenolysis provides access to the enantiomerically pure amino alcohol.

Scheme 8

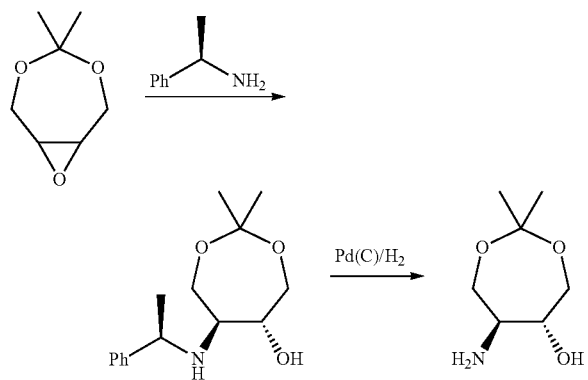

Various protected lactones and esters can be treated with ammonia to give amido alcohols, which can be converted to the corresponding amino alcohols on treatment with lithium aluminium hydride (Scheme 9).

Scheme 9

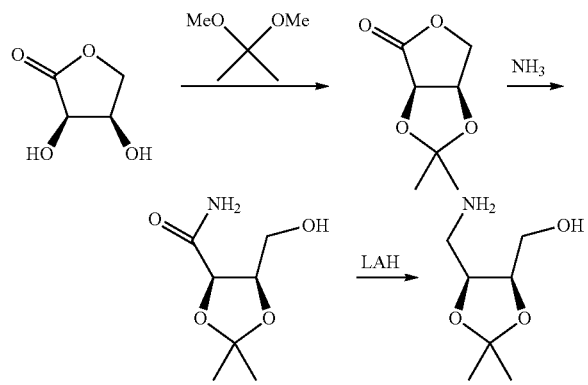

General Aspects

The compounds of the invention are useful in both free base form and in the form of salts.

It will be appreciated that the compounds of the invention include all optical isomers and stereoisomers of the formula (I).

It will also be appreciated that the representation of a compound of formula (I), where B and/or D is a hydroxy group, is of the enol-type tautomeric form of a corresponding amide, and this will largely exist in the amide form. The use of the enol-type tautomeric representation is simply to allow fewer structural formulae to represent the compounds of the invention.

The active compounds may be administered to a patient by a variety of routes, including orally, parenterally, by inhalation spray, topically, rectally, nasally, buccally or via an implanted reservoir. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams. The specific dosage required for any particular patient will depend upon a variety of factors, including the patient's age, body weight, general health, sex, etc.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

EXAMPLES

The following examples further illustrate the invention. It is to be appreciated that the invention is not limited to the examples.

General Methods

Anhydrous solvents were obtained commercially. Air sensitive reactions were carried out under argon. Organic solutions were dried over MgSO$_4$ and the solvents were evaporated under reduced pressure. Chromatography solvents were distilled prior to use. Thin layer chromatography (t.l.c.) was performed on glass or aluminium sheets coated with 60 $F_{254}$ silica. Organic compounds were visualised under uv light or by use of a dip of cerium(IV) sulfate (0.2%, w/v) and ammonium molybdate (5%) in sulfuric acid (2M), one of $I_2$ (0.2%) and KI (7%) in $H_2SO_4$ (M), or 0.1% ninhydrin in EtOH. Flash column chromatography was performed on Scharlau or Merck silica gel 60 (40-60 μm). Optical rotations were recorded on a Perkin-Elmer 241 polarimeter with a path length of 1 dm and are in units of $10^{-1}$ deg $cm^2$ $g^{-1}$; concentrations are in g/100 ml. NMR spectra were recorded on a Bruker AC300E. Unless otherwise stated, $^1$H spectra at 300 MHz were measured in $CDCl_3$, $CD_3OD$ (internal reference $Me_4Si$, δ 0) or $D_2O$ (no internal reference), and $^{13}C$ spectra at 75.5 MHz in $CDCl_3$ (reference, solvent centre line, δ 77.4), $CD_3OD$ (reference, solvent centre line δ 49.5) or $D_2O$ (no internal reference). Positive electrospray mass spectra were recorded on a Waters Q-TOF Premier Tandem Mass Spectrometer.

Example 1

Synthesis of rac-(2R,3S)-3-(4-hydroxy-5H-pyrrolo[3,2-d]pyrimidin-7-yl)methylamino)butane-1,2,4-triol Example 1.1

Synthesis of 1,4-bis-methoxymethoxy-cis-but-2-ene

This compound was prepared according to the method described in C. Saluzzo, A-M. La Spina, D. Picq, G. Alvernhe, D. Anker, D. Wolf and G. Haufe, *Bull. Chim. Soc. Fr.*, 1994, 131, 831-843.

Example 1.2

Synthesis of meso-2,3-bis((methoxymethoxy)methyl)oxirane

To a stirred solution of the product from Example 1.1 (3.66 g, 20.8 mmol) in DCM (40 ml) was added m-chloroperbenzoic acid (57%, 7.55 g, 24.9 mmol) portionwise. The resulting solution was stirred at ambient temperature for 16 hours. The reaction mixture was evaporated and partitioned between ether and saturated aqueous sodium bicarbonate, the ethereal

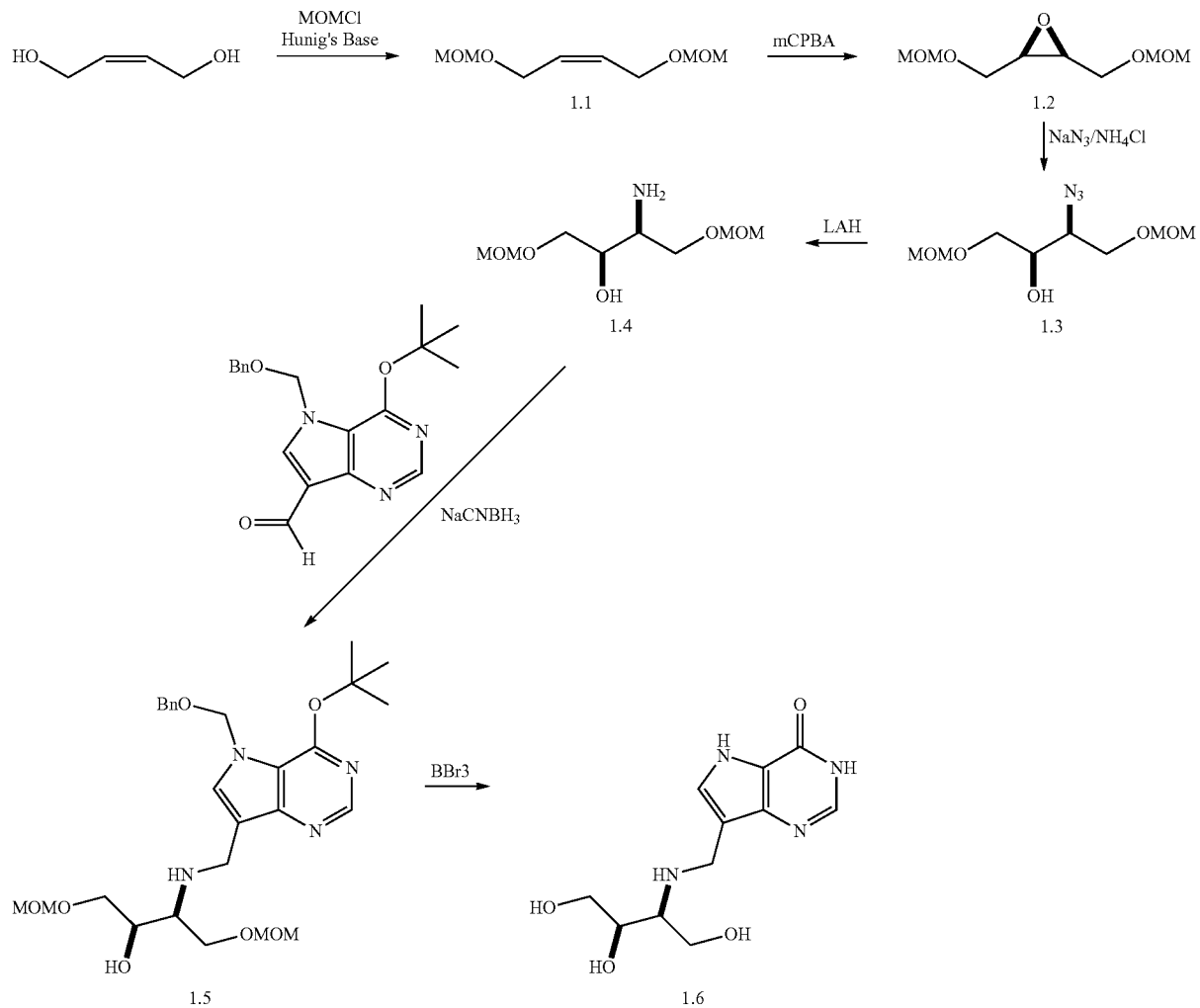

layer was dried (MgSO$_4$) and concentrated. The residue was purified by flash silica chromatography, eluting with 17% ethyl acetate in petroleum ether giving the title compound as a colourless oil (1.88 g, 47%). $^1$H NMR (300 MHz, CDCl$_3$) 3.26 (2H, m), 3.39 (6H, s), 3.65 (2H, m), 3.75 (2H, dd, J 4.3, 11.6 Hz), 4.67 (4H, ABq).

Example 1.3

Synthesis of rac-(6R,7S)-7-azido-2,4,9,11-tetraoxadodecan-6-ol

The product from Example 1.2 (1.88 g, 9.77 mmol), ammonium chloride (1.83 g, 34.2 mmol) and sodium azide (2.22 g, 34.2 mmol) were heated in dimethylformamide (15 ml) at 110° C. for 5 hours. The reaction mixture was diluted with ethyl acetate and washed with water (5×), dried (MgSO$_4$) and evaporated. The residue was purified by flash silica chromatography, eluting with 2:1 petrol:ethyl acetate giving the title compound as a colourless oil (786 mg, 34%). $^1$H NMR (300 MHz, CDCl$_3$) 2.77 (1H, br s), 3.39 (3H, s), 3.40 (3H, s), 3.64 (3H, m), 3.80 (2H, m), 3.91 (1H, m), 4.67 (2H, m), 4.68 (2H, m); $^{13}$C NMR (75 MHz, CDCl$_3$) 55.9, 62.8, 68.1, 70.1, 70.8, 97.1, 97.5.

Example 1.4

Synthesis of (6R,7SR)-7-amino-2,4,9,11-tetraoxadodecan-6-ol

To a stirred solution of the product from Example 1.3 (392 mg, 1.67 mmol) in tetrahydrofuran (10 ml) was added lithium aluminium hydride (1.0M in ether, 3.33 ml) dropwise. The resulting solution was stirred at ambient temperature for 1 hour. The reaction mixture was partitioned between aqueous sodium bicarbonate and ethyl acetate and the aqueous layer evaporated. The residue was triturated with hot ethyl acetate (4×) and the solution evaporated to give the title compound as a colourless oil (261 mg, 75%). $^1$H NMR (300 MHz, CDCl$_3$) 3.07 (1H, m), 3.38 (3H, s), 3.38 (3H, s), 3.53 (1H, dd, J 6.8, 9.7 Hz), 3.67 (5H, m), 4.64 (2H, s), 4.66 (2H, s); $^{13}$C NMR (75 MHz, CDCl$_3$) 52.7, 55.7, 55.7, 70.7, 70.9, 70.9, 97.1, 97.3.

Example 1.5

Synthesis of (6RS,7SR)-7-((5-(benzyloxymethyl)-4-tert-butoxy-5H-pyrrolo[3,2-d]pyrimidin-7-yl)methylamino)-2,4,9,11-tetraoxadodecan-6-ol The product from Example 1.4 (151 mg, 0.722 mmol) and aldehyde (GB. Evans et al., *J. Med. Chem.* 2005, 48, 4679-4689) (204 mg, 0.601 mmol) were evaporated from methanol (10 ml) three times before addition of methanol (10 ml), acetic acid (5 drops) and sodium cyanoborohydride (76 mg, 1.20 mmol). The resulting solution was stirred at ambient temperature for 16 hours and evaporated on to silica. The residue was purified by flash silica chromatography, eluting with 95:5 dichloromethane:methanol (plus 1% triethylamine) giving the title compound as a colourless oil (319 mg, 100%). $^1$H NMR (300 MHz, CDCl$_3$) 1.69 (9H, s), 2.93 (1H, m), 3.35 (3H, s), 3.36 (3H, s), 3.62 (2H, m), 3.75 (3H, m), 3.98 (1H, d, J Hz), 4.18 (1H, d, J Hz), 4.47 (2H, s), 4.62 (2H, s), 4.65 (2H, s), 5.73 (2H, s), 7.29 (6H, m), 8.46 (1H, s).

Example 1.6

Synthesis of 7-(((2RS,3SR)-1,3,4-trihydroxybutan-2-ylamino)methyl)-3H-pyrrolo[3,2-d]pyrimidin-4(5H)-one The product from Example 1.5 (104 mg, 0.195 mmol) was stirred in DCM (10 ml) at −78° C. and boron tribromide (1.0M in DCM, 1.95 ml) added dropwise. The reaction was stirred at −78° C. for 45 minutes before addition of methanol (10 ml). The solvents were evaporated and the residue co-evaporated with methanol (2×). The residue was partitioned between water and DCM and the aqueous layer evaporated. The residue was stirred in methanolic ammonia for 10 minutes and then evaporated on to silica and purified by flash silica chromatography, eluting with 5:4.5:0.5 DCM:methanol:ammonia giving the title compound as a white solid (27 mg, 52%). $^1$H NMR (300 MHz, CDCl$_3$) 2.76 (1H, q, J 5.2 Hz), 3.48 (1H, dd, J 6.3, 11.9 Hz), 3.60 (2H, m), 3.70 (2H, m), 3.85 (2H, ABq), 7.34 (1H, s), 7.78 (1H, s); $^{13}$C NMR (75 MHz, CDCl$_3$) 40.2, 59.8, 59.8, 63.5, 71.2, 113.1, 117.5, 129.2, 142.4, 143.5, 155.4; m/z (ES$^+$) 537 (2MH$^+$, 20%), 269 (MH$^+$, 100%); HRMS (ESI$^+$) C$_{11}$H$_{16}$N$_4$O$_4$ requires 269.1241. found 269.1250. The product, compound 1.6, is a 1:1 mixture of the enantiomers of Examples 17 and 18 below.

Example 2

Synthesis of 7-(((2,4-dihydroxybutyl)(methyl)amino)methyl)-3H-pyrrolo[3,2-d]pyrimidin-4(5H)-one

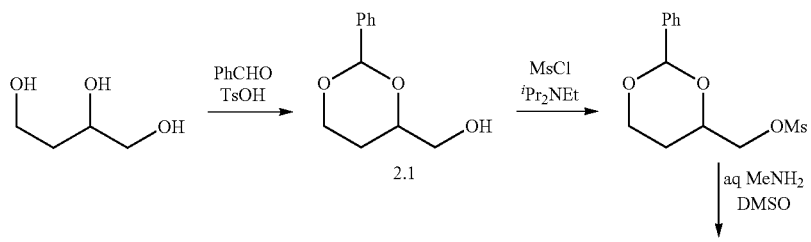

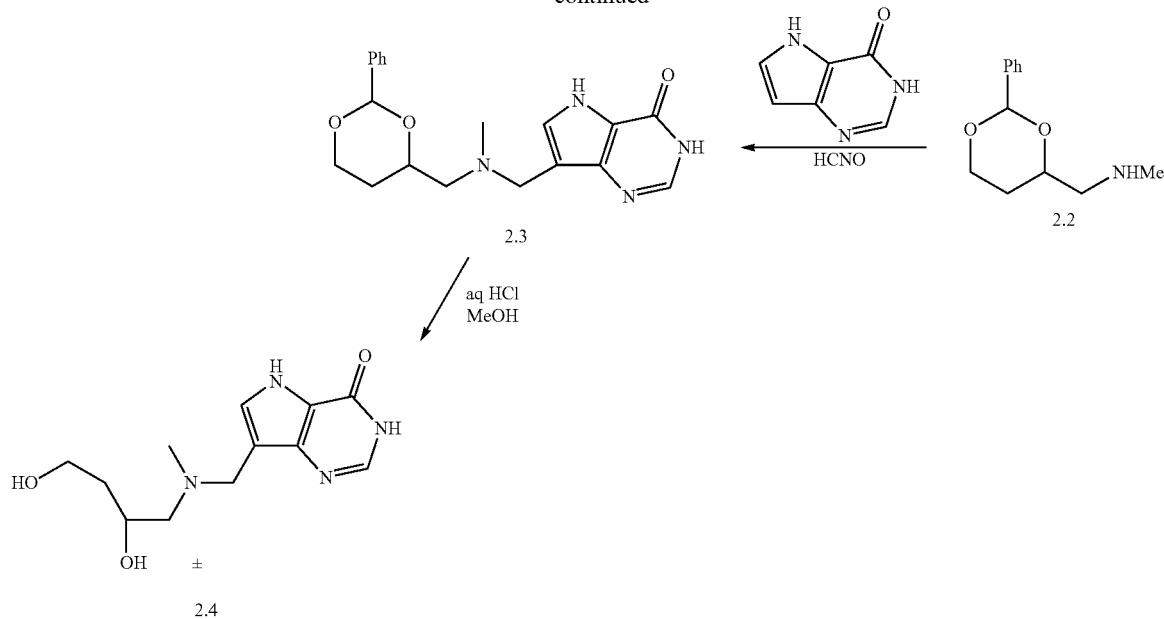

Example 2.1

Synthesis of 4-hydroxymethyl-2-phenyl-1,3-dioxane

A mixture of 1,2,4-butanetriol (3.0 g, 28.3 mmol) and benzaldehyde (11.48 ml, 113 mmol) in dry toluene (50 mL) with p-toluenesulfonic acid monohydrate (0.269 g, 1.413 mmol) was heated under reflux in a Dean-Stark apparatus. After ~1 h, the solution was washed with sat. aq NaHCO$_3$, dried and concentrated under high vac to remove most of the benzaldehyde. Chromatography gave syrupy title compound (2.88 g, 14.83 mmol, 52.5% yield). The NMR's were the same as reported (*Tetrahedron Asymm*. 1996, 7, 3209-3246).

Example 2.2

Synthesis of 4-methylaminomethyl-2-phenyl-1,3-dioxane

To a solution of 4-hydroxymethyl-2-phenyl-1,3-dioxane (0.80 g, 4.12 mmol) in dichloromethane (20 mL) was added diisopropylethylamine (1.702 ml, 10.30 mmol) and the solution was cooled in an ice bath. Methanesulfonyl chloride (0.414 ml, 5.35 mmol) was added and the solution was allowed to warm to RT. After 1 h, it was washed with 2M aq HCl, saturated aq NaHCO$_3$, dried and concentrated to a syrup (1.15 g). A solution of (0.9 g, 3.30 mmol) of this material in DMSO (8 mL) containing 40% aq methylamine (2.85 ml, 33.0 mmol) was stoppered and heated at ~75-80° C. for 24 h. The solution was cooled, chloroform was added and washed twice with water, dried and concentrated. Chromatography afforded title compound (0.465 g, 2.24 mmol, 68%) as a syrup. $^1$H NMR (CDCl$_3$) δ 7.50-7.47 (2H, m), 7.39-7.30 (3H, m), 5.52 (1H, s), 4.31-4.25 (1H, m), 4.09-3.93 (2H, m), 2.80 (1H, dd, J=12.3, 8.0 Hz), 2.67 (1H, dd, J=12.3, 3.4 Hz), 2.45 (3H, s), 1.96-1.83 (2H, m), 1.49 (1H, dd, J=13.2, 1.2 Hz); $^{13}$C NMR δ 139.0, 129.2, 128.6, 126.5, 101.6, 76.8, 67.2, 57.0, 36.8, 29.5.

Example 2.3

Synthesis of 7-((methyl((2-phenyl-1,3-dioxan-4-yl)methyl)amino)-methyl)-3H-pyrrolo[3,2-d]pyrimidin-4(5H)-one A mixture of 4-methylaminomethyl-2-phenyl-1,3-dioxane (0.368 g, 1.775 mmol), 9-deazahypoxanthine (0.288 g, 2.131 mmol), acetic acid (0.508 ml, 8.88 mmol) and 37% aq formaldehyde (0.264 ml, 3.55 mmol) in dioxane (10 mL) was stirred and heated in stoppered flask at 80° C. More 37% aq formaldehyde (0.132 ml, 1.775 mmol) was added and the stoppered flask was heated again at 80° C. for ~24 h. The solution was concentrated to dryness and chromatography (10% 7M NH$_3$/MeOH in CH$_2$Cl$_2$) separated the less polar byproducts, but the product and deazahypoxanthine eluted together. Chromatography of this material eluting with CHCl$_3$/EtOAc/MeOH 5:2:1, then 4:2:3 followed by 20% 7M NH$_3$/MeOH, gave the title compound as a white solid (0.406 g, 1.146 mmol, 64.5% yield). $^1$H NMR (CDCl$_3$/CD$_3$OD) δ 7.84 ((1H, s), 7.48-7.45 (2H, m), 7.39 (1H, s), 7.37-7.28 (3H, m), 5.56 (1H, s), 4.30-4.11 (2H, m), 4.02 (1H, dt, J=11.9, 2.5 Hz), 3.91 and 3.83 (1H each, d, J=13.8 Hz), 2.73 (1H, dd, J=13.5, 7.5 Hz), 2.57 (1H, dd, J=13.5, 3.4 Hz), 2.39 (3H, s), 1.74 (ddd, J=12.5, 4.9 Hz), 1.53 (1H, d, J=12.4 Hz); $^{13}$C NMR δ 156.8, 146.2, 143.2, 140.6, 130.6, 130.5, 129.8, 128.0, 119.7, 113.9, 103.0, 77.4, 68.7, 62.5, 52.0, 44.3, 31.5.

Example 2.4

Synthesis of 7-(((2,4-dihydroxybutyl)(methyl)amino)methyl)-3H-pyrrolo[3,2-d]pyrimidin-4(5H)-one A solution of 9-deaza-9-{[(methyl(2-phenyl-1,3-dioxan-4-yl)methyl)amino]methyl}-hypoxanthine (0.070 g, 0.198 mmol) in methanol (2 mL) and conc aq HCl (2 mL) was allowed to stand at RT. After ~2 h, it was diluted with water, extracted (×2) with chloroform, and then the aq. phase was concentrated to dryness. Chromatography (CH$_2$Cl$_2$/MeOH/aq NH$_3$ 5:4:1) gave 7-(((2,4-dihydroxybutyl)(methyl)amino)

methyl)-3H-pyrrolo[3,2-d]pyrimidin-4(5H)-one as a white solid (0.040 g, 0.150 mmol, 76% yield). $^1$H NMR (D$_2$O) δ 8.00 (1H, s), 7.71 (1H, s), 4.51 (1H, d, J=13.9 Hz), 4.44 (1H, d, J=14.0 Hz), 4.19 (1H, br s), 3.68 (2H, t, J=6.4 Hz), 3.17 (2H, br s), 2.86 (3H, s), 1.71-1.61 (2H, m); $^{13}$C NMR δ 155.3, 144.6, 143.4, 132.4, 118.2, 104.2, 72.0, 63.1, 60.0, 58.0, 36.8.

Example 3

Synthesis of (R)-7-((2,3-dihydroxypropylamino)methyl)-3H-pyrrolo[3,2-d]pyrimidin-4(5H)-one hydrochloride

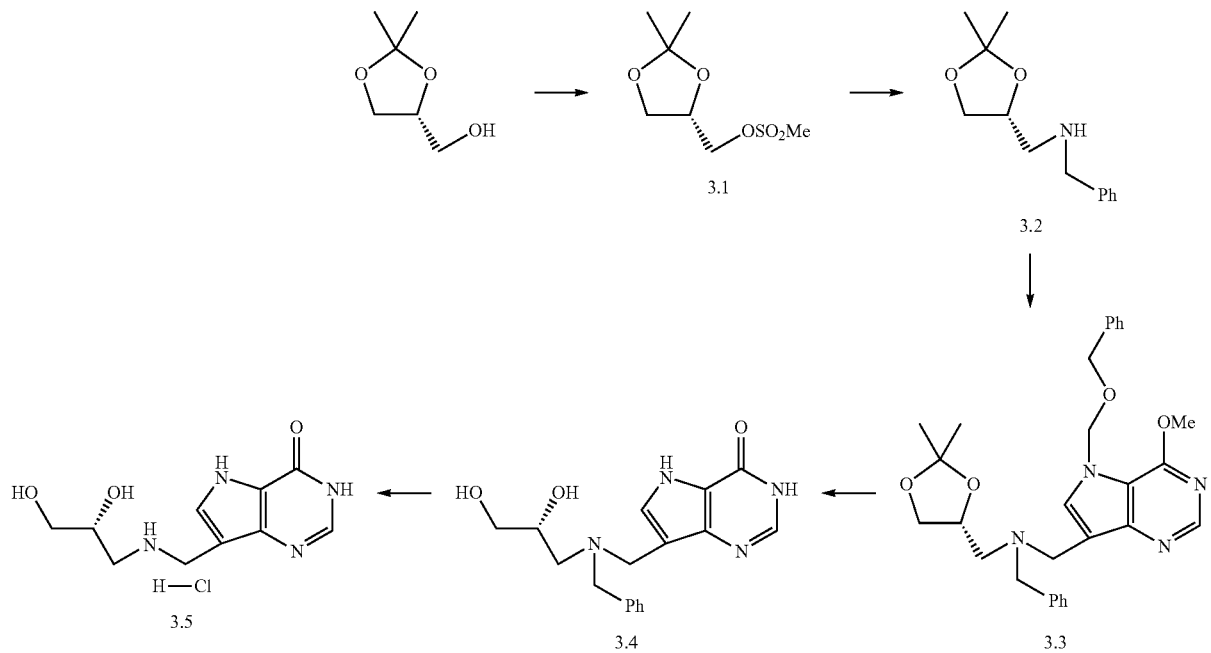

Example 3.1

Synthesis of (S)-(2,2-dimethyl-1,3-dioxolan-4-yl)methyl methanesulfonate

The title compound was prepared from (R)-(2,2-dimethyl-1,3-dioxolan-4-yl)methanol (Sigma-Aldrich, 99% ee) by a known literature procedure (H. S. Kim, D. Barak, T. K. Harden, J. L. Boyer and K. A. Jacobson, *J. Med. Chem.*, 2001, 44, 3092). $^1$H NMR (CDCl$_3$, 300 MHz), δ ppm, 4.37 (m, 1H), 4.23 (d, 2H, J 5.3 Hz), 4.11 (dd, 1H, J 8.7, 6.5 Hz), 3.83 (dd, 1H, J 8.7, 5.4 Hz), 3.07 (s, 3H), 1.45 (s, 3H), 1.37 (s, 3H). $^{13}$C NMR (CDCl$_3$, 75.5 MHz), δ ppm, 110.2, 73.2, 69.2, 65.8, 37.6, 31.5, 26.6, 25.1. [α]$_D^{25}$ +3.1 (c, 0.72, CHCl$_3$).

Example 3.2

Synthesis of (R)—N-benzyl-1-(2,2-dimethyl-1,3-dioxolan-4-yl)methanamine

The title compound was prepared in the same way as that method described for preparing the (S)-enantiomer (M. Lemaire, F. Posada, J.-G. Gourcy and G. Jeminet, *Synlett*, 1995, 627). A solution of (S)-(2,2-dimethyl-1,3-dioxolan-4-yl)methyl methanesulfonate (3.0 g, 14.27 mmol) and benzylamine (6.23 ml, 57.1 mmol) were refluxed together in CH$_3$CN (38 ml) for 48 h. Tlc (EtOAc-hex 8:2) showed a new product (uv/molybdate or ninhydrin) with Rf ~0.3 together with a little higher running sm. The solvent was evaporated and the residue dissolved in EtOAc and washed with aqueous sat. NaHCO$_3$, dried and the solvent evaporated. The residue was chromatographed (EtOAc-hex, 6:4 then 8:2) to give (R)—N-benzyl-1-(2,2-dimethyl-1,3-dioxolan-4-yl)methanamine (2.56 g, 11.57 mmol, 81% yield) as a yellow oil. [α]$_D^{21}$ −3.7 (c, 0.885, CHCl$_3$). $^1$H NMR (CDCl$_3$, 300 MHz), δ ppm, 7.32-7.20 (m, 5H), 4.25, (m, 1H), 4.03 (dd, 1H, J 8.0, 6.4 Hz), 3.82 (s, 2H), 3.68 (dd, 1H, J 8.0, 6.8 Hz), 2.74 (d, 2H, J 5.7 Hz), 1.40 (s, 3H), 1.35 (s, 3H). $^{13}$C NMR (CDCl$_3$, 75.5 MHz), δ ppm, 140.6, 128.8, 128.4, 127.3, 109.5, 75.8, 67.9, 54.4, 52.1, 27.3, 25.8.

Example 3.3

(R)—N-benzyl-1-(5-(benzyloxymethyl)-4-methoxy-5H-pyrrolo[3,2-d]pyrimidin-7-yl)-N-((2,2-dimethyl-1,3-dioxolan-4-yl)methyl)methanamine To a solution of (R)—N-benzyl-1-(2,2-dimethyl-1,3-dioxolan-4-yl)methanamine (0.372 g, 1.682 mmol) and 5-(benzyloxymethyl)-4-methoxy-5H-pyrrolo[3,2-d]pyrimidine-7-carbaldehyde (0.5 g, 1.682 mmol) in 1,2-dichloroethane (30 ml) was added sodium triacetoxyborohydride (0.463 g, 2.186 mmol) and anhydrous MgSO$_4$ (1 g). The mixture was stirred for 6 h. Tlc (EtOAc-hexanes, 8:2) showed the reaction essentially over. After diluting with CH$_2$Cl$_2$ the mixture was washed with aqueous sat. NaHCO$_3$, brine, dried and the solvent evaporated. The residue was chromatographed (EtOAc-hex, 1:1, uv and molybdate) to give (R)—N-benzyl-1-(5-(benzyloxymethyl)-4-methoxy-5H-pyrrolo[3,2-d]pyrimidin-7-yl)-N-((2,2-dimethyl-1,3-dioxolan-4-yl)methyl)methanamine (0.631 g, 1.255 mmol, 74.7% yield) as a colourless gum. [α]$_D^{21}$ −21.9 (c, 0.905, MeOH). $^1$H NMR (CDCl$_3$, 300 MHz), δ ppm, 8.55 (s, 1H), 7.41 (s, 1H), 7.37-7.18 (m, 10H), 5.73 (s, 2H), 4.46 (s, 2H), 4.38-4.29 (m, 1H), 4.10, (s, 3H), 4.05-3.98 (m, 2H), 3.79 (d, 1H, J 13.9 Hz), 3.63 (d, 1H, J 13.9 Hz), 3.53, (t, 1H, J 7.9 Hz), 2.73 (dd, 1H, J 13.3, 5.9 Hz), 2.64 (dd, 1H, J 13.3, 5.9 Hz), 1.32 (s, 6H). $^{13}$C NMR (CDCl$_3$, 75.5 MHz), δ ppm, 156.2 (C), 150.7 (C), 150.0 (CH), 139.6 (C), 136.9 (C), 132.2 (CH), 128.8 (CH), 128.4 (CH), 128.2 (CH), 128.0 (CH), 127.7 (CH), 126.9 (CH), 115.7 (C), 114.7 (C), 109.0 (C), 77.0 (CH$_2$), 74.7 (CH$_2$), 70.1 (CH$_2$), 68.4 (CH$_2$), 59.2 (CH$_2$), 56.2 (CH$_2$) 53.5 (CH$_3$), 47.8 (CH$_2$), 26.8 (CH$_3$), 25.6 (CH$_3$). +ESMS Found 503.2643 (M+H)$^+$ C$_{29}$H$_{35}$N$_4$O$_4$ requires 503.2658.

Example 3.4

(R)-7-((benzyl(2,3-dihydroxypropyl)amino)methyl)-3H-pyrrolo[3,2-d]pyrimidin-4(5H)-one (R)—N-benzyl-1-(5-(benzyloxymethyl)-4-methoxy-5H-pyrrolo[3,2-d]pyrimidin-7-yl)-N-((2,2-dimethyl-1,3-dioxolan-4-yl)methyl)methanamine (0.6 g, 1.194 mmol) was heated to 100° C. in HCl (15 ml, 37%) for 3 h. Tlc (CH$_2$Cl$_2$-6M NH$_3$ in MeOH, 9:1) showed reaction over. The solvent was evaporated and the residue dissolved in MeOH, neutralized with Amberlyst A21 resin, filtered and the solvent evaporated. The residue was chromatographed (CH$_2$Cl$_2$-6M NH$_3$ in MeOH, 9:1 then 85:15) to give (R)-3-(benzyl((4-hydroxy-5H-pyrrolo[3,2-d]pyrimidin-7-yl)methyl)amino)propane-1,2-diol (0.36 g, 1.096 mmol, 92% yield) as a colourless solid. [α]$_D^{22}$ +13.0 (c 0.715, MeOH). $^1$H NMR (CD$_3$OD, 300 MHz), δ ppm, 7.90 (s, 1H), 7.37 (s, 1H), 7.31-7.16 (m, 5H), 3.97-3.78 (m, 3H), 3.69 (d, 1H, J 13.8 Hz), 3.63 (d, 1H, J 13.8 Hz), 3.50 (dd, 1H, J 11.2, 4.8 Hz), 3.42 (dd, 1H, J 11.2, 5.7 Hz), 2.60 (d, 2H, J 6.4 Hz). $^{13}$C NMR (CD$_3$OD, 75.5 MHz), δ ppm, 156.1 (C), 145.5 (C), 142.5 (C), 140.2 (C), 130.2 (CH), 129.4 (CH), 129.2 (CH), 128.1 (CH), 119.3 (C), 115.0 (C), 70.6 (CH), 66.3 (CH$_2$), 60.0 (CH$_2$), 57.6 (CH$_2$), 49.0 (CH$_2$). +ESMS Found 329.1600 C$_{17}$H$_{21}$N$_4$O$_3$ (M+H)$^+$ requires 329.1614.

Example 3.5

(R)-7-((2,3-dihydroxypropylamino)methyl)-3H-pyrrolo[3,2-d]pyrimidin-4(5H)-one hydrochloride (R)-3-(Benzyl((4-hydroxy-5H-pyrrolo[3,2-d]pyrimidin-7-yl)methyl)amino)propane-1,2-diol (0.1 g, 0.305 mmol) was dissolved in hot water (20 ml), cooled to rt and 10% Pd—C (50 mg) added. Hydrogen was added from a balloon and the mixture stirred at rt. After 4 h tlc (CH$_2$Cl$_2$-MeOH-cNH$_3$, 5:4.5:0.5) showed reaction over. The hydrogen was replaced with Ar and the mixture heated to 80° C. to ensure product was in solution then the mixture filtered through Celite and the solvent evaporated to give (R)-3-((4-hydroxy-5H-pyrrolo[3,2-d]pyrimidin-7-yl)methylamino)propane-1,2-diol as a colourless solid (0.072 g, 99%). The product was converted to its hydrochloride salt with 5% HCl. $^1$H NMR (D$_2$O+DCl, 300 MHz), δ ppm, 9.07 (s, 1H), 7.91 (s, 1H), 4.53 (s, 2H), 4.06 (m, 1H), 3.69-3.57 (m, 2H), 3.33 (dd, 1H, J 12.9, 2.9 Hz), 3.17 (dd, 1H, J 12.9, 9.8 Hz). $^{13}$C NMR (D$_2$O+DCl, 75.5 MHz), δ ppm, 153.8 (C), 146.1 (CH), 134.1 (C), 133.1 (CH), 119.6 (C), 104.1 (C), 68.5 (CH), 64.5 (CH$_2$), 50.2 (CH$_2$), 41.8 (CH$_2$). [α]$_D^{18}$ +12.6 (c, 0.565, H$_2$O). +ESMS Found 261.0952 (M+Na)$^+$ C$_{10}$H$_{14}$N$_4$O$_3$Na requires 261.0964.

Example 4

Synthesis of 7-(((2R,3R)-1,3,4-trihydroxybutan-2-ylamino)methyl)-3H-pyrrolo[3,2-d]pyrimidin-4(5H)-one hydrochloride

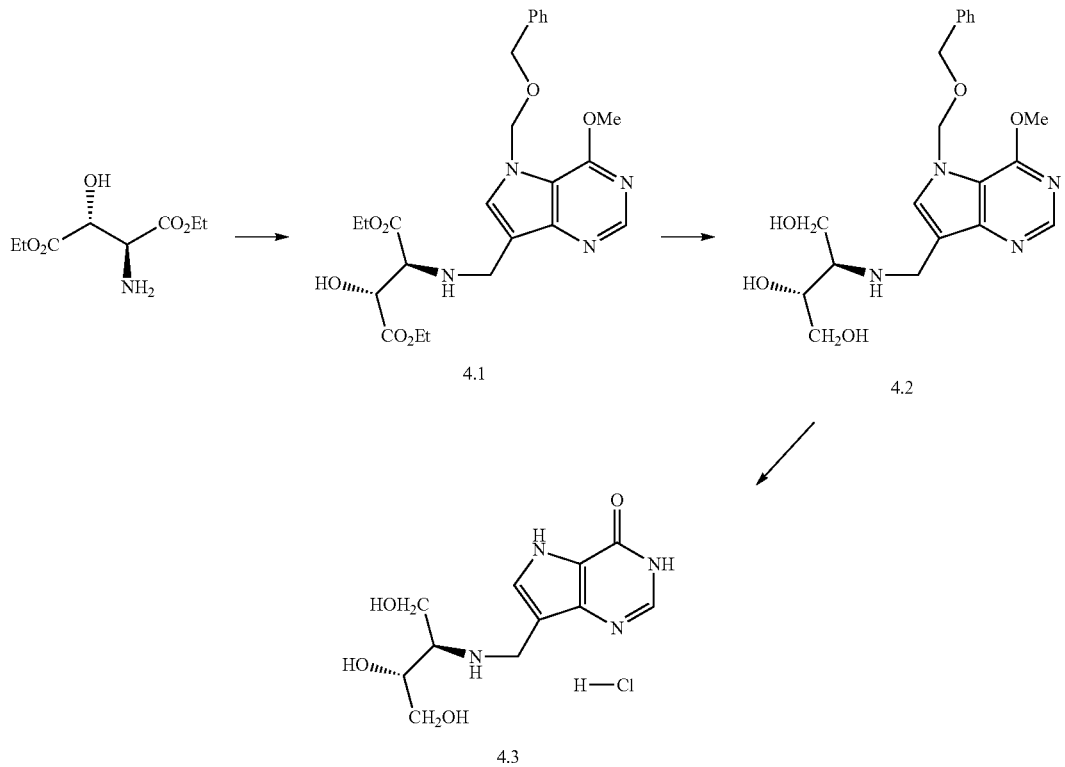

Example 4.1

Synthesis of (2S,3R)-diethyl 2-((5-(benzyloxymethyl)-4-methoxy-5H-1-pyrrolo[3,2-d]pyrimidin-7-yl)methylamino)-3-hydroxysuccinate Sodium triacetoxyborohydride (0.545 g, 2.57 mmol) was added to a solution of (2S,3R)-diethyl 2-amino-3-hydroxysuccinate (0.406 g, 1.978 mmol), the latter prepared from diethyl-L-tartrate by known methods (A. Breuning, R. Vicik and T. Schirmeister, *Tetrahedron Asymm.*, 2003, 14, 3301 and Z. Tang, Z.-H. Yang, X.-H. Chen, L.-F. Cun, A.-Q. Mi, Y.-Z. Jiang and L.-Z. Gong, *J. Am. Chem. Soc.*, 2005, 127, 9285) and 5-(benzyloxymethyl)-4-methoxy-5H-pyrrolo[3,2-d]pyrimidine-7-carbaldehyde (0.588 g, 1.978 mmol) in 1,2-dichloroethane (30 ml) and the mixture stirred at rt for 1 h. Tlc (EtOAc) showed all amine to have gone (ninhydrin) but still some aldehyde present and a new main product in between. More (2S,3R)-diethyl 2-amino-3-hydroxysuccinate (121 mg) added. The mixture was stirred a further 3 h then diluted with $CH_2Cl_2$ and washed with aqueous sat. $NaHCO_3$, dried and evaporated. The residue was chromatographed (EtOAc-hexanes, 9:1 then EtOAc) to give (2S,3R)-diethyl 2-((5-(benzyloxymethyl)-4-methoxy-5H-pyrrolo[3,2-d]pyrimidin-7-yl)methylamino)-3-hydroxysuccinate (0.668 g, 1.373 mmol, 69.4% yield) as a pale yellow gum. $[\alpha]_D^{21}$ −5.9 (c 0.54, EtOH). $^1$H NMR ($CDCl_3$, 300 MHz), δ ppm, 8.55 (s, 1H), 7.34 (s, 1H), 7.33-7.23 (m, 5H), 5.70 (s, 2H), 4.62 (d, 1H, J 3.4 Hz), 4.48 (s, 2H), 4.23-4.15 (m, 5H), 4.10 (s, 3H), 3.99 (d, 1H, J 13.8 Hz), 3.85 (d, 1H, J 3.3 Hz), 2.25 (br. s, 2H, exchanged to $D_2O$), 1.26 (t, 3H, J 7.1 Hz), 1.25 (t, 3H, J 7.1 Hz). $^{13}$C NMR ($CDCl_3$, 75.5 MHz), δ ppm, 171.9 (C), 171.1 (C), 156.2 (C), 150.0 (CH), 149.8 (C), 136.9 (C), 130.9 (CH), 128.4 (CH), 127.9 (CH), 127.6 (CH), 116.1 (C), 77.0 ($CH_2$), 72.0 (CH), 70.2 ($CH_2$), 63.8 (CH), 61.4 ($CH_2$), 61.3 ($CH_2$), 53.5 ($CH_3$), 42.6 ($CH_2$), 14.1 ($CH_3$). +ESMS Found 487.2174 $(M+H)^+$ $C_{24}H_{31}N_4O_7$ requires 487.2193.

Example 4.2

Synthesis of (2R,3R)-3-((5-(benzyloxymethyl)-4-methoxy-5H-pyrrolo[3,2-d]pyrimidin-7-yl)methylamino)butane-1,2,4-triol To a refluxing solution of (2S,3R)-diethyl 2-((5-(benzyloxymethyl)-4-methoxy-5H-pyrrolo[3,2-d]pyrimidin-7-yl)methylamino)-3-hydroxysuccinate (0.6 g, 1.233 mmol) in THF (10 ml) and methanol (0.499 ml, 12.33 mmol) was added lithium borohydride (0.134 g, 6.17 mmol) in portions over about 1 h. Tlc ($CH_2Cl_2$-MeOH-c$NH_3$, 9:1:0.1) still showed (uv, ninhydrin or molybdate) sm. More MeOH (0.5 ml) was added and small portions of $LiBH_4$ (total ~134 mg) added over about 1 h until tlc showed reaction finished. The solvent was evaporated and the residue chromatographed ($CH_2Cl_2$-MeOH-c$NH_3$, 95:5:0.5, then 85:15:0.5) to give a colourless gum which soon crystallized (214 mg, 41%). The gum was of sufficient purity to proceed to the next step, but a small quantity was recrystallised by dissolving a portion of the crude (2R,3R)-3-((5-(benzyloxymethyl)-4-methoxy-5H-pyrrolo[3,2-d]pyrimidin-7-yl)methylamino)butane-1,2,4-triol in MeOH and evaporating the solvent to leave a mobile gum. The gum was dissolved in hot ethyl acetate, cooled to rt and seeded. The colourless solid was filtered off and dried to give clusters of very tiny crystals under the microscope. Mpt 108-109° C. $[\alpha]_D^{18}$ −6.1 (c 0.59, MeOH). $^1$H NMR ($CD_3OD$, 300 MHz), δ ppm, 8.42 (s, 1H), 7.64 (s, 1H), 7.28-7.16 (m, 5H), 5.75 (s, 2H), 4.50 (s, 2H), 4.10 (s, 3H), 3.83-3.68 (m, 3H), 3.63 (d, 2H, J 5.5 Hz), 3.31 (pentet, 1H, J 1.6 Hz). $^{13}$C NMR ($CD_3OD$, 75.5 MHz), δ ppm, 158.0 (C), 150.8 (CH), 150.7 (C), 138.8 (C), 134.2 (CH), 129.3 (CH), 128.8 (CH), 128.6 (CH), 117.0 (C), 116.1 (C), 78.5 ($CH_2$), 72.1 (CH), 71.5 ($CH_2$), 65.6 ($CH_2$), 62.3 (CH), 61.0 ($CH_2$), 54.3 ($CH_3$), 41.6 ($CH_2$). +ESMS Found 403.1980 $(M+H)^+$ $C_{20}H_{27}N_4O_5$ requires 403.1981.

Example 4.3

Synthesis of 7-(((2R,3R)-1,3,4-trihydroxybutan-2-ylamino)methyl)-3H-pyrrolo[3,2-d]pyrimidin-4(5H)-one hydrochloride (2R,3R)-3-((5-(benzyloxymethyl)-4-methoxy-5H-pyrrolo[3,2-d]pyrimidin-7-yl)methylamino)butane-1,2,4-triol (0.1 g, 0.248 mmol) was heated under reflux in HCl (4 ml, 37%) for 2 h. Tlc ($CH_2Cl_2$-MeOH-c$NH_3$, 5:4.5:0.5) showed reaction over. The solvent was evaporated and the residue dissolved in MeOH and neutralized with Amberlyst A21 resin. The mixture was filtered, the solvent evaporated and the residue chromatographed ($CH_2Cl_2$-MeOH-c$NH_3$, 7:3:0.3 then 5:4.5:0.5) to give the free base form of the product as a colourless solid which was converted with 5% HCl to 7-(((2R,3R)-1,3,4-trihydroxybutan-2-ylamino)methyl)-3H-pyrrolo[3,2-d]pyrimidin-4(5H)-one hydrochloride as a colourless solid (0.055 g, 0.180 mmol, 72.6% yield). $[\alpha]_D^{22}$ +15.4 (c 0.56, $H_2O$). $^1$H NMR ($D_2O$, 300 MHz), δ ppm, 8.82 (s, 1H), 7.87 (s, 1H), 4.61 (s, 2H), 4.19 (m, 1H), 4.06-3.89 (m, 2H), 3.72 (d, 2H, J 5.6 Hz), 3.56 (m, 1H). $^{13}$C NMR ($D_2O$, 75.5 MHz), δ ppm, 154.4 (C), 145.6 (CH), 136.0 (C), 133.6 (CH), 119.4 (C), 104.9 (C), 69.4 (CH), 63.4 ($CH_2$), 61.4 (CH), 58.0 ($CH_2$), 40.4 ($CH_2$). +ESMS Found 269.1252 $(M+H)^+$ $C_{11}H_{17}N_4O_4$ requires 269.1250—free base.

Example 5

(S)-7-((2,3-dihydroxypropylamino)methyl)-3H-pyrrolo[3,2-d]pyrimidin-4(5H)-one hydrochloride

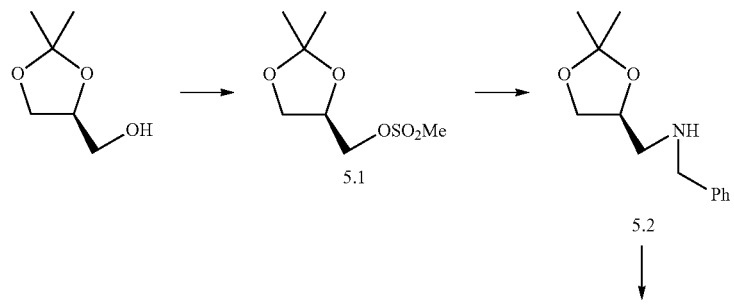

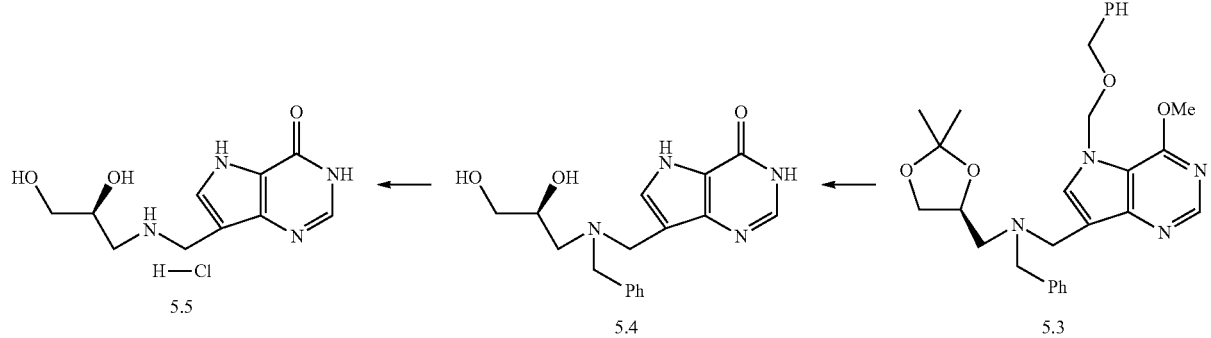

Example 5.1

(R)-(2,2-dimethyl-1,3-dioxolan-4-yl)methyl methanesulfonate

The title compound was prepared from (S)-(2,2-dimethyl-1,3-dioxolan-4-yl)methanol (Sigma-Aldrich, 99% ee) by a known literature procedure (H. S. Kim, D. Barak, T. K. Harden, J. L. Boyer and K. A. Jacobson, *J. Med. Chem.*, 2001, 44, 3092). $[\alpha]_D^{21}$ −3.1 (c, 0.83, CHCl$_3$). The $^1$H NMR and $^{13}$C NMR were identical to that of compound 3.1.

Example 5.2

(S)—N-benzyl-1-(2,2-dimethyl-1,3-dioxolan-4-yl) methanamine

The title compound was prepared in the same way as described by M. Lemaire, F. Posada, J.-G. Gourcy and G. Jeminet, *Synlett*, 1995, 627. A solution of (R)-(2,2-dimethyl-1,3-dioxolan-4-yl)methyl methanesulfonate (3.9 g, 18.55 mmol) and benzylamine (8.10 ml, 74.2 mmol) was refluxed in CH$_3$CN (50 ml) for 48 h. The solvent was evaporated and the residue dissolved in EtOAc and washed with aqueous sat. NaHCO$_3$, dried and the solvent evaporated. The residue was chromatographed (EtOAc-hex, 6:4 then 8:2) to give (S)—N-benzyl-1-(2,2-dimethyl-1,3-dioxolan-4-yl)methanamine (3.1 g, 14.01 mmol, 76% yield) as a yellow oil. $[\alpha]_D^{21}$ +4.3 (c, 0.69, CHCl$_3$). The $^1$H NMR and $^{13}$C NMR were identical to that of compound 3.2.

Example 5.3

(S)—N-benzyl-1-(5-(benzyloxymethyl)-4-methoxy-5H-pyrrolo[3,2-d]pyrimidin-7-yl)-N-((2,2-dimethyl-1,3-dioxolan-4-yl)methyl)methanamine To a solution of (S)—N-benzyl-1-(2,2-dimethyl-1,3-dioxolan-4-91)methanamine (0.670 g, 3.03 mmol) and 5-(benzyloxymethyl)-4-methoxy-5H-pyrrolo[3,2-d]pyrimidine-7-carbaldehyde (0.9 g, 3.03 mmol) in 1,2-dichloroethane (30 ml) was added sodium triacetoxyborohydride (0.834 g, 3.94 mmol) and anhydrous MgSO$_4$ (2 g). The mixture was stirred for 5 h. After diluting with CH$_2$Cl$_2$ the mixture was washed with aqueous sat. NaHCO$_3$, brine, dried and the solvent evaporated. The residue was chromatographed (EtOAc-hex, 1:1, uv and molybdate) to give (S)—N-benzyl-1-(5-(benzyloxymethyl)-4-methoxy-5H-pyrrolo[3,2-d]pyrimidin-7-yl)-N-((2,2-dimethyl-1,3-dioxolan-4-yl)methyl)-methanamine (1.18 g, 2.34 mmol, 78% yield) as a pale yellow gum. $[\alpha]_D^{21}$ +21.6 (c, 0.92, MeOH). The $^1$H NMR and $^{13}$C NMR were identical to that of compound 3. +ESMS Found 503.2635 (M+H)$^+$ C$_{29}$H$_{35}$N$_4$O$_4$ requires 503.2658.

Example 5.4

(S)-7-((benzyl(2,3-dihydroxypropyl)amino)methyl)-3H-pyrrolo[3,2-d]pyrimidin-4(5H)-one (S)—N-benzyl-1-(5-(benzyloxymethyl)-4-methoxy-5H-pyrrolo[3,2-d]pyrimidin-7-yl)-N-((2,2-dimethyl-1,3-dioxolan-4-yl)methyl)methanamine (1.1 g, 2.189 mmol) was heated to 100° C. in HCl (15 ml, 37%) for 3 h. Tlc (CH$_2$Cl$_2$-6M NH$_3$ in MeOH, 9:1) showed reaction over. The solvent was evaporated and the residue dissolved in MeOH, neutralized with Amberlyst A21 resin, filtered and the solvent evaporated. The residue was chromatographed (CH$_2$Cl$_2$-6M NH$_3$ in MeOH, 9:1 then 85:15) to give (S)-3-(benzyl((4-hydroxy-5H-pyrrolo[3,2-d]pyrimidin-7-yl)methyl)amino)propane-1,2-diol (0.427 g, 1.3 mmol, 59.4% yield) as a colourless solid. $[\alpha]_D^{20}$ 12.7 (c 0.715, MeOH). The $^1$H NMR and $^{13}$C NMR were identical to that of compound 3.4. +ESMS Found 329.1618 C$_{17}$H$_{21}$N$_4$O$_3$ (M+H) requires 329.1614.

Example 5.5

(S)-7-((2,3-dihydroxypropylamino)methyl)-3H-pyrrolo[3,2-d]pyrimidin-4(5H)-one hydrochloride (S)-3-(benzyl((4-hydroxy-5H-pyrrolo[3,2-d]pyrimidin-7-yl)methyl)amino)propane-1,2-diol (0.1 g, 0.305 mmol) was dissolved in MeOH (10 ml), diluted with water (10 ml) and 10% Pd—C (50 mg) added. H$_2$ from a balloon added and the mixture stirred for 45 min. The H$_2$ was replaced with Ar and the mixture filtered through Celite. The Celite was extracted with portions of hot water and the combined filtrates evaporated to a solid (53 mg). The solid was chromatographed on silica gel (CH$_2$Cl$_2$-MeOH-cNH$_3$, 5:4.5:0.5) to give the free base form of the product as a colourless solid. The product was converted with 5% HCl to its hydrochloride as a colourless foam and crystallized from MeOH to give (S)-3-((4-hydroxy-5H-pyrrolo[3,2-d]pyrimidin-7-yl)methylamino) propane-1,2-diol hydrochloride (35 mg, 41.8%). Mpt 241-242° C. $[\alpha]_D^{20}$ −12.9 (c, 0.535, H$_2$O). The $^1$H NMR and $^{13}$C NMR were identical to that of compound 3.5. +ESMS Found 239.1136 (M+H)+ C10H15N43N requires 239.1144.

Example 6

Synthesis of 7-((1,3-dihydroxy-2-(hydroxymethyl) propan-2-ylamino)methyl)-3H-pyrrolo[3,2-d]pyrimidin-4(5H)-one

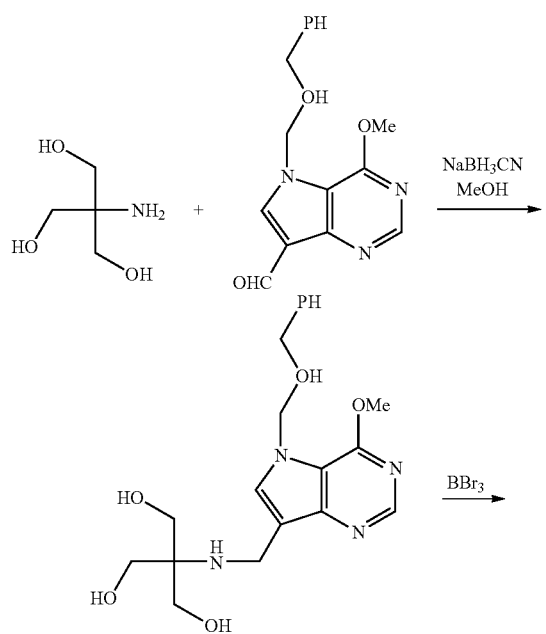

6.1

6.2

Example 6.1

Synthesis of 2-((5-(benzyloxymethyl)-4-methoxy-5H-pyrrolo[3,2-d]pyrimidin-7-yl)methylamino)-2-(hydroxymethyl)propane-1,3-diol Sodium cyanoborohydride was added to a suspension of 5-(benzyloxymethyl)-4-methoxy-5H-pyrrolo[3,2-d]pyrimidine-7-carbaldehyde (50 mg, 168 μmol) and 2-amino-2-(hydroxymethyl)propane-1,3-diol (20.37 mg, 168 μmol) in methanol (5 mL) and stirred overnight at r.t. The crude reaction was absorbed onto silica and eluted with 20% MeOH/EtOAc to afford 2-((5-(benzyloxymethyl)-4-methoxy-5H-pyrrolo[3,2-d]pyrimidin-7-yl)methylamino)-2-(hydroxymethyl)propane-1,3-diol (24 mg, 59.6 μmol, 35.5% yield) as a syrup. $^1$H NMR (d4-MeOH) 8.42 (s, 1H), 7.65 (s, 1H), 7.23 (m, 5H), 5.74 (s, 2H), 4.51 (s, 2H), 4.11 (s, 3H), 4.04 (s, 2H), 3.68 (s, 6H). $^{13}$C NMR (d4-MeOH) 158.4, 151.2, 150.9, 139.1, 134.4, 129.7, 129.2, 129.0, 117.5, 116.4, 78.9, 71.9, 62.9, 62.6, 54.8, 36.6.

Example 6.2

Synthesis of 2-((4-hydroxy-5H-pyrrolo[3,2-d]pyrimidin-7-yl)methylamino)-2-(hydroxymethyl)propane-1,3-diol Boron tribromide (1 mL, 1.0 mmol) was added dropwise to a solution of 2-((5-(benzyloxymethyl)-4-methoxy-5H-pyrrolo[3,2-d]pyrimidin-7-yl)methylamino)-2-(hydroxymethyl)propane-1,3-diol (30 mg, 74.5 μmol) in dichloromethane (5 mL) and stirred at r.t. A white solid precipitated from the reaction after 1 h and the reaction was then quenched with methanol, concentrated in vacuo and co-distilled with methanol (3×25 mL) to afford a crude residue. The residue was dissolved in methanol absorbed onto silica and chromatographed eluting with 5:4.5:0.5 DCM:MeOH:NH4OH to afford 2-((4-hydroxy-5H-pyrrolo[3,2-d]pyrimidin-7-yl)methylamino)-2-(hydroxymethyl)propane-1,3-diol (7 mg, 26.1 μmol, 35.0% yield) as a white solid which was converted to the HCl salt for NMR analysis. Mpt 223-224° C. (plates from EtOH). $^1$H NMR (D2O, referenced to internal acetone at 2.225 ppm) δ 9.06, (s, 1H), 7.92 (s, 1H), 4.59 (s, 2H), 3.91 (s, 6H). $^{13}$ NMR (D2O, referenced to internal acetone at δ 31.5) δ 153.7, 146.0, 134.2, 133.0, 119.4, 104.7, 67.6, 59.3, 36.4. +ESMS Found 269.1263 (M+H)+ C11H17N4O4 requires 269.1250.

Example 7

Synthesis of 3-((4-hydroxy-5H-pyrrolo[3,2-d]pyrimidin-7-yl)methylamino)-butanol and -ethanol

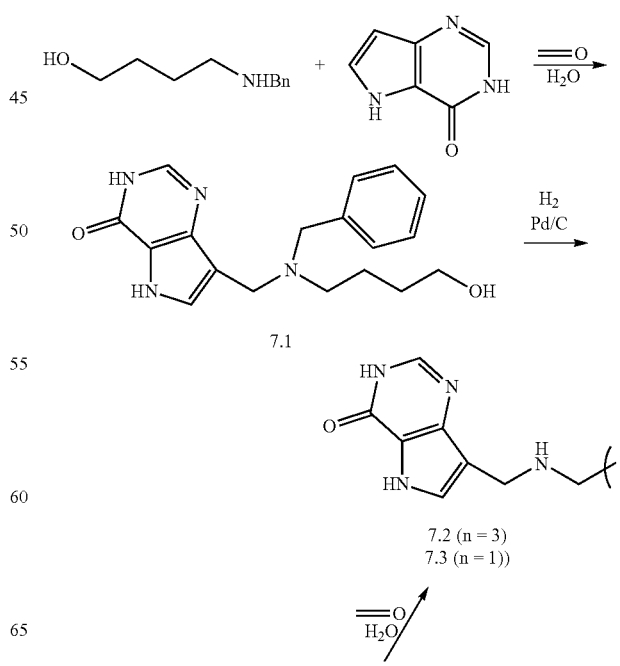

7.2 (n = 3)
7.3 (n = 1))

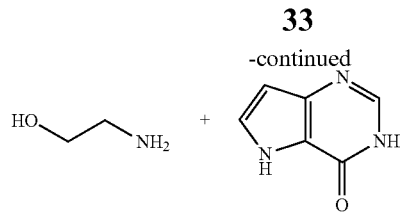

Example 7.1

Synthesis of 7-((benzyl(4-hydroxybutyl)amino)methyl)-3H-pyrrolo[3,2-d]pyrimidin-4(5H)-one A mixture of 3-(benzylamine)butanol (172 mg, 0.96 mmol), 9-deazahypoxanthine (100 mg, 0.74 mmol) and 37% aq formaldehyde (72 µl, 0.96 mmol) in water (5 ml) was stirred and heated in stoppered flask at 85° C. overnight. The solution was evaporated to dryness and the residue was chromatographed on silica (DCM-MeOH 9:1 to 8:2) to give 7-((benzyl(4-hydroxybutyl)amino)methyl)-3H-pyrrolo[3,2-d]pyrimidin-4(5H)-one (130 mg, 0.40 mmol, 55% yield) as a white solid. $^1$H NMR (300 MHz, CD$_3$OD+DCl) 1.50 (2H, m), 1.93 (2H, m), 3.20 (2H, q, J 7 Hz), 3.55 (2H, t, J 6 Hz), 4.50 (1H, d, J 13 Hz), 4.62 (1H, d, J 13 Hz), 4.72 (1H, d, J 14.1 Hz), 4.79 (1H, d, J 14.1 Hz), 7.45 (3H, m), 7.63 (2H, m), 8.00 (1H, s), 9.10 (1H, s); $^{13}$C NMR (75 MHz, CD$_3$OD+DCl) 22.2, 30.8, 50.0, 53.6, 58.2, 62.3, 100.2, 103.7, 120.4, 130.7, 131.4, 132.7, 133.5, 134.5, 147.1, 153.0.

Example 7.2

Synthesis of 7-((4-hydroxybutylamino)methyl)-3H-pyrrolo[3,2-d]pyrimidin-4(5H)-one To 7-((benzyl(4-hydroxybutyl)amino)methyl)-3H-pyrrolo[3,2-d]pyrimidin-4(5H)-one (230 mg, 0.70 mmol) in iso-propanol (3 ml) was added 10% Pd—C (50 mg). The mixture was stirred at 50° C. under an atmospheric pressure of H$_2$ overnight. Then the solution was filtered on a pad of Celite and the pad washed with MeOH (10 ml). The filtrate was evaporated to dryness and the residue was chromatographed on silica (DCM-MeOH 8:2+1% cNH$_3$) to give 7-(((4-hydroxybutyl)amino)methyl)-3H-pyrrolo[3,2-d]pyrimidin-4(5H)-one (133 mg, 0.56 mmol, 80% yield) as a white solid. $^1$H NMR (300 MHz, CD$_3$OD+DCl) 1.64 (2H, m), 1.87 (2H, m), 3.19 (2H, t, J 7.6 Hz), 3.63 (2H, t, J 5.9 Hz), 4.48 (2H, s), 7.87 (1H, s), 9.05 (1H, s); $^{13}$C NMR (75 MHz, CD$_3$OD+DCl) 24.7, 30.7, 30.9, 42.1, 62.5, 105.6, 120.2, 133.4, 133.8, 146.8, 153.3.

Example 7.3

Synthesis of 7-((2-hydroxyethylamino)methyl)-3H-pyrrolo[3,2-d]pyrimidin-4(5H)-one A mixture of ethanolamine (78 µl, 0.96 mmol), 9-deazahypoxanthine (100 mg, 0.74 mmol) and 37% aq formaldehyde (72 µl, 0.96 mmol) in water (5 ml) was stirred and heated in stoppered flask at 85° C. overnight. The solution was evaporated to dryness and the residue was chromatographed on silica (DCM-MeOH-cNH$_3$ 6:3.5:0.5) to give 7-((2-hydroxyethylamino)methyl)-3H-pyrrolo[3,2-d]pyrimidin-4(5H)-one (100 mg, 0.48 mmol, 65% yield) as a pale brown solid. $^1$H NMR (300 MHz, CD$_3$OD) 2.80 (2H, t, J 5.5 Hz), 3.68 (2H, t, J 5.5 Hz), 3.97 (2H, s), 7.42 (1H, s), 7.88 (1H, s); $^{13}$C NMR (75 MHz, MeOD+DCl) 42.0, 50.7, 58.43, 105.2, 120.5, 133.8, 135.0, 147.1, 153.0

Example 8

Synthesis of 7-((3-hydroxy-2-(hydroxymethyl)propylamino)methyl)-3H-pyrrolo[3,2-d]pyrimidin-4(5H)-one

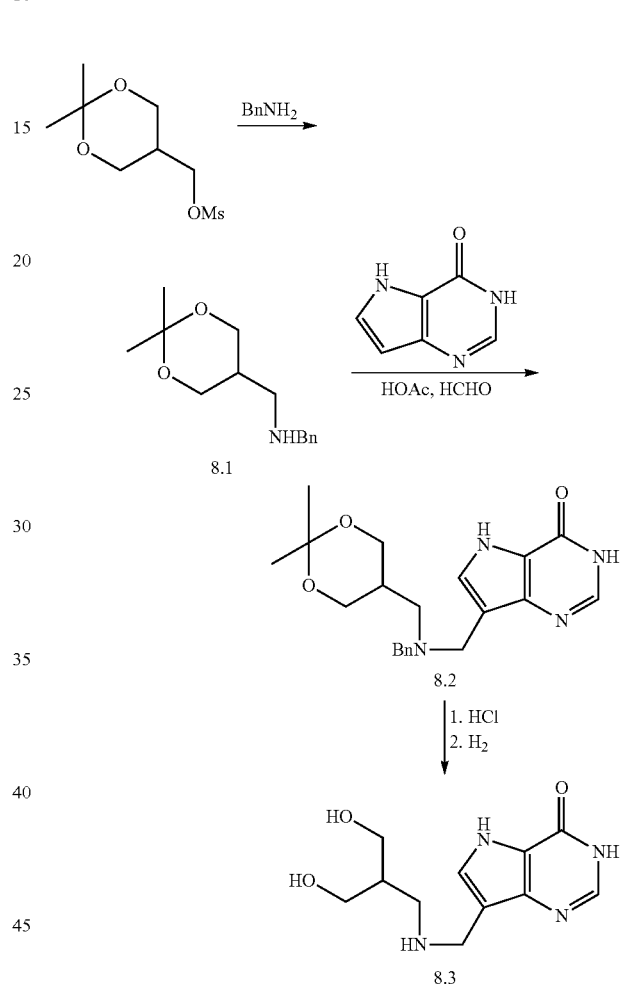

Example 8.1

Synthesis of N-benzyl(2,2-dimethyl-1,3-dioxan-5-yl)methanamine

A solution of (2,2-dimethyl-1,3-dioxan-5-yl)methyl methanesulfonate (1.70 g, 7.58 mmol) in benzylamine (10 mL, 92 mmol) was stirred at 80° C. and monitored by TLC. After 2 h the reaction was complete therefore concentrated in vacuo. The residue was diluted with toluene (containing a small amount of ethyl acetate) and washed with water, dried and concentrate in vacuo. Column chromatography on silica eluting with ethyl acetate afforded N-benzyl(2,2-dimethyl-1,3-dioxan-5-yl)methanamine (1.51 g, 85% yield) as a yellow oil. $^{13}$C NMR (CD$_3$OD) δ 140.8, 129.4 (2XCH), 128.1, 99.3, 64.0 (2XCH$_2$), 54.7, 33.7, 25.6, 23.0

Example 8.2

Synthesis of 7-((benzyl((2,2-dimethyl-1,3-dioxan-5-yl)methyl)amino)methyl)-3H-pyrrolo[3,2-d]pyrimidin-4(5H)-one Acetic acid (0.122 mL, 2125 μmol) was added dropwise to a solution of N-benzyl(2,2-dimethyl-1,3-dioxan-5-yl)methanamine (100 mg, 425 μmol) in 1,4-dioxane (2 mL, 2.34E+04 μmol) followed by addition of 3H-pyrrolo[3,2-d]pyrimidin-4(5H)-one (115 mg, 850 μmol). The resulting suspension was heated to 95° C. (bath temp) and held at that temperature overnight. The reaction was cooled to ambient temperature. Column chromatography on silica eluting with 5% 7N NH$_3$/MeOH to afforded, presumably, 7-((benzyl((2,2-dimethyl-1,3-dioxan-5-yl)methyl)amino)methyl)-3H-pyrrolo[3,2-d]pyrimidin-4(5H)-one (56 mg, 146 μmol, 34.5% yield) which was committed to the next step without further characterisation.

Example 8.3

Synthesis of 7-((3-hydroxy-2-(hydroxymethyl)propylamino)methyl)-3H-pyrrolo[3,2-d]pyrimidin-4(5H)-one cHCl was added to a stirred solution of 7-((benzyl((2,2-dimethyl-1,3-dioxan-5-yl)methyl)amino)methyl)-3H-pyrrolo[3,2-d]pyrimidin-4(5H)-one (50 mg, 131 μmol) in methanol (2 mL). After 0.5 h the reaction was concentrated in vacuo and co-distilled with methanol. The crude reaction was absorbed as a methanol solution onto silica gel and purified by chromatography on silica eluting with 20% 7N NH$_3$/MeOH to afford, presumably, 7-(((2,2-dimethyl-1,3-dioxan-5-yl)methylamino)methyl)-3H-pyrrolo[3,2-d]pyrimidin-4(5H)-one (19 mg, 42.4% yield) as a white solid, which was committed to the next step without characterisation. A solution of 7-(((2,2-dimethyl-1,3-dioxan-5-yl)methylamino)methyl)-3H-pyrrolo[3,2-d]pyrimidin-4(5H)-one (19 mg, 55.5 μmol) and 10% palladium on carbon (56 mg, 526 μmol) in water (2 mL, 1.11E+05 μmol) was stirred under an atmosphere of hydrogen (0.101 mg, 50.2 μmol) for 72 h. The reaction was filtered through Celite® and the filtrate concentrated in vacuo to yield a crude residue which was purified by chromatography on silica gel, eluting with 5:4.5:0.5 DCM:MeOH:NH$_4$OH to afford 7-((3-hydroxy-2-(hydroxymethyl)propylamino)methyl)-3H-pyrrolo[3,2-d]pyrimidin-4(5H)-one hydrochloride (4 mg, 27.6% yield) as a white solid. $^{13}$C NMR (D$_2$O) δ 152.6, 145.0, 133.2, 131.7, 118.4, 102.8, 60.8 (2×CH$_2$), 47.6, 41.1, 39.8.

Example 9

Synthesis of 7-(((3-hydroxy-2-(hydroxymethyl)propyl)(methyl)-amino)methyl)-3H-pyrrolo[3,2-d]pyrimidin-4(5H)-one

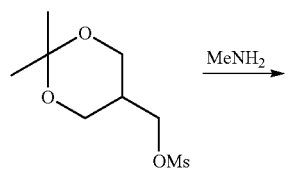

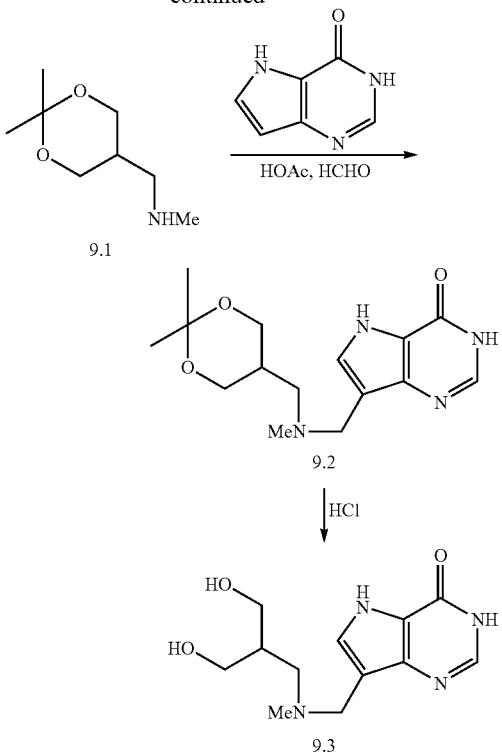

Example 9.1

Synthesis of (2,2-dimethyl-1,3-dioxan-5-yl)-N-methylmethanamine

Methylamine solution (3 mL, 34.8 mmol) was added to a solution of (2,2-dimethyl-1,3-dioxan-5-yl)methyl methanesulfonate (0.9 g, 4.01 mmol, prepared as per B. Xu et al. *J. Med. Chem.* 2002, 45, 5694) in DMSO (7 mL) and stirred at 75° C. overnight. The reaction was diluted with CHCl$_3$ and the CHCl$_3$ washed with water (×2), dried and concentrated in vacuo to afford approximately 670 mg of crude product. The crude material was columned on silica eluting with DCM, 20% MeOH/DCM, and 20% 7N NH3 in MeOH/DCM to afford (2,2-dimethyl-1,3-dioxan-5-yl)-N-methylmethanamine (330 mg, 52% yield) as an oily residue. $^{13}$C NMR (CD$_3$OD) δ 99.7, 64.4 (2×CH$_2$), 52.3, 36.9, 36.0, 26.0, 23.5.

Example 9.2

Synthesis of 7-((((2,2-dimethyl-1,3-dioxan-5-yl)methyl)(methyl)-amino)methyl)-3H-pyrrolo[3,2-d]pyrimidin-4(5H)-one Acetic acid (0.180 mL, 3140 μmol) was added dropwise to a solution of (2,2-dimethyl-1,3-dioxan-5-yl)-N-methylmethanamine (100 mg, 628 μmol) in 1,4-dioxane (2 mL, 2.34E+04 μmol) followed by the addition of 3H-pyrrolo[3,2-d]pyrimidin-4(5H)-one (170 mg, 1256 μmol). The resulting suspension was heated to 95° C. (bath temp) and held at that temp overnight. Following absorption onto silica, chromatography eluting with 10% 7N NH3 in MeOH/DCM afforded one major product, presumably 7-((benzyl((2,2-dimethyl-1,3-dioxan-5-yl)methyl)amino)methyl)-3H-pyrrolo[3,2-d]pyrimidin-4(5H)-one (120 mg, 62% yield). which was committed to the next step without further characterization.

Example 9.3

Synthesis of 7-(((3-hydroxy-2-(hydroxymethyl)propyl)(methyl)-amino)methyl)-3H-pyrrolo[3,2-d]pyrimidin-4(5H)-one Hydrochloric acid 30% (10.00 µl, 326 µmol) was added to a solution of 7-(((((2,2-dimethyl-1,3-dioxan-5-yl)methyl)(methyl)amino)methyl)-3H-pyrrolo[3,2-d]pyrimidin-4(5H)-one (100 mg, 326 µmol) in methanol (13.21 µl, 326 µmol) and the resulting reaction left to stand for 30 min. The reaction was concentrated in vacuo to afford a solid. The solid was redissolved in methanol and absorbed onto silica. Chromatography eluting with 20% 7N NH$_3$ in MeOH to afford the title compound as a solid (80 mg, 92% yield). $^{13}$C NMR (D$_2$O) δ155.1, 144.4, 143.3, 132.1, 118.0, 104.4, 61.3 (2×CH$_2$), 56.7, 50.5, 40.9, 38.3.

Example 10

Synthesis of 7-((1,3-dihydroxypropan-2-ylamino)methyl)-3H-pyrrolo[3,2-d]pyrimidin-4(5H)-one hydrochloride

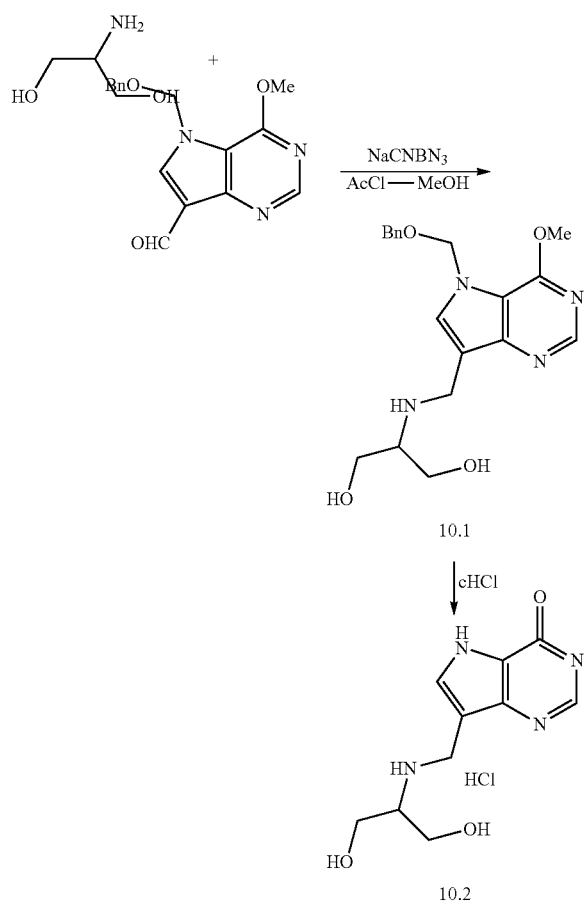

Example 10.1

Synthesis of 2-((5-(benzyloxymethyl)-4-methoxy-5H-pyrrolo[3,2-d]pyrimidin-7-yl)methylamino)propane-1,3-diol Acetyl chloride (0.117 ml, 1.65 mmol) was added to a stirred solution of 2-aminopropane-1,3-diol (0.3 g, 3.29 mmol) and 5-(benzyloxymethyl)-4-methoxy-5H-pyrrolo[3,2-d]pyrimidine-7-carbaldehyde (0.196 g, 0.659 mmol, prepared as in G. B. Evans, R. H. Furneaux, A, Lewandowicz, V. L. Schramm and P. C. Tyler, *J. Med. Chem.*, 2003, 46, 3412) in MeOH (5 ml). Sodium cyanoborohydride (0.062 g, 0.988 mmol) was added and the mixture was stirred at rt overnight. The solvent was evaporated and the residue chromatographed on silica gel (CH$_2$Cl$_2$-MeOH-28% NH$_4$OH, 95:5:0.5 then 9:1:0.05) to give 2-((5-(benzyloxymethyl)-4-methoxy-5H-pyrrolo[3,2-d]pyrimidin-7-yl)methylamino)-propane-1,3-diol (0.188 g, 77%) as a colourless solid. $^1$H NMR (CD$_3$OD) δ 8.42, (s, 1H), 7.65 (s, 1H), 7.25-7.16 (m, 5H), 5.75 (s, 2H), 4.50 (s, 2H), 4.10 (s, 3H), 4.03 (s, 2H), 3.68 (dd, J=11.2, 5.9 Hz, 2H), 3.58 (dd, J=11.2, 5.9 Hz, 2H), 2.81 (pentet, J=5.6 Hz, 1H). $^{13}$C NMR (CD$_3$OD, 75.5 MHz, referenced to centre line of CD$_3$OD at δ 49.0) δ 157.9, 150.8, 150.6, 138.7, 134.1, 129.3, 128.8, 128.6, 117.0, 116.2, 78.5, 71.5, 62.5 (CH$_2$X2), 61.3, 54.3, 41.4. +ESMS Found 373.1865 (M+H)$^+$ C$_{19}$H$_{25}$N$_4$O$_4$ requires 373.1876.

Example 10.2

Synthesis of 7-((1,3-dihydroxypropan-2-ylamino)methyl)-3H-pyrrolo[3,2-d]pyrimidin-4(5H)-one hydrochloride The product from Example 10.1 (0.18 g, 0.483 mmol) was heated under reflux in 37% HCl for 1.5 h. The solvent was evaporated and the residue dissolved in a 1:1 mixture of MeOH:H$_2$O, neutralised with Amberlyst A21 resin, filtered and the solvent evaporated. The residue was chromatographed on silica gel ($^i$PrOH-water-28% NH$_4$OH, 92:0.4:0.4) to give the free base form of the product which was converted with 5% HCl to 7-((1,3-dihydroxypropan-2-ylamino)methyl)-3H-pyrrolo[3,2-d]pyrimidin-4(5H)-one hydrochloride (0.085 g, 64.0%) as a colourless solid. $^1$H NMR (D$_2$O, referenced to internal acetone at δ 2.225) δ 8.74, (s, 1H), 7.85 (s, 1H), 4.58 (s, 2H), 3.98 (dd, J=12.7, 4.6 Hz, 2H), 3.89 (dd, J=12.6, 5.9 Hz, 2H), 3.53 (m, 1H). $^{13}$C NMR (D$_2$O, referenced to internal acetone at δ 31.5) δ 154.5, 145.4, 136.8, 133.4, 119.3, 105.3, 60.9, 58.9, 39.8. +ESMS Found 239.1153 (M+H)$^+$ C$_{10}$H$_{15}$N$_4$O$_3$ requires 239.1144—free base.

Example 11

Synthesis of 7-(((1,3-dihydroxypropan-2-yl)(2-hydroxyethyl)amino)methyl)-3H-pyrrolo[3,2-d]pyrimidin-4(5H)-one hydrochloride

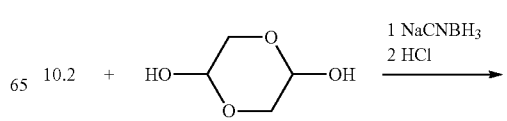

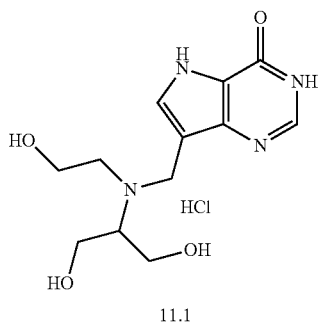

11.1

Example 11.1

Synthesis of 2-(((4-hydroxy-5H-pyrrolo[3,2-d]pyrimidin-7-yl)methyl)(2-hydroxyethyl)amino)propane-1,3-diol hydrochloride Sodium cyanoborohydride (0.011 g, 0.18 mmol) was added to a solution of the product from Example 10.2 (0.041 g, 0.15 mmol) and 1,4-dioxane-2,5-diol (0.027 g, 0.22 mmol, Sigma-Aldrich) in MeOH (3 ml) and stirred at it for 16 h. The solvent was evaporated and the residue chromatographed on silica gel ($^i$PrOH-28% aq. NH$_4$OH-water, 98:1:1) to give the crude product as a yellow solid (~21 mg). The solid was triturated with a little 7M NH$_3$-EtOH solution to leave the free base form of the title compound as a colourless solid (~12 mg). This solid was dissolved in excess 5% aq. HCl then the solvent evaporated to give 7-(((1,3-dihydroxypropan-2-yl)(2-hydroxyethyl)amino)methyl)-3H-pyrrolo[3,2-d]pyrimidin-4(5H)-one hydrochloride as a solid (15 mg, 32%). $^1$H NMR (D$_2$O, referenced to HOD at 4.72 ppm) δ 8.49 (s, 1H), 7.82 (s, 1H), 4.77 (s, 2H), 3.98-3.88 (m, 6H), 3.77 (sextet, J=6.1 Hz, 1H), 3.56 (br. s, 2H). $^{13}$C NMR (D$_2$O), δ 154.4, 144.4, 139.5, 132.8, 118.6, 104.1, 64.3, 56.7, 55.7, 52.6, 47.1. +ESMS Found 283.1407 (M+H)$^+$ C$_{12}$H$_{19}$N$_4$O$_4$ requires 283.1406.

Example 12

Synthesis of 7-((1,3-dihydroxy-2-(methylthiomethyl)propan-2-ylamino)methyl)-3H-pyrrolo[3,2-d]pyrimidin-4(5H)-one

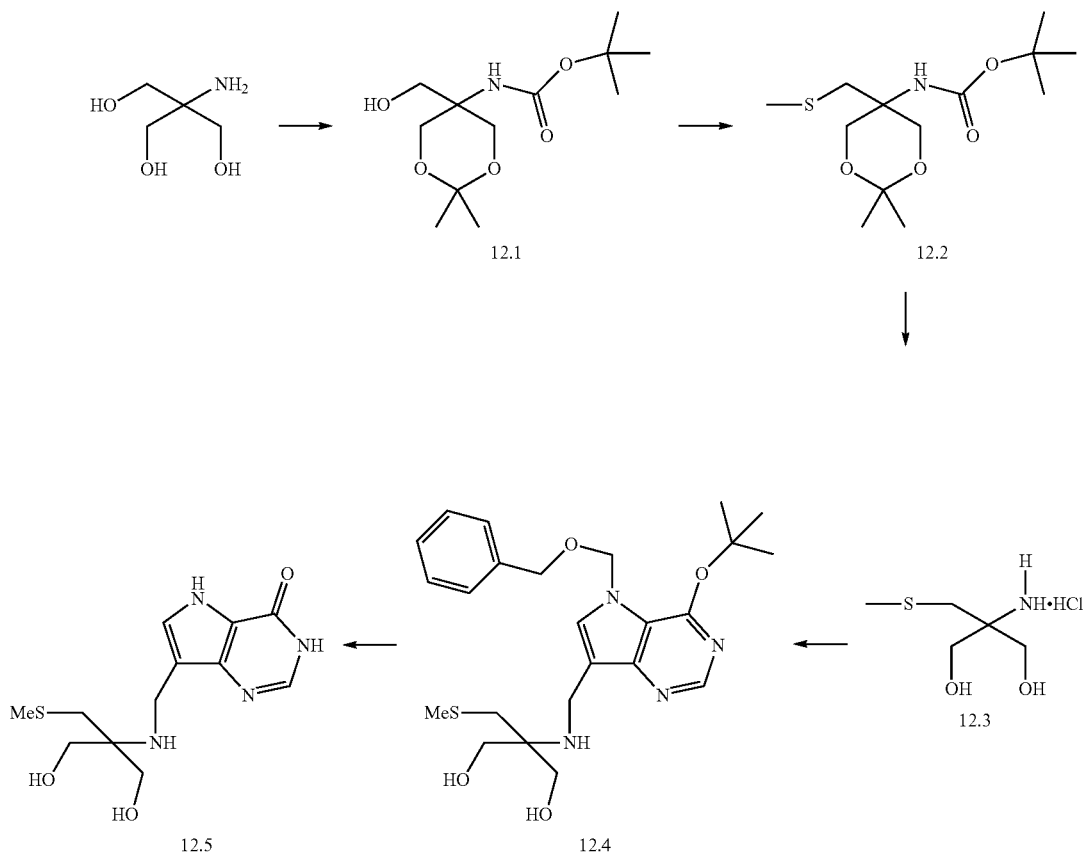

Example 12.1

Synthesis of N-(5-(hydroxymethyl)-2,2-dimethyl-1,3-dioxan-5-yl)pivalamide

A solution of 2-amino-2-(hydroxymethyl)propane-1,3-diol (15.7 g, 130 mmol) and di-tert-butyl dicarbonate (31.1 g, 143 mmol) in methanol (400 mL) and water (40 mL) was stirred at ambient temperature for 72 h. The contents of the flask were concentrated under reduced pressure and the resulting white solid was dissolved in minimal hot ethyl acetate and allowed to recrystallise overnight. The crystals were filtered and washed with petroleum ether to give N-(1,3-dihydroxy-2-(hydroxymethyl)propan-2-yl)pivalamide (26.5 g, 130 mmol, 100%) as fluffy, white needles. To a solution of N-(1,3-dihydroxy-2-(hydroxymethyl)propan-2-yl)pivalamide (9.50 g, 42.0 mmol) and 2,2-dimethoxypropane (16.0 mL, 129 mmol) in DMF (100 mL) was added pyridinium para-toluenesulfonate (0.540 g, 2.15 mmol) at RT. The reaction was stirred at ambient temperature for 15 h. after which time the reaction was complete by TLC (petroleum ether:ethyl acetate, 4:1, visualised with Erlichs). The reaction mixture was diluted with diethyl ether, washed three times with aqueous sodium bicarbonate, once with brine, dried over magnesium sulphate, filtered and concentrated under reduced pressure. The resulting semi-solid was recrystallised from minimal hot petroleum ether to give N-(5-(hydroxymethyl)-2,2-dimethyl-1,3-dioxan-5-yl)pivalamide (7.32 g, 65%) as white crystals. $^1$H NMR (CDCl$_3$): δ 5.31 (br s, 1H, NH), 4.18 (br s, 1H, OH), 3.85 (d, J=11.5 Hz, 2H), 3.80 (d, J=11.5 Hz, 2H), 3.70 (d, 6.6 Hz, 2H), 1.46 (s, 12H), 1.44 (s, 3H). $^{13}$C NMR (CDCl$_3$): δ 154.0, 98.8, 80.5, 64.8, 64.5 (2C), 53.4, 28.3 (3C), 26.9, 20.3.

Example 12.2

Synthesis of tert-butyl 2,2-dimethyl-5-(methylthiomethyl)-1,3-dioxan-5-ylcarbamate To a solution of N-(5-(hydroxymethyl)-2,2-dimethyl-1,3-dioxan-5-yl)pivalamide (1.03 g, 4.20 mmol) and triethylamine (1.52 mL, 10.9 mmol) in CH$_2$Cl$_2$ (10 mL) was added methanesulfonyl chloride (0.425 mL, 5.46 mmol) dropwise at 0° C. The reaction was allowed to warm to room temperature and was complete after 1.5 h as indicated by TLC (petroleum ether:ethyl acetate, 4:1, visualised with Erlichs). The reaction mixture was diluted with CH$_2$Cl$_2$, washed with water and brine, dried over magnesium sulfate, filtered and concentrated under reduced pressure to yield (2,2-dimethyl-5-pivalamino-1,3-dioxan-5-yl)-methyl methanesulfonate (1.35 g, 4.17 mmol, 99%) as a pale yellow solid. To a solution of (2,2-dimethyl-5-pivalamino-1,3-dioxan-5-yl)-methyl methanesulfonate (0.566 g, 1.67 mmol), in DMF (3 mL) was added sodium thiomethoxide (0.292 g, 4.17 mmol) at room temperature under argon for 15 h. TLC (petroleum ether:ethyl acetate, 4:1, visualised with Erlichs) indicated the reaction was complete so the contents of the flask were diluted with ethyl acetate, washed three times with aqueous sodium bicarbonate and once with brine. The organic layer was dried over magnesium sulfate, filtered and concentrated under reduced pressure. The resulting pale yellow solid was purified by flash column chromatography (CH$_2$Cl$_2$:methanol, 5:1) to give tert-butyl 2,2-dimethyl-5-(methylthiomethyl)-1,3-dioxan-5-ylcarbamate (0.460 g, 95%) as a white solid. $^1$H NMR (CDCl$_3$): δ 4.86 (brs, 1H, NH), 4.01 (d, J=11.7 Hz, 2H), 3.82 (d, J=11.7 Hz, 2H), 3.02 (s, 2H), 2.16 (s, 3H), 1.50 (s, 3H), 1.45 (s, 9H), 1.41 (s, 3H). $^{13}$C NMR (CDCl$_3$): δ 154.8, 98.5, 95.3, 65.4 (2C), 52.4, 37.3, 28.4 (3C), 24.6, 22.6, 17.5.

Example 12.3

Synthesis of 2-amino-2-(methylthiomethyl)propane-1,3-diol, hydrochloride salt

A solution of tert-butyl 2,2-dimethyl-5-(methylthiomethyl)-1,3-dioxan-5-ylcarbamate (2.64 g, 9.06 mmol) in methanol (10 mL) was added to a solution of concentrated hydrochloric acid (8 mL) in methanol (100 mL) and concentrated under reduced pressure to give a yellow oil, which was purified by flash column chromatography (CH$_2$Cl$_2$:methanol:7 M methanolic ammonia, 5:2:1). The residue was reconverted to the hydrochloride salt by treatment with a solution of concentrated hydrochloric acid (1 mL) and methanol (5 mL) and concentration under reduced pressure to give the 2-amino-2-(methylthiomethyl)propane-1,3-diol, hydrochloride salt (1.37 g, 9.06 mmol, 100%). $^1$H NMR (D$_2$O): δ 3.74 (s, 4H), 2.88 (s, 2H), 2.19 (s, 3H). $^{13}$C NMR (DMSO), δ ppm, 64.4 (2×CH$_2$), 57.9, 48.9, 17.5. +ESMS Found 152.0744 (M—Cl$^-$) C$_5$H$_{14}$NO$_2$S requires 152.0745.

Example 12.4

Synthesis of 2-((5-(benzyloxymethyl)-4-tert-butoxy-5H-pyrrolo[3,2-d]pyrimidin-7-yl)methylamino)-2-(methylthiomethyl)propane-1,3-diol To a solution of 2-amino-2-(methioxymethyl)-1,3-propanediol (265 mg, 0.156 mmol) and 5-(benzyloxymethyl)-4-tert-butoxy-5H-pyrrolol[3,2-d]pyrimidine-7-carbaldehyde (505 mg, 0.149 mmol) in methanol (10 mL) was added sodium cyanoborohydride (140 mg, 0.223 mmol) and the mixture stirred at ambient temperature for 5 h. TLC(CH$_2$Cl$_2$:methanol:7 M methanolic ammonia, 19:1:0.5, visualised with UV and Erlichs) indicated the reaction was essentially over so the contents of the flask were concentrated under reduced pressure and submitted to gradient flash column chromatography (CH$_2$Cl$_2$:methanol:7 M methanolic ammonia, 20:1:0.5 to 10:1:0.5) to give 2-((5-(benzyloxymethyl)-4-tert-butoxy-5H-pyrrolo[3,2-d]pyrimidin-7-yl)methylamino)-2-(methylthiomethyl)propane-1,3-diol (440 mg, 62%) as a yellow gum. $^1$H NMR (CD$_3$OD) δ 8.36 (s, 1H), 7.58 (s, 1H), 7.24-7.21 (m, 5H), 5.77 (s, 2H), 4.50 (s, 2H), 3.68 (d, J=10.8 Hz, 2H), 3.63 (d, J=10.8 Hz, 2H), 2.75 (s, 2H), 2.15 (s, 3H), 1.70 (s, 9H). $^{13}$C NMR (CD$_3$OD, δ5.5 MHz): δ 157.6, 150.3, 139.0, 133.5, 129.4 (2C), 128.7, 128.5 (2C), 118.2, 116.4, 84.6, 78.5, 71.2, 63.0, 55.4, 37.9, 36.1, 29.0, 17.4. +ESMS Found 475.2379 (M+H$^+$) C$_{24}$H$_{35}$N$_4$O$_4$S requires 475.2379.

Example 12.5

Synthesis of 7-((1,3-dihydroxy-2-(methylthiomethyl)propan-2-ylamino)methyl)-3H-pyrrolo[3,2-d]pyrimidin-4(5H)-one A solution of 2-((5-(benzyloxymethyl)-4-tert-butoxy-5H-pyrrolo[3,2-d]pyrimidin-7-yl)methylamino)-2-(methylthiomethyl)propane-1,3-diol (200 mg, 0.421 mmol) in methanol (1 mL) was added to a solution of concentrated hydrochloric acid (2 mL) in methanol (5 mL) and the reaction was heated at 100° C. for 3 h. The contents of the flask were concentrated under reduced pressure, redissolved in methanol (5 mL) and Amberlyst 21 resin (~1 g) was added. After stirring for 1 h at ambient temperature the resin was removed by filtration, the filtrate concentrated under reduced pressure and then redissolved in 7 M methanolic ammonia (5 mL) and stirred for 30 min. TLC(CH$_2$Cl$_2$:7 M methanolic ammonia, 4:1, visualised with Erlichs) indicated the reaction was complete so the solution was concentrated under reduced pressure and the residue dry-loaded on to a silica column. Purification by flash column chromatography (CH$_2$Cl$_2$:7 M methanolic ammonia, 3:1, visualised with Erlichs) gave 7-((1,3-dihydroxy-2-(methylthiomethyl)propan-2-ylamino)methyl)-3H-pyrrolo[3,2-d]pyrimidin-4(5H)-one (62.0 mg, 49%) as a white foam. $^1$H NMR (D$_2$O, drop of DCl) δ 8.91 (1H), 7.79 (1H), 4.43 (2H), 3.84 (d, J=12.7 Hz, 2H), 3.79 (d, J=12.7 Hz, 2H), 2.92 (s, 2H), 2.13 (s, 3H). $^{13}$C NMR (D$_2$O, drop of DCl): δ 152.8, 145.2, 133.3, 131.8, 118.5, 103.5, 67.4, 59.2, 35.4, 33.5, 17.0. +ESMS Found 299.1185 (M+Fr) C$_{12}$H$_{19}$N$_4$O$_3$S requires 299.1178.

Example 13

Synthesis of (R)-7-(((2,3-dihydroxypropyl)(2-hydroxyethyl)amino)methyl)-3H-pyrrolo[3,2-d]pyrimidin-4(5H)-one

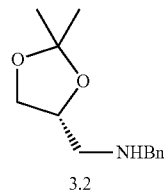

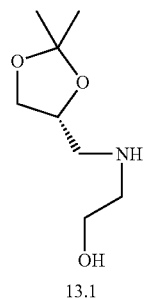 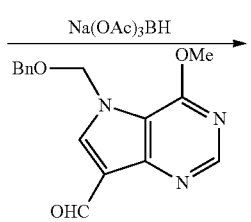

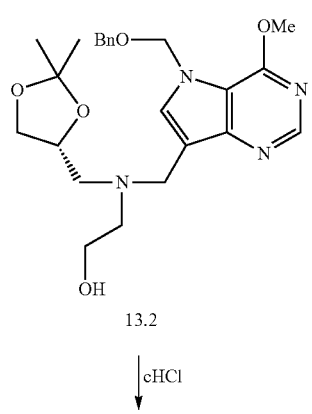

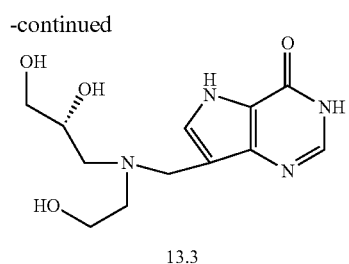

Example 13.1

Synthesis of (R)-2-((2,2-dimethyl-1,3-dioxolan-4-yl)methylamino)ethanol

Potassium carbonate (0.125 g, 0.904 mmol) was added to a solution of the product from Example 3.2 (0.2 g, 0.904 mmol) and 2-bromoethanol (0.096 ml, 1.356 mmol) in CH$_3$CN (4 ml) and the mixture heated under reflux for 64 h. After cooling, the mixture was diluted with EtOAc and washed with sat. NaHCO$_3$, dried and the solvent evaporated. The residue was chromatographed on silica gel (EtOAc-hexanes 1:1 then 7:3) to give crude (R)-2-(benzyl((2,2-dimethyl-1,3-dioxolan-4-yl)methyl)amino)ethanol as a colourless oil (203 mg, 85%). The oil was dissolved in MeOH (5 ml), 10% Pd—C (50 mg) added and the mixture stirred under hydrogen added from a balloon for 1 h. The hydrogen was replaced with Ar and the mixture filtered through Celite, the solvent evaporated and the residue chromatographed on silica gel (CH$_2$Cl$_2$-MeOH-28% NH$_4$OH, 97:3:0.5, then 9:1:0.1) and the product distilled on a kugelrohr apparatus at 120° C./0.05 mmHg to give (R)-2-((2,2-dimethyl-1,3-dioxolan-4-yl)methylamino)ethanol (0.103 g, 78%) as a colourless gum. $^1$H NMR (CD$_3$OD) δ 4.24 (pentet, J=6.2 Hz, 1H), 4.06 (dd, J=8.2, 6.3 Hz, 1H), 3.71-3.59 (m, 3H), 2.76-2.66 (m, 4H), 1.39 (s, 3H), 1.33 (s, 3H). $^{13}$C NMR (CD$_3$OD, referenced to the centre line of CD$_3$OD at 49.0 ppm) δ 110.4, 76.4, 68.6, 61.6, 53.4, 52.5, 27.3, 25.7. +ESMS Found 176.1278 C$_8$H$_{18}$NO$_3$ (M+H)$^+$ requires 176.1287. [α]$_D^{20}$ +9.5 (c, 0.525, MeOH).

Example 13.2

Synthesis of (R)-2-(((5-(benzyloxymethyl)-4-methoxy-5H-pyrrolo[3,2-d]pyrimidin-7-yl)methyl)((2,2-dimethyl-1,3-dioxolan-4-yl)methyl)amino)ethanol Sodium triacetoxyborohydride (0.126 g, 0.594 mmol) and MgSO$_4$ (500 mg) were added to a solution of the product from Example 13.1 (0.08 g, 0.457 mmol) and 5-(benzyloxymethyl)-4-methoxy-5H-pyrrolo[3,2-d]pyrimidine-7-carbaldehyde (0.136 g, 0.457 mmol, prepared as in G. B. Evans, R. H. Furneaux, A, Lewandowicz, V. L. Schramm and P. C. Tyler, *J. Med. Chem.*, 2003, 46, 3412) in 1,2-dichloroethane (3 ml) and the mixture stirred at rt overnight. The mixture was diluted with CH$_2$Cl$_2$ and washed with sat. NaHCO$_3$ solution, dried and the solvent evaporated. The residue was chromatographed on silica gel (EtOAc then EtOAc-MeOH-28% NH$_4$OH, 97:3:0.01) to give (R)-2-(((5-(benzyloxymethyl)-4-methoxy-5H-pyrrolo[3,2-d]pyrimidin-7-yl)methyl)((2,2-dimethyl-1,3-dioxolan-4-yl)methyl)amino)ethanol (0.180 g, 86%) as a colourless gum which turned pale yellow on standing. $^1$H NMR (CDCl$_3$) δ 8.53 (s, 1H), 7.36-7.23 (s, 6H), 5.71 (s, 2H), 4.60 (v.br.s, 1H, exchanged to D$_2$O), 4.46 (s, 2H), 4.20 (pentet, 1H, J=6.3 Hz), 4.10 (s, 3H), 4.02 (d, 1H, J=14.1

Hz), 3.88-3.67 (m, 4H), 3.26 (dd, 1H, J=8.0, 6.9 Hz), 2.86-2.70 (m, 3H), 2.61 (dd, 1H, J=13.2, 6.7 Hz), 1.32 (s, 3H), 1.28 (s, 3H). $^{13}$C NMR (CDCl$_3$, referenced to the centre line of CDCl$_3$ at 77.0 ppm) δ 156.3, 150.2, 149.9, 136.8, 131.5, 128.5, 128.0, 127.7, 116.2, 115.1, 108.9, 76.9, 74.2, 70.1, 68.4, 59.9, 57.2, 56.5, 53.6, 47.8, 26.8, 25.4. +ESMS Found 457.2467 C$_{24}$H$_{33}$N$_4$O$_5$ (M+H)$^+$ requires 457.2451.

Example 13.3

Synthesis of (R)-7-(((2,3-dihydroxypropyl)(2-hydroxyethyl)amino)methyl)-3H-pyrrolo[3,2-d]pyrimidin-4(5H)-one The product from Example 13.2 (0.165 g, 0.361 mmol) was dissolved in 37% HCl (4 ml) and heated to 100° C. for 1.5 h. The solvent was evaporated and the residue dissolved in MeOH and a little water and neutralized with Amberlyst A21 resin. The mixture was filtered and the solvent was evaporated. The residue was chromatographed on silica gel ($^i$PrOH—H$_2$O-28% NH$_4$OH 9:0.5:0.5 then 8:1.5:0.5) to give (R)-7-(((2,3-dihydroxypropyl)(2-hydroxyethyl)amino)methyl)-3H-pyrrolo[3,2-d]pyrimidin-4(5H)-one (0.074 g, 72.5%) as a colourless solid. [α]$_D^{20}$ +18.4 (c, 0.56, H$_2$O). $^1$H NMR (D$_2$O+NaOD, referenced to internal acetonitrile at 2.06 ppm) δ 8.07 (s, 1H), 7.35 (s, 1H), 3.94-3.65 (m, 3H), 3.68 (t, J=6.2 Hz, 2H), 3.50 (dd, J=11.7, 4.2 Hz, 1H), 3.40 (dd, J=11.6, 6.2 Hz, 1H), 2.75-2.48 (m, 4H). $^{13}$C NMR (D$_2$O, 75.5 MHz, referenced to internal acetone at 31.5 ppm) δ 156.3, 145.4, 143.7, 132.0, 118.6, 109.2, 68.9, 65.1, 58.5, 56.7, 56.3, 48.8. +ESMS Found 283.1398 C$_{12}$H$_{19}$N$_4$O$_4$ (M+H)$^+$ requires 283.1406.

Example 14

Synthesis of (S)-7-(((2,3-dihydroxypropyl)(2-hydroxyethyl)amino)methyl)-3H-pyrrolo[3,2-d]pyrimidin-4(5H)-one

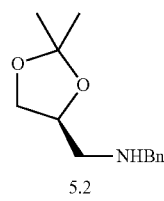

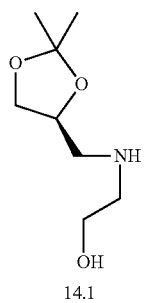

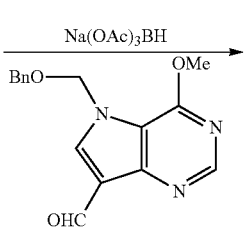

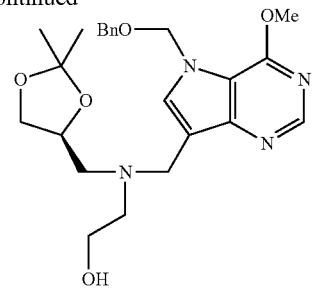

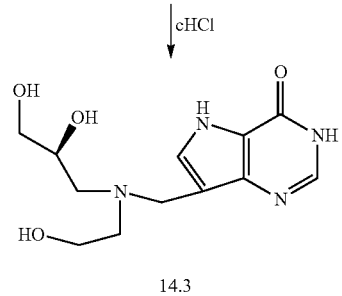

Example 14.1

Synthesis of (S)-2-((2,2-dimethyl-1,3-dioxolan-4-yl)methylamino)ethanol

The product from Example 5.2 (200 mg, 0.904 mmol) was treated with 2-bromoethanol (0.096 ml, 1.356 mmol) and potassium carbonate (0.125 g, 0.904 mmol) to give crude (S)-2-(benzyl((2,2-dimethyl-1,3-dioxolan-4-yl)methyl) amino)ethanol (0.172 g, 71.7%) which was then hydrogenolysed in exactly the same way as for the (R)-enantiomer in Example 13.1 to give 70 mg (62%) of compound 14.1. The $^1$H and $^{13}$C NMR were identical to the (R)-enantiomer in Example 13.1. +ESMS Found 176.1274 C$_8$H$_{18}$NO$_3$ (M+H)$^+$ requires 176.1287. [α]$_D^{20}$ −9.6 (c, 0.555, MeOH).

Example 14.2

Synthesis of (S)-2-(((5-(benzyloxymethyl)-4-methoxy-5H-pyrrolo[3,2-d]pyrimidin-7-yl)methyl)((2,2-dimethyl-1,3-dioxolan-4-yl)methyl)amino)ethanol The product from Example 14.1 (0.048 g, 0.274 mmol) was reductively aminated with 5-(benzyloxymethyl)-4-methoxy-5H-pyrrolo[3,2-d]pyrimidine-7-carbaldehyde (0.081 g, 0.274 mmol) and sodium triacetoxyborohydride (0.075 g, 0.356 mmol) in the same way as described for the R-enantiomer in Example 13.2. to give (S)-2-(((5-(benzyloxymethyl)-4-methoxy-5H-pyrrolo[3,2-d]pyrimidin-7-yl)methyl)((2,2-dimethyl-1,3-dioxolan-4-yl)methyl)amino)ethanol (100 mg, 80%) as a colourless gum which slowly turned pale yellow. The $^1$H and $^{13}$C NMR were as described for the R-enantiomer in Example 13.2. +ESMS Found 457.2469 C$_{24}$H$_{33}$N$_4$O$_5$ (M+H)$^+$ requires 457.2451.

Example 14.3

Synthesis of (S)-7-(((2,3-dihydroxypropyl)(2-hydroxyethyl)amino)methyl)-3H-pyrrolo[3,2-d]pyrimidin-4(5H)-one The product from Example 14.2 (100 mg, 0.219 mmol) was converted into the title compound (42 mg, 67.9%) in the same way as that described for the R-enantiomer in Example 13.3. The $^1$H and $^{13}$C NMR were in agreement with those described for the R-enantiomer in Example 13.3. +ESMS Found 283.1404 $C_{12}H_{19}N_4O_4$ (M+H)$^+$ requires 283.1406. $[\alpha]_D^{20}$ −17.9 (c, 0.545, H$_2$O).

Example 15

Synthesis of 7-(((2S,3S)-1,3,4-trihydroxybutan-2-ylamino)methyl)-3H-pyrrolo[3,2-d]pyrimidin-4(5H)-one

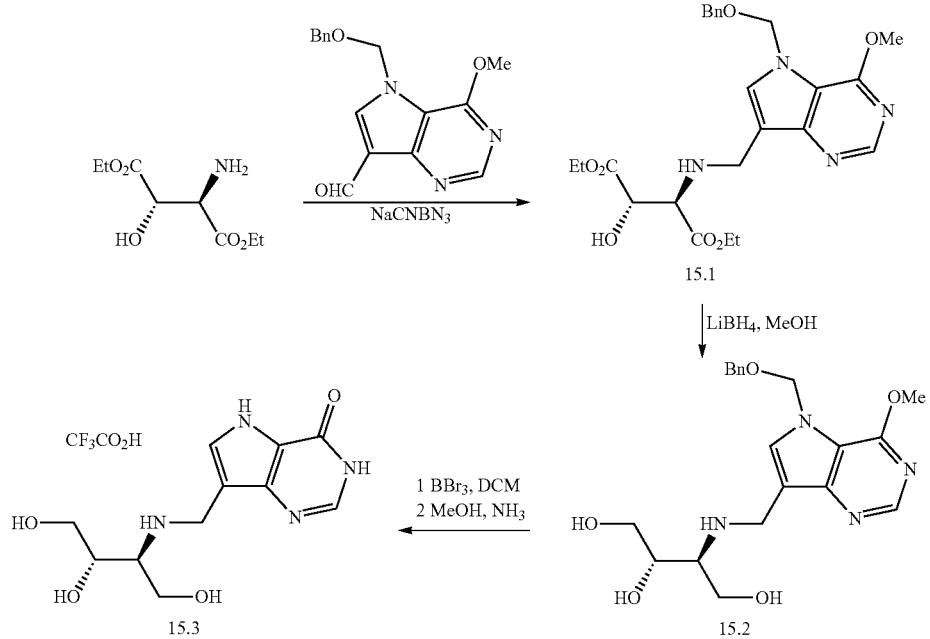

Example 15.1

Synthesis of (2R,3S)-diethyl 2-((5-(benzyloxymethyl)-4-methoxy-5H-pyrrolo[3,2-d]pyrimidin-7-yl)methylamino)-3-hydroxysuccinate A mixture of (2R,3S)-diethyl 2-amino-3-hydroxysuccinate (prepared as described in A. Breuning, R. Vicik and T. Schirmeister, *Tetrahedron Asymm.*, 2003, 14, 3301 and Z. Tang, Z.-H. Yang, X.-H. Chen, L.-F. Cun, A.-Q. Mi, Y.-Z. Jiang and L.-Z. Gong, *J. Am. Chem. Soc.*, 2005, 127, 9285) (0.109 g, 0.53 mmol), sodium cyanoborohydride (0.055 g, 0.88 mmol) and 5-(benzyloxymethyl)-4-methoxy-5H-pyrrolo[3,2-d]pyrimidin-7-carbaldehyde (0.131 g, 0.44 mmol) were evaporated from methanol (3×). The residue was dissolved in methanol (10 ml) and acetic acid added (5 drops). The reaction mixture was stirred at ambient temperature for 2 h. The reaction mixture was evaporated on to silica gel and chromatographed (ethyl acetate-petrol, 2:1 then ethyl acetate-triethylamine, 1:99) giving a colourless oil (0.166 g, 77%). $^1$H NMR (CDCl$_3$) δ 8.55 (s, 1H), 7.34 (s, 1H), 7.33-7.23 (m, 5H); 5.70 (s, 2H), 4.62 (d, J=3.4 Hz, 1H), 4.48 (s, 2H), 4.23-4.15 (m, 5H), 4.10 (s, 3H), 3.99 (d, J=13.8 Hz, 1H), 3.85 (d, J=2.3 Hz, 1H), 2.25 (brs, 2H), 1.26 (t, J=7.1 Hz, 3H), 1.25 (t, J=7.1 Hz, 3H).

Example 15.2

Synthesis of (2S,3S)-3-((5-(benzyloxymethyl)-4-methoxy-5H-pyrrolo[3,2-d]pyrimidin-7-yl)methylamino)butane-1,2,4-triol To a stirred solution of the product from Example 15.1 (0.166 g, 0.34 mmol) in diethyl ether (10 ml) was added methanol (0.14 ml, 3.41 mmol) and then lithium borohydride (0.85 ml, 1.71 mmol, 2.0M in THF). After 30 mins the reaction mixture was diluted with methanol and then concentrated. The residue was dissolved in methanol, diluted with concentrated aqueous ammonia (1 ml) and evaporated on to silica gel. The material was chromatographed on silica gel (DCM-methanol-conc. ammonia, 85:15:2, then 70:30:2, then 50:50:4). This gave three distinct compounds; firstly the title compound and then two different salt forms of the title compound. The three compounds were combined to give a colourless oil (0.103 g, 75%). $^1$H NMR (CD$_3$OD) δ 8.42 (s, 1H), 7.64 (s, 1H), 7.28-7.16 (m, 5H), 5.75 (s, 2H), 4.50 (s, 2H), 4.10 (s, 3H), 3.83-3.68 (m, 3H), 3.63 (d, J=5.5 Hz, 2H), 3.31 (pentet, J=1.6 Hz, 1H).

Example 15.3

Synthesis of the trifluoroacetic acid salt of 7-(((2S,3S)-1,3,4-trihydroxybutan-2-ylamino)methyl)-3H-pyrrolo[3,2-d]pyrimidin-4(5H)-one To a stirred solution of the product from Example 15.2 (0.103 g, 0.26 mmol) in DCM (10 ml) at −78° C. was added boron tribromide (2.56 ml, 2.56 mmol, 1.0M in DCM). After 15 mins the reaction mixture was warmed to ambient temperature and co-evaporated with methanol (3×). The residue was stirred in methanol (7N ammonia solution) for 10 mins and evaporated on to silica gel. The material was chromatographed on silica gel (chloroform-methanol-conc. ammonia, 10:9:1) and then on Polar-RP HPLC (TFA-methanol-water, 0.1:1:99 increasing to 0.1:1:4) giving a white solid (0.018 mg, 26%). ¹H NMR (D₂O) δ 8.32 (s, 1H), 7.74 (s, 1H), 4.53 (s, 2H), 4.13 (dq, J=5.7, 1.1 Hz, 1H), 3.95 (ddd, J=12.5, 4.5, 1.1 Hz, 1H), 3.86 (ddd, J=11.2, 7.2, 1.1 Hz, 1H), 3.64 (m, 2H), 3.46 (m, 1H).

Example 16

Synthesis of (2RS,3SR)-1,3,4-trihydroxy-N,N-dimethyl-N-((4-oxo-4,5-dihydro-3H-pyrrolo[3,2-d]pyrimidin-7-yl)methyl)butan-2-aminium iodide

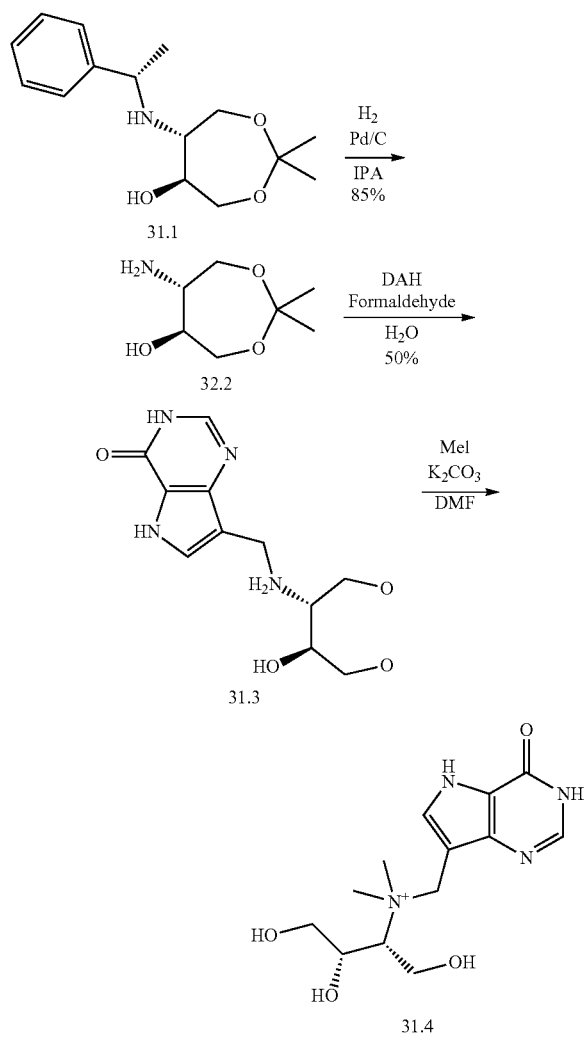

Example 16.1

Synthesis of (5S,6R)-2,2-dimethyl-6-((S)-1-phenylethylamino)-1,3-dioxepan-5-ol

This compound was prepared according to the method described in T. Inaba, A. Birchler, Y. Yamada, S. Sagawa, K. Yokota, K. Ando and I. Uchida, *J. Org. Chem.*, 1998, 63, 7582-7583.

Example 16.2

Synthesis of (5S,6R)-6-amino-2,2-dimethyl-1,3-dioxepan-5-ol

To (5S,6R)-2,2-dimethyl-6-((S)-1-phenylethylamino)-1,3-dioxepan-5-ol (500 mg, 1.88 mmol) in iso-propanol (5 ml) was added 10% Pd—C (100 mg). The mixture was stirred at 50° C. under an atmospheric pressure of H₂ overnight. Then the solution was filtered on a pad of Celite and the pad washed with MeOH (20 ml). The filtrate was evaporated to dryness to give (5S,6R)-6-amino-2,2-dimethyl-1,3-dioxepan-5-ol (300 mg, 1.86 mmol, 99% yield) as a white solid. ¹H NMR (CDCl₃) 1.03 (3H, s), 1.06 (3H, s), 2.61 (1H, d, OH), 2.75 (1H, m), 3.38 (1H, m), 3.46 (1H, dd, J 5.3 and 12.5 Hz), 3.57 (1H, dd, J 5.9 and 12.5 Hz), 3.75 (1H, dd, J 2.3 and 12.5 Hz), 3.80 (1H, dd, J 1.8 and 12.5 Hz). ¹³C NMR (CDCl₃) 25.0, 25.1, 56.1, 61.6, 62.8, 74.6, 101.7.

Example 16.3

Synthesis of 7-(((2RS,3SR)-1,3,4-trihydroxybutan-2-ylamino)methyl)-3H-pyrrolo[3,2-d]pyrimidin-4(5H)-one A mixture of (5S,6R)-6-amino-2,2-dimethyl-1,3-dioxepan-5-ol (155 mg, 0.96 mmol), 9-deazahypoxanthine (100 mg, 0.74 mmol) and 37% aq formaldehyde (140 µl, 1.85 mmol) in water (2 ml) was stirred and heated in stoppered flask at 85° C. overnight. The solution was evaporated to dryness. The residue was stirred in methanolic ammonia for 10 minutes and then evaporated. The residue was chromatographed on silica (DCM-MeOH-cNH₃ 6:3.5:0.5) to give the racemic 7-(((2RS,3SR)-1,3,4-trihydroxybutan-2-ylamino)methyl)-3H-pyrrolo[3,2-d]pyrimidin-4(5H)-one (55 mg, 0.20 mmol, 30% yield) as a white solid ¹H NMR (CDCl₃) 2.76 (1H, q, J 5.2 Hz), 3.48 (1H, dd, J 6.3, 11.9 Hz), 3.60 (2H, m), 3.70 (2H, m), 3.85 (2H, ABq), 7.34 (1H, s), 7.78 (1H, s). ¹³C NMR (CDCl₃) δ0.2, 59.8, 59.8, 63.5, 71.2, 113.1, 117.5, 129.2, 142.4, 143.5, 155.4. m/z (ESI⁺) 537 (2MH⁺, 20%), 269 (MH⁺, 100%). HRMS (ESI⁺) C₁₁H₁₆N₄O₄ requires 269.1241. found 269.1250.

Example 16.4

Synthesis of (2RS,3SR)-1,3,4-trihydroxy-N,N-dimethyl-N-((4-oxo-4,5-dihydro-3H-pyrrolo[3,2-d]pyrimidin-7-yl)methyl)butan-2-aminium iodide To a mixture of rac-(2R,3S)-3-((4-hydroxy-5H-pyrrolo[3,2-d]pyrimidin-7-yl)methylamino)butane-1,2,4-triol (50 mg, 0.19 mmol) and potassium carbonate (130 mg, 0.93 mmol) in DMF (5 mL) was added iodomethane (15 µl, 0.20 mmol). The mixture was stirred at 60° C. overnight. Then the solvent was evaporated and the residue was purified by chromatography with DCM-MeOH-cNH₃ (9:1:0.1). to give (2RS,3SR)-1,3,4-trihydroxy-N,N-dimethyl-N-((4-oxo-4,5-dihydro-3H-pyrrolo[3,2-d]pyrimidin-7-yl)methyl)butan-2-aminium iodide (30 mg, 0.10 mmol, 57% yield) as a colourless oil. ¹H NMR (CD₃OD) 3.02 (1H, m), 3.62 (6H, s), 3.50-3.80 (5H, m), 4.01 (1H, d, J 13 Hz), 4.17 (1H, d, J 13 Hz). ¹³C NMR (CD₃OD) 34.2, 38.1, 59.6, 65.5, 66.5, 71.3, 115.2, 119.6, 129.7, 145.1, 146.5, 156.4.

Example 17

Synthesis of 7-(((2R,3S)-1,3,4-trihydroxybutan-2-ylamino)methyl)-3H-pyrrolo[3,2-d]pyrimidin-4(5H)-one

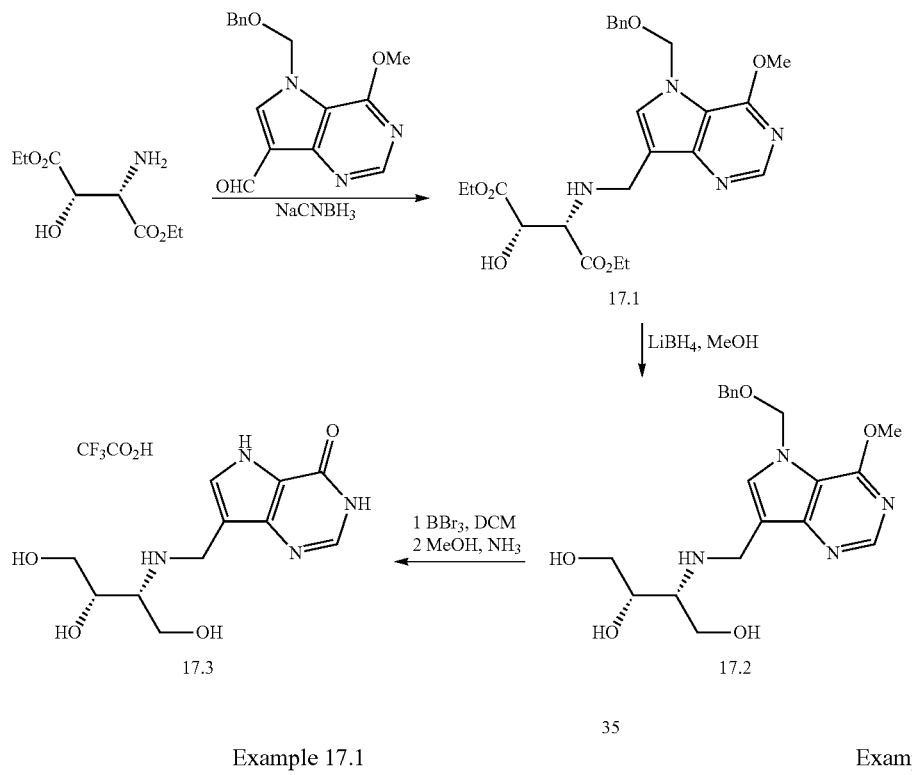

Example 17.1

Synthesis of (2R,3S)-diethyl 2-((5-(benzyloxymethyl)-4-methoxy-5H-pyrrolo[3,2-d]pyrimidin-7-yl)methylamino)-3-hydroxysuccinate A mixture of (2S,3S)-diethyl 2-amino-3-hydroxysuccinate (prepared as described in A. Baruch, S. H. L. Verhelst, M. Bogyo, K. A. H. Chehade, *Synthesis*, 2005, 2, 240-244 and Z. Tang, Z.-H. Yang, X.-H. Chen, L.-F. Cun, A.-Q. Mi, Y.-Z. Jiang and L.-Z. Gong, *J. Am. Chem. Soc.*, 2005, 127, 9285) (0.871 g, 4.24 mmol), sodium cyanoborohydride (0.444 g, 7.07 mmol) and 5-(benzyloxymethyl)-4-methoxy-5H-pyrrolo[3,2-d]pyrimidin-7-carbaldehyde (1.051 g, 3.54 mmol) was evaporated from methanol (3×). The residue was dissolved in methanol (20 ml) and acetic acid added (10 drops). The reaction mixture was stirred at ambient temperature for 18 h. The reaction mixture was evaporated on to silica gel and chromatographed (triethylamine-methanol-DCM, 1:3:99) giving a colourless oil (2.577 g, 150%). $^1$H NMR revealed the product was contaminated with (co-polar) starting amine and some borohydride residues. $^1$H NMR (CDCl$_3$) δ 8.52 (s, 1H), 7.38-7.23 (m, 6H), 5.69 (s, 2H), 4.52 (br. s, 1H), 4.47 (s, 2H), 4.32-4.10 (m, 6H), 4.10 (s, 3H), 3.73 (br. s, 1H), 1.27 (t, J=7.2 Hz, 3H), 1.21 (t, J=7.2 Hz, 3H).

Example 17.2

Synthesis of (2S,3R)-3-((5-(benzyloxymethyl)-4-methoxy-5H-pyrrolo[3,2-d]pyrimidin-7-yl)methylamino)butane-1,2,4-triol To a stirred solution of the product from Example 17.1 (1.718 g, 3.53 mmol) in diethyl ether (30 ml) was added methanol (1.43 ml, 35.3 mmol) and then lithium borohydride (8.83 ml, 17.7 mmol, 2.0M in THF). After 1 h methanol (1.43 ml, 35.3 mmol) was added to the reaction mixture and stirring continued. After 1 h further the reaction mixture was diluted with methanol and then concentrated. The residue was dissolved in methanol (20 ml), diluted with hydrochloric acid (20 ml, 1M) and concentrated. The residue was chromatographed on silica gel (methanol [7N ammonia]-DCM, 15:85) giving a white solid (0.940 g, 66%). $^1$H NMR (CD$_3$OD) δ 8.43 (s, 1H), 7.69 (s, 1H), 7.28-7.15 (m, 5H), 5.77 (s, 2H), 4.52 (s, 2H), 4.12 (ABq, 2H), 4.11 (s, 31-1), 3.80 (dd, J=11.7, 5.3 Hz, 1H), 3.80-3.60 (m, 3H), 3.59 (dd, J=11.0, 4.9 Hz, 1H), 2.90 (q, J=4.9 Hz, 1H). $^{13}$C NMR (CD$_3$OD) δ 158.4, 151.4, 151.0, 139.1, 135.0, 129.7, 129.2, 129.1, 117.5, 115.3, 79.0, 72.5, 72.0, 65.6, 62.0, 61.6, 54.8, 42.1.

Example 17.3

Synthesis of the trifluoroacetic acid salt of 7-(((2R,3S)-1,3,4-trihydroxybutan-2-ylamino)methyl)-3H-pyrrolo[3,2-d]pyrimidin-4(5H)-one To a stirred solution of the product from Example 17.2 (0.940 g, 2.34 mmol) in DCM (30 ml) at −78° C. was added boron tribromide (23.4 ml, 23.4 mmol, 1.0M in DCM). After 15 mins the reaction mixture was warmed to ambient temperature and coevaporated with methanol (3×). The residue was stirred in methanol (7N ammonia solution) for 10 mins and evaporated on to silica gel. The material was chromatographed on silica gel (chloroform-methanol-conc. ammonia, 10:9:1) and then on Polar-RP HPLC (TFA-methanol-water, 0.1:3:97 increasing to 0.1:50:50) giving a crystalline white solid (0.234 mg, 26%). $^1$H NMR (D$_2$O) δ ppm 8.03 (s, 1H), 7.59 (s, 1H), 4.41 (ABq, 2H), 3.88 (dd, J=13.2, 4.2 Hz, 1H), 3.80 (m, 1H), 3.72 (dd, J=13.2, 5.3 Hz, 1H), 3.60 (dd, J=12.5, 3.4 Hz, 2H), 3.47 (dd, J=12.5, 4.5 Hz, 1H), 3.26 (m, 1H). +ESMS found 269.1258 (M+H)$^+$ C$_{11}$H$_{17}$N$_4$O$_4$ requires 269.1250.

Example 18

Synthesis of 7-(((2S,3R)-1,3,4-trihydroxybutan-2-ylamino)methyl)-3H-pyrrolo[3,2-d]pyrimidin-4(5H)-one

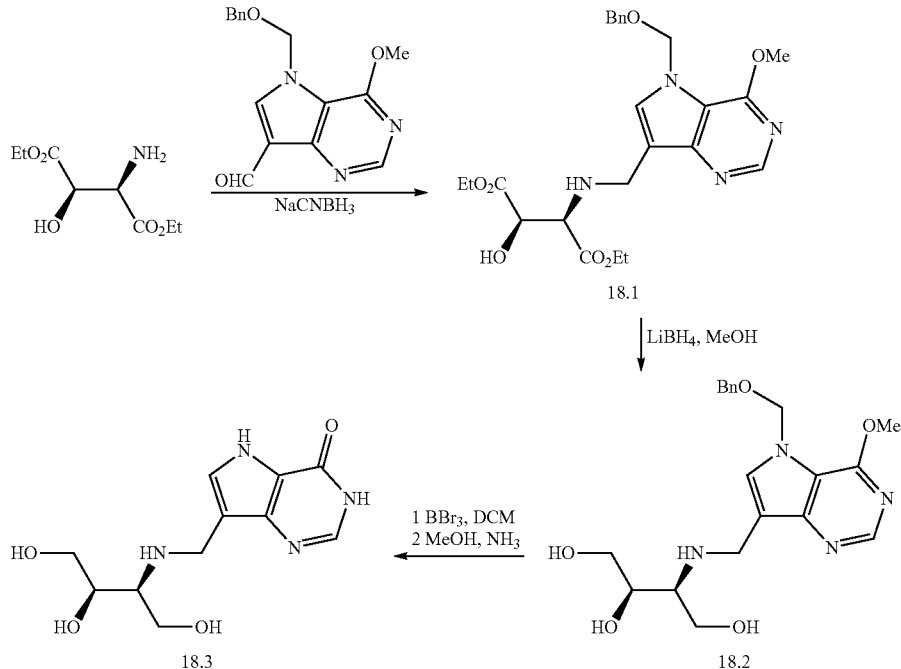

Example 18.1

Synthesis of (2S,3R)-diethyl 2-((5-(benzyloxymethyl)-4-methoxy-5H-1-pyrrolo[3,2-d]pyrimidin-7-yl)methylamino)-3-hydroxysuccinate A mixture of (2R,3R)-diethyl 2-amino-3-hydroxysuccinate (prepared as described in A. Baruch, S. H. L. Verhelst, M. Bogyo, K. A. H. Chehade, *Synthesis*, 2005, 2, 240-244 and Z. Tang, Z.-H. Yang, X.-H. Chen, L.-F. Cun, A.-Q. Mi, Y.-Z. Jiang and L.-Z. Gong, *J. Am. Chem. Soc.*, 2005, 127, 9285) (0.083 g, 0.40 mmol), sodium cyanoborohydride (0.042 g, 0.67 mmol) and 5-(benzyloxymethyl)-4-methoxy-5H-pyrrolo[3,2-d]pyrimidin-7-carbaldehyde (0.100 g, 0.34 mmol) was evaporated from methanol (3×). The residue was dissolved in methanol (10 ml) and acetic acid added (5 drops). The reaction mixture was stirred at ambient temperature for 16 h. The reaction mixture was evaporated on to silica gel and chromatographed (triethylamine-ethyl acetate-petrol, 1:66:33) giving a colourless oil (0.114 g, 70%). $^1$H NMR revealed the product was slightly contaminated with (co-polar) starting amine. $^1$H NMR (CDCl$_3$) δ 8.52 (s, 1H), 7.38-7.23 (m, 6H), 5.69 (s, 2H), 4.52 (br. s, 1H), 4.47 (s, 2H), 4.32-4.10 (m, 6H), 4.10 (s, 3H), 3.73 (br. s, 1H), 1.27 (t, J=7.2 Hz, 3H), 1.21 (t, J=7.2 Hz, 3H).

Example 18.2

Synthesis of (2R,3S)-3-((5-(benzyloxymethyl)-4-methoxy-5H-pyrrolo[3,2-d]pyrimidin-7-yl)methylamino)butane-1,2,4-triol To a stirred solution of the product from Example 18.1 (0.114 g, 0.23 mmol) in diethyl ether (10 ml) was added methanol (0.10 ml, 2.34 mmol) and then lithium borohydride (0.59 ml, 1.17 mmol, 2.0M in THF). After 30 mins the reaction mixture was diluted with methanol and evaporated on to silica gel. The material was chromatographed (conc. ammonia-methanol-DCM, 0.5:5:95 then 0.5:15:85) giving a colourless gum (0.056 g, 59%). $^1$H NMR (CD$_3$OD) δ 8.43 (s, 1H), 7.69 (s, 1H), 7.28-7.15 (m, 5H), 5.77 (s, 2H), 4.52 (s, 2H), 4.12 (ABq, 2H), 4.11 (s, 3H), 3.80 (dd, J=11.7, 5.3 Hz, 1H), 3.80-3.60 (m, 3H), 3.59 (dd, J=11.0, 4.9 Hz, 1H), 2.90 (q, J=4.9 Hz, 1H). $^{13}$C NMR (CD$_3$OD) δ 158.4, 151.4, 151.0, 139.1, 135.0, 129.7, 129.2, 129.1, 117.5, 115.3, 79.0, 72.5, 72.0, 65.6, 62.0, 61.6, 54.8, 42.1.

Example 18.3

Synthesis of 7-(((2S,3R)-1,3,4-trihydroxybutan-2-ylamino)methyl)-3H-pyrrolo[3,2-d]pyrimidin-4(5H)-one To a stirred solution of the product from Example 18.2 (0.056 g, 0.14 mmol) in DCM (7 ml) at −78° C. was added boron tribromide (1.39 ml, 1.39 mmol, 1.0M in DCM). After 15 mins the reaction mixture was warmed to ambient temperature and coevaporated with methanol (3×). The residue was stirred in methanol (7N ammonia solution) for 10 mins and evaporated on to silica gel. The material was chromatographed on silica gel (chloroform-methanol-conc. ammonia, 10:9:1) giving a white solid (17 mg, 46%). $^1$H NMR (D$_2$O) δ 8.03 (s, 1H), 7.59 (s, 1H), 4.41 (ABq, 2H), 3.88 (dd, J=13.2, 4.2 Hz, 1H), 3.80 (m, 1H), 3.72 (dd, J=13.2, 5.3 Hz, 1H), 3.60 (dd, J=12.5, 3.4 Hz, 2H), 3.47 (dd, J=12.5, 4.5 Hz, 1H), 3.26 (m, 1H). +ESMS found 269.1262 (M+H)$^+$ C$_{11}$H$_{17}$N$_4$O$_4$ requires 269.1250.

Example 19

Synthesis of 7-(((2S,3R)-2,3-dihydroxy-4-(methylthio)butylamino)methyl)-3H-pyrrolo[3,2-d]pyrimidin-4(5H)-one

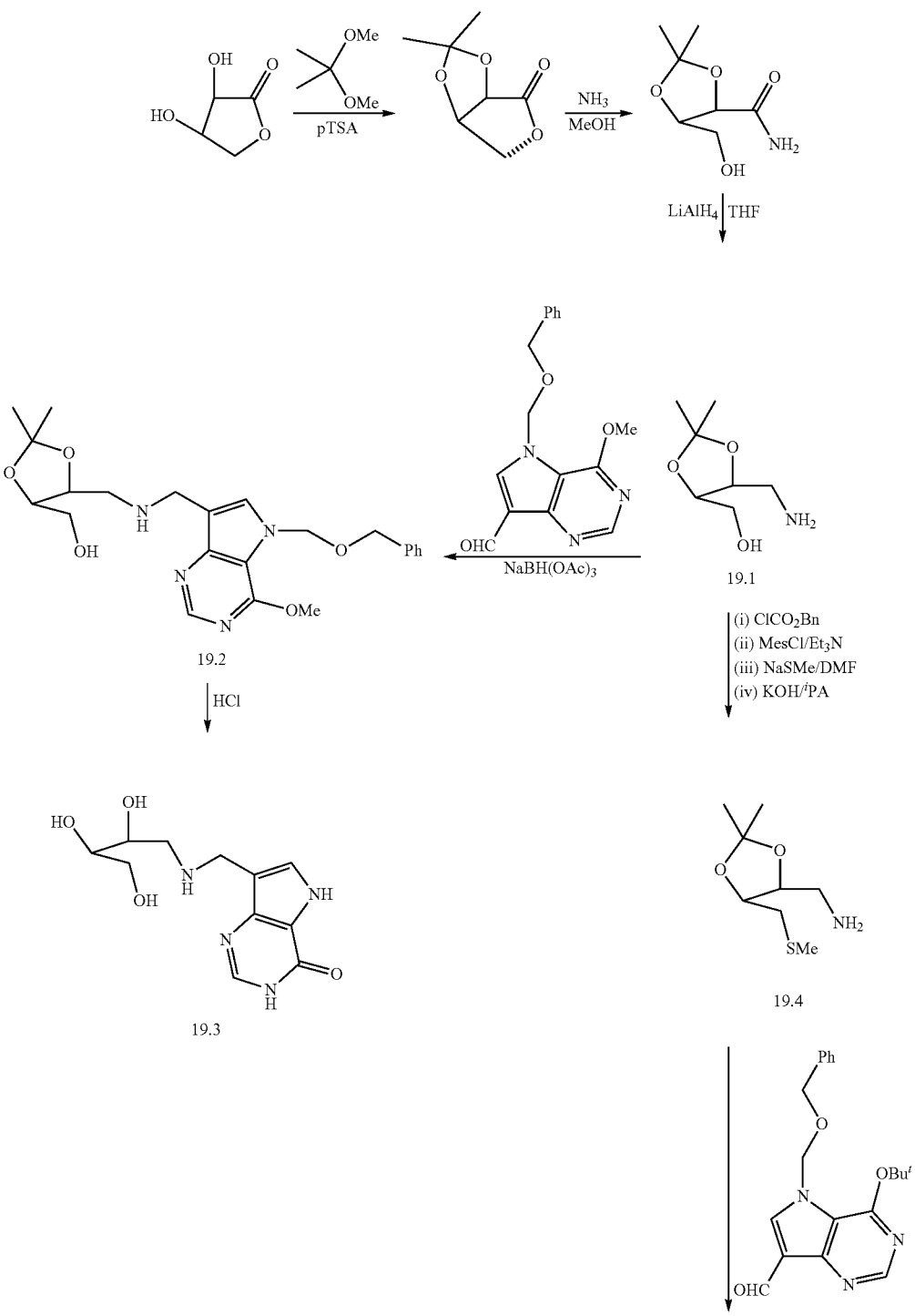

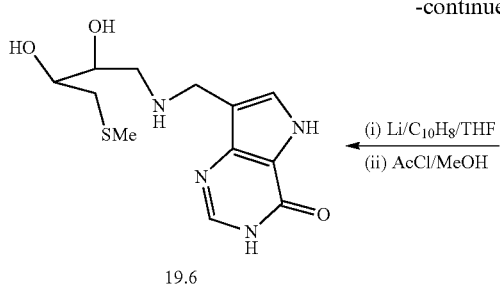

19.6

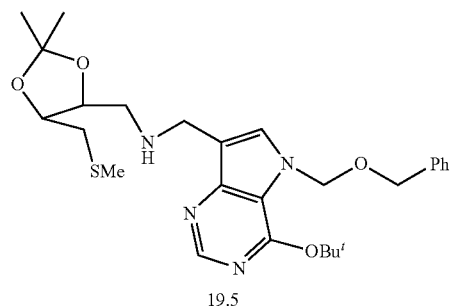

19.5

(i) Li/C$_{10}$H$_8$/THF
(ii) AcCl/MeOH

Example 19

Synthesis of (2S,3R)—O-isopropylidene-4-hydroxybutylamine

A solution of 2,3-O-isopropylidene-D-erythronamide (D. L. Mitchell Canad. J. Chem., 1963, 41,214) (2.80 g, 16.0 mmol) in anhydrous THF (ca 45 ml) was added dropwise over about 30 minutes to a stirred suspension of lithium aluminium hydride (2.43 g, 64.0 mmol) in THF (40 ml) maintained at ambient temperature. The mixture was then refluxed overnight before being cooled and worked up in the Fieser manner. The inorganic materials were removed by filtration and the filtrate concentrated to give (2S,3R)—O-isopropylidene-4-hydroxybutylamine (2.17 g, 84%) as a mobile syrup which was considered to be pure enough for subsequent reaction. $^1$H NMR (CDCl$_3$) δ 4.31 (td, J=6.7, 4.2 Hz, 1H), 4.23 (td, J=6.6, 3.9 Hz, 1H), 3.71 (d of ABq, lower field branch J=12.0, 7.0 Hz, higher field branch J=12.0, 4.2 Hz, 2H), 3.01 (d of ABq, lower field branch J=12.6, 7.1 Hz, higher field branch J=12.6, 4.9 Hz, 2H), 1.45 (s, 3H), 1.36 (s, 3H). $^{13}$C NMR (CDCl$_3$) δ 108.3, 77.6, 77.5, 60.8, 41.2, 27.8, 25.3.

Example 19.2

Synthesis of N-[5-(Benzylyoxymethyl)-4-methoxy-5H-pyrrolo[3,2-d]pyrimidin-7-yl]methylamino(2S,3R)-2,3-O-isopropylidene-2,3,4-butanetriol To a mixture of 5-(benzyloxymethyl)-4-methoxy-5H-pyrrolo[3,2-d]pyrimidine-7-carbaldehyde (0.39 g, 1.30 mmol), (2S,3R)-2,3-O-isopropylidene-1-amino-2,3,4-butanetriol (0.21 g, 1.30 mmol) in 1,2-dichloroethane (8 ml) containing anhydrous magnesium sulphate (0.5 g) was added, in a single portion, sodium triacetoxyborohydride (0.36 g, 1.70 mmol) and the whole stirred overnight at ambient temperature. The mixture was diluted with DCM and washed with saturated sodium bicarbonate solution before being dried and concentrated to dryness. The mixture was fractionated by flash chromatography over silica (without preabsorption) eluting with 2-to-5% MeOH/EtOAc to give the title compound (0.23 g, 39.9%) as an immobile syrup. $^1$H 8.53 (s, 1H), 7.42 (s, 1H), 7.40-7.18 (m, 5H), 5.69 (s, 2H), 4.49 (s, 2H), 4.34 (m, 2H), 4.13 (s, 3H), 3.99 (s, 2H), 3.95 (brs, 1H), 3.73 (d of ABq, J=12.0, 4.7 Hz, lower field branch of ABq and J=12.0, 3.7 Hz, higher field branch of ABq, 2H), 2.97 (d of ABq, J=12.2, 7.6 Hz, lower field branch of ABq and J=12.2, 3.1 Hz, higher field branch of ABq), 1.41 (s, 3H), 1.34 (s, 3H). $^{13}$C NMR (CDCl$_3$) δ 156.7, 150.5, 150.3, 137.3, 131.5, 128.81, 128.3, 128.0, 116.3, 115.1, 108.3, 78.0, 77.5, 76.2, 70.6, 60.8, 53.9, 48.4, 43.5, 27.8, 25.3. HR-ESMS MH+ 443.2327 C$_{23}$H$_{31}$N$_4$O$_5$ requires MH+ 443.2294 Δ 0.9 ppm (MNa+ 465.2111 observed also).

Example 19.3

Synthesis of 7-(((2S,3R)-2,3,4-trihydroxybutylamino)methyl)-3H-pyrrolo[3,2-d]pyrimidin-4(5H)-one Concentrated hydrochloric acid (10 ml) was added to N-[5-(benzylyoxymethyl)-4-methoxy-5H-pyrrolo[3,2-d]pyrimidin-7-yl]methylamino-(2S,3R)-2,3-O-isopropylidene-2,3,4-butanetriol (0.48 g, 1.08 mmol) and the solution refluxed for two hours before being cooled, concentrated and then redissolved in methanol (10 ml) and water (2 ml). The solution was neutralised to pH 7 with A-21 resin and then recovered by filtration. The crude product was preabsorbed onto silica and fractionated over silica eluting with DCM/MeOH/0.88 NH3 (5:4:1). The title compound was recovered as a white solid by slow precipitation (overnight) from the eluting solvent in selected eluate fractions. $^1$H NMR (D2O/DCl) δ 8.82 (s, 1H), 7.66 (s, 1H), 3.73 (7-line multiplet, two overlapping 4-line multiplets, J=3 Hz 1H), 3.51-3.33 (m, 3H), 3.18 (dd, J=12.9, 2:9 Hz, 1H), 2.96 (dd, J=12.9, 9.6 Hz, 1H). $^{13}$C NMR (D2O/DCl) δ 152.9, 145.5, 133.2, 132.3, 118.6, 103.2, 73.3, 68.0, 62.5, 49.4, 40.9. HR-ESMS MH+ 269.1242 C$_{11}$H$_{17}$N$_4$O$_4$ requires MH+ 269.1250 Δ 3 ppm. C$_{11}$H$_{16}$N$_4$O$_4$ requires C, 49.25; H, 6.01, N 20.89%. Found C, 48.79; H, 6.25; N, 20.74.

Example 19.4

Synthesis of (2S,3R)-2,3-O-isopropylidene-1-amino-4-methylthiobutane-2,3-diol To a vigorously stirred solution of (2S,3R)—O-isopropylidene-4-hydroxybutylamine (1.2 g, 7.44 mmol) in toluene (10 ml) was added water (10 ml), potassium carbonate (1.55 g, 11.2 mmol) and then, in a single slug, benzyl chloroformate (2.54 g, 50% solution in toluene, 7.44 mmol). Stirring was continued for 90 min after which time the mixture was diluted with DCM and washed with saturated sodium bicarbonate and brine before being dried and concentrated to a syrup, 1.97 g (90%). This CBz-protected amine was considered to be pure enough for subsequent reaction but could be purified by chromatography over silica using 40% EtOAc/hexane as eluant. $^1$H NMR (CDCl$_3$) δ 7.37 (brs, 5H), 5.12 (s, 2H), 4.24 (m, 2H), 3.71 (m, 2H), 3.51 (m, 1H), 3.36 (m, 1H), 1.46 (s, 3H), 1.36 (s, 3H). $^{13}$C NMR (CDCl$_3$) δ 156.9, 136.8, 129.4, 128.8, 128.5, 109.0, 77.3, 76.2, 67.3, 61.1, 41.3, 28.2, 25.6.

A sample of the N-CBz derivative (4.44 g, 15.1 mmol) was dissolved in dry DCM (40 ml) containing triethylamine (1.5 equiv, 3.17 ml, 22.6 mmol) and the solution cooled in an ice-bath under a blanket of argon. Methanesulphonyl chloride (1.2 equiv, 1.4 ml, 18.1 mmol) was added dropwise over several minutes, at which point the cooling bath was removed and the mixture stirred for 30 min at ambient temperature. The solution was diluted with DCM, washed with saturated sodium bicarbonate solution and then dried and concentrated to give the N-CBz, O-mesylate as a colourless, mobile syrup (5.83 g) which was considered to be pure enough for subsequent reaction. $^1$H NMR (CDCl$_3$) δ 7.37 (s, 5H), 5.14 (s, 2H), 4.43-4.15 (m, 3H), 3.55 (m, 1H), 3.15 (m, 1H), 3.03 (s, 3H), 1.46 (s, 3H), 1.35 (s, 3H).

The N-CBz, O-mesylate ester (5.83 g) was dissolved in anhydrous DMF (60 ml) and immersed in a water bath (so as to dissipate heat) while sodium thiomethoxide (2 equiv, 2.19 g, 31.3 mmol based upon the mesylate precursor) was added in three (or so) portions and, thereafter, was allowed to stir at ambient temperature over a weekend. The mixture was diluted with ether and the resulting organic phase was washed five times with water before being dried and concentrated to a mobile syrup (4.56 g). The two-component product mixture was fractionated by chromatography over silica, employing a gradient elution of 10-to-40% EtOAc/hexane, to give the N-CBz, 4-thiomethyl derivative (1.02 g, 21%). $^1$H NMR (CDCl$_3$) δ 7.38 (s, 5H), 5.18 (s, 3H), 4.34 (q, J=6.0 Hz, 1H), 4.20 (m, 1H), 3.54 (m, 1H), 3.15 (m, 1H), 2.66 (m, 2H), 2.18 (s, 3H), 1.44 (s, 3H), 1.34 (s, 3H). HR-ESMS MNa+ 348.1241 C$_{16}$H$_{23}$NO$_4$SNa requires MNa+ 348.1245 Δ 1.1 ppm. The major product recovered from this reaction was consistently found to be the isopropylidene derivative of cis 3,4-dihydroxypyrrolidine.

The crude thiomethylated N-CBz protected amine (1.03 g, 3.17 mmol) was dissolved in isopropanol (25 ml) and to this was added aqueous potassium hydroxide (2M, 10 ml, 20.0 mmol). The two-phase mixture was refluxed for 24 hours after which time the solution was cooled and concentrated to the point where the bulk of the isopropanol had been removed. The product was extracted into ether and the ether phase dried and concentrated to a mobile, light yellow syrup (0.73 g). This crude product was purified by flash chromatography after preabsorption on silica eluting, firstly, with DCM (to remove the benzyl alcohol) and then with 2-to-6% [7M NH$_3$/MeOH] in DCM, visualising with ninhydrin. In this manner, (2S,3R) 2,3-O-isopropylidene-2,3-dihydroxy-4-methylthiobutylamine (0.39 g, 64.3%) was obtained as a light yellow syrup. $^1$H NMR (CDCl$_3$) δ 4.32 (q, J=6.5 Hz, 1H), 4.13 (q J=6.3 Hz 1H), 2.82 (d, J=6.4 Hz, 2H), 2.64 (d, J=6.1 Hz, 2H), 2.18 (s, 3H), 1.47 (s, 3H), 1.37 (s, 3H). $^{13}$C NMR (CDCl$_3$) δ 108.7, 80.0, 77.4, 42.2, 34.3, 28.7, 26.0, 16.7. HR-ESMS MH+ 192.1057 C$_8$H$_{17}$NO$_2$S requires MH+ 192.1058 Δ 0.5 ppm.

Example 19.5

Synthesis of N-[5-(Benzylyoxymethyl)-4-t-butoxy-5H-pyrrolo[3,2-d]pyrimidin-7-yl]methylamino(2S,3R)-2,3-O-isopropylidene-4-methylthio-2,3-butanediol To a mixture of 5-(benzyloxymethyl)-4-t-butoxy-5H-pyrrolo[3,2-d]pyrimidine-7-carbaldehyde (0.85 g, 2.51 mmol), (2S,3R)-2,3-O-isopropylidene-1-amino-4-methylthio-2,3-butanediol (0.37 g, 1.93 mmol) in 1,2-dichloroethane (25 ml) containing anhydrous magnesium sulphate (0.6 g) was added, in a single portion, sodium triacetoxyborohydride (0.53 g, 2.51 mmol) and the whole stirred overnight at ambient temperature. The mixture was diluted with DCM and washed with saturated sodium bicarbonate solution before being dried and concentrated (1.32 g). The mixture was fractionated by flash chromatography over silica (with preabsorption) eluting with DCM/ethyl acetate/7M NH$_3$-MeOH (49:49:2) to give the title compound (0.60 g, 60.3%) as an immobile syrup. $^1$H NMR (CDCl$_3$) δ 8.47 (s, 1H), 7.34 (s, 1H), 7.33-7.18 (m, 5H), 5.76 (s, 2H), 4.49 (s, 2H), 4.31 (sextet, J=6 Hz, 2H), 4.04 (s, 2H), 2.82 (d, J=5.9 Hz, 2H), 2.62 (d, J=5.6 Hz, 2H), 2.15 (s, 3H), 1.70 (s, 9H), 1.41 (s, 3H), 1.34 (s, 3H). $^{13}$C NMR (CDCl$_3$) δ 156.2, 150.4, 150.0, 137.6, 130.9, 128.8, 128.2, 127.8, 116.5, 108.8, 83.2, 77.5, 77.4, 77.1, 70.3, 49.2, 43.9, 34.6, 29.1, 28.6, 26.0, 16.7. HR-ESMS MH+ 515.2697 C$_{27}$H$_{33}$N$_4$O$_4$S requires MH+ 515.2692 Δ 1.0 ppm.

Example 19.6

Synthesis of 7-(((2S,3R)-2,3-dihydroxy-4-(methylthio)butylamino)methyl)-3H-pyrrolo[3,2-d]pyrimidin-4(5H)-one To a solution of lithium naphthalenide [prepared from the reaction of lithium (0.081 g, 11.7 mmol) with naphthalene (1.94 g, 15.2 mmol) in solution in anhydrous THF (25 ml)] maintained under argon at −78° was added, dropwise over a period of 2 minutes, a solution of N-[5-(benzylyoxymethyl)-4-t-butoxy-5H-pyrrolo[3,2-d]pyrimidin-7-yl]methylamino (2S,3R)-2,3-O-isopropylidene-4-methylthio-2,3-butanediol (0.60 g, 1.17 mmol) in anhydrous THF (5 ml). The solution was stirred at −78° for 60 minutes after which time tlc [DCM 7M NH$_3$-MeOH, 9:1) revealed the complete consumption of starting material. The mixture was quenched by the addition of 2-3 ml water and then allowed to warm to ambient temperature before being concentrated almost to dryness. The mixture was then stirred with methanolic ammonia (7M, 20 ml) for 15 minutes and then reconcentrated. The crude product was redissolved in DCM and preabsorbed onto silica and then fractionated by elution with the DCM 7M NH$_3$-MeOH, 9:1 cocktail to give the intermediate N-[4-hydroxy-5H-pyrrolo[3,2-d]pyrimidin-7-yl]methylamino(2S,3R)-2,3-O-isopropylidene-4-methylthio-2,3-butanediol (0.18 g, 45.5%) as an immobile gum. $^1$H NMR (d4-MeOH) δ 7.92 (s, 1H), 7.43 (s, 1H), 4.32 (m, 2H), 3.96 (ABq, J=13.6 Hz, 2H), 2.75 (d, J=6.2 Hz, 2H), 2.62 (d, J=6.4 Hz, 2H), 2.17 (s, 3H), 1.35 (s, 6H). $^{13}$C NMR (d4-MeOH) δ 156.3, 145.3, 143.3, 128.8, 119.8, 116.74, 110.0, 78.7, 78.5, 49.1, 44.2, 35.0, 29.3, 26.7, 16.9. HR-ESMS MH+ 339.1503 C$_{15}$H$_{23}$N$_4$O$_3$S requires MH+ 339.1491 Δ 3.5 ppm; also see MNa+ 361.1325.

N-[4-Hydroxy-5H-pyrrolo[3,2-d]pyrimidin-7-yl]methylamino(2S,3R)-2,3-O-isopropylidene-4-methylthio-2,3-butanediol (0.18 g, 0.53 mmol) was suspended in MeOH (15 ml) and to this was added a solution of acetyl chloride (0.38 ml, 5.3 mmol) in MeOH (10 ml) following which solution was achieved within a few minutes. Stirring was continued for 5 hours and then the solution was neutralised with A-21 resin, filtered and preabsorbed directly onto silica. The crude product was fractionated by flash chromatography using a stepped gradient elution which commenced with DCM/MeOH (80:20+1 7M NH$_3$-MeOH) and ended with (60:40+1 7M NH$_3$-MeOH) and recovered by slow precipitation from the elution solvent in a selected cluster of receivers. In this manner, the title compound was isolated as a colourless solid (0.023 g, 13.5%). $^1$H NMR (d$_4$-MeOH+DCl) δ 9.13 (s, 1H), 7.97 (s, 1H), 4.58 (s, 2H), 3.96 (m, 1H), 3.73 (m, 1H), 3.46 (dd, J=12.6, 3.3 Hz, 1H), 3.05 (dd J=12.6, 9.0 Hz, 1H), 2.85 (dd, J=13.9, 3.7 Hz, 1H), 2.57 (dd, J 13.9, 5.2 Hz, 1H), 2.15 (s, 3H). $^{13}$C NMR (d$_4$-MeOH+DCl) δ 153.0, 146.9, 134.1, 132.9, 120.1, 105.1, 74.2, 70.6, 51.0, 42.3, 39.2, 16.7. HR-ESMS MNa+ 321.1009 C$_{12}$H$_{18}$N$_4$O$_3$SNa requires 321.0997 Δ 3.7 ppm.

Example 20
Synthesis of 7-(((2RS,3RS)-2,3,4-trihydroxybutylamino)methyl)-3H-pyrrolo[3,2-d]pyrimidin-4(5H)-one and 7-(((2RS,3RS)-2,3-dihydroxy-4-(methylthio)butylamino)methyl)-3H-pyrrolo[3,2-d]pyrimidin-4(5H)-one
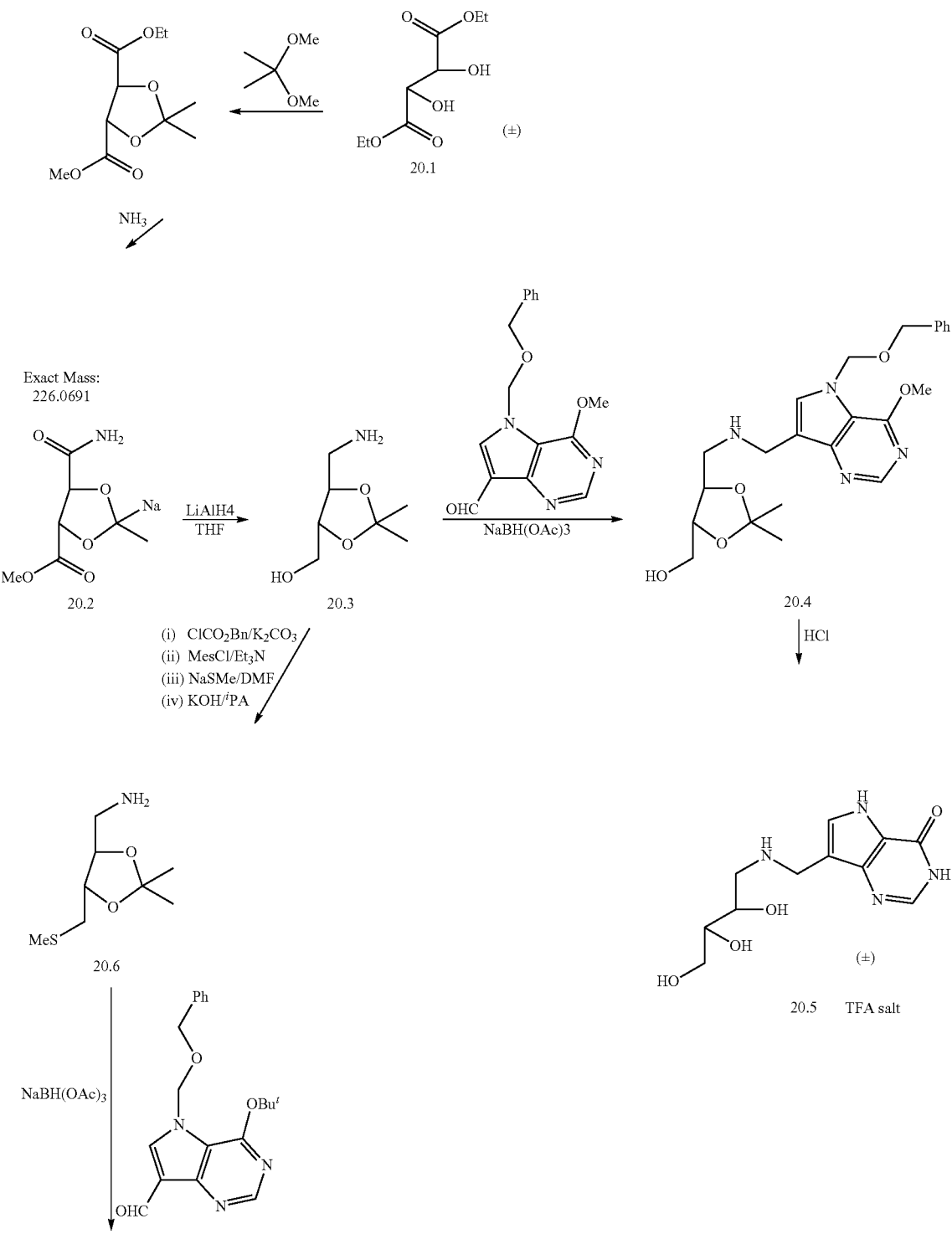

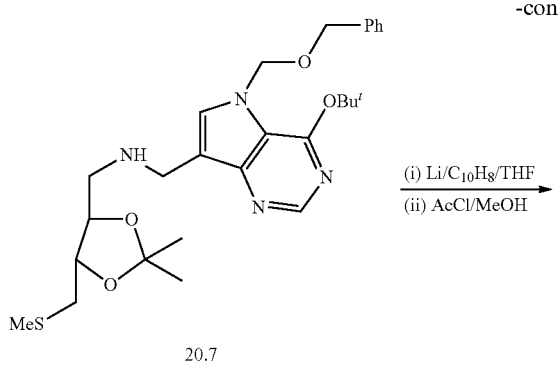

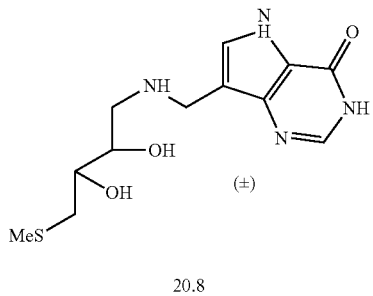

Example 20.1

Synthesis of (2R/S,3R/S)-Ethyl, methyl 2,3-O-isopropylidenetartrate

To a solution containing (+) and (−) diethyl tartrate (1.0 g each, 9.7 mmol) and dimethoxypropane (2.0 g, 19.4 mmol) in benzene (30 ml) was added p-toluenesulphonic acid (0.1 g) and the mixture refluxed for 3 hr. The solution was cooled and diluted with EtOAc (200 ml) and washed with a saturated brine/sodium bicarbonate cocktail before being dried and concentrated to a homogeneous, mobile liquid (1.78 g, 79%). A sample was distilled by Kugelrohr (120-140°/18 mm) to give the mixed ethyl methyl ester as a colourless liquid. In subsequent larger-scale preparations, the crude product was considered to be pure enough for further reaction. $^1$H NMR (CDCl$_3$) δ 4.79-4.74 (m, 2H), 4.26 (q, J=7.1 Hz, 2H), 3.81 (s, 3H) 1.48 (s, 6H), 1.32 (t, J=7.1 Hz, 3H). $^{13}$C NMR (CDCl$_3$) δ 170.4, 170.0, 114.1, 77.6, 77.4, 62.3, 53.1, 26.7, 14.4.

Example 20.2

Synthesis of (2R/S,3R/S) Methyl 2,3-O-isopropylidenetartramide

The 2,3-O-isopropylidenetartrate esters (1.78 g, 7.66 mmol) were dissolved in MeOH (10 ml) and stirred at ambient temperature as methanolic ammonia (7M, 1.09 ml, 7.66 mmol) was added. The solution was stirred for two days at ambient temperature before being directly preabsorbed onto a small quantity of silica and the crude product fractionated by gradient elution with 50% ethyl acetate/hexane to give the tartramide (0.67 g, 43%) as an oil that readily solidified. $^1$H NMR (CDCl$_3$) δ 6.52 (brs, 2H), 6.34 (brs, 2H), 4.73 (s, 2H), 3.84 (s, 3H), 1.52 (s, 3H), 1.48 (s, 3H). $^{13}$C NMR (CDCl$_3$) δ 173.0, 170.9, 113.9, 77.8, 77.4, 53.2, 27.0, 26.5. HRMS C$_8$H$_{13}$NO$_5{}^{23}$NaS (M$^{23}$Na)$^+$ requires 226.0691. found 226.0696.

Example 20.3

Synthesis of (2R/S,3R/S) 2,3-O-Isopropylidene-1-amino-2,3,4-butanetriol

The tartramide ester (0.83 g, 4.08 mmol) was dissolved in anhydrous THF (10 ml) and added dropwise to a suspension of LAH in THF (60 ml) at ambient temperature. The mixture was then refluxed for 4 hrs before being cooled in an ice-bath and quenched carefully using the three-step Feiser method. The inorganic materials were removed by filtration, rinsed thoroughly with ether and the filtrate was dried and concentrated to a homogeneous, colourless syrup (0.6 g, 91%) that was used in subsequent reaction. $^1$H NMR (CDCl$_3$) δ 3.68 (m, 2H), 3.47 (dd, J=10.8, 4.2 Hz and upper field br 10.8, 5.2 Hz, 2H), 3.13 (brs, 2H), 2.70 (d of ABq, lower field br J 12.8, 4.8 Hz and upper field br 12.8, 5.2 Hz, 2H), 1.30 (s, 3H), 1.29 (s, 3H). $^{13}$C NMR (CDCl$_3$) δ 107.9, 70.8, 80.2, 62.3, 43.9, 27.5, 27.4. LR-ESMS MH+ 162.1112.

Example 20.4

Synthesis of N-[5-(Benzylyoxymethyl)-4-methoxy-5H-pyrrolo[3,2-d]pyrimidin-7-yl]methylamino(2R/S,3R/S)-2,3-O-isopropylidene-2,3,4-butanetriol To a mixture of 5-(benzyloxymethyl)-4-methoxy-5H-pyrrolo[3,2-d]pyrimidine-7-carbaldehyde (0.59 g, 1.98 mmol), (2RS,3RS)-2,3 isopropylidene-1-amino-2,3,4-butanetriol (0.41 g, 2.54 mmol) in 1,2-dichloroethane (10 ml) containing anhydrous magnesium sulphate (1.0 g) was added, in a single portion, sodium triacetoxyborohydride (0.70 g, 3.31 mmol) and the whole stirred overnight at ambient temp. The mixture was diluted with DCM and washed with saturated sodium bicarbonate solution before being dried and concentrated to an immobile syrup (0.92 g). The N-[5-(benzylyoxymethyl)-4-methoxy-5H-pyrrolo[3,2-d]pyrimidin-7-yl]methyl-1-amino(2R/S,3R/S)-2,3-O-isopropylidene-2,3,4-butanetriol was recovered by flash chromatography (without preabsorption) over silica eluting with 2-to-5% MeOH/EtOAc as an immobile, colourless syrup (0.65 g, 58%). $^1$H NMR (CDCl$_3$) δ 8.56 (s, 1H), 7.38 (s, 1H), 7.37-7.21 (m, 5H), 5.74 (s, 2H), 4.53 (s, 2H), 4.14 (s, 3H), 4.05 (s, 2H), 3.84 (m, 3H), 3.62 (m, 1H, higher field br of CH$_2$ ABq; 3.15 dd J 12.1, 3.0 Hz, lower field br of CH$_2$ ABq, 1H), 2.74 m, higher field br of CH$_2$ ABq, 1H), 1.41 (s, 3H), 1.30 (s, 3H). $^{13}$C NMR (CDCl$_3$) δ 156.7, 150.5, 150.3, 137.3, 131.5, 128.8, 128.4, 128.1, 116.3, 115.2, 108.9, 82.2, 80.1, 77.4, 70.7, 62.8, 34.0, 50.6, 43.7, 27.3, 27.1. LR-ESMS MNa$^+$ 465.2144, MH$^+$ 443.2153 (C$_{23}$H$_{31}$N$_4$O$_5$).

Example 20.5

Synthesis of 7-(((2RS,3RS)-2,3,4-trihydroxybutylamino)methyl)-3H-pyrrolo[3,2-d]pyrimidin-4(5H)-one A solution of N-[5-(benzyloxymethyl)-4-methoxy-5H-pyrrolo[3,2-d]pyrimidin-7-yl]methyl-1-amino(2R/S,3R/S)-2,3-isopropylidene-2,3,4-butanetriol (0.48 g, 1.085 mmol) in concentrated hydrochloric acid (10 ml) was refluxed for 3 hours. The solution was then cooled and concentrated, redissolved in methanol (10 ml) containing water (3 ml) and neutralised with Amberlyst A-21 resin. The resin was removed by filtration and the filtrate concentrated to an immobile syrup (0.35 g), a portion of which was purified by RP-HPLC [1% MeOH, Phenomenex Synergi 4µ POLAR RP 80A, 250×30 mm] to give 7-(((2RS,3RS)-2,3,4-trihydroxybutylamino)methyl)-3H-pyrrolo[3,2-d]pyrimidin-4(5H)-one (triflate salt) as a colourless foam. $^1$H NMR (CD$_3$OD) δ 8.08 (s, 1H), 7.55 (s, 1H), 4.32 (s, 2H), 3.93 (m, 1H), 3.59-3.44 (m, 1H), 3.53 (s, 2H), 3.14 (d, J=5.9 Hz, 2H). $^{13}$C NMR (CD$_3$OD) δ 162.2, 161.7, 161.2, 160.7, 155.6, 144.8, 143.3, 131.6, 120.1, 107.7, 74.3, 71.1, 63.9, 51.0, 42.3. HR-ESMS MH+ 269.1241 C$_{11}$H$_{17}$N$_4$O$_4$ requires 269.1250.

Example 20.6

Synthesis of (2R/S,3R/S)-2,3-O-isopropylidene-1-amino-4-methylthiobutane-2,3-diol To a vigorously stirred solution of (2R/S,3R/S)-2,3-O-isopropylidene-1-amino-2,3,4-butanetriol (6.92 g, 43.0 mmol) in toluene (70 ml) was added water (70 ml), potassium carbonate (8.91 g, 1.5 equiv, 64.5 mmol) and then benzyl chloroformate (50% w/w in toluene, 14.7 g, 43.0 mmol). After stirring for three hours at ambient temperature, the mixture was diluted with DCM and then washed with water and the organic phase separated, dried and then concentrated to a mobile syrup (12.1 g, quantitative), the $^1$H NMR spectrum for which indicated that the compound—N-carbobenzyloxy (2R/S,3R/S)2,3-O-isopropylidene-1-amino-2,3,4-butanetriol—was pure enough for subsequent reaction. A sample of this compound (4.29 g, 14.5 mmol) was dissolved in dry DCM containing triethylamine (1.5 equiv, 3.06 ml, 21.8 mmol), and then cooled in an ice-bath under a blanket of argon. Methanesulphonyl chloride (1.2 equiv, 1.36 ml, 17.5 mmol) was added dropwise over several minutes at which point the cooling bath was removed and the mixture stirred for 30 min at ambient temperature. The solution was diluted with DCM, washed with saturated sodium bicarbonate solution and then dried and concentrated to a colourless, mobile syrup (5.09 g) which was considered to be pure enough for subsequent reaction. $^1$H NMR (CDCl$_3$) δ 7.37 (s, 5H), 5.14 (brs, 3H), 4.34 (brs, 2H), 3.99 (m, 2H), 3.46 (m, 2H), 3.07 (s, 3H), 1.42 (s, 6H). $^{13}$C NMR (CDCl$_3$) δ 157.0, 136.7, 129.0, 128.6, 128.5, 110.4, 76.9, 76.0, 68.5, 67.4, 46.4, 38.1, 27.5, 27.2. The mesylate ester (5.09 g) was dissolved in anhydrous DMF (50 ml) and immersed in a water bath (so as to dissipate heat) while sodium thiomethoxide (2 equiv, 2.04 g, 29.0 mmol based upon the mesylate precursor) was added in three (or so) portions. The temperature rose to no greater than 22° C. and, thereafter, was allowed to stir at ambient temperature over a weekend. The mixture was diluted with ether and the resulting organic phase was washed five times with water before being dried and concentrated to a mobile syrup (2.79 g, 59%). $^1$H NMR (CDCl$_3$) δ 7.38 (s, 5H), 5.18 (s, 3H), 3.93 (brs, 2H), 3.57 (m, lower field branch of an ABq, 1H), 3.41 m, higher field branch of ABq, 1H), 2.74 (brs, 2H), 2.17 (s, 3H), 1.40 (s, 3H), 1.39 (s, 3H). The crude thiomethylated N-CBz protected amine (4.07 g, 12.52 mmol) was dissolved in isopropanol (70 ml) and to this was added aqueous potassium hydroxide (2M, 31.2 ml, 62.4 mmol). The two-phase mixture was refluxed for 4-5 hours after which time the solution was cooled and concentrated to the point where the bulk of the isopropanol had been removed. The product was extracted into ether and the ether phase dried and concentrated to a mobile, light yellow syrup (3.26 g). This crude product was purified by flash chromatography after preabsorption on silica eluting, firstly, with DCM (to remove the benzyl alcohol) and then with 2-to-6% [7M NH3/MeOH] in DCM, visualising with ninhydrin. (2R/S,3R/S) 2,3-O-Isopropylidene-2,3-dihydroxy-4-methylthiobutylamine (1.84 g, 77%) was obtained as a light yellow syrup. $^1$H NMR (CDCl$_3$) δ 3.95 (m, 1H), 3.82 (2×4 line m, J 7.7, 3.5 Hz and 7.6, 3.5 Hz, 1H), 2.99 (dd, J=13.3, 3.3 Hz, 1H), 2.83 (dd, J=13.3, 6.3 Hz, 1H), 2.72 (dxABq, J=13.6, 5.8 Hz, 2H), 2.19 (s, 3H), 1.42 (s, 3H), 1.42 (s, 3H). $^{13}$C NMR (CDCl$_3$) 109.4, 82.8, 77.8, 44.6, 37.4, 27.7, 27.6, 16.9. ESMS MH+ 192.1057 C$_8$H$_{18}$NO$_2$S requires MH+ 192.1057.

Example 20.7

Synthesis of N-[5-(Benzylyoxymethyl)-4-t-butoxy-5H-pyrrolo[3,2-d]pyrimidin-7-yl]methylamino(2R/S, 3R/S)-2,3-O-isopropylidene-4-methylthio-2,3-butanediol To a mixture of 5-(benzyloxymethyl)-4-t-butoxy-5H-pyrrolo[3,2-d]pyrimidine-7-carbaldehyde (0.95 g, 2.79 mmol), (2R/S,3R/S)-2,3-O-isopropylidene-1-amino-4-methylthio-2,3-butanediol (0.41 g, 2.14 mmol) in 1,2-dichloroethane (25 ml) containing anhydrous magnesium sulphate (0.6 g) was added, in a single portion, sodium triacetoxyborohydride (0.59 g, 3.31 mmol) and the whole stirred overnight at ambient temperature. The mixture was diluted with DCM and washed with saturated sodium bicarbonate solution before being dried and concentrated (1.51 g). The mixture was fractionated by flash chromatography over silica (with preabsorption) eluting with DCM/ethyl acetate/7M NH3-MeOH (10:10:0.15) to give the title compound (0.55 g, 49.9%) as an immobile syrup. $^1$H NMR (CDCl$_3$) δ 8.48 (s, 1H), 7.34 (s, 1H), 7.34-7.19 (m, 5H), 5.74 (s, 2H), 4.51 (s, 2H), 4.07 (s, 2H), 3.98 (brs, 1H), 2.93 (m, 1H), 2.73 (d, J=5.3 Hz, 1H), 2.14 (s, 3H), 1.72 (s, 9H), 1.43 (s, 6H). $^{13}$C NMR (CDCl$_3$) δ 155.8, 150.0, 149.6, 137.2, 130.5, 128.5, 127.9, 127.4, 117.0, 116.2, 109.1, 82.8, 80.2, 78.5, 77.0, 69.9, 51.5, 43.6, 37.0, 28.7, 27.4, 27.2, 16.6. HR-ESMS MH+ found 515.2675 C$_{27}$H$_{39}$N$_4$O$_4$S requires MH+ 515.2692.

Example 20.8

Synthesis of 7-(((2RS,3RS)-2,3-dihydroxy-4-(methylthio)butylamino)methyl)-3H-pyrrolo[3,2-d]pyrimidin-4(5H)-one To a solution of lithium naphthalenide [prepared from the reaction of lithium (0.081 g, 11.7 mmol) with naphthalene (1.94 g, 15.2 mmol) in solution in anhydrous THF (25 ml)] maintained under argon at −78° C. was added, dropwise over a period of 2 minutes, a solution of N-[5-(benzylyoxymethyl)-4-t-butoxy-5H-pyrrolo[3,2-d]pyrimidin-7-yl]methylamino(2R/S,3R/S)-2,3-O-isopropylidene-4-methylthio-2, 3-butanediol (0.55 g, 1.08 mmol) in anhydrous THF (5 ml). The solution was stirred at −78° C. for 60 minutes after which time tlc [DCM 7M NH$_3$-MeOH, 9:1) revealed the complete consumption of starting material. The mixture was quenched by the addition of 2-3 ml water and then allowed to warm to ambient temperature before being concentrated almost to dryness. The mixture was then stirred with methanolic ammonia (7M, 20 ml) for 15 minutes and then reconcentrated. The crude product was redissolved in DCM, preabsorbed onto silica and then fractionated by elution with the DCM 7M NH$_3$-MeOH, 9:1 cocktail to give the intermediate N-(4-hydroxy-5H-pyrrolo[3,2-d]pyrimidin-7-yl)methylamino(2R/S,3R/S)-2,3-O-isopropylidene-4-methylthio-2, 3-butanediol (0.13 g, 35.6%) as an immobile gum. $^1$H NMR (CDCl$_3$) δ 7.92 (s, 1H), 7.41 (s, 1H), 4.04-3.82 (m, 2H), 3.95 (s, 2H), 2.93 (dd, J=12.3, 3.3 Hz, 1H), 2.27 dd J=12.3, 7.5 Hz, 1H), 2.14 (s, 3H), 1.37 (s, 3H), 1.34 (s, 3H). $^{13}$C NMR (CDCl$_3$) δ 156.5, 145.6, 145.3, 129.0, 119.6, 116.5, 110.7, 81.5, 80.5, 52.5, 44.1, 38.0, 28.0, 27.9, 16.9. HR-ESMS MH+ 339.1487 C$_{15}$H$_{23}$N$_4$O$_3$S requires 339.1491.

N-[4-Hydroxy-5H-pyrrolo[3,2-d]pyrimidin-7-yl]methylamino(2R/S,3R/S)-2,3-O-isopropylidene-4-methylthio-2,3-butanediol (0.13 g, 0.38 mmol) was suspended in MeOH (5 ml) and to this was added a solution of acetyl chloride (0.27 ml, 3.8 mmol) in MeOH (5 ml) at which point solution was achieved within a few minutes. Stirring was continued for 5 hours and then the solution was neutralised with A-21 resin, filtered and preabsorbed directly onto silica. The crude product was fractionated by flash chromatography using a stepped gradient elution which commenced with DCM/MeOH (80:20+1 7M NH3-MeOH) and ended with (60:40+1 7M NH$_3$-MeOH) and recovered by slow precipitation from the elution solvent in a selected cluster of receivers. In this manner, the title compound was isolated as a colourless solid (0.028 g, 22%). $^1$H NMR (d$_4$-MeOH+DCl) δ 9.14 (s, 1H), 7.94 (s, 1H), 4.57 (s, 2H), 4.14 (m, 1H), 3.72 (td, J=6.9, 2.1 Hz, 1H), 3.32 (m, 1H), 2.74 (dd, J=13.9, 3.7 Hz, 1H), 2.63 (dd, J=13.9, 5.2 Hz, 1H), 2.14 (s, 3H). $^{13}$C NMR (d$_4$-MeOH+DCl) δ 153.0, 147.0, 133.9, 133.0, 120.0, 105.1, 72.7, 69.2, 51.7, 42.2, 38.2, 16.3. HR-ESMS MH+ 299.1180 C$_{12}$H$_{18}$N$_4$O$_3$S requires 299.1178.

Example 21

Synthesis of 7-(((2RS,3RS)-3,4-dihydroxy-2-(hydroxymethyl)butylamino)methyl)-3H-pyrrolo[3,2-d]pyrimidin-4(5H)-one hydrochloride Example 21.1

Synthesis of (±)-((4R/S,5P/S)-2-benzylisoxazolidine-4,5-diyl)dimethanol

A mixture of N-benzylhydroxylamine hydrochloride (13.59 g, 85.15 mmol) and sodium acetate (9.31 g, 114 mmol) were stirred together in ethanol (75 mL) at rt for 15 mins. Aqueous 37% formaldehyde solution (12.68 ml, 170 mmol) was added and stirring continued for 30 mins, then cis-2-butene-1,4-diol (4.67 ml, 56.8 mmol) added and the mixture heated under reflux for 16 h. The solvent was evaporated and the residue dissolved in CHCl$_3$ and washed with aq. sat. NaHCO$_3$, dried (MgSO$_4$) and the solvent evaporated to give a brown syrup suitable for use without further purification (12.5 g, 98%). An aliquot was purified by chromatography on silica gel (EtOAc then EtOAc-MeOH, 95:5) to give (±)-((4R/S, 5R/S)-2-benzylisoxazolidine-4,5-diyl)dimethanol as a colourless syrup. $^{13}$C NMR (CDCl$_3$, referenced to the centre line of CDCl$_3$ at 77.0 ppm) δ 136.5, 129.0, 128.4, 127.6, 78.5, 62.4, 61.3, 60.4, 56.8, 45.8.

Example 21.2

Synthesis of (±)-(2R/S, 3R/S)-3-((benzylamino)methyl)butane-1,2,4-triol

Zinc dust (11.13 g, 170 mmol) was added to a solution of the product from Example 21.1 (12.5 g, 56.1 mmol) in acetic acid (150 ml)—exotherm to ~67° C.—and the mixture stirred at rt for 1 h. The mixture was filtered, the solvent evaporated and the residue chromatographed on silica gel (CH$_2$Cl$_2$-7M NH$_3$ in MeOH, 9:1 then 8:2) to give (±)-(2R/S, 3R/S)-3-((benzylamino)methyl)butane-1,2,4-triol as a colourless syrup (5.8 g, 45%). $^1$H NMR (CDCl$_3$) δ 7.33-7.23 (m, 5H),

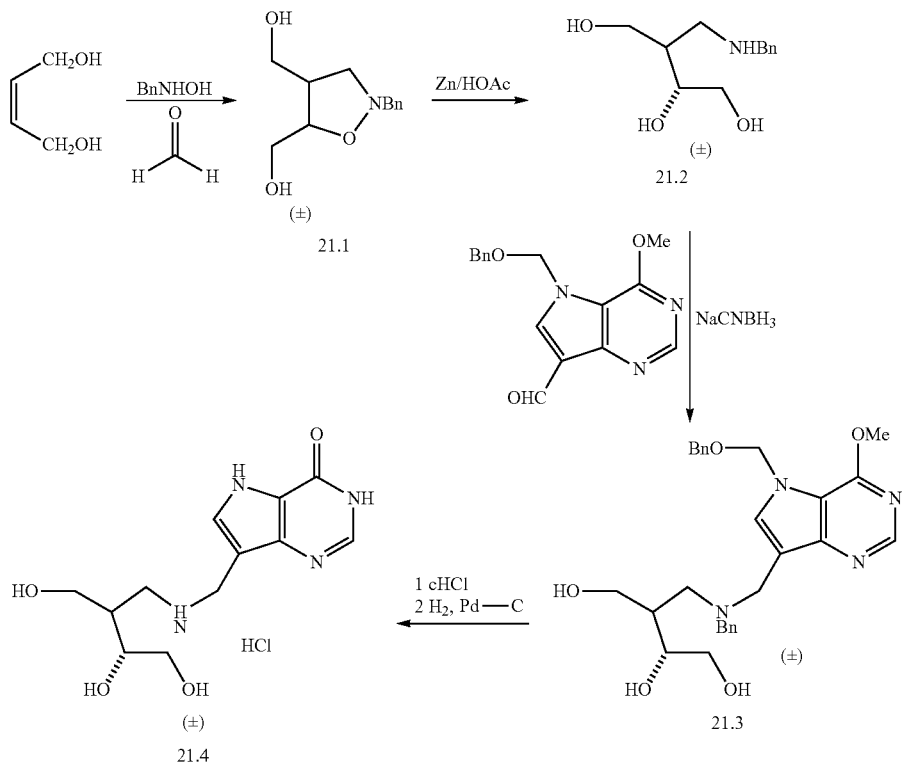

4.11 (br. s, 4H), 3.76-3.66 (m, 5H), 3.61-3.51 (m, 2H), 2.81-2.70 (m, 2H), 1.82 (sextet, J=5.5 Hz, 1H). $^{13}$C NMR (CDCl$_3$, referenced to the centre line of CDCl$_3$ at 77.0 ppm) δ 138.8, 128.5, 128.2, 127.3, 73.3, 64.5, 63.1, 54.0, 49.7, 43.3.

Example 21.3

Synthesis of (±)-(2R/S, 3R/S)-3-((benzyl((5-(benzyloxymethyl)-4-methoxy-5H-pyrrolo[3,2-d]pyrimidin-7-yl)methyl)amino)methyl)butane-1,2,4-triol Acetyl chloride (0.021 ml, 0.301 mmol), 5-(benzyloxymethyl)-4-methoxy-5H-pyrrolo[3,2-d]pyrimidine-7-carbaldehyde (0.179 g, 0.602 mmol, prepared as in G. B. Evans, R. H. Furneaux, A, Lewandowicz, V. L. Schramm and P. C. Tyler, *J. Med. Chem.*, 2003, 46, 3412), the product from Example 21.2 (0.136 g, 0.602 mmol) and sodium cyanoborohydride (0.057 g, 0.903 mmol) were successively added to MeOH (6 ml). The mixture was stirred at it for 64 h. The solvent was evaporated and the residue chromatographed on silica gel (CH$_2$Cl$_2$-7M NH$_3$ in MeOH, 96:4) to give (±)-(2R/S, 3R/S)-3-((benzyl ((5-(benzyloxymethyl)-4-methoxy-5H-pyrrolo[3,2-d] pyrimidin-7-yl)methyl)amino)methyl)butane-1,2,4-triol (0.159 g, 52%) as a colourless gum. $^1$H NMR (CD$_3$OD) δ 8.43 (s, 1H), 7.58 (s, 1H), 7.32-7.12 (m, 10H), 5.75 (s, 2H), 4.50 (s, 2H), 4.10 (s, 3H), 3.85 (s, 2H), 3.71 (dd, J=10.9, 4.8 Hz, 1H), 3.65-3.51 (m, 4H), 3.48-3.37 (m, 2H), 2.69-2.57 (m, 2H), 2.19 (m, 1H). $^{13}$C NMR (CD$_3$OD, referenced to the centre line of CD$_3$OD at 49.0 ppm) δ 157.9, 151.3, 150.9, 139.8, 138.7, 135.1, 130.4, 129.3, 128.7, 128.6, 128.2, 116.8, 114.2, 78.6, 74.1, 71.6, 65.4, 63.7, 59.9, 55.5, 54.3, 48.5, 42.1. +ESMS Found 507.2604 (M+H)$^+$ C$_{28}$H$_{35}$N$_4$O$_5$ requires 507.2607.

Example 21.4

Synthesis of 7-(((2RS,3RS)-3,4-dihydroxy-2-(hydroxymethyl)butylamino)methyl)-3H-pyrrolo[3,2-d] pyrimidin-4(5H)-one hydrochloride The product from Example 21.3 (0.15 g, 0.296 mmol) was heated under reflux in 37% aq. HCl (4 ml) for 1.5 h. The solvent was evaporated to a cream coloured foam which was dissolved in a 1:1 mixture of MeOH:water (10 ml) and the solution neutralised with Amberlyst A21 resin. The resin was filtered off and 10% Pd—C (50 mg) added to the filtrate and the mixture stirred under hydrogen added from a balloon for 1 h. The Pd-catalyst was filtered off over Celite and the solvent evaporated. The residue was chromatographed on silica gel (CH$_2$Cl$_2$-MeOH-28% aq. NH$_4$OH, 5:4.5:0.5) to give the free base form of the product as a colourless solid which was dissolved in excess 5% aq. HCl followed by evaporation of the solvent to give the racemic 7-(((2RS,3RS)-3,4-dihydroxy-2-(hydroxymethyl)butylamino)methyl)-3H-pyrrolo[3,2-d]pyrimidin-4(5H)-one hydrochloride as a colourless solid (26 mg, 28%). $^1$H NMR (D$_2$O, referenced to internal acetone at 2.225 ppm) δ 8.82 (s, 1H), 7.86 (s, 1H), 4.48 (s, 2H), 3.81-3.72 (m, 2H), 3.65-3.49 (m, 3H), 3.31-3.19 (m, 2H), 2.25 (m, 1H). $^{13}$C NMR (D$_2$O, referenced to internal acetone at 31.5 ppm) δ 154.3, 145.6, 136.0, 133.6, 119.4, 104.8, 72.0, 64.1, 61.2, 48.5, 42.1, 41.6. +ESMS Found 283.1406 C$_{12}$H$_{19}$N$_4$O$_4$ (M+H)$^+$ requires 283.1406—free base.

Example 22

Synthesis of 7-(((2RS,3SR)-3,4-dihydroxy-2-(hydroxymethyl)butylamino)methyl)-3H-pyrrolo[3,2-d] pyrimidin-4(5H)-one

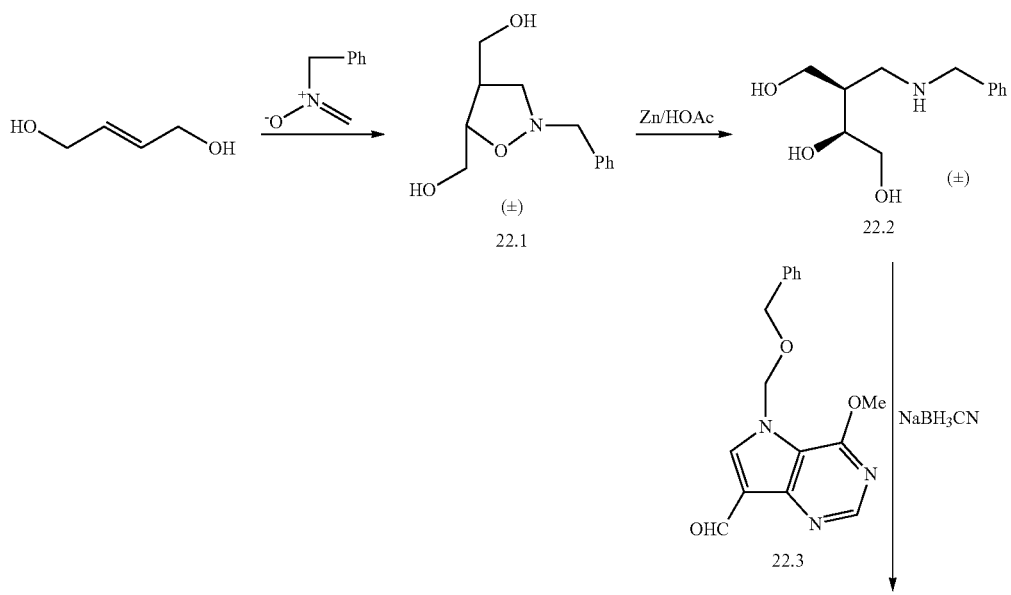

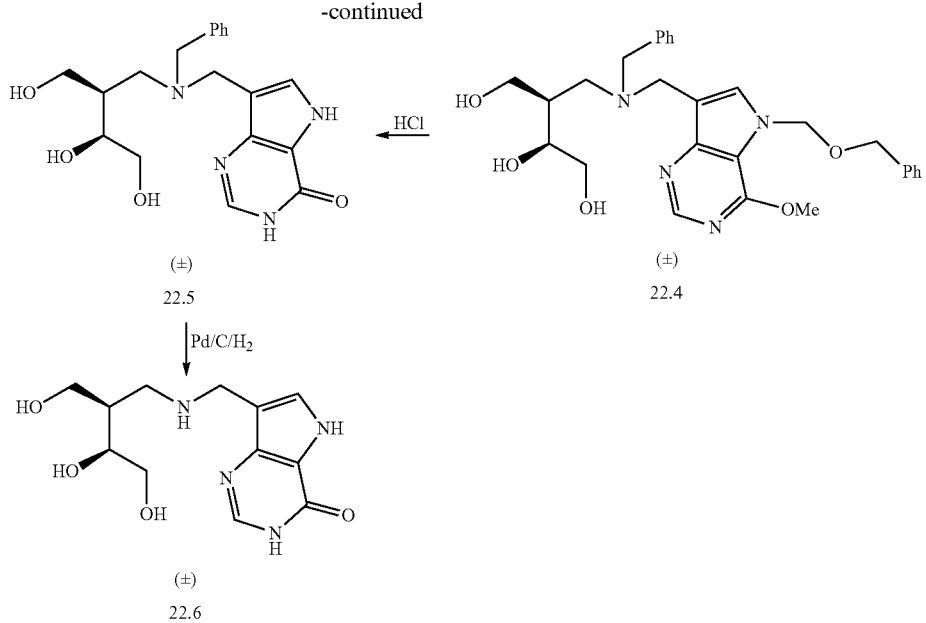

Example 22.1

Synthesis of N-Benzyl trans-4,5-bis(hydroxymethyl)isoxazolidine

A mixture of N-benzylhydroxylamine (4.4 g, 27.7 mmol) and anhydrous NaOAc (3.0 g, 36.7 mmol) in 35 ml EtOH was stirred at ambient temperature for 15 min, after which time formaldehyde (4.1 ml, 55.1 mmol) was added and the mixture stirred for another 30 min. A solution of (E)-but-2-ene-1,4-diol (1.63 g, 18.50 mmol) in ethanol (20 ml) was then introduced to the mixture in a single slug and the resulting solution refluxed for 18 hours. The mixture was cooled, concentrated and taken up in DCM and the solution washed sodium bicarbonate solution, dried and concentrated to an immobile oil (5.25 g). The crude product was fractionated by chromatography over silica eluting firstly with EtOAc and then with 5% MeOH/EtOAc and the title compound was isolated as an immobile syrup (1.95 g). The chromatography was repeated with only EtOAc as eluant and the compound isolated (1.46 g, 35%) as an homogeneous syrup. $^1$H NMR (CDCl$_3$) δ 7.41-7.22 (m, 5H), 4.10-3.82 (m, 2H), 3.80-3.60 (m, 4H), 3.5-2.3 (m, 5H). $^{13}$C NMR 137.0, 129.3, 128.8, 128.0, 81.6, 64.1, 63.0, 58.7, 47.7.

Example 22.2

Synthesis of (±)-3-[(Benzylamino)methyl]butane-1,2,4-triol

Zinc dust (0.47 g, 7.2 mmol) was added to a solution of N-benzyl trans-4,5-bis(hydroxymethyl)isoxazolidine (0.32 g, 1.43 mmol) in acetic acid (6 ml) and the mixture stirred vigorously for 1.5 hrs after which time the starting material had been consumed. The mixture was filtered through a plug of celite and the filtrate concentrated to dryness before being redissolved in DCM, preabsorbed onto silica and then fractionated by chromatography, eluting isocratically with M/7M NH$_3$-MeOH, (4:1) to give the aminotriol (0.26 g, 81%) as an immobile syrup. $^1$H NMR (CDCl$_3$) δ 3.90 (q, J=4.0 Hz, 1H), 3.80 (s, 2H), 3.75 (d, J=5.1 Hz, 2H), 3.66 (dq, J=11.7, 3.9 Hz, 2H), 2.94 (d, J=6.9 Hz, 2H), 1.78 (m, 1H). $^{13}$C NMR 138.9, 129.1, 128.7, 127.9, 73.7, 65.4, 65.3, 54.4, 48.9, 43.9. –ESMS—clean spectrum shows only MH+ (226) and MNa+ (248), C$_{12}$H$_{19}$NO$_3$.

Example 22.3

Synthesis of 5-(Benzyloxymethyl)-4-chloro-5H-pyrrolo[3,2-d]pyrimidine-7-carbaldehyde To a suspension of 4-chloro-5H-pyrrolo[3,2-d]pyrimidine (4.04 g, 26.3 mmol) in THF (60 ml) maintained cold in an ice-bath was added, portionwise over a period of 20 min, sodium hydride (1:58 g, 60% disp, 39.5 mmol) and the mixture stirred for an additional 15 min. Benzylchloromethyl ether (6.87 g, 6.12 ml, 26.3 mmol) was then added dropwise over a period of 15 min, at which point the ice-bath was removed and the mixture stirred at ambient temperature for an hour. Recooled the solution in ice, quenched with water (2 ml) and then extracted the mixture with (a large volume of) DCM (phase boundary clarified by filtration through celite) and concentrated the organic phase to dryness. The crude product was redissolved in DCM (100 ml) and cooled in an ice-bath before adding, portionwise, NBS (4.7 g, 26.41 mmol). The resulting solution was stirred for 2 hrs whilst warming to ambient temperature and then concentrated directly onto silica. The crude was fractionated by chromatography over silica eluting with 20% EtOAc/hexane to give the title compound as an oil (5.28 g, 56.9%) which readily solidified. $^1$H NMR (CDCl$_3$) δ 8.77 (s, 1H), 7.60 (s, 1H), 7.40-7.14 (m, 5H), 5.85 (s, 2H), 4.55 (s, 2H). $^{13}$C NMR (CDCl$_3$) δ 151.3, 135.9, 129.0, 128.7, 128.1, 77.2, 71.3: quats not evident.

7-Bromo-5-(benzyloxymethyl)-4-chloro-5H-pyrrolo[3,2-d]pyrimidine (3.73 g, 10.6 mmol) was dissolved in anhydrous anisole (48 ml) and then diluted with Et$_2$O (145 ml) before being cooled to −78° C. at which point N-butyllithium (1.48M in hexane, 9.2 ml, 13.6 mmol) was added dropwise such that the temperature did not exceed −70° C. Within 2 minutes of the addition, DMF (8.5 ml, 0.123 mol) was introduced quickly (T≤−68° and the mixture stirred whilst warming to −40°, at which point water (20 ml) was added. The mixture was then extracted with EtOAc and the extract washed with brine and then dried and concentrated to an orange solid. Purification of this material was accomplished by chromatography over silica, eluting with 20→40% EtOAc/hexane, to give (a heart fraction of) the title aldehyde (1.83 g, 57.3%) as an off-white solid. $^1$H NMR (CDCl$_3$) δ 10.35 (s, 1H), 8.89 (s, 1H), 8.14 (s, 1H), 7.35-7.20 (m, 5H), 5.90 (s, 2H), 4.60 (s, 2H).

Example 22.4

Synthesis of (±)-3-{Benzyl([5-benzyloxymethyl]-4-methoxy-5H-pyrrolo[3,2-d]pyrimidin-7-yl)methyl)aminomethyl}butane-1,2,4-triol To a solution of (±)-3-[(benzylamino)methyl]butane-1,2,4-triol (0.25 g, 1.11 mmol), 5-benzyloxy-4-methoxy-5H-pyrrolo[3,2-d]pyrimidine 7-carbaldehyde (0.33 g, 1.11 mmol) in methanol (11 ml) was added a 40 μL slug of acetyl chloride and this was followed by the addition of sodium cyanoborohydride (0.105 g, 1.67 mmol) in a single shot. The mixture was stirred at ambient temperature for three days before being diluted with DCM and washed with saturated sodium bicarbonate solution. The solution was dried and concentrated and then fractionated by chromatography over silica eluting with 4% 7M NH$_3$-MeOH in DCM to give the title compound (0.31 g, 55%) as an immobile syrup. $^1$H NMR (CDCl$_3$) δ 8.56 (s, 1H), 7.46-7.17 (m, 11H), 5.74 (s, 2H), 5.33 (s, 2H), 4.14 (s, 3H), 4.05 (d, J=14.2 Hz, 1H), 3.92 (d, J=14.2 Hz, 1H), 3.80-3.41 (m, 7H), 2.90 (dd, J=13.2, 9.0 Hz, 1H), 2.72 (dd, J=12.9, 5.1 Hz, 1H), 2.38 (m, 1H). $^{13}$C NMR (CDCl$_3$) δ 156.9, 150.9, 150.7, 138.0, 137.2, 133.5, 129.7, 129.0, 128.9, 128.4, 128.0, 127.9, 112.3, 77.2, 74.3, 70.7, 65.1, 64.5, 59.4, 54.3, 54.1, 46.0, 40.9. HR-ESMS MH+ 507.2592, C$_{28}$H$_{35}$N$_4$O$_5$ requires 507.2607 Δ=3.0 ppm.

Example 22.5/22.6

Synthesis of 7-(((2RS,3SR)-3,4-dihydroxy-2-(hydroxymethyl)butylamino)methyl)-3H-pyrrolo[3,2-d]pyrimidin-4(5H)-one A solution of 3-{benzyl([5-benzyloxymethyl]-4-methoxy-5H-pyrrolo[3,2-d]pyrimidin-7-yl)methyl)aminomethyl}butane-1,2,4-triol (0.31 g, 0.612 mmol) was refluxed in concentrated hydrochloric acid (8 ml) for 2.5 hr and concentrated to dryness. The residue was redissolved in methanol (10 ml) and water (2 ml) and treated with A21 resin to the point of neutrality. The resin was recovered by filtration and the filtrate concentrated and redissolved in methanol (6 ml) and water (3 ml), 10% Pd/C (0.1 g) added and the mixture hydrogenolysed for 2 hr. The solution was filtered through a pad of celite and concentrated to an immobile syrup (0.16 g). The product was fractionated over silica eluting with DCM/MeOH/0.88NH$_3$ (5:4.5:0.5) and the title compound, as free base, recovered as a colourless solid (0.06 g, 34.7%). $^1$H NMR (D$_2$O+DCl) δ 8.64 (s, 1H), 7.76 (s, 1H), 4.40 (s, 2H), 3.75-3.48 (m, 5H), 3.27-3.20 (m, 2H), 2.13-2.02 (m, 1H). $^{13}$C NMR (D$_2$O+DCl) δ 153.73, 144.6, 136.3, 132.5, 118.5, 104.28, 71.2, 63.9, 61.4, 47.2, 41.2:40.2. HR-ESMS MH+ 283.1413 C$_{12}$H$_{19}$N$_4$O$_4$ requires MH+283.1406 Δ 2.5 ppm.

Example 23

Synthesis of 7-(((2RS,3RS)-3,4-dihydroxy-2-(methylthiomethyl)butylamino)methyl)-3H-pyrrolo[3,2-d]pyrimidin-4(5H)-one

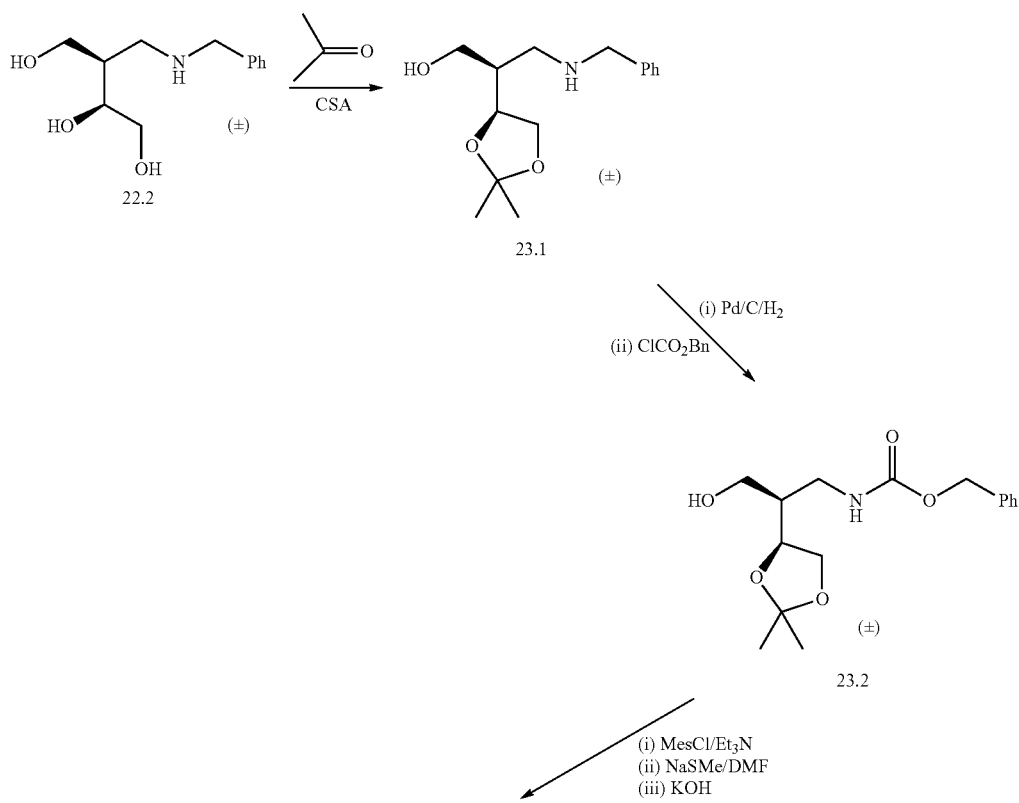

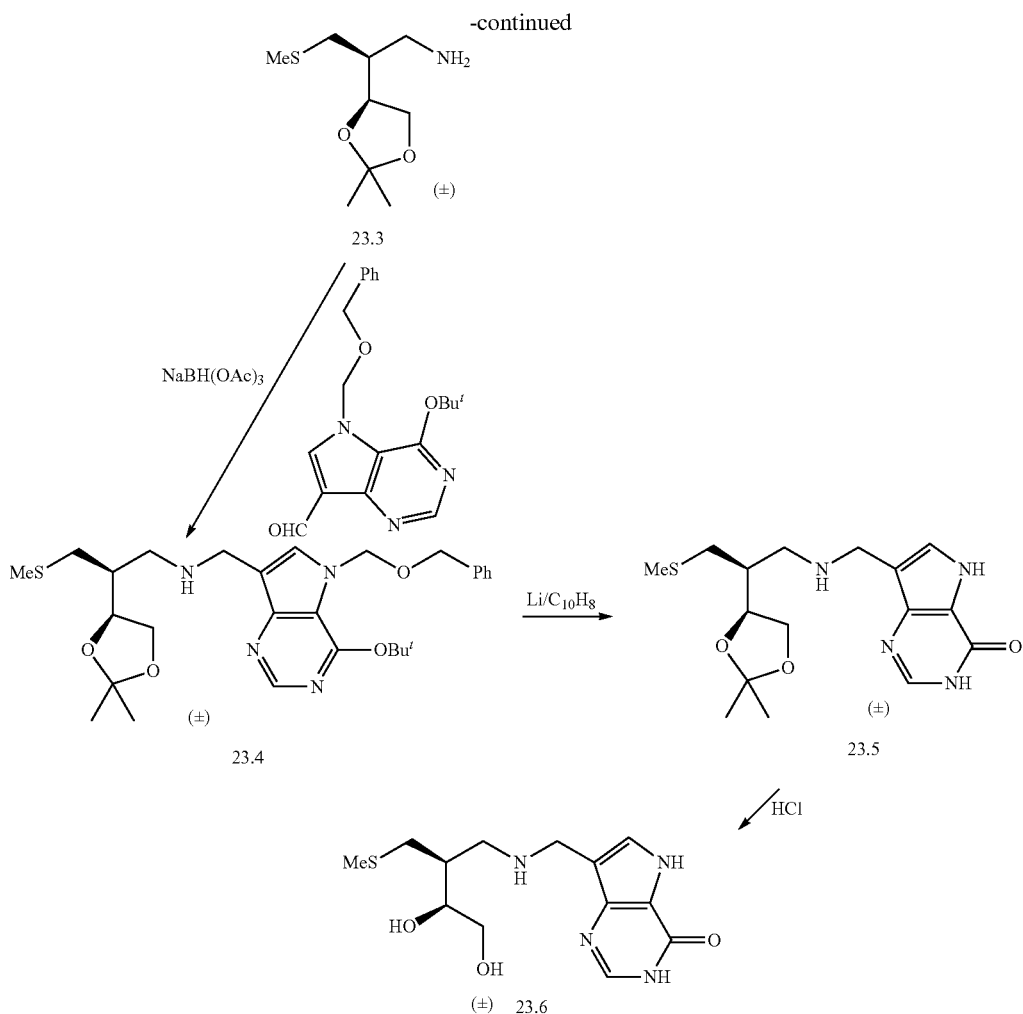

Example 23.1

Synthesis of (±)-N-Benzyl-2-(2,2-dimethyl-1,3-dioxolan-4-yl)-3-hydroxypropane-1-amine A solution of (±)-3-[(benzylamino)methyl]butane-1,2,4-triol (Example 22.2, 0.97 g, 4.31 mmol) and (±)-camphorsulphonic acid monohydrate (1.62 g, 6.47 mmol) in acetone (30 ml) was stirred at ambient temperature for three days after which time the solution was diluted with DCM and washed with sodium bicarbonate solution. The organic phase was dried and concentrated to a syrup (1.1 g) which was fractionated by chromatography over silica, eluting with EtOAc to give the acetonide (0.52 g, 45.6%) as a mobile yellow oil. $^1$H NMR (CDCl$_3$) δ 7.26-7.07 (m, 5H), 3.92 (m, 2H), 3.74-3.46 (m, 5H), 2.94 (dd, J=12.0, 3.0 Hz, 1H), 2.76 (dd, J=12.0, 6.0 Hz, 1H), 1.76 (m, 1H), 1.28 (s, 3H), 1.22 (s, 3H). $^{13}$C NMR (CDCl$_3$) δ 139.6, 128.9, 128.6, 127.7, 109.3, 75.6, 68.4, 66.0, 54.6, 51.2, 43.5, 27.0, 25.8. LR-ESMS MH+ 266.1844.

Example 23.2

Synthesis of (±)-N-Benzyl-2(2,2-dimethyl-1,3-dioxolan-4-yl)-3-hydroxypropyl carbamate A solution of (±)-N-benzyl-2(2,2-dimethyl-1,3-dioxolan-4-yl)-3-hydroxypropane-1-amine (2.07 g, 7.8 mmol) in 45 ml MeOH was hydrogenolysed in the presence of 10% Pd/C (0.39 g) 18 hrs after which time no starting material remained. The solution was filtered through pad of celite and concentrated, then redissolved in toluene (13 ml). Water (13 ml) was then added followed by potassium carbonate (1.62 g, 11.7 mmol) and benzylchloroformate (50% w/w in toluene, 2.64 ml, 7.8 mmol) and the mixture stirred vigorously for 3 hrs. The mixture was diluted with EtOAc and washed with sodium bicarbonate solution and brine and then dried and concentrated (2.47 g). The CBz-protected amine was recovered following chromatography over silica eluting with 40% EtOAc/hexane to give the compound (2.12 g, 82%) as a colourless syrup. $^1$H NMR (CDCl$_3$) δ 7.39 (brs, 5H), 5.24 (m, 1H), 5.14 (s, 2H), 4.08 (m, 2H), 3.73 (m, 1H), 3.62-3.34 (m, 4H), 3.26 (t, J=6.3 Hz, 1H), 1.83 (m, 1H), 1.42 (s, 3H), 1.34 (s, 3H). $^{13}$C NMR (CDCl$_3$) δ 158.3, 136.7, 129.0, 128.6, 128.5, 109.3, 75.7, 68.5, 67.5, 61.0, 45.6, 39.3, 27.0, 25.8. LR-ESMS MNa+ 332.1180 C$_{16}$H$_{23}$NO$_5$Na.

Example 23.3

Synthesis of (±)-2(2,2-Dimethyl-1,3-dioxolan-4-yl)-3-(methylthio)propane-1-amine Methanesulphonyl chloride (0.182 ml, 2.33 mmol) was added to an ice-cooled solution of (±)-N-benzyl-2(2,2-dimethyl-1,3-dioxolan-4-yl)-3-hydroxypropyl carbamate (0.6 g, 1.94 mmol) and Et$_3$N (0.41 ml, 2.91 mmol) in DCM (8 ml) and the solution was then allowed to warm to ambient. After 1 hr, the solution was diluted with DCM, washed with sodium bicarbonate solution then dried and concentrated (0.87 g). This product was dissolved in 3.5 ml DMF (3.5 ml) and then sodium thiomethoxide (0.272 g, 3.85 mmol) was added. Stirring was continued for 2 hr, after which time the mixture was diluted with ether and washed with water (×5) and brine, then dried and concentrated to an oil (0.70 g)—the mesylate-to-thiomethoxide transformation confirmed from an examination of NMR data. The residue was dissolved in isopropanol (12 ml) and to this was added KOH (2M, 5.4 ml) and the solution heated at reflux for 24 hrs. The solution was cooled and concentrated to the point where most of the isopropanol had been removed, at which point Et$_2$O was added and the product extracted. The organic phase was dried and concentrated and the product fractionated by chromatography over silica, eluting firstly with DCM (to remove the benzyl alcohol) and then with 4% 7M NH$_3$ MeOH/DCM to recover the title compound (0.32 g, 80%) as a pale yellow syrup. $^1$H NMR (CDCl$_3$) δ 4.15 (m, 2H), 3.70 (m, 1H), 2.90 (d, J=5.1 Hz, 2H), 2.54 (d, J=2.6 Hz, 1H), 2.52 (d, J=1.0 Hz, 1H), 2.11 (s, 3H), 1.73 (m, 1H), 1.46 (s, 3H), 1.36 (s, 3H). $^{13}$C NMR (CDCl$_3$) δ 109.1, 77.3, 68.4, 44.5, 42.5, 34.4, 27.0, 25.8, 16.7.

Example 23.4

Synthesis of N-{(5-(Benzyloxymethyl)-4-t-butoxy-5H-1-pyrrolo{3,2-d}pyrimidin-7-yl}methyl-2-(2,2-dimethyl-1,3-dioxolan-4-yl)-3-(methylthio)propan-1-amine To a mixture comprising (±)-2(2,2-dimethyl-1,3-dioxolan-4-yl)-3-(methylthio)propane-1-amine (0.37 g, 1.80 mmol), 5-(benzyloxymethyl)-4-t-butoxy-5H-pyrrolo[3,2-d]pyrimidin-7-carbaldehyde (0.795 g, 1.3 equiv, 2.34 mmol) in 1,2-dichloroethane (15 ml) was added, in a single portion, sodium triacetoxyborohydride (1.3 equiv, 2.34 mmol, 0.49 g) and then 0.5 g anhydrous magnesium sulphate. The mixture was stirred overnight at ambient temperature before being diluted with DCM and washed with sodium bicarbonate solution. The organic phase was dried and concentrated to an immobile syrup (1.25 g) crude. This crude product was fractionated by chromatography over silica in a column prepared in DCM/EtOAc/7MNH$_3$-MeOH (4.95:4.95:0.1)—the crude being added to the column in DCM before advancing to the more polar eluant. The title compound (0.56 g, 58.8%) was isolated as an immobile syrup. $^1$H NMR (CDCl$_3$) δ 8.46 (s, 1H), 7.36-7.18 (m, 6H), 5.74 (s, 2H), 4.47 (s, 2H), 4.21 (q, J=6.6 Hz, 1H), 4.07 (dd J=8.0, 6.3 Hz, 1H), 3.99 (s, 2H), 3.67 (t, J=7.7 Hz, 1H), 2.86 (m, 2H), 2.55 (d, J=6.4 Hz, 2H), 2.07 (s, 3H), 1.69 (s, 9H), 1.36 (s, 3H), 1.32 (s, 3H). $^{13}$C NMR (CDCl$_3$) δ 156.1, 150.4, 149.87, 137.6, 130.7, 128.8, 128.2, 127.8, 117.4, 116.8, 109.0, 83.1, 77.6, 77.4, 70.2, 68.1, 50.0, 44.2, 42.1, 34.9, 29.1, 26.9, 25.8, 16.7.

Example 23.5

Synthesis of N-{4-Hydroxy-5H-pyrrolo{3,2-d}pyrimidin-7-yl}methyl-2-(2,2-dimethyl-1,3-dioxolan-4-yl)-3-(methylthio)propan-1-amine To a solution of lithium naphthalenide [prepared from the reaction of lithium (0.073 g, 10.6 mmol) with naphthalene (1.63 g, 12.7 mmol) in solution in anhydrous THF (25 ml)] maintained under argon at −78° C. was added, dropwise over a period of 2 minutes, a solution of N-{(5-(benzyloxymethyl)-4-t-butoxy-5H-pyrrolo{3,2-d}pyrimidin-7-yl}methyl-2-(2,2-dimethyl-1,3-dioxolan-4-yl)-3-(methylthio)propan-1-amine (0.56 g, 1.06 mmol) in 3 ml THF. After stirring for 1 hr at −78° C., the solution was quenched by the addition of water (2 ml) and then allowed to warm to ambient temperature before being concentrated to dryness. The mixture was stirred with 7M NH$_3$-MeOH for 20 minutes and then reconcentrated. The crude product was then redissolved in DCM and preabsorbed onto a small quantity of silica before being fractionated by chromatography over silica, eluting, firstly with DCM [to remove naphthalene] and then with 3% 7M NH$_3$-MeOH/DCM to give (a heart fraction of) the title compound (0.1 g, 26%) as an immobile syrup. This was considered to be pure enough for subsequent reaction. $^1$H NMR (CD$_3$OD) δ 7.88 (s, 1H), 7.38 (s, 1H), 4.11 (m, 2H), 3.94 (s, 2H), 3.68 (m, 1H), 2.86 (d, J=6.0 Hz, 2H), 2.53 (m, 2H), 2.06 (s, 3H), 1.96 (m, 1H), 1.32 (s, 3H), 1.29 (s, 3H). $^{13}$C NMR (CD$_3$OD) δ 156.5, 145.3, 143.1, 128.8, 119.7, 116.5, 110.4, 79.6, 69.5, 51.5, 44.3, 42.9, 35.9, 27.2, 26.0, 16.5. HR-ESMS MH+ 353.1650 C$_{16}$H$_{25}$N$_4$O$_3$S requires MH+ 353.1647 Δ 0.8 ppm.

Example 23.6

Synthesis of 7-(((2RS,3RS)-3,4-dihydroxy-2-(methylthiomethyl)butylamino)methyl)-3H-pyrrolo[3,2-d]pyrimidin-4(5H)-one To a stirred suspension of N-{4-hydroxy-5H-pyrrolo[3,2-d]pyrimidin-7-yl}methyl-2-(2,2-dimethyl-1,3-dioxolan-4-yl)-3-(methylthio)propan-1-amine (0.1 g, 0.28 mmol) in methanol (7 ml) was added a solution of acetyl chloride (0.22 g, 2.8 mmol) in methanol (3 ml) and the solution stirred at ambient temperature for 2.5 hr. Amberlyst A-21 resin was added and the solution made neutral before being filtered free of resin and concentrated to a light yellow gum (0.072 g). This was dissolved in aqueous methanol (1:1) and preabsorbed onto silica for chromatography over silica. Gradient elution with DCM/MeOH/0.88 NH$_3$ cocktails ranging from 9:1:0.1 through to 6:4:0.1 in composition furnished the title compound as a precipitate (free base) in the latter fractions. This was recovered by filtration and dried to give a colourless solid (0.026 g). $^1$H NMR (CD$_3$OD+DCl) δ 7.93 (s, 1H), 7.42 (s, 1H), 3.94 (s, 2H), 3.82 (q, J=4.8 Hz 1H), 3.58 (m, 2H), 2.89 (m, 2H), 2.66 (dd J=13.2, 6.6 Hz, 1H), 2.55 (dd J=13.2, 7.5 Hz, 1H), 2.13 (s, 3H), 1.94 (m, 1H). $^{13}$C NMR (CD$_3$OD+DCl) δ 156.6, 145.2, 143.4, 129.1, 119.7, 115.8, 75.0, 65.9, 50.0, 45.9, 41.5, 36.6, 16.3. HR-ESMS MH+ 313.1332 C$_{13}$H$_{21}$N$_4$O$_3$S requires MH+ 313.1334 Δ 0.6 ppm.

Example 24

Synthesis of 7-(((2R,3S)-3,4-dihydroxy-1-(methylthio)butan-2-ylamino)methyl)-3H-pyrrolo[3,2-d]pyrimidin-4(5H)-one hydrochloride

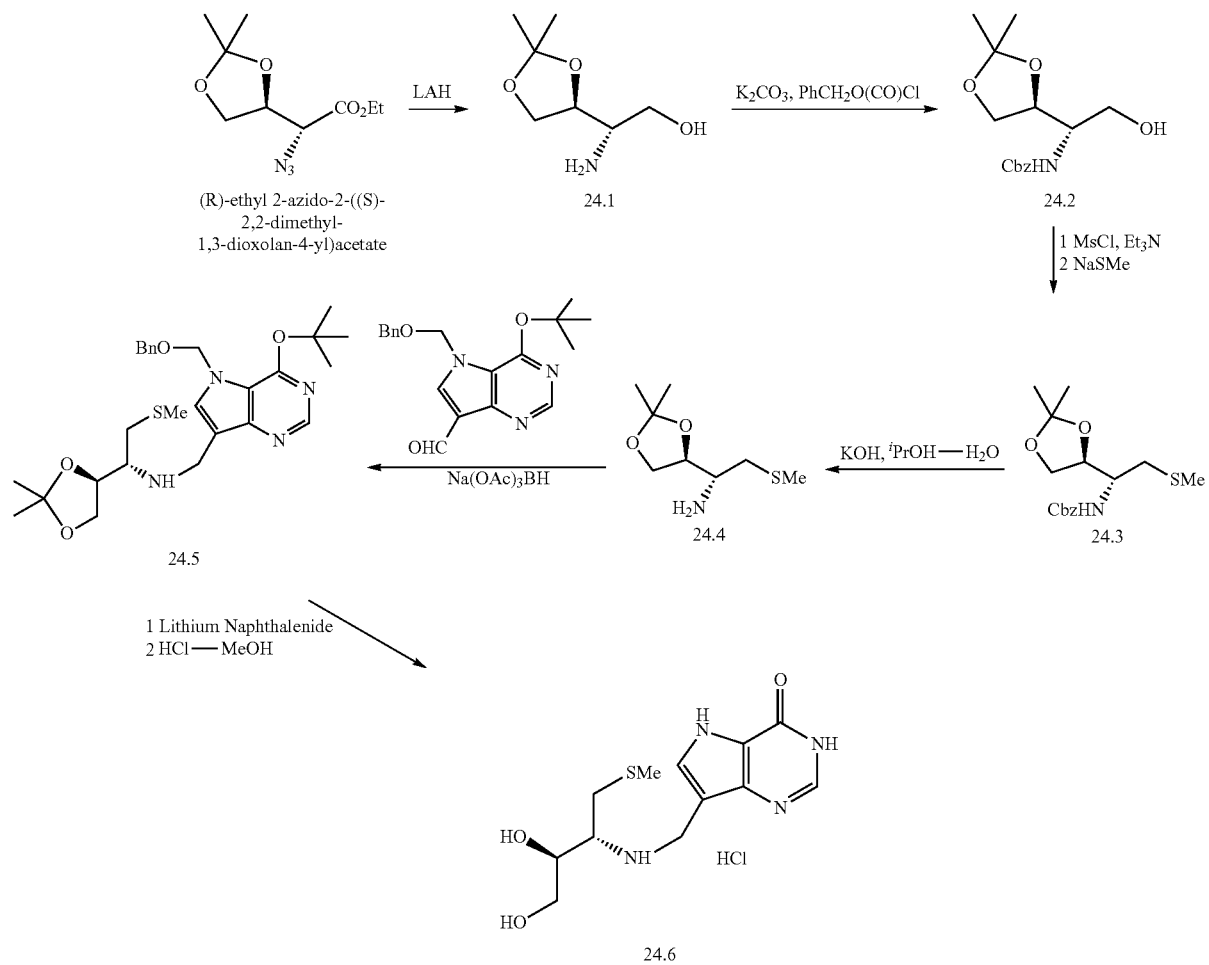

Example 24.1

Synthesis of (S)-2-amino-2-((S)-2,2-dimethyl-1,3-dioxolan-4-yl)ethanol

Diethyl D-tartrate [(2S,3S)-diethyl 2,3-dihydroxysuccinate] was converted to (2R,3S)-diethyl 2-azido-3-hydroxysuccinate according to the literature method (A. Breuning, R. Vicik and T. Schirmeister, *Tetrahedron: Asymm.*, 2003, 14, 3301) and then into (R)-ethyl 2-azido-2-((S)-2,2-dimethyl-1,3-dioxolan-4-yl)acetate according to the method described by S. Saito, T. Ishikawa, A. Kuroda, K. Koga and T. Moriwake, *Tetrahedron*, 1992, 48, 4067 for the corresponding enantiomer. This latter compound was converted into (S)-2-amino-2-((S)-2,2-dimethyl-1,3-dioxolan-4-yl)ethanol in the same way as described for the enantiomer in Example 25.1. The $^1$H NMR was identical to the enantiomer product of Example 25.1.

Example 24.2

Synthesis of benzyl (S)-1-((S)-2,2-dimethyl-1,3-dioxolan-4-yl)-2-hydroxyethylcarbamate The product from Example 24.1 was converted into benzyl (S)-1-((S)-2,2-dimethyl-1,3-dioxolan-4-yl)-2-hydroxyethylcarbamate as a colourless solid in the same way described for the enantiomer in Example 25.2. The $^1$H and $^{13}$C NMR were identical to those of the enantiomer product of Example 25.2. +ESMS Found 318.1317 (M+Na)$^+$ $C_{15}H_{21}NNaO_5$ requires 318.1317. $[\alpha]_D^{20}$ +12.5 (c 1.205, MeOH).

Example 24.3

Synthesis of benzyl (R)-1-((S)-2,2-dimethyl-1,3-dioxolan-4-yl)-2-(methylthio)ethylcarbamate The product from Example 24.2 was converted into benzyl (R)-1-((S)-2,2-dimethyl-1,3-dioxolan-4-yl)-2-(methylthio)ethylcarbamate as a colourless solid in the same way as described for its enantiomer in Example 25.3. The $^1$H NMR, $^{13}$C NMR and mpt were identical to the enantiomer product of Example 25.3. +ESMS Found 348.1249 (M+Na)$^+$ $C_{16}H_{23}NNaO_4S$ requires 348.1245. $[\alpha]_D^{20}$ −31.9 (c 0.59, MeOH).

Example 24.4

Synthesis of (R)-1-((S)-2,2-dimethyl-1,3-dioxolan-4-yl)-2-(methylthio)ethanamine The product from Example 24.3 was converted into (R)-1-((S)-2,2-dimethyl-1,3-dioxolan-4-yl)-2-(methylthio)ethanamine as a pale yellow oil in the same way described for the enantiomer in Example 25.4. The $^1$H and $^{13}$C NMR were identical to the enantiomer product of Example 25.4. +ESMS Found 192.1064 $C_8H_{18}NO_2S$ (M+H)$^+$ requires 192.1058. $[\alpha]_D^{20}$ −27.1 (c 1.085, MeOH).

Example 24.5

Synthesis (R)—N-((5-(benzyloxymethyl)-4-tert-butoxy-5H-pyrrolo[3,2-d]pyrimidin-7-yl)methyl)-1-((S)-2,2-dimethyl-1,3-dioxolan-4-yl)-2-(methylthio)ethanamine The product from Example 24.4 was converted to (R)—N-((5-(benzyloxymethyl)-4-tert-butoxy-5H-pyrrolo[3,2-d]pyrimidin-7-yl)methyl)-1-((S)-2,2-dimethyl-1,3-dioxolan-4-yl)-2-(methylthio)ethanamine as a pale yellow gum in the same way described for the enantiomer in Example 25.5. The $^1$H and $^{13}$C NMR were identical to the enantiomer product of Example 25.5. +ESMS Found 515.2697 (M+H)$^+$ $C_{27}H_{39}N_4O_4S$ requires 515.2692. $[\alpha]_D^{20}$ −5.4 (c, 0.445, MeOH).

Example 24.6

Synthesis of 7-(((2R,3S)-3,4-dihydroxy-1-(methylthio)butan-2-ylamino)methyl)-3H-pyrrolo[3,2-d]pyrimidin-4(5H)-one hydrochloride The product from Example 25.5 was converted into 7-(((2R,3S)-3,4-dihydroxy-1-(methylthio)butan-2-ylamino)methyl)-3H-pyrrolo[3,2-d]pyrimidin-4(5H)-one hydrochloride in the same way described for the enantiomer in Example 25.6. The $^1$H and $^{13}$C NMR were identical to the enantiomer product of Example 25.6. +ESMS Found 299.1176 $C_{12}H_{19}N_4O_3S$ (M+H)$^+$ free base requires 299.1178.

Example 25

Synthesis of (2R,3S)-3-((4-hydroxy-5H-pyrrolo[3,2-d]pyrimidin-7-yl)methylamino)-4-(methylthio)butane-1,2-diol hydrochloride

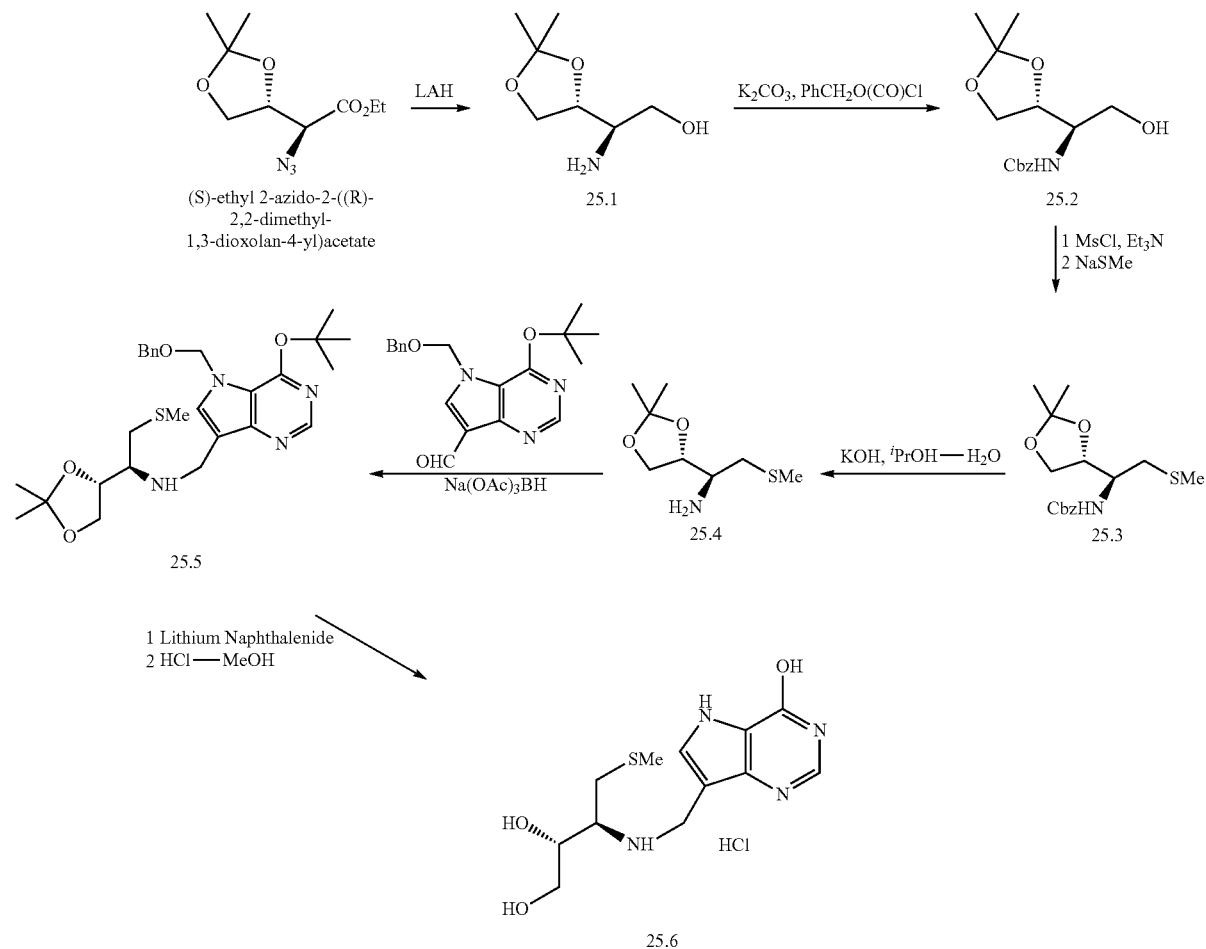

Example 25.1

Synthesis of (R)-2-amino-2-((R)-2,2-dimethyl-1,3-dioxolan-4-yl)ethanol

Diethyl L-tartrate [(2R,3R)-diethyl 2,3-dihydroxysuccinate] was converted to (2S,3R)-diethyl 2-azido-3-hydroxysuccinate according to the literature method (A. Breuning, R. Vicik and T. Schirmeister, *Tetrahedron: Asymm.*, 2003, 14, 3301) and then into (S)-ethyl 2-azido-2-((R)-2,2-dimethyl-1,3-dioxolan-4-yl)acetate according to the method described by S. Saito, T. Ishikawa, A. Kuroda, K. Koga and T. Moriwake, *Tetrahedron*, 1992, 48, 4067. This latter compound (1.8 g, 7.85 mmol) was dissolved in dry THF (12 ml) and cooled in an ice-bath. Lithium aluminium hydride (31.4 ml, 31.4 mmol, 1M in diethyl ether) was added and the mixture warmed to rt and stirred for 30 mins., then heated under reflux for 3 h. The mixture was cooled in an ice bath and water (1.2 ml), 15% aq. NaOH (1.2 ml), and water (4 ml) added successively. The mixture was diluted with diethyl ether, filtered through Celite and the Celite washed with hot $CHCl_3$ (3×). The combined filtrates were dried ($MgSO_4$), filtered and the solvent evaporated to a colourless oil. The oil was chromatographed on silica gel ($CH_2Cl_2$-MeOH-28% aq. $NH_4OH$, 96:4:0.5 then 9:1:0.05) to give a pale yellow oil which was distilled on a Kugelrohr apparatus at 120° C./0.1 mmHg to afford (R)-2-amino-2-((R)-2,2-dimethyl-1,3-dioxolan-4-yl) ethanol (0.415 g, 61%) as a colourless oil. $^1$H NMR ($CDCl_3$, referenced to the centre line of $CDCl_3$ at 77.0 ppm) δ 4.10-3.98 (m, 2H), 3.87 (dd, J=7.4, 5.7 Hz, 1H), 3.71 (dd, J=10.9, 4.4 Hz, 1H), 3.54 (dd, J=10.9, 5.7 Hz, 1H), 2.95 (m, 1H), 1.94 (brs, 3H, exchanged to $D_2O$), 1.42 (s, 3H), 1.35 (s, 3H). $^{13}$C NMR ($CDCl_3$) δ 109.0, 77.8, 66.6, 64.4, 54.6, 26.5, 25.2. +ESMS Found 162.1130 (M+H)$^+$ $C_7H_{16}NO_3$ requires 162.1130. $[\alpha]_D^{20}$ −9.5 (c, 1.47, $CHCl_3$). Lit., $[\alpha]_D$ −10.5, c 1.5, $CHCl_3$ for the product made from D-ascorbic acid according to M. Banwell, C. De Savi, D. Hockless and K. Watson, *Chem. Commun.*, 1998, 645.

Example 25.2

Synthesis of benzyl (R)-1-((R)-2,2-dimethyl-1,3-dioxolan-4-yl)-2-hydroxyethylcarbamate Following a method described for the preparation of a diastereomer of the title compound (T. Inaba, Y. Yamada, H. Abe, S. Sagawa and H. Cho, *J. Org. Chem.*, 2000, 65, 1623) benzyl chloroformate (2.51 ml, 7.44 mmol, 50% in toluene) was added to a vigorously stirred solution of the product from Example 25.1 (1.2 g, 7.44 mmol) and potassium carbonate (1.286 g, 9.31 mmol) in a mixture of toluene (12 ml) and water (12 ml). Stirring was continued at rt for 16 h. Triethylamine (10.46 ml, 74.4 mmol) was added, the aqueous phase saturated with salt and the organic layer was diluted with EtOAc and separated, dried ($MgSO_4$) and the solvent evaporated. The residue was chromatographed on silica gel (EtOAc-hexanes, 4:6 then 6:4) to give benzyl (R)-1-((R)-2,2-dimethyl-1,3-dioxolan-4-yl)-2-hydroxyethylcarbamate a colourless gum which soon crystallized (1.63 g, 74%). $^1$H NMR ($CDCl_3$) δ 7.38-7.28 (m, 5H), 5.38 (brd, J=6.3 Hz, 1H, exchanged to $D_2O$), 5.10 (s, 2H,), 4.19 (m, 1H), 4.05 (brdd, J=8.5, 6.5 Hz, 1H), 3.93-3.82 (m, 2H), 3.79-3.67 (m, 2H, simplified slightly after $D_2O$ exchange), 2.52 (brs, 1H, exchanged to $D_2O$), 1.42, (s, 3H), 1.33 (s, 3H). $^{13}$C NMR ($CDCl_3$, referenced to the centre line of $CDCl_3$ at 77.0 ppm) δ 156.4, 136.2, 128.5, 128.2, 128.1, 109.7, 76.1, 67.0, 62.0, 54.3, 26.5, 25.0. +ESMS Found 318.1332 (M+Na)$^+$ $C_{15}H_{21}NNaO_5$ requires 318.1317. $[\alpha]_D^{20}$ −12.5 (c 1.22, MeOH).

Example 25.3

Synthesis of benzyl (S)-1-((R)-2,2-dimethyl-1,3-dioxolan-4-yl)-2-(methylthio)ethylcarbamate Following a similar method described for the preparation of a diastereomer of the title compound (T. Inaba, Y. Yamada, H. Abe, S. Sagawa and H. Cho, *J. Org. Chem.*, 2000, 65, 1623) methanesulfonyl chloride (0.470 ml, 6.03 mmol) was added to a solution of the product from Example 25.2 (1.62 g, 5.49 mmol) and triethylamine (1.147 ml, 8.23 mmol) in $CH_2Cl_2$ (15 ml) at 0° C. The mixture was warmed to rt and stirred for 0.5 h. then washed with sat aq. $NaHCO_3$, dried ($MgSO_4$) and the solvent evaporated to give the crude mesylate. This was dissolved in DMF (5 ml) and sodium thiomethoxide (0.577 g, 8.23 mmol) added. The mixture was stirred at rt for 1 h then diluted with diethyl ether (100 ml) and washed with water (5×5 ml), brine (1×), dried ($MgSO_4$) and the solvent evaporated to a yellow gum. The residue was chromatographed on silica gel (EtOAc-Hexanes, 15:85) to give benzyl (S)-1-((R)-2,2-dimethyl-1,3-dioxolan-4-yl)-2-(methylthio)ethylcarbamate (1.26 g, 71%) as a colourless solid. An analytical sample was recrystallized from $Et_2O$-hexanes to give colourless fine needles. M.p. 70-71° C. $^1$H NMR ($CDCl_3$) δ 7.39-7.26 (m, 5H), 5.12 (d, J=12.3 Hz, 1H), 5.09 (d, J=12.3 Hz, 1H), 5.00 (br. s, 1H, exchanged to $D_2O$), 4.13 (m, 1H), 4.05 (dd, J=8.5, 6.3 Hz, 1H), 3.96-3.83 (m, 2H), 2.78 (d, J=5.4 Hz, 2H), 2.13 (s, 3H), 1.41 (s, 3H), 1.33 (s, 3H). $^{13}$C NMR ($CDCl_3$) δ 156.1, 136.3, 128.5, 128.2, 128.1, 109.8, 76.5, 67.0 ($CH_2 \times 2$), 52.9, 36.0, 26.5, 25.1, 16.5. +ESMS Found 348.1230 (M+Na)$^+$ $C_{16}H_{23}NNaO_4S$ requires 348.1245. $[\alpha]_D^{20}$ +32.4 (c 0.555, MeOH).

Example 25.4

Synthesis of (S)-1-((R)-2,2-dimethyl-1,3-dioxolan-4-yl)-2-(methylthio)ethanamine The product from Example 25.3 (1.26 g, 3.87 mmol) was dissolved in iPrOH (21 ml) and 2M aq. KOH (10 ml) and heated to 80° C. for 64 h. The solvent was evaporated and the residue dissolved in diethyl ether (100 ml) and washed with water (×1), brine (×1) dried ($MgSO_4$) and the solvent evaporated. The residue was chromatographed on silica gel (EtOAc-hexanes, 1:1 then EtOAc-MeOH, 99:1) to give (S)-1-((R)-2,2-dimethyl-1,3-dioxolan-4-yl)-2-(methylthio)ethanamine (0.578 g, 78%) as a pale yellow oil. $^1$H NMR ($CDCl_3$) δ 4.07 (dd, J=7.6, 6.1 Hz, 1H), 3.97 (q, 0.1-=6.2 Hz, 1H), 3.88 (dd, J=7.6, 6.2 Hz, 1H), 2.99 (m, 1H), 2.81 (dd, J=13.4, 3.4 Hz, 1H), 2.41 (dd, J=13.4, 8.9 Hz, 1H), 2.12 (s, 3H), 1.42 (s, 3H), 1.41 (s, 2H, exchanged to $D_2O$), 1.35 (s, 3H). $^{13}$C NMR ($CDCl_3$, referenced to the centre of $CDCl_3$ at 77.0 ppm) δ 109.2, 78.8, 66.6, 52.4, 39.4, 26.6, 25.2, 15.8. +ESMS Found 192.1051 $C_8H_{18}NO_2S$ (M+H)$^+$ requires 192.1058. $[\alpha]_D^{20}$ +27.9 (c 0.92, MeOH).

Example 25.5

Synthesis (S)—N-((5-(benzyloxymethyl)-4-tert-butoxy-5H-pyrrolo[3,2-d]pyrimidin-7-yl)methyl)-1-((R)-2,2-dimethyl-1,3-dioxolan-4-yl)-2-(methylthio)ethanamine To a solution of the product from Example 25.4 (0.1 g, 0.523 mmol) and 5-(benzyloxymethyl)-4-tert-butoxy-5H- pyrrolo[3,2-d]pyrimidine-7-carbaldehyde (0.177 g, 0.523 mmol, prepared as described in G. B. Evans, R. H. Furneaux, A. Lewandowicz, V. L. Schramm and P. C. Tyler, *J. Med. Chem.*, 2003, 46, 5271) in 1,2-dichloroethane (3 ml) was added sodium triacetoxyborohydride (0.144 g, 0.680 mmol) and MgSO$_4$ (200 mg). The mixture was stirred 16 h at rt then diluted with CH$_2$Cl$_2$ and washed with aq. sat NaHCO$_3$, dried (MgSO$_4$) and the solvent evaporated. The residue was chromatographed on silica gel (EtOAc-hexanes, 9:1) to give (S)—N-((5-(benzyloxymethyl)-4-tert-butoxy-5H-pyrrolo[3,2-d]pyrimidin-7-yl)methyl)-1-((R)-2,2-dimethyl-1,3-dioxolan-4-yl)-2-(methylthio)ethanamine (0.162 g, 60%) as a pale yellow gum. $^1$H NMR (CDCl$_3$) δ 8.47 (s, 1H), 7.35 (s, 1H), 7.32-7.22 (m, 5H), 5.73 (s, 2H), 4.47 (s, 2H), 4.19 (q, J=6.4 Hz, 1H), 4.12-4.06 (m, 2H), 3.98 (d, J=13.7 Hz, 1H), 3.89 (dd, J=8.0, 6.4 Hz, 1H), 2.95-2.81 (m, 2H), 2.76 (dd, J=13.5, 6.0 Hz, 1H), 2.10 (s, 3H), 2.04 (br. s, 1H, exchanged to D$_2$O), 1.69, (s, 9H), 1.40 (s, 3H), 1.34 (s, 3H). $^{13}$C NMR (CDCl$_3$), δ 155.8, 149.9, 149.6, 137.2, 130.4, 128.4, 127.8, 127.4, 116.9, 116.4, 109.0, 82.8, 77.0, 76.9, 69.9, 67.2, 58.3, 41.2, 35.7, 28.7, 26.6, 25.2, 16.4. +ESMS Found 515.2668 (M+H)$^+$ C$_{27}$H$_{39}$N$_4$O$_4$S requires 515.2692. [α]$_D^{20}$ +5.8 (c, 0.685, MeOH).

Example 25.6

Synthesis of (2R,3S)-3-4(4-hydroxy-5H-pyrrolo[3,2-d]pyrimidin-7-yl)methylamino)-4-(methylthio)butane-1,2-diol hydrochloride Lithuium naphthalenide solution (H.-J. Liu, J. Yip and K.-S. Shia, *Tetrahedron Lett.*, 1997, 38, 2253) was prepared by adding tiny pieces of lithium (0.016 g, 2.332 mmol) to a solution of naphthalene (0.374 g, 2.91 mmol) in dry THF (6 ml) with stirring at rt for 3 h to give a very dark green solution. The solution was cooled to −78° C. and the product from Example 25.5 (0.15 g, 0.291 mmol) in dry THF (1 ml) added. The mixture was stirred for 10 mins then water (1 ml) added to give a colourless solution which was warmed to rt. The solvent was evaporated and the residue stirred with a solution of 7M NH$_3$-MeOH (10 ml) for 10 mins. The solvent was evaporated and the residue triturated with toluene (2×10 ml) and the solvent decanted off and discarded. The residue was chromatographed on silica gel (CH$_2$Cl$_2$-7M NH$_3$ in MeOH, 9:1) to give 7-(((S)-1-((R)-2,2-dimethyl-1,3-dioxalan-4-yl-2-(methylthio)ethylamino)methyl)-5H-pyrrolo[3,2-d]pyrimidin-4-ol as a colourless solid (76 mg, 0.225 mmol). This was dissolved in MeOH (10 ml) containing acetyl chloride (0.2 ml, 2.81 mmol) and the solution stirred for 4 h at rt. After neutralizing with Amberlyst A21 resin, the mixture was filtered and the solvent evaporated. The residue was chromatographed on silica gel (CH$_2$Cl$_2$-MeOH-28% aq. NH$_4$OH 85:15:2) to give the free base form of the title compound as a colourless solid which was converted to (2R,3S)-3-((4-hydroxy-5H-pyrrolo[3,2-d]pyrimidin-7-yl)methylamino)-4-(methylthio)butane-1,2-diol hydrochloride (41 mg, 42%) with 5% aq. HCl. $^1$H NMR (D$_2$O, referenced to internal acetone at 2.225 ppm), δ 8.95 (s, 1H), 7.93 (s, 1H), 4.69 (d, J=14.5 Hz, 1H), 4.64 (d, J=14.5 Hz, 1H), 4.27 (m, 1H), 3.82-3.70 (m, 2H), 3.62 (m, 1H), 3.04-2.86 (m, 2H), 2.02 (s, 3H). $^{13}$C NMR (D$_2$O, referenced to internal acetone at 31.5 ppm), δ 154.0, 145.9, 134.7, 133.9, 119.5, 104.4, 69.7, 63.1, 59.1, 40.8, 31.3, 15.6. +ESMS Found 299.1192 C$_{12}$H$_{19}$N$_4$O$_3$S (M+H)$^+$ free base requires 299.1178. [α]$_D^{20}$ +39.0 (c 0.6, MeOH).

Example 26

Synthesis of 7-(((2S,3S)-3,4-dihydroxy-1-(methylthio)butan-2-ylamino)methyl)-3H-pyrrolo[3,2-d]pyrimidin-4(5H)-one

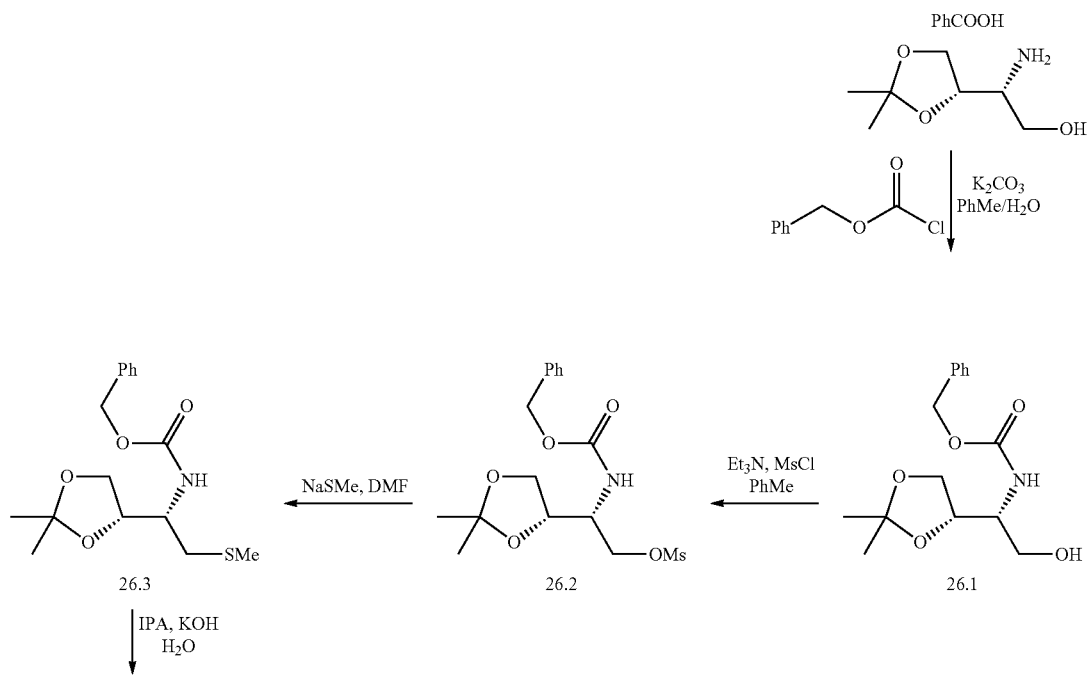

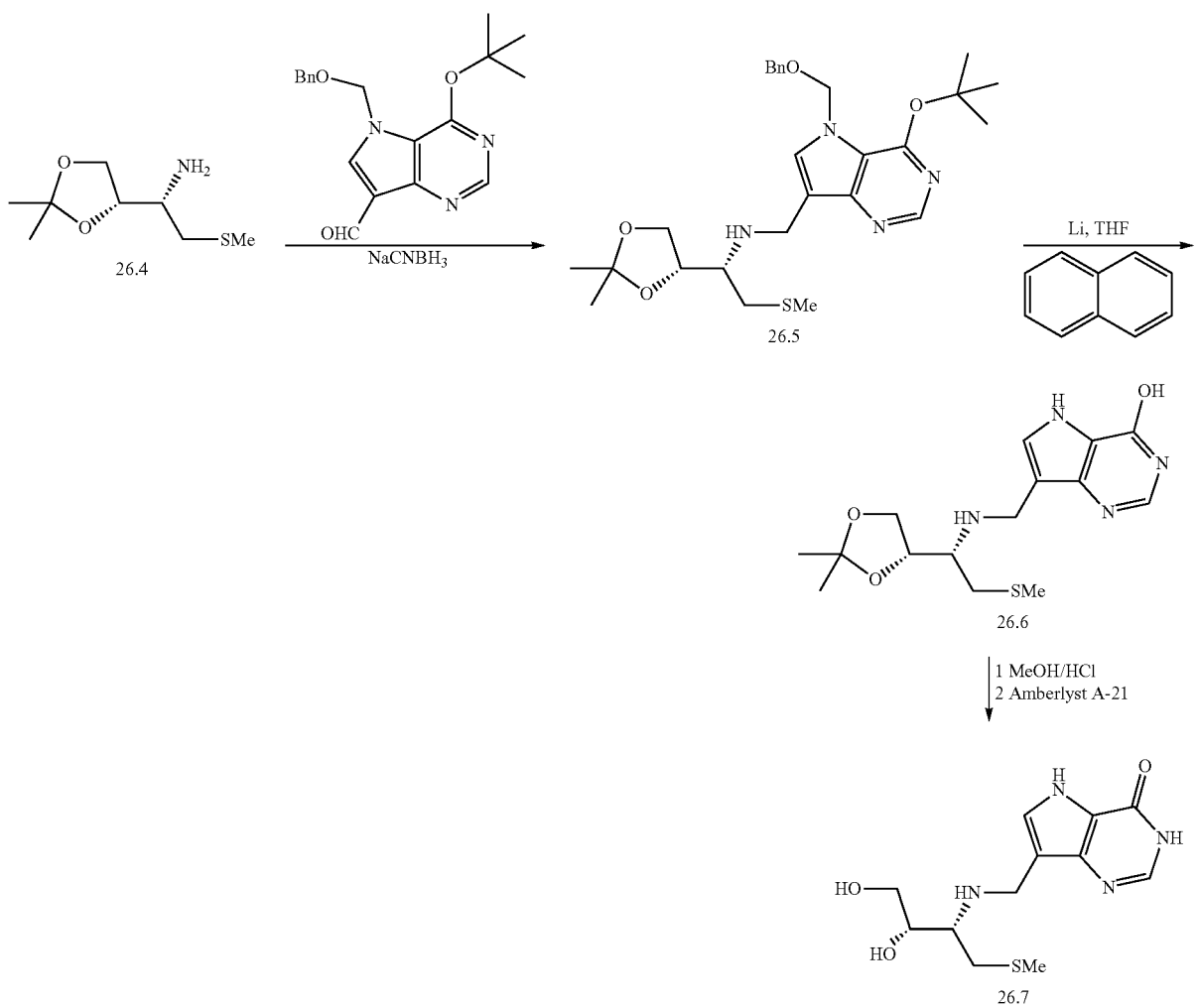

Example 26.1

Synthesis of benzyl (R)-1-((S)-2,2-dimethyl-1,3-dioxolan-4-yl)-2-hydroxyethylcarbamate The known method by T. Inaba, Y. Yamada, H. Abe, S. Sagawa and H. Cho, *J. Org. Chem.*, 2000, 65, 1623 for the preparation of the enantiomer of title compound was followed. To a stirred solution of the benzoic acid salt of (R)-2-amino-2-((S)-2,2-dimethyl-1,3-dioxolan-4-yl)ethanol (prepared as described in T. Inaba, Y. Yamada, H. Abe, S. Sagawa and H. Cho, *J. Org. Chem.*, 2000, 65, 1623) (1.616 g, 5.70 mmol) in toluene:water (1:1, 20 ml) was added potassium carbonate (0.985 g, 7.13 mmol) and then benzyl chloroformate (0.90 ml, 6.27 mmol). The reaction mixture was stirred vigorously for 16 h before addition of triethylamine (0.08 ml, 0.58 mmol) and sodium chloride (1.5 g, 25.6 mmol). After 30 minutes the layers were separated and the aqueous phase extracted with toluene. The combined organic extracts were dried (MgSO$_4$) and concentrated to give a colourless oil (1.926 g, 114%). The extra mass was determined to be residual toluene. The $^1$H NMR was in agreement with that for the enantiomer described in T. Inaba, Y. Yamada, H. Abe, S. Sagawa and H. Cho, *J. Org. Chem.*, 2000, 65, 1623.

Example 26.2

Synthesis of (R)-2-(benzyloxycarbonylamino)-2-((S)-2,2-dimethyl-1,3-dioxolan-4-yl)ethyl methanesulfonate To a stirred solution of the product from Example 26.1 (1.926 g, 6.52 mmol) in toluene (15 ml) at 0° C. was added triethylamine (1.09 ml, 7.83 mmol) and then mesyl chloride (0.56 ml, 7.17 mmol) dropwise. Once addition was complete the reaction mixture was warmed to ambient temperature and stirred for 1.5 h. The reaction mixture was washed with water and saturated aqueous sodium bicarbonate, dried (MgSO$_4$) and evaporated to give a colourless oil (2.24 g, 92%). $^1$H NMR (CDCl$_3$) δ 7.41-7.13 (m, 5H), 5.13 (ABq, 2H), 5.10 (br. s, 1H), 4.32 (dt, J=6.4, 1.9 Hz, 1H), 4.26 (d, J=6.8 Hz, 2H), 4.07 (dd, J=8.3, 6.8 Hz, 2H), 3.73 (dd, J=8.7, 6.8 Hz, 1H), 2.98 (s, 3H), 1.43 (s, 3H), 1.33 (s, 3H).

Example 26.3

Synthesis of benzyl (S)-1-((S)-2,2-dimethyl-1,3-dioxolan-4-yl)-2-(methylthio)ethyl carbamate To a stirred solution of the product from Example 26.2 (2.24 g, 6.00 mmol) in dimethylformamide (10 ml) was added sodium thiomethoxide (0.547 g, 7.80 mmol). The reaction mixture was stirred at ambient temperature for 16 h. The reaction mixture was diluted with ethyl acetate and washed with water (4×), dried (MgSO$_4$) and evaporated. The residue was chromatographed on silica gel (ethyl acetate-petrol, 1:4) giving a colourless oil (1.595 g, 82%). $^1$H NMR (CDCl$_3$) δ 7.35 (m, 5H), 5.12 (ABq, 2H), 5.07 (br. s, 1H), 4.47 (brt, J=7.2 Hz, 1H), 4.05 (t, J=7.2 Hz, 1H), 3.83 (brq, J=7.2 Hz, 1H), 3.70 (dd, J=8.3, 6.8 Hz, 1H), 2.69 (d, J=7.6 Hz, 2H), 2.15 (s, 3H), 1.42 (s, 3H), 1.34 (s, 3H).

Example 26.4

Synthesis of (S)-1-((S)-2,2-dimethyl-1,3-dioxolan-4-yl)-2-(methylthio)ethanamine A stirred solution of the product from Example 26.3 (1.595 g, 4.90 mmol) in isopropanol (27 ml) and 2M potassium hydroxide (12 ml) was heated at 80° C. for 64 h. The reaction mixture was concentrated to remove isopropanol. The residue was diluted with water and extracted with diethyl ether (2×), dried (MgSO$_4$) and evaporated. The residue was chromatographed on silica gel (ethyl acetate-petrol, 2:1 then methanol-ethyl acetate, 1:99) giving a pale yellow oil (0.575 g, 61%). $^1$H NMR (CDCl$_3$) δ 4.06 (m, 2H), 3.79 (m, 1H), 2.90 (m, 1H), 2.61 (dd, J=13.2, 4.5 Hz, 1H), 2.44 (dd, J=13.2, 8.7 Hz, 1H), 2.12 (s, 3H), 1.43 (s, 3H), 1.36 (s, 3H). $^{13}$C NMR (CDCl$_3$) δ 109.5, 79.0, 66.9, 52.7, 39.9, 26.9, 25.6, 16.3, 14.6.

Example 26.5

Synthesis of (S)—N-((5-(benzyloxymethyl)-4-tert-butoxy-5H-pyrrolo[3,2-d]pyrimidin-7-yl)methyl)-1-((S)-2,2-dimethyl-1,3-dioxolan-4-yl)-2-(methylthio)ethanamine A mixture of the product from Example 26.4 (0.130 g, 0.68 mmol), sodium cyanoborohydride (0.071 g, 1.13 mmol) and 5-(benzyloxymethyl)-4-tert-butyloxy-5H-pyrrolo[3,2-d]pyrimidin-7-carbaldehyde (0.192 g, 0.57 mmol) were evaporated from methanol (3×). The residue was dissolved in methanol (10 ml) and acetic acid added (5 drops). The reaction mixture was stirred at ambient temperature for 2 h. The reaction mixture was evaporated on to silica gel and chromatographed (methanol-triethylamine-DCM, 3:1:96) giving a yellow oil (0.274 g, 94%). $^1$H NMR indicated that the product contained some (co-polar) starting amine. $^1$H NMR (CDCl$_3$) δ 8.47 (s, 1H), 7.38 (s, 1H), 7.34-7.22 (m, 5H), 5.73 (s, 2H), 4.47 (s, 2H), 4.34 (q, J=6.8 Hz, 1H), 4.10 (Abq, 2H), 4.03 (m, 1H), 3.82 (m, 1H), 2.87 (q, J=5.7 Hz, 1H), 2.72 (dd, J=13.2, 5.7 Hz, 1H), 2.60 (dd, J=13.2, 6.0 Hz, 1H), 2.05 (s, 3H), 1.69 (s, 9H), 1.39 (s, 3H), 1.34 (s, 3H).

Example 26.6

Synthesis of 7-(((S)-1-((S)-2,2-dimethyl-1,3-dioxolan-4-yl)-2-(methylthio)ethylamino)methyl)-5H-pyrrolo[3,2-d]pyrimidin-4-ol To a stirred solution of Naphthalene (0.682 g, 5.32 mmol) in THF (10 ml) was added lithium metal (0.030 g, 4.26 mmol). The mixture was stirred at ambient temperature until an intense green colour persisted. The mixture was cooled to −30° C. and the product from Example 26.5 (0.274 g, 0.53 mmol) added dropwise as a solution in THF (3 ml). The reaction mixture was stirred at −30° C. for 1 h before addition of saturated aqueous ammonium chloride. The reaction mixture was extracted with diethyl ether (3×), dried (MgSO$_4$) and evaporated. The residue was dissolved in acetonitrile, washed with petrol (3×) and evaporated. The residue was stirred in methanol (7N ammonia solution), evaporated on to silica and chromatographed (methanol [7N ammonia solution]-DCM, 1:9) giving a white solid (0.055 g, 31%). $^1$H NMR (CD$_3$OD) δ 7.91 (s, 1H), 7.44 (s, 1H), 4.21 (q, J=6.8 Hz, 1H), 4.03 (d, J=6.0, 2H), 4.01 (m, 1H), 3.73 (dd, J=8.3, 6.8 Hz, 1H), 2.79 (m, 1H), 2.64 (dd, J=13.6, 5.3 Hz, 1H), 2.53 (dd, J=13.6, 6.8 Hz, 1H), 1.96 (s, 3H), 1.32 (s, 6H). $^{13}$C NMR (CD$_3$OD) δ 156.4, 145.4, 143.0, 129.1, 119.7, 116.8, 110.7, 79.5, 68.1, 58.4, 42.1, 36.3, 27.2, 25.9, 16.0.

Example 26.7

Synthesis of 7-(((2S,3S)-3,4-dihydroxy-1-(methylthio)butan-2-ylamino)methyl)-3H-pyrrolo[3,2-d]pyrimidin-4(5H)-one The product from Example 26.6 (0.055 g, 0.16 mmol) was stirred in a 1% hydrogen chloride solution in methanol (10 ml) for 1.5 h at ambient temperature. The reaction mixture was neutralised with Amberlyst A-21 ion exchange resin. The resin was filtered and the reaction solution concentrated. The residue was chromatographed (methanol [3.5N ammonia solution]-DCM, 1:4) giving a white solid (0.035 g, 72%). $^1$H NMR (CD$_3$OD) δ ppm 7.98 (s, 1H), 7.60 (s, 1H), 4.44 (ABq, 2H), 3.97 (q, J=3.8 Hz, 1H), 3.76 (dd, J=11.7, 4.2 Hz, 1H), 3.67 (dd, J=11.7, 3.8 Hz, 1H), 3.44 (m, 1H), 2.92 (m, 2H), 2.08 (s, 3H). $^{13}$C NMR (CD$_3$OD) δ 156.2, 145.6, 144.0, 130.7, 120.0, 109.8, 70.1, 66.0, 60.0, 41.4, 33.9, 16.0. +ESMS Found 299.1194: (M+H)$^+$ C$_{12}$H$_{19}$N$_4$O$_3$S requires 299.1178:

Example 27
Synthesis of 7-(((2R,3R)-3,4-dihydroxy-1-(methylthio)butan-2-ylamino)methyl)-3H-pyrrolo[3,2-d]pyrimidin-4(5H)-one
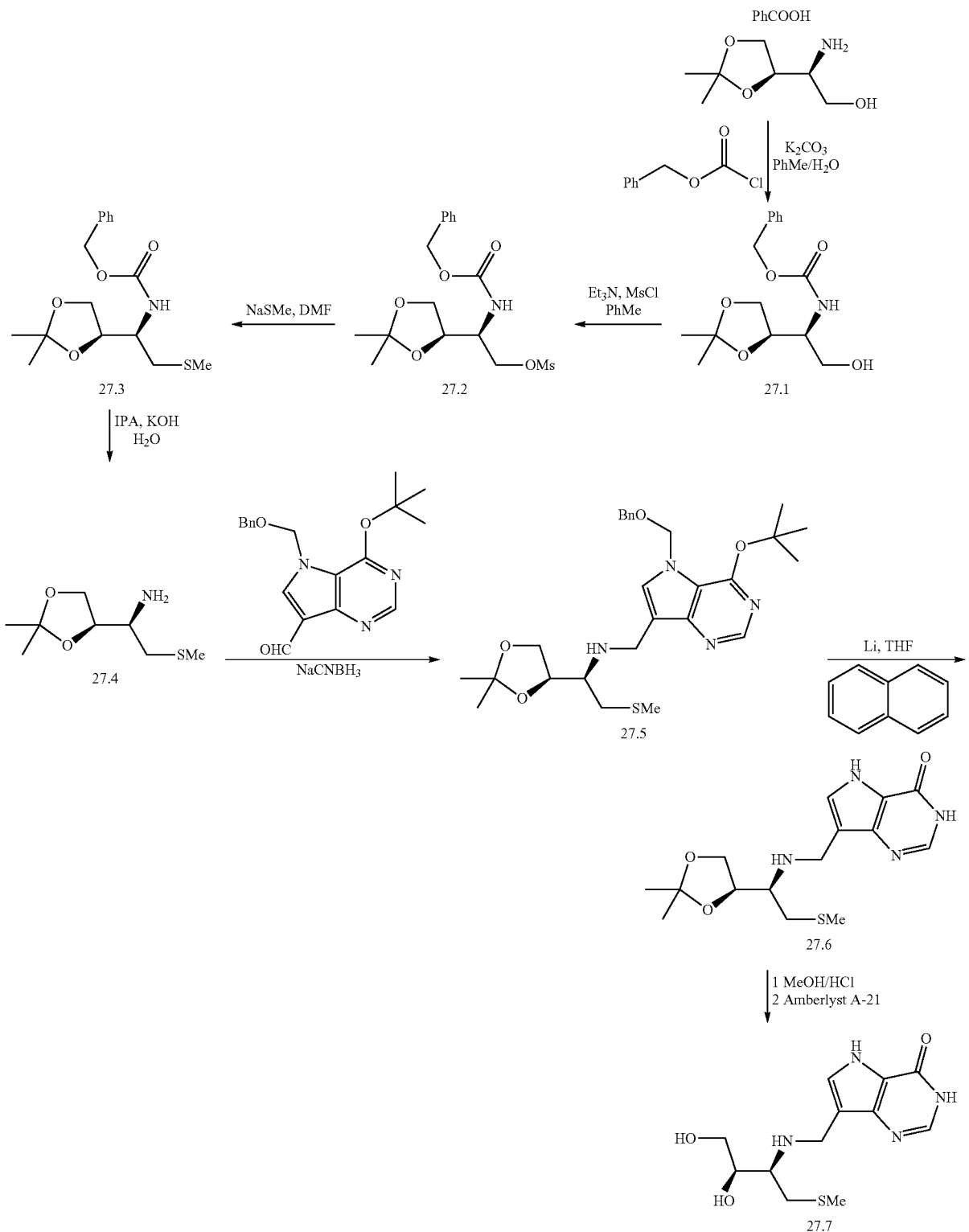

Example 27.1

Synthesis of benzyl (S)-1-((R)-2,2-dimethyl-1,3-dioxolan-4-yl)-2-hydroxyethylcarbamate The known method by T. Inaba, Y. Yamada, H. Abe, S. Sagawa and H. Cho, *J. Org. Chem.*, 2000, 65, 1623 for the preparation of the title compound was followed. To a stirred solution of the benzoic acid salt of (S)-2-amino-2-((R)-2,2-dimethyl-1,3-dioxolan-4-yl)ethanol (prepared as described in T. Inaba, Y. Yamada, H. Abe, S. Sagawa and H. Cho, *J. Org. Chem.*, 2000, 65, 1623) (2.083 g, 7.35 mmol) in toluene:water (1:1, 20 ml) was added potassium carbonate (1.27 g, 9.19 mmol) and then benzyl chloroformate (1.16 ml, 8.09 mmol). The reaction mixture was stirred vigorously for 3 h before addition of triethylamine (0.10 ml, 0.72 mmol) and sodium chloride (1.5 g, 25.6 mmol). After 10 minutes the layers were separated and the aqueous phase extracted with toluene. The combined organic extracts were dried ($MgSO_4$) and concentrated to give a colourless oil (2.17 g, 100%). The $^1H$ NMR was in agreement with that for the compound described in T. Inaba, Y. Yamada, H. Abe, S. Sagawa and H. Cho, *J. Org. Chem.*, 2000, 65, 1623.

Example 27.2

Synthesis of (S)-2-(benzyloxycarbonylamino)-2-((R)-2,2-dimethyl-1,3-dioxolan-4-yl)ethyl methanesulfonate To a stirred solution of the product from Example 27.1 (2.17 g, 7.35 mmol) in toluene (20 ml) at 0° C. was added triethylamine (1.23 ml, 8.82 mmol) and then mesyl chloride (0.63 ml, 8.08 mmol) dropwise. Once addition was complete the reaction mixture was warmed to ambient temperature and stirred for 1.5 h. The reaction mixture was washed with water and saturated aqueous sodium bicarbonate, dried ($MgSO_4$) and evaporated to give a colourless oil (2.58 g, 94%). $^1H$ NMR ($CDCl_3$) δ 7.41-7.13 (m, 5H), 5.13 (ABq, 2H), 5.10 (br. s, 1H), 4.32 (dt, J=6.4, 1.9 Hz, 1H), 4.26 (d, J=6.8 Hz, 2H), 4.07 (dd, J=8.3, 6.8 Hz, 2H), 3.73 (dd, J=8.7, 6.8 Hz, 1H), 2.98 (s, 3H), 1.43 (s, 3H), 1.33 (s, 3H).

Example 27.3

Synthesis of benzyl (R)-1-((R)-2,2-dimethyl-1,3-dioxolan-4-yl)-2-(methylthio)ethylcarbamate To a stirred solution of the product from Example 27.2 (2.58 g, 6.91 mmol) in dimethylformamide (10 ml) was added sodium thiomethoxide (0.630 g, 8.98 mmol). The reaction mixture was stirred at ambient temperature for 16 h. The reaction mixture was diluted with ethyl acetate and washed with water (4×), dried ($MgSO_4$) and evaporated. The residue was chromatographed on silica gel (ethyl acetate-petrol, 1:4) giving a colourless oil (2.007 g, 89%). $^1H$ NMR ($CDCl_3$) δ 7.35 (m, 5H), 5.12 (ABq, 2H), 5.07 (br. s, 1H), 4.47 (bit, J=7.2 Hz, 1H), 4.05 (t, J=7.2 Hz, 1H), 3.83 (brq, J=7.2 Hz, 1H), 3.70 (dd, J=8.3, 6.8 Hz, 1H), 2.69 (d, J=7.6 Hz, 2H), 2.15 (s, 3H), 1.42 (s, 3H), 1.34 (s, 3H).

Example 27.4

Synthesis of (R)-1-((R)-2,2-dimethyl-1,3-dioxolan-4-yl)-2-(methylthio)ethanamine A stirred solution of the product from Example 27.3 (2.007 g, 6.17 mmol) in isopropanol (34 ml) and 2M potassium hydroxide (15 ml) was heated at 80° C. for 64 h. The reaction mixture was concentrated to remove isopropanol. The residue was diluted with water and extracted with diethyl ether (3×), dried ($MgSO_4$) and evaporated. The residue was chromatographed on silica gel (ethyl acetate-petrol, 2:1 then methanol-ethyl acetate, 2:98) giving a pale yellow oil (0.913 g, 77%). $^1H$ NMR ($CDCl_3$) δ 4.06 (m, 2H), 3.79 (m, 1H), 2.90 (m, 1H), 2.61 (dd, J=13.2, 4.5 Hz, 1H), 2.44 (dd, J=13.2, 8.7 Hz, 1H), 2.12 (s, 3H), 1.43 (s, 3H), 1.36 (s, 3H). $^{13}C$ NMR ($CDCl_3$) δ 109.5, 79.0, 66.9, 52.7, 39.9, 26.9, 25.6, 16.3, 14.6.

Example 27.5

(R)—N-((5-(benzyloxymethyl)-4-tert-butoxy-5H-pyrrolo[3,2-d]pyrimidin-7-yl)methyl)-1-((R)-2,2-dimethyl-1,3-dioxolan-4-yl)-2-(methylthio)ethanamine A mixture of the product from Example 27.4 (0.130 g, 0.68 mmol), sodium cyanoborohydride (0.071 g, 1.13 mmol) and 5-(benzyloxymethyl)-4-tert-butyloxy-5H-pyrrolo[3,2-d]pyrimidin-7-carbaldehyde (0.192 g, 0.57 mmol) were evaporated from methanol (3×). The residue was dissolved in methanol (10 ml) and acetic acid added (5 drops). The reaction mixture was stirred at ambient temperature for 2 h. The reaction mixture was evaporated on to silica gel and chromatographed (methanol-triethylamine-DCM, 3:1:96) giving an orange oil (0.272 g, 93%). $^1H$ NMR indicated that the product contained some (co-polar) starting amine. $^1H$ NMR ($CDCl_3$) δ 8.47 (s, 1H), 7.38 (s, 1H), 7.34-7.22 (m, 5H), 5.73 (s, 2H), 4.47 (s, 2H), 4.34 (q, J=6.8 Hz, 1H), 4.10 (Abq, 2H), 4.03 (m, 1H), 3.82 (m, 1H), 2.87 (q, J=5.7 Hz; 1H), 2.72 (dd, J=13.2, 5.7 Hz, 1H), 2.60 (dd, J=13.2, 6.0 Hz, 1H), 2.05 (s, 3H), 1.69 (s, 9H), 1.39 (s, 3H), 1.34 (s, 3H).

Example 27.6

7-(((R)-1-((R)-2,2-dimethyl-1,3-dioxolan-4-yl)-2-(methylthio)ethylamino)methyl)-3H-pyrrolo[3,2-d]pyrimidin-4(5H)-one To a stirred solution of Naphthalene (0.677 g, 5.28 mmol) in THF (10 ml) was added lithium metal (0.029 g, 4.23 mmol). The mixture was stirred at ambient temperature until an intense green colour persisted. The mixture was cooled to −78° C. and the product from Example 27.5 (0.272 g, 0.53 mmol) added dropwise as a solution in THF (3 ml). The reaction mixture was stirred at −78° C. for 1 h before addition of saturated aqueous ammonium chloride. The reaction mixture was extracted with diethyl ether (3×), dried ($MgSO_4$) and evaporated. The residue was dissolved in acetonitrile, washed with petrol (3×) and evaporated. The residue was stirred in methanol (7N ammonia solution), evaporated on to silica and chromatographed (methanol [7N ammonia solution]-DCM, 1:9) giving a white solid (0.049 g, 27%). $^1H$ NMR ($CD_3OD$) δ 7.91 (s, 1H), 7.44 (s, 1H), 4.21 (q, J=6.8 Hz, 1H), 4.03 (d, J=6.0, 2H), 4.01 (m, 1H), 3.73 (dd, J=8.3, 6.8 Hz, 1H), 2.79 (m, 1H), 2.64 (dd, J=13.6, 5.3 Hz, 1H), 2.53 (dd, J=13.6, 6.8 Hz, 1H), 1.96 (s, 3H), 1.32 (s, 6H). $^{13}C$ NMR ($CD_3OD$) δ 156.4, 145.4, 143.0, 129.1, 119.7, 116.8, 110.7, 79.6, 68.1, 58.4, 42.1, 36.3, 27.2, 25.9, 16.0.

Example 27.7

Synthesis of 7-(((2R,3R)-3,4-dihydroxy-1-(methylthio)butan-2-ylamino)methyl)-3H-pyrrolo[3,2-d]pyrimidin-4(5H)-one The product from Example 27.6 (0.049 g, 0.15 mmol) was stirred in a 1% hydrogen chloride solution in methanol (10 ml) for 3 h at ambient temperature. The reaction mixture was neutralised with Amberlyst A-21 ion exchange resin. The resin was filtered and the reaction solution concentrated. The residue was chromatographed (methanol [3,5N ammonia solution]-DCM, 1:4) giving a white solid (0.036 g, 83%). $^1$H NMR revealed this compound to be identical to the enantiomer from Example 26.7. +ESMS Found 299.1180 (M+H)$^+$ $C_{12}H_{19}N_4O_3S$ requires 299.1178.

Example 28

Synthesis of 7-(((2RS,3SR)-3,4-dihydroxy-2-(methylthiomethyl)butylamino)methyl)-3H-pyrrolo[3,2-d]pyrimidin-4(5H)-one phase mixture stirred vigorously for 3 h. The mixture was diluted with EtOAc and washed with aq. sat. NaHCO$_3$, dried (MgSO$_4$) and the solvent evaporated. The residue was chromatographed on silica gel (EtOAc-hexanes, 6:4) to give (±)-benzyl (R/S)-2-((R/S)-2,2-dimethyl-1,3-dioxolan-4-yl)-3-hydroxypropylcarbamate (0.423 g, 73%) as a pale yellow oil. $^1$H NMR (CDCl$_3$) δ ppm 7.40-7.28 (m, 5H), 5.11 (s, 3H, became a s, 2H after D$_2$O exchange), 4.17-4.05 (m, 2H), 3.75 (brt, J=6.2 Hz, became brd after D$_2$O exchange, 3H), 3.31 (brt, J=6.2 Hz, became a brd after D$_2$O exchange, 2H), 2.77 (bit, 1H, exchanged to D$_2$O), 1.87 (m, 1H), 1.41 (s, 3H), 1.34 (s, 3H). $^{13}$C NMR (CDCl$_3$, referenced to the centre line of CDCl$_3$ at 77.0 ppm) δ 157.2, 136.3, 128.5, 128.2, 128.1,

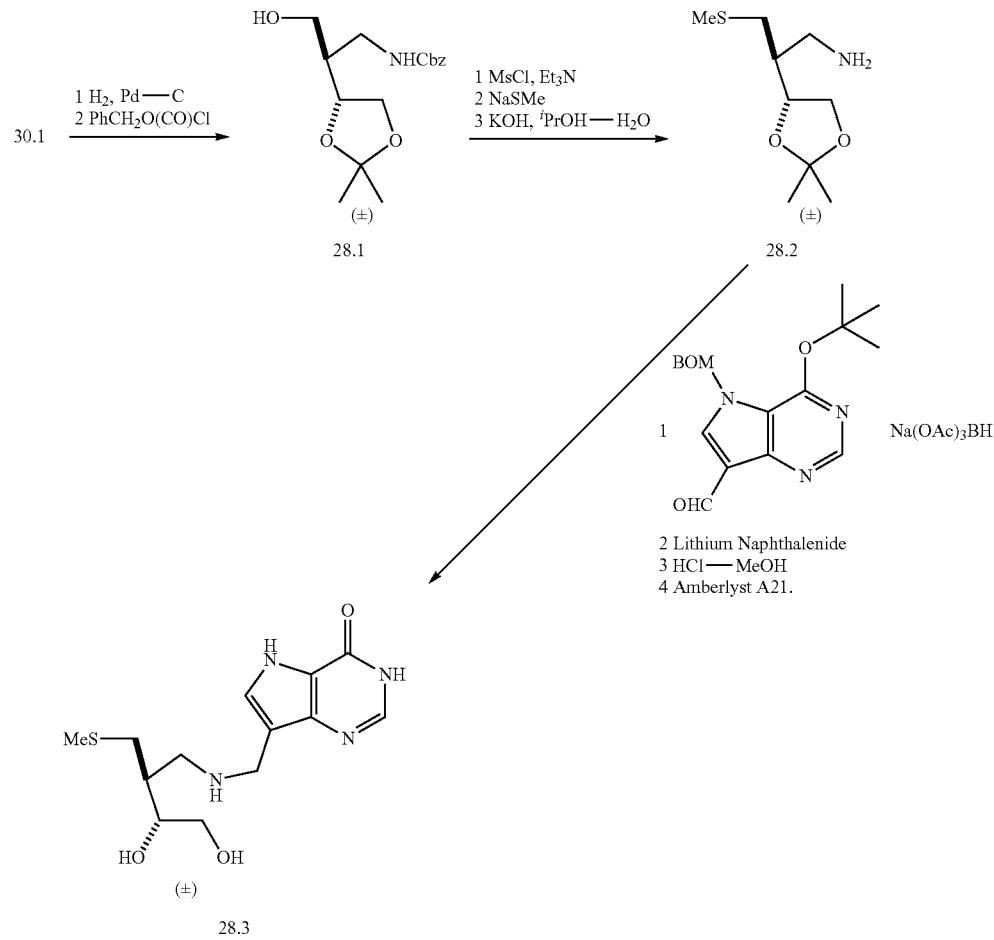

108.9, 76.1, 67.6, 67.0, 60.9, 43.9, 39.5, 26.5, 25.3. +ESMS Found 332.1464 (M+Na)$^+$ $C_{16}H_{23}NaNO_5$ requires 332.1474.

Example 28.2

Synthesis of (±)-(S/R)-2-((R/S)-2,2-dimethyl-1,3-dioxolan-4-yl)-3-(methylthio)propan-1-amine Methanesulfonyl chloride (0.121 ml, 1.552 mmol) was added to a solution of the product from Example 28.1 (0.4 g, 1.293 mmol) and triethylamine (0.273 ml, 1.940 mmol) in CH$_2$Cl$_2$ (5 ml) whilst cooled in an ice bath. The mixture was warmed to rt and stirred for 30 mins. The mixture was diluted Example 28.1

Synthesis of (±)-benzyl (R/S)-2-((R/S)-2,2-dimethyl-1,3-dioxolan-4-yl)-3-hydroxypropylcarbamate The product from Example 30.1 (0.5 g, 1.884 mmol) was dissolved in MeOH (10 ml), 10% Pd—C (100 mg) added and the mixture stirred under hydrogen added from a balloon for 16 h. Filtration through Celite and evaporation of the solvent gave a colourless gum (320 mg). The residue was dissolved in a mixture of toluene (3 ml) and water (3 ml) then potassium carbonate (0.391 g, 2.83 mmol) and benzyl chloroformate (0.637 ml, 1.884 mmol, 50% in toluene) added and the 2 with CH$_2$Cl$_2$ and washed with aq. sat. NaHCO$_3$, dried (MgSO$_4$) and the solvent evaporated to give the crude mesylate. This was dissolved in DMF (2 ml), sodium thiomethoxide (0.181 g, 2.59 mmol) and the mixture stirred for 1.5 h at rt. Diethyl ether (60 ml) was added and the mixture washed with water (4×5 ml), brine (1×5 ml), dried (MgSO$_4$) and the solvent evaporated. The residue was dissolved in a mixture of $^i$PrOH (8 ml) and 2M aq. KOH (3.6 ml) and heated to 80° C. for 64 h. The solvent was evaporated and the residue dissolved in diethyl ether (60 ml) and washed with water (×1), brine (×1), dried (MgSO$_4$) and the solvent evaporated. The residue was chromatographed on silica gel (CH$_2$Cl$_2$-7M NH$_3$ in MeOH, 97:3) to give (±)-(S/R)-2-((R/S)-2,2-dimethyl-1,3-dioxolan-4-yl)-3-(methylthio)propan-1-amine (0.189 g, 71%) as a colourless oil. $^1$H NMR (CDCl$_3$) δ 4.20 (q, J=6.7 Hz, 1H), 4.06 (dd, J=8.1, 6.4 Hz, 1H), 3.70 (t, J=7.7 Hz, 1H), 2.83-2.74 (m, 3H), 2.61 (dd, J=13.1, 8.1 Hz, 1H), 2.13 (s, 3H), 1.79 (m, 1H), 1.41 (s, 3H), 1.35 (s, 3H), 1.21 (b. s, 2H, exchanged to D$_2$O). $^{13}$C NMR (CDCl$_3$) δ 108.6, 76.5, 67.6, 44.2, 41.9, 33.3, 26.6, 25.3, 16.4. +ESMS Found 206.1223 (M+H)+C$_9$H$_{20}$NO$_2$S requires 206.1215.

Example 28.3

Synthesis of 7-(((2RS,3SR)-3,4-dihydroxy-2-(methylthiomethyl)butylamino)methyl)-3H-pyrrolo[3,2-d]pyrimidin-4(5H)-one Sodium triacetoxyborohydride (0.134 g, 0.633 mmol) was added to a solution of 5-(benzyloxymethyl)-4-tert-butoxy-5H-pyrrolo[3,2-d]pyrimidine-7-carbaldehyde (0.165 g, 0.487 mmol, prepared as described in G. B. Evans, R. H. Furneaux, A. Lewandowicz, V. L. Schramm and P. C. Tyler, *J. Med. Chem.*, 2003, 46, 5271) and the product from Example 28.2 (0.1 g, 0.487 mmol) in 1,2-dichloroethane (4 ml). MgSO$_4$ (150 mg) added and the mixture stirred for 16 h at rt. CH$_2$Cl$_2$ was added and the mixture was washed with aq. sat. NaHCO$_3$, dried (MgSO$_4$) and the solvent evaporated. The residue was chromatographed on silica gel (EtOAc-CH$_2$Cl$_2$-7M NH$_3$ in MeOH, 4.95:4.95:0.1 then 5.95:3.95:0.1) to give a yellow gum (191 mg) which by $^1$H NMR consisted of (±)-(S/R)—N-((5-benzyloxymethyl)-4-tert-butoxy-5H-pyrrolo[3,2-d]pyrimidin-7-yl)methyl)-2-((R/S)-2,2-dimethyl-1,3-dioxolan-4-yl)-3-(methylthio)propan-1-amine contaminated with ~8 wt % of the product from Example 28.2. Without further purification it was dissolved in dry THF (1 ml) and added to a solution of lithium naphthalenide [prepared from lithium (0.023 g, 3.33 mmol) and naphthalene (0.512 g, 3.99 mmol) in dry THF (8 ml) according to H.-J. Liu, J. Yip and K.-S Shia, *Tetrahedron Lett.*, 1997, 38, 2253] at −78° C. and the dark green mixture was stirred for 10 min. Water (2 ml) was added to give a colourless solution and the mixture warmed to rt. The solvent was evaporated and the residue stirred with 7M NH$_3$-MeOH solution (10 ml) for 10 mins. The solvent was evaporated and the residue chromatographed on silica gel (CH$_2$Cl$_2$ then CH$_2$Cl$_2$-7M NH$_3$-MeOH, 9:1) to give intermediate (±)-7(((S/R)-2-((R/S)-2,2-dimethyl-1,3-dioxolan-4-yl)-3-(methylthio)propylamino)methyl)-5H-pyrrolo[3,2-d]pyrimidin-4-ol (72 mg). The latter was dissolved in MeOH (10 ml) containing acetyl chloride (0.237 ml, 3.33 mmol) and stirred at rt for 4 h. The solution was neutralized with Amberlyst A21 resin, filtered and the solvent evaporated. The residue was chromatographed on silica gel (CH$_2$Cl$_2$-7M NH$_3$-MeOH, 8:2) to give racemiv 7-(((2RS,3SR)-3,4-dihydroxy-2-(methylthiomethyl)butylamino)methyl)-3H-pyrrolo[3,2-d]pyrimidin-4(5H)-one as a colourless solid (17 mg, 16%). $^1$H NMR (D$_2$O, referenced to internal acetone at 2.225 ppm) δ 8.07 (s, 1H), 7.71 (s, 1H), 4.43 (s, 2H), 3.88 (m, 1H), 3.68-3.54 (m, 2H), 3.37-3.25 (m, 2H), 2.71 (dd, J=13.7, 4.6 Hz, 1H), 2.47 (dd, J=13.7, 9.3 Hz, 1H), 2.25 (m, 1H), 2.04 (s, 3H). $^{13}$C NMR (D$_2$O, referenced to internal acetone at 31.5 ppm) δ 156.3, 145.1, 144.1, 132.2, 119.0, 107.0, 73.0, 63.5, 48.6, 42.3, 39.1, 32.8, 15.8. +ESMS Found 313.1324 (M+H)$^+$ C$_{13}$H$_{21}$N$_4$O$_3$S, requires 313.1334.

Example 29

Synthesis of 7-((benzyl((2RS,3SR)-3,4-dihydroxy-2-(methylthiomethyl)butyl)amino)methyl)-3H-pyrrolo[3,2-d]pyrimidin-4(5H)-one

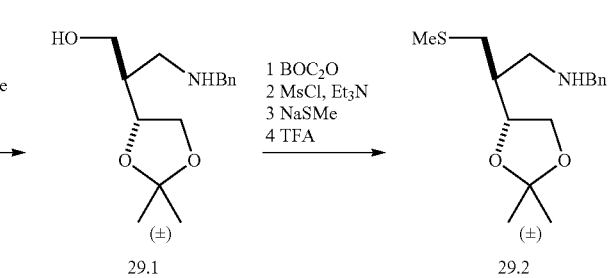

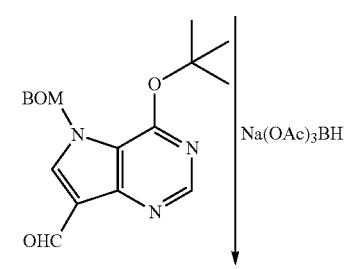

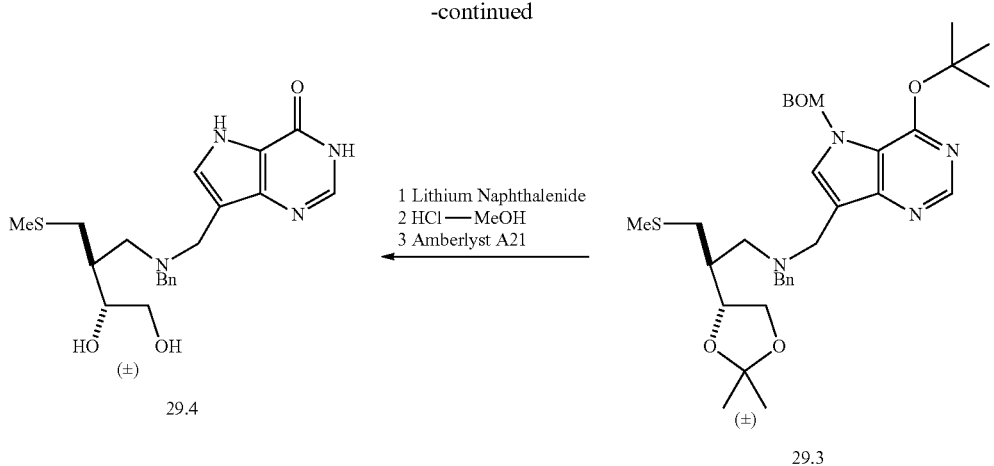

(±) 29.4

(±) 29.3

Example 29.1

Synthesis of (±)-(R/S)-3-(benzylamino)-2((R/S)-2,2-dimethyl-1,3-dioxalan-4-yl)propan-1-ol To a solution of the product from Example 21.2 (0.74 g, 3.28 mmol) in acetone (15 mL) and 2,2-dimethoxypropane (5 mL) was added 1R-(−)-camphorsulfonic acid (0.916 g, 3.94 mmol) and the mixture stirred at rt for 1 h. Triethylamine (0.916 ml, 6.57 mmol) was added and the solvent was evaporated. The residue was dissolved in CHCl$_3$ and washed with 10% aq Na$_2$CO$_3$, dried (MgSO$_4$) and the solvent evaporated. The residue was chromatographed on silica gel (CHCl$_3$-EtOAc-MeOH, 5:2:1) to give (±)-(R/S)-3-(benzylamino)-2-((R/S)-2,2-dimethyl-1,3-dioxalan-4-yl)propan-1-ol as a syrup (0.55 g, 63%). $^1$H NMR (CDCl$_3$) δ 7.36-7.23 (m, 5H), 4.04-3.97 (m, 2H), 3.89 (dd, J=10.9, 4.3 Hz, 1H), 3.82-3.62 (m, 4H), 3.10 (br. s, 2H), 2.79 (dd, J=11.8, 4.0 Hz, 1H), 2.71 (dd, J=11.8, 8.8 Hz, 1H), 1.94 (m, 1H), 1.39 (s, 3H), 1.33 (s, 3H). $^{13}$C NMR (CDCl$_3$, referenced to the centre line of CDCl$_3$ at 77.0 ppm) δ 139.1, 128.5, 128.1, 127.3, 108.8, 76.2, 67.8, 64.8, 54.0, 50.5, 43.3, 26.5, 25.3.

Example 29.2

Synthesis of (±)-(S/R)—N-benzyl-2-((R/S)-2,2-dimethyl-1,3-dioxolan-4-yl)-3-(methylthio)propan-1-amine The product from Example 30.1 (0.5 g, 1.884 mmol) and di-tert-butyl dicarbonate (0.452 g, 2.073 mmol) were stirred together in MeOH (10 ml) for 1 h. The solvent was evaporated and the residue of (±)-tert-butyl benzyl ((R/S)-2-((R/S)-2,2-dimethyl-1,3-dioxolan-4-yl)-3-hydroxypropyl)carbamate was dissolved in CH$_2$Cl$_2$ (10 ml) and triethylamine (0.394 ml, 2.83 mmol) added. The mixture was cooled in an ice bath and methanesulfonyl chloride (0.176 ml, 2.261 mmol) was added dropwise. The mixture was warmed to rt and stirred for 30 min. then washed with aq. sat. NaHCO$_3$, dried (MgSO$_4$) and the solvent evaporated to give crude (±)-(R/S)-3-(benzyl(tert-butoxycarbonyl)amino)-2-((R/S)-2,2-dimethyl-1,3-dioxolan-4-yl)propyl methanesulfonate. The latter was dissolved in DMF (3 ml) and sodium thiomethoxide (0.264 g, 3.77 mmol) added. After stirring at rt for 3 h the mixture was diluted with diethyl ether (50 ml) and washed with water (4×5 ml), dried (MgSO$_4$) then the solvent evaporated. The residue was chromatographed on silica gel (EtOAc-hexanes, 15:85) to give (±)-tert-butyl benzyl((S/R)-2-((R/S)-2,2-dimethyl-1,3-dioxolan-4-yl)-3-(methylthio)propyl)carbamate as a colourless gum (421 mg) which was dissolved in a mixture of CH$_2$Cl$_2$ (10 ml) and TFA (1 ml) and stirred for 70 mins. The mixture was diluted with CH$_2$Cl$_2$ and washed with aq. sat. NaHCO$_3$, dried (MgSO$_4$) and the solvent evaporated. The residue was chromatographed on silica gel (toluene-acetone, 13:1) to give (±)-(S/R)—N-benzyl-2-((R/S)-2,2-dimethyl-1,3-dioxolan-4-yl)-3-(methylthio)propan-1-amine (0.13 g, 23%) as a pale yellow oil. $^1$H NMR (CDCl$_3$) δ 7.39-7.20 (m, 5H), 4.17 (q, J=6.8 Hz, 1H), 4.03 (dd, J=8.1, 6.2 Hz, 1H), 3.77 (s, 2H), 3.68 (t, J=7.8 Hz, 1H), 2.78 (dd, J=13.1, 4.3 Hz, 1H), 2.73-2.64 (m, 2H), 2.60 (dd, J=13.1 7.9 Hz, 1H), 2.11 (s, 3H), 1.92 (m, 1H), 1.70 (br. s, 1H, exchanged to D$_2$O), 1.38 (s, 3H), 1.34 (s, 3H). $^{13}$C NMR (CDCl$_3$, referenced to the centre line of CDCl$_3$ at 77.0 ppm) δ 140.3, 128.4, 128.1, 126.9, 108.5, 76.9, 67.8, 54.2, 49.3, 42.1, 34.3, 26.6, 25.4, 16.5. +ESMS Found 296.1683 C$_{16}$H$_{26}$NO$_2$S (M+H)$^+$ requires 296.1684.

Example 29.3

Synthesis of (±)-(S/R)—N-benzyl-N-((5-(benzyloxymethyl)-4-tert-butoxy-5H-pyrrolo[3,2-d]pyrimidin-7-yl)methyl)-2-((R/S)-2,2-dimethyl-1,3-dioxolan-4-yl)-3-(methylthio)propan-1-amine Sodium triacetoxyborohydride (0.140 g, 0.660 mmol) was added to a solution of 5-(benzyloxymethyl)-4-tert-butoxy-5H-pyrrolo[3,2-d]pyrimidine-7-carbaldehyde (0.172 g, 0.508 mmol, prepared as described in G. B. Evans, R. H. Furneaux, A. Lewandowicz, V. L. Schramm and P. C. Tyler, *J. Med. Chem.*, 2003, 46, 5271) and the product from Example 30.2 (0.15 g, 0.508 mmol) in 1,2-dichloroethane (4 ml). MgSO$_4$ (200 mg) was added and the mixture stirred for 4 h. The mixture was diluted with CH$_2$Cl$_2$ and washed with aq. sat. NaHCO$_3$, dried (MgSO$_4$) and the solvent evaporated. The residue was chromatographed on silica gel (EtOAc-hexanes, 25:75) to give (±)-(S/R)—N-benzyl-N-((5-(benzyloxymethyl)-4-tert-butoxy-5H-pyrrolo[3,2-d]pyrimidin-7-yl)methyl)-2-((R/S)-2,2-dimethyl-1,3-dioxolan-4-yl)-3-(methylthio)propan-1-amine (0.2 g, 63%) as a yellow gum. $^1$H NMR (CDCl$_3$) δ 8.48 (s, 1H), 7.39-7.19 (m, 11H), 5.76 (s, 2H), 4.47 (s, 2H), 4.07-3.91 (m, 2H), 3.89 (d, J=14.3 Hz, 1H), 3.80 (d, J=14.3 Hz, 1H), 3.72 (t, J=7.6 Hz, 1H), 3.67 (d, J=13.8 Hz, 1H), 3.55 (d, J=13.8 Hz, 1H), 2.79 (dd, J=13.1, 3.8

Hz, 1H), 2.60 (dd, J=12.9, 6.5 Hz, 1H), 2.52 (dd, J=13.1, 6.8 Hz, 1H), 2.43 (dd, J=12.9, 7.2 Hz, 1H), 2.17-2.05 (m, 1H), 2.06 (s, 3H), 1.70 (s, 9H), 1.34 (s, 3H), 1.27 (s, 3H). $^{13}$C NMR (CDCl$_3$, referenced to the centre line of CDCl$_3$ at 77.0 ppm) δ 155.7, 150.7, 149.6, 139.5, 137.2, 131.7, 128.9, 128.4, 128.2, 127.8, 127.4, 126.8, 116.6, 114.0, 108.0, 82.7, 77.0, 76.8, 69.9, 68.0, 59.1, 54.4, 47.1, 40.5, 34.6, 28.7, 26.6, 25.5, 16.8. +ESMS Found 619.3315 C$_{35}$H$_{47}$N$_4$O$_4$S (M+H)$^+$ requires 619.3318.

Example 29.4

Synthesis of 7-((benzyl((2RS,3SR)-3,4-dihydroxy-2-(methylthiomethyl)butyl)amino)methyl)-3H-pyrrolo[3,2-d]pyrimidin-4(5H)-one A solution of lithium naphthalenide (H.-J. Liu, J. Yip and K.-S Shia, *Tetrahedron Lett.*, 1997, 38, 2253) was prepared by adding tiny pieces of lithium (0.018 g, 2.59 mmol) to a solution of naphthalene (0.414 g, 3.23 mmol) in dry THF (8 ml) under Ar and stirring for 3 h at rt. The resulting dark green solution was cooled to –78° C. and the product from Example 30.3 (0.2 g, 0.32 mmol) dissolved in THF (1.5 ml) was added. After 10 mins water (1 ml) was added, the mixture allowed to warm to rt then the solvent evaporated. The residue was dissolved in 7M NH$_3$-MeOH solution (10 ml) and left at rt for 10 mins then the solvent evaporated and the residue chromatographed on silica gel (CH$_2$Cl$_2$ then CH$_2$Cl$_2$-7M NH$_3$ in MeOH, 9:1) to, give intermediate (±)-7-((benzyl((S/R)-2,((R/S)-2,2-dimethyl-1,3-dioxolan-4-yl)-3-(methylthio)propyl)amino)methyl)-5H-pyrrolo[3,2-d]pyrimidin-4-ol as a yellow foam (120 mg). A portion of the latter compound (0.031 g, 0.07 mmol) was dissolved in 2% HCl-MeOH solution (6 ml) and stirred for 30 mins then neutralized with Amberlyst A21 resin. The resin was filtered off, the solvent evaporated and the residue chromatographed on silica gel (CH$_2$Cl$_2$-7M NH$_3$ in MeOH, 9:1 then 85:15) to give racemic 7-((benzyl((2RS, 3SR)-3,4-dihydroxy-2-(methylthiomethyl)butyl)amino)methyl)-3H-pyrrolo[3,2-d]pyrimidin-4(5H)-one as a colourless solid (11 mg, 39%). $^1$H NMR (CD$_3$OD) δ 7.89 (s, 1H), 7.38 (s, 1H), 7.37-7.20 (m, 5H), 3.93 (d, J=13.9 Hz, 1H), 3.78 (d, J=13.4 Hz, 1H), 3.72-3.64 (m, 2H), 3.45 (d, J=13.4 Hz, 1H), 3.41-3.28 (m, 2H+ CD$_3$OD), 2.74-2.52 (m, 3H), 2.39 (dd, J=13.2, 7.8 Hz, 1H), 2.18 (m, 1H), 2.05 (s, 3H). $^{13}$C NMR (CD$_3$OD, referenced to the centre line of CD$_3$OD at 49.0 ppm) δ 156.0, 145.6, 142.7, 140.0, 130.6, 129.7, 129.3, 128.2, 119.1, 114.6, 74.9, 65.1, 59.9, 56.1, 48.3, 40.4, 35.4, 16.3. +ESMS Found 403.1812 (M+H)$^+$ C$_{20}$H$_{27}$N$_4$O$_3$S requires 403.1804.

Example 30

(S)-7-(1-(1,3-dihydroxypropan-2-ylamino)-2-hydroxyethyl)-3H-pyrrolo[3,2-d]pyrimidin-4(5H)-one hydrochloride

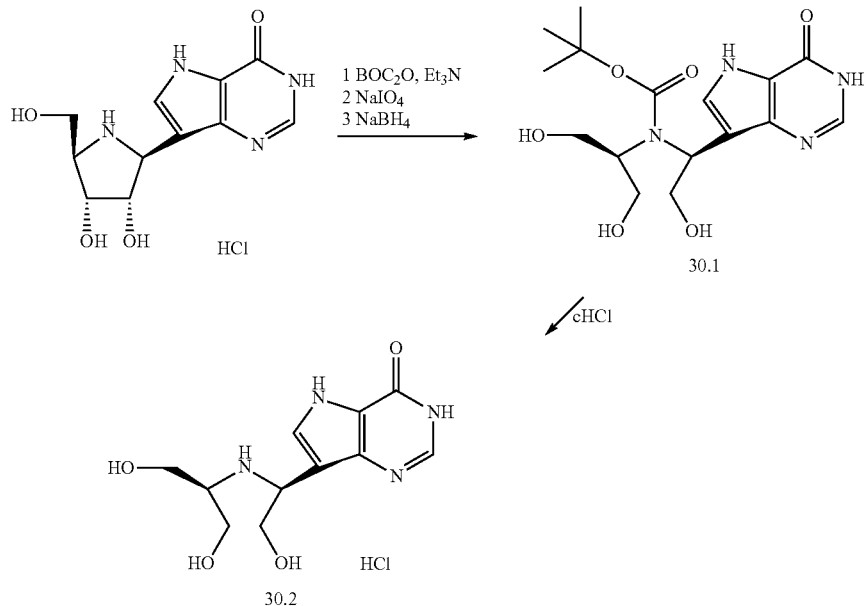

Example 30.1

Synthesis of (S)-tert-butyl 1,3-dihydroxypropan-2-yl (2-hydroxy-1-(4-oxo-4,5-dihydro-3H-pyrrolo[3,2-d]pyrimidin-7-yl)ethyl)carbamate Di-tert-butyl Bicarbonate (0.091 g, 0.416 mmol) was added to a solution of (2S,3S,4R,5R)-2-(4-hydroxy-5H-pyrrolo[3,2-d]pyrimidin-7-yl)-5-(hydroxymethyl)pyrrolidine-3,4-diol hydrochloride (0.07 g, 0.231 mmol, synthesized according to G. B. Evans, R. N. Furneaux, G. J. Gainsford, V. L. Schramm and P. C. Tyler, *Tetrahedron*, 2000, 56, 3053) and triethylamine (0.065 ml, 0.462 mmol) in a mixture of water (1 ml) and MeOH (3 ml). The solution was stirred for 30 mins., then the solvent evaporated to give 116 mg of a colourless solid which consisted, as estimated by $^1$H NMR, of about 78 mg, 0.213 mmol of (2S,3S,4R,5R)-tert-butyl 3,4-dihydroxy-2-(4-hydroxy-5H-pyrrolo[3,2-d]pyrimidin-7-yl)-5-(hydroxymethyl)pyrrolidine-1-carboxylate with the rest being triethylamine hydrochloride. This mixture was dissolved in MeOH (4 ml) and water (3 ml) and sodium periodate (0.055 g, 0.255 mmol) added. After stirring for 15 mins a precipitate formed. Sodium borohydride (0.024 g, 0.639 mmol) was added and the mixture stirred for 15 mins then filtered through Celite and the solvent evaporated. The residue was chromatographed on silica gel (CH$_2$Cl$_2$-MeOH, 85:15) to give (S)-tert-butyl 1,3-dihydroxypropan-2-yl(2-hydroxy-1-(4-oxo-4,5-dihydro-3H-pyrrolo[3,2-d]pyrimidin-7-yl)ethyl)carbamate (0.072 g, 92%) as a colourless solid. $^1$H NMR (CD$_3$OD) δ 7.89 (s, 1H), 7.50 (br.s 1H), 5.32 (br. s, 0.5 H), 5.08 (br. s, 0.5H), 4.28 (br.s 1H), 4.17-3.50 (br. m, 6H), 1.39 (br. d, 9H). +ESMS Found 369.1760 (M+H)$^+$ C$_{16}$H$_{25}$N$_4$O$_6$ requires 369.1774. [α]$_D^{20}$ +35.8 (c, 0.505, MeOH).

Example 30.2

(S)-7-(1-(1,3-dihydroxypropan-2-ylamino)-2-hydroxyethyl)-3H-pyrrolo[3,2-d]pyrimidin-4(5H)-one hydrochloride The product from Example 31.1 (0.068 g, 0.185 mmol) was dissolved in a mixture of MeOH (2 ml) and 37% HCL (0.2 ml). After a few mins the solvent was evaporated to a yellow foam which was crystallized from EtOH to give (S)-7-(1-(1,3-dihydroxypropan-2-ylamino)-2-hydroxyethyl)-3H-pyrrolo[3,2-d]pyrimidin-4(5H)-one hydrochloride as a colourless solid (42 mg, 75% as clumps of very tiny crystals when viewed under the microscope). M.p. >300° C. $^1$H NMR (D$_2$O+DCl, referenced to internal acetone at 2.225 ppm) δ 8.95 (s, 1H), 7.96 (s, 1H), 5.09 (t, 1H, J=4.7 Hz), 4.24 (dd, 1H, J=12.2, 4.3 Hz), 4.11 (dd, 1H, J=12.2, 5.1 Hz), 3.97-3.77 (m, 4H), 3.46 (pentet, 1H, J=5.3 Hz). $^{13}$C NMR (D$_2$O+DCl, referenced to internal acetone at 31.5 ppm) δ 154.0, 146.0, 133.4, 132.5, 119.7, 106.6, 62.1, 60.1, 59.3, 59.1, 54.7. +ESMS Found 269.1239 (M+H)$^+$ C$_{11}$H$_{17}$N$_4$O$_4$ requires 269.1250—free base form. [α]$_D^{20}$ +24.1 (c 0.435, H$_2$O+1 drop 37% HCl).

Example 31

Inhibition Studies

The inhibitor dissociation constants reported in Table 1 below are for phosphorolysis of inosine by PNP and were based on reaction rates measurements with different inhibitor concentrations. Reactions were started by addition of 0.05 μg of human or *Plasmodium falciparum* purine nucleoside phosphaorylase (HsPNP and PfPNP, respectively; final concentration 1.4 nM) to 1 mM inosine in 50 mM KPO$_4$, pH=7.5 buffer with xanthine oxidase added to final concentration 60 mU/mL at 25° C. In the coupled assay, hypoxanthine formed by phosphorolysis of inosine was oxidized to uric acid and followed spectrophotometrically at 293 nm (extinction coefficient for uric acid $\epsilon_{293}$=12.9 mM$^{-1}$). The dissociation constant for slow-onset tight-binding inhibitors was determined from reaction rates after slow onset inhibition had occurred according to the equation υ=(k$_{cat}$×S)/(K$_m$(1+I/K$_d$)+S), where υ is the steady state reaction rate after the slow-onset inhibition period has reached equilibrium, k$_{cat}$ is the rate at substrate saturation, S is substrate concentration, K$_m$ is the Michaelis constant for inosine (38 microM under these conditions), I is inhibitor concentration and K$_d$ is the equilibrium dissociation constant for the tightly-inhibited PNP-inhibitor complex. For inhibitors without slow-onset properties, fits to the same equation were made, but using initial reaction rates.

TABLE 1

Inhibition constants with human and malarial PNP

Structure (Using Fischer projection formula)

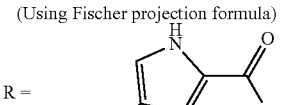

R =

| Example No | Configuration | | K$_d$ vs HsPNP | K$_d$ vs PfPNP |
|---|---|---|---|---|
| Achiral Amines | | | | |
| 7.3 | | HO(CH$_2$)$_2$NHR | 1.1 ± 0.1 nM | 430 ± 50 nM |
| 7.2 | | HO(CH$_2$)$_4$NHR | 25 ± 1 nM | 770 ± 66 nM |
| 8 | | 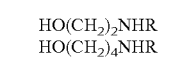 | 14.1 ± 1.2 nM | 210 ± 50 nM |
| 9 | | 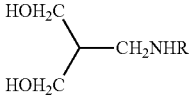 | 3.7 ± 0.7 nM | 2.0 ± 0.6 microM |
| 6 | | 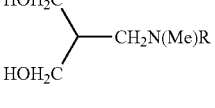 | 0.62 ± 0.17 nM | 163 ± 80 nM |
| 12 | | 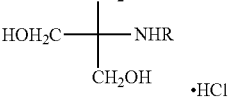 | 3.0 ± 0.2 nM | 4.3 ± 0.2 microM |

TABLE 1-continued

Inhibition constants with human and malarial PNP

Structure (Using Fischer projection formula)

R = 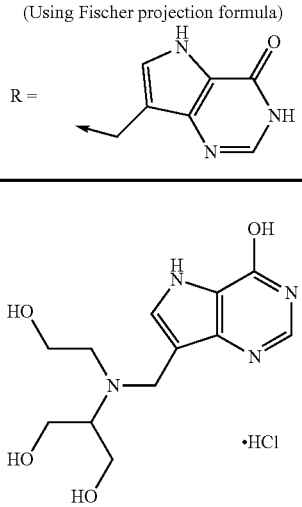

| Example No | Configuration | Structure | $K_d$ vs HsPNP | $K_d$ vs PfPNP |
|---|---|---|---|---|
| 11 | | 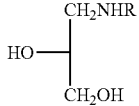 | 469 ± 58 pM | 1.0 ± 0.2 microM |
| Glycerol Derivatives | | | | |
| 3 | L-glycero | 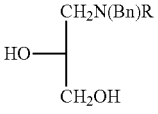 CH$_2$NHR / HO— / CH$_2$OH | 14.9 ± 1.7 nM | 1.8 ± .8 microM |
| 3.4 | N-Benzyl-L-glycero | CH$_2$N(Bn)R / HO— / CH$_2$OH | 300 ± 50 nM | 2 ± 0.2 microM |
| 13 | N-(3-hydroxyethyl)-L-glycero | 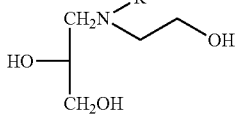 | 165 ± 30 nM | 550 ± 80 nM |
| 5 | D-glycero | CH$_2$NHR / —OH / CH$_2$OH | 4.2 ± 0.3 nM | 260 ± 30 nM |
| 14 | N-(3-hydroxyethyl)-D-glycero | 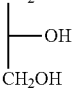 | 96 ± 22 nM | 1.38 ± 0.31 microM |
| 2-Amino-2-deoxy-tetritol derivatives | | | | |
| 15 | D-erythro | CH$_2$OH / —NHR / —OH / CH$_2$OH | 5.2 ± 0.7 nM | 4.8 ± 1.8 microM |

TABLE 1-continued

Inhibition constants with human and malarial PNP

Structure
(Using Fischer projection formula)

R = [7-deazahypoxanthine-CH2- group]

| Example No | Configuration | Structure | $K_d$ vs HsPNP | $K_d$ vs PfPNP |
|---|---|---|---|---|
| 4 | L-erythro | CH2OH / RHN— / HO— / CH2OH | 4.3 ± 0.7 nM | 770 ± 175 nM |
| 17 | D-threo (DATMe-Immucillin-H) | CH2OH / RHN— / —OH / CH2OH | 8.6 ± 0.6 pM | 55 ± 12 nM |
| 18 | L-threo | CH2OH / —NHR / HO— —OH / CH2OH | 1.0 ± 0.03 nM | 210 ± 40 nM |

1-Amino-1-deoxy-tetritol derivatives

| 19.3 | D-erythro | CH2NHR / —OH / —OH / CH2OH | 31 ± 3 nM | 12 ± 2 microM |
| 20.5 | D,L-threo | CH2NHR / HO— / —OH / CH2OH  and  CH2NHR / —OH / HO— / CH2OH | 84 ± 7 nM | 32 ± 2 microM |
| 2 | 3-Deoxy-N-Methyl-DL-glycero | CH2N(Me)R / ~OH / CH2 / CH2OH | 227 ± 40 nM | 770 ± 175 nM |

TABLE 1-continued

Inhibition constants with human and malarial PNP

Structure
(Using Fischer projection formula)

R = [deazahypoxanthine-methyl group]

| Example No | Configuration | Structure | $K_d$ vs HsPNP | $K_d$ vs PfPNP |
|---|---|---|---|---|
| *2-Aminomethyl-2-deoxy-tetritol derivatives* | | | | |
| 21 | D,L-erythro | CH$_2$OH / RHNH$_2$C— / HO— / CH$_2$OH  &  CH$_2$OH / —CH$_2$NHR / —OH / CH$_2$OH | 0.78 ± 0.15 nM | 2.2 ± 0.3 microM |
| 22 | D,L-threo | CH$_2$OH / RHNH$_2$C— / —OH / CH$_2$OH  &  CH$_2$OH / —CH$_2$NHR / HO— / CH$_2$OH | 0.90 ± 0.02 microM | 3.5 ± 0.2 microM |
| *2-Amino-2-deoxy-1-methylthio-tetritol derivatives* | | | | |
| 24 | D-erythro | CH$_2$SMe / —NHR / —OH / CH$_2$OH | 15 ± 1 nM | 19 ± 1 nM |
| 25 | L-erythro | CH$_2$SMe / RHN— / HO— / CH$_2$OH | 74 ± 5 nM | 13 ± 3 microM |
| 26 | D-threo | CH$_2$SMe / RHN— / —OH / CH$_2$OH | 71 ± 7 nM | 10 ± 3 microM |

TABLE 1-continued

Inhibition constants with human and malarial PNP

R = [pyrrolo[3,2-d]pyrimidin-4(5H)-one-7-ylmethyl group] (Structure using Fischer projection formula)

| Example No | Configuration | Structure | $K_d$ vs HsPNP | $K_d$ vs PfPNP |
|---|---|---|---|---|
| 27 | L-threo | CH₂SMe / —NHR / HO— / CH₂OH | 142 ± 31 nM | 3.5 ± 1 microM |

2-Aminomethyl-2-deoxy-1-methylthio-tetritol derivatives

| Example No | Configuration | Structure | $K_d$ vs HsPNP | $K_d$ vs PfPNP |
|---|---|---|---|---|
| 28 | D,L-erythro | CH₂SMe / RHNH₂C— / HO— / CH₂OH  and  CH₂SMe / —CH₂NHR / —OH / CH₂OH | 5.6 ± 1.2 nM | 6.3 ± 1.2 microM |
| 23 | DL-threo | CH₂SMe / RHNH₂C— / —OH / CH₂OH  and  CH₂SMe / —CH₂NHR / HO— / CH₂OH | 159 ± 12 nM | 3.0 ± 0.3 microM |
| 29 | N-Benzyl-D,L-erythro | CH₂SMe / R(iBn)NH₂C— / HO— / CH₂OH  and  CH₂SMe / —CH₂N(Bn)R / —OH / CH₂OH | 22 ± 1 nM | 1.1 ± 0.1 microM |

TABLE 1-continued

Inhibition constants with human and malarial PNP

Structure (Using Fischer projection formula)

R = [4-oxo-pyrrolo[3,2-d]pyrimidin-7-yl]methyl

| Example No | Configuration | Structure | $K_d$ vs HsPNP | $K_d$ vs PfPNP |
|---|---|---|---|---|
| *4-Amino-4-deoxy-1-methythio-tetritol derivatives* | | | | |
| 19 | L-erythro | CH$_2$SMe / HO— / HO— / CH$_2$NHR | 51 ± 4 nM | 5.3 ± 0.9 microM |
| 20.8 | D,L-threo | CH$_2$SMe / HO— / —OH / CH$_2$NHR  and  CH$_2$SMe / HO— / —OH / CH$_2$NHR | 789 ± 46 nM | 7.4 ± 1.3 microM |
| *Other* | | | | |
| 30 | 2',3'-seco-Immucillin-H | (structure shown) | 0.21 ± 0.08 nM | 297 ± 99 nM |

Example 32

Oral Availability of (2S,3R)-3-((4-hydroxy-5H-pyrrolo[3,2-d]pyrimidin-7-yl)-methylamino)butane-1,2,4-triol (Compound 17.3)

A solution of 25 microliters containing 50 nanomoles of (2S,3R)-3-((4-hydroxy-5H-pyrrolo[3,2-d]pyrimidin-7-yl)-methylamino)butane-1,2,4-triol (compound 17.3) in 10% sucrose was pipetted into the mouth of three Balb-c mice that had been fasted overnight. A control group was treated with 25 microliters of 10% sucrose without inhibitor. Another group of three mice were treated by interperitoneal injection of 100 microliters of phosphate-buffered saline (PBS; 137 mM NaCl, 10 mM phosphate buffer, and 2.7 mM KCl) containing 50 nanomoles of compound 17.3. Small samples (8 μL) of blood were collected from the tail and added to 8 μL of PBS containing 1 U heparin and 0.3% Triton X-100. The mixture was kept on ice for 25 min and assayed immediately or stored at −80° C. for subsequent analysis. Samples assayed immediately or after storage at −80° C. gave equivalent results. For PNP catalytic activity of whole blood samples, 3 μL samples of the lysate were added to the complete reaction mixture (1.0 mL volume) containing 1 mM inosine, 50 mM phosphate, pH=7.4 and 60 mU/ml xanthine oxidase. After mixing, the reaction progress was followed spectrophotometrically at 293 nm. Reactions were monitored for 4 minutes to measure the initial rate of purine nucleoside phosphorylase activity. All reaction rates were normalized to enzyme activity per hemoglobin absorbance at 412 and 540 nanometers, measured in the same cuvette used for the enzyme assay mixtures and directly following the 4 min assay period. FIG. 1 shows that compound 17.3 is orally available and inhibits PNP in mice for more than 24 hours.

Although the invention has been described by way of example, it should be appreciated the variations or modifications may be made without departing from the scope of the invention. Furthermore, when known equivalents exist to specific features, such equivalents are incorporated as if specifically referred to in the specification.

INDUSTRIAL APPLICABILITY

The invention relates to compounds that are inhibitors of PNPs and/or NHs. The compounds are therefore expected to be useful in the treatment of diseases in which the inhibition of PNPs or NHs is desirable. Such diseases include cancer, bacterial infection, protozoal infection (including malaria), and T-cell mediated diseases.

The invention claimed is:
1. A compound of the formula (I):

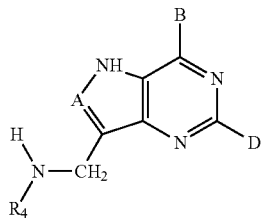

where:
R⁴ is dihydroxypropyl, dihydroxybutyl, trihydroxybutyl, dihydroxypentyl or trihydroxypentyl;
A is N or CH;
B is OH or alkoxy; and
D is H, OH, NH$_2$, or SCH$_3$;
or a tautomer thereof, or a pharmaceutically acceptable salt thereof, or an ester prodrug form thereof.
2. A compound as claimed in claim 1 where A is CH.
3. A compound as claimed in claim 1 where A is N.
4. A compound as claimed in claim 1 where B is OH.
5. A compound as claimed in claim 1 where D is H or NH$_2$.
6. A compound as claimed in claim 1 where D is OH or SCH$_3$.
7. A compound selected from the group consisting of:
rac-(2R,3S)-3-((4-hydroxy-5H-pyrrolo[3,2-d]pyrimidin-7-yl)methylamino)butane-1,2,4-triol;
7-(((2,4-dihydroxybutyl)(methyl)amino)methyl)-3H-pyrrolo[3,2-d]pyrimidin-4(5H)-one;
(R)3-((4-hydroxy-5H-pyrrolo[3,2-d]pyrimidin-7-yl)methylamino)-propane-1,2-diol hydrochloride;
(2R,3R)-3-((4-hydroxy-5H-pyrrolo[3,2-d]pyrimidin-7-yl)methylamino)butane-1,2,4-triol hydrochloride;
2-amino-7-(2,3-dihydroxy-1-(2-hydroxyethylamino)propyl)-3H-pyrrolo[3,2-d]pyrimidin-4(5H)-one;
7-(2,3-dihydroxy-1-(2-hydroxyethylamino)propyl)-3H-pyrrolo[3,2-d]pyrimidin-4(5H)-one;
2-amino-7-(1-amino-2,3,5-trihydroxypentyl)-3H-pyrrolo[3,2-d]pyrimidin-4(5H)-one;
7-(1-amino-2,3,5-trihydroxypentyl)-3H-pyrrolo[3,2-d]pyrimidin-4(5H)-one;
2-amino-7-(4-amino-2,3,5-trihydroxypentyl)-3H-pyrrolo[3,2-d]pyrimidin-4(5H)-one;
7-(4-amino-2,3,5-trihydroxypentyl)-3H-pyrrolo[3,2-d]pyrimidin-4(5H)-one;
2-amino-7-(1-(1,3-dihydroxypropan-2-ylamino)-2-hydroxyethyl)-3H-pyrrolo[3,2-d]pyrimidin-4(5H)-one;
7-(1-(1,3-dihydroxypropan-2-ylamino)-2-hydroxyethyl)-3H-pyrrolo[3,2-d]pyrimidin-4(5H)-one;
2-amino-7-(((2,4-dihydroxybutyl)(methyl)amino)methyl)-3H-pyrrolo[3,2-d]pyrimidin-4(5H)-one;
2-amino-7-((2,4-dihydroxybutylamino)methyl)-3H-pyrrolo[3,2-d]pyrimidin-4(5H)-one;
7-((2,4-dihydroxybutylamino)methyl)-3H-pyrrolo[3,2-d]pyrimidin-4(5H)-one;
2-amino-7-((3,4-dihydroxy-2-(hydroxymethyl)butylamino)methyl)-3H-pyrrolo[3,2-d]pyrimidin-4(5H)-one;
7-((3,4-dihydroxy-2-(hydroxymethyl)butylamino)methyl)-3H-pyrrolo[3,2-d]pyrimidin-4(5H)-one;
2-amino-7-((3-hydroxy-2-(hydroxymethyl)propylamino)methyl)-3H-pyrrolo[3,2-d]pyrimidin-4(5H)-one;
7-((3-hydroxy-2-(hydroxymethyl)propylamino)methyl)-3H-pyrrolo[3,2-d]pyrimidin-4(5H)-one;
2-amino-7-(((3-hydroxy-2-(hydroxymethyl)propyl)(methyl)amino)methyl)-3H-pyrrolo[3,2-d]pyrimidin-4(5H)-one;
7-(((3-hydroxy-2-(hydroxymethyl)propyl)(methyl)amino)methyl)-3H-pyrrolo[3,2-d]pyrimidin-4(5H)-one;
2-amino-7-(3,4-dihydroxy-5-(methylthiomethyl)pyrrolidin-2-yl)-3H-pyrrolo[3,2-d]pyrimidin-4(5H)-one;
7-(3,4-dihydroxy-5-(methylthiomethyl)pyrrolidin-2-yl)-3H-pyrrolo[3,2-d]pyrimidin-4(5H)-one;
2-amino-7-(2,3-dihydroxy-1-(2-(methylthio)ethylamino)propyl)-3H-pyrrolo[3,2-d]pyrimidin-4(5H)-one;
7-(2,3-dihydroxy-1-(2-(methylthio)ethylamino)propyl)-3H-pyrrolo[3,2-d]pyrimidin-4(5H)-one;
2-amino-7-(1-amino-2,3-dihydroxy-5-(methylthio)pentyl)-3H-pyrrolo[3,2-d]pyrimidin-4(5H)-one;
7-(1-amino-2,3-dihydroxy-5-(methylthio)pentyl)-3H-pyrrolo[3,2-d]pyrimidin-4(5H)-one;
2-amino-7-(2-hydroxy-1-(1-hydroxy-3-(methylthio)propan-2-ylamino)ethyl)-3H-pyrrolo[3,2-d]pyrimidin-4(5H)-one;
7-(2-hydroxy-1-(1-hydroxy-3-(methylthio)propan-2-ylamino)ethyl)-3H-pyrrolo[3,2-d]pyrimidin-4(5H)-one;
2-amino-7-((3,4-dihydroxy-1-(methylthio)butan-2-ylamino)methyl)-3H-pyrrolo[3,2-d]pyrimidin-4(5H)-one;
7-((3,4-dihydroxy-1-(methylthio)butan-2-ylamino)methyl)-3H-pyrrolo[3,2-d]pyrimidin-4(5H)-one;
2-amino-7-(((2-hydroxy-4-(methylthio)butyl)(methyl)amino)methyl)-3H-pyrrolo[3,2-d]pyrimidin-4(5H)-one;
7-(((2-hydroxy-4-(methylthio)butyl)(methyl)amino)methyl)-3H-pyrrolo[3,2-d]pyrimidin-4(5H)-one;
2-amino-7-((2-hydroxy-4-(methylthio)butylamino)methyl)-3H-pyrrolo[3,2-d]pyrimidin-4(5H)-one;
7-((2-hydroxy-4-(methylthio)butylamino)methyl)-3H-pyrrolo[3,2-d]pyrimidin-4(5H)-one;
2-amino-7-((3,4-dihydroxy-2-(methylthiomethyl)butylamino)methyl)-3H-pyrrolo[3,2-d]pyrimidin-4(5H)-one;
7-((3,4-dihydroxy-2-(methylthiomethyl)butylamino)methyl)-3H-pyrrolo[3,2-d]pyrimidin-4(5H)-one;
2-amino-7-((3-hydroxy-2-(methylthiomethyl)propylamino)methyl)-3H-pyrrolo[3,2-d]pyrimidin-4(5H)-one;
7-((3-hydroxy-2-(methylthiomethyl)propylamino)methyl)-3H-pyrrolo[3,2-d]pyrimidin-4(5H)-one;
7-(((3-hydroxy-2-(methylthiomethyl)propyl)(methyl)amino)methyl)-3H-pyrrolo[3,2-d]pyrimidin-4(5H)-one;

2-amino-7-(((3-hydroxy-2-(methylthiomethyl)propyl)(methyl)amino)methyl)-3H-pyrrolo[3,2-d]pyrimidin-4(5H)-one;
7-(((2R,3R)-1,3,4-trihydroxybutan-2-ylamino)methyl)-3H-pyrrolo[3,2-d]pyrimidin-4(5H)-one;
7-(((2S,3S)-1,3,4-trihydroxybutan-2-ylamino)methyl)-3H-pyrrolo[3,2-d]pyrimidin-4(5H)-one;
7-(((2R,3S)-1,3,4-trihydroxybutan-2-ylamino)methyl)-3H-pyrrolo[3,2-d]pyrimidin-4(5H)-one;
7-(((2S,3R)-1,3,4-trihydroxybutan-2-ylamino)methyl)-3H-pyrrolo[3,2-d]pyrimidin-4(5H)-one;
2-amino-7-(((2R,3R)-1,3,4-trihydroxybutan-2-ylamino)methyl)-3H-pyrrolo[3,2-d]pyrimidin-4(5H)-one;
2-amino-7-(((2S,3S)-1,3,4-trihydroxybutan-2-ylamino)methyl)-3H-pyrrolo[3,2-d]pyrimidin-4(5H)-one;
2-amino-7-(((2R,3S)-1,3,4-trihydroxybutan-2-ylamino)methyl)-3H-pyrrolo[3,2-d]pyrimidin-4(5H)-one;
2-amino-7-(((2S,3R)-1,3,4-trihydroxybutan-2-ylamino)methyl)-3H-pyrrolo[3,2-d]pyrimidin-4(5H)-one;
5-amino-3-(((2R,3R)-1,3,4-trihydroxybutan-2-ylamino)methyl)-1H-pyrazolo[4,3-d]pyrimidin-7(6H)-one;
5-amino-3-(((2S,3S)-1,3,4-trihydroxybutan-2-ylamino)methyl)-1H-pyrazolo[4,3-d]pyrimidin-7(6H)-one;
5-amino-3-(((2R,3S)-1,3,4-trihydroxybutan-2-ylamino)methyl)-1H-pyrazolo[4,3-d]pyrimidin-7(6H)-one;
5-amino-3-(((2S,3R)-1,3,4-trihydroxybutan-2-ylamino)methyl)-1H-pyrazolo[4,3-d]pyrimidin-7(6H)-one;
7-((1,3-dihydroxy-2-(hydroxymethyl)propan-2-ylamino)methyl)-3H-pyrrolo[3,2-d]pyrimidin-4(5H)-one;
2-amino-7-((1,3-dihydroxy-2-(hydroxymethyl)propan-2-ylamino)methyl)-3H-pyrrolo[3,2-d]pyrimidin-4(5H)-one;
3-((1,3-dihydroxy-2-(hydroxymethyl)propan-2-ylamino)methyl)-1H-pyrazolo[4,3-d]pyrimidin-7(6H)-one;
7-((4-hydroxybutylamino)methyl)-3H-pyrrolo[3,2-d]pyrimidin-4(5H)-one;
2-amino-7-((4-hydroxybutylamino)methyl)-3H-pyrrolo[3,2-d]pyrimidin-4(5H)-one;
3-((4-hydroxybutylamino)methyl)-1H-pyrazolo[4,3-d]pyrimidin-7(6H)-one;
7-((2-hydroxyethylamino)methyl)-3H-pyrrolo[3,2-d]pyrimidin-4(5H)-one;
2-amino-7-((2-hydroxyethylamino)methyl)-3H-pyrrolo[3,2-d]pyrimidin-4(5H)-one;
3-((2-hydroxyethylamino)methyl)-1H-pyrazolo[4,3-d]pyrimidin-7(6H)-one;
7-((3-hydroxy-2-(hydroxymethyl)propylamino)methyl)-3H-pyrrolo[3,2-d]pyrimidin-4(5H)-one;
2-amino-7-((3-hydroxy-2-(hydroxymethyl)propylamino)methyl)-3H-pyrrolo[3,2-d]pyrimidin-4(5H)-one;
3-((3-hydroxy-2-(hydroxymethyl)propylamino)methyl)-1H-pyrazolo[4,3-d]pyrimidin-7(6H)-one;
7-(((3-hydroxy-2-(hydroxymethyl)propyl)(methyl)amino)methyl)-3H-pyrrolo[3,2-d]pyrimidin-4(5H)-one;
2-amino-7-(((3-hydroxy-2-(hydroxymethyl)propyl)(methyl)-amino)methyl)-3H-pyrrolo[3,2-d]pyrimidin-4(5H)-one;
3-(((1,3-dihydroxypropan-2-yl)(methyl)amino) methyl)-1H-pyrazolo[4,3-d]pyrimidin-7(6H)-one;
7-((3-hydroxy-2-(hydroxymethyl)propylamino)methyl)-3H-pyrrolo[3,2-d]pyrimidin-4(5H)-one;
2-amino-7-((3-hydroxy-2-(hydroxymethyl)propylamino)methyl)-3H-pyrrolo[3,2-d]pyrimidin-4(5H)-one;
3-((1,3-dihydroxypropan-2-ylamino)methyl)-1H-pyrazolo[4,3-d]pyrimidin-7(6H)-one;
7-(((3-hydroxy-2-(hydroxymethyl)propyl)(methyl)-amino)methyl)-3H-pyrrolo[3,2-d]pyrimidin-4(5H)-one;
2-amino-7-(((3-hydroxy-2-(hydroxymethyl)propyl)(methyl)-amino)methyl)-3H-pyrrolo[3,2-d]pyrimidin-4(5H)-one;
3-(((1,3-dihydroxypropan-2-yl)(methyl)amino)methyl)-1H-pyrazolo[4,3-d]pyrimidin-7(6H)-one;
7-(((3-hydroxy-2-(hydroxymethyl)propyl)(hydroxymethyl)amino)methyl)-3H-pyrrolo[3,2-d]pyrimidin-4(5H)-one;
2-amino-7-(((3-hydroxy-2-(hydroxymethyl)propyl)(hydroxymethyl)amino)methyl)-3H-pyrrolo[3,2-d]pyrimidin-4(5H)-one;
5-amino-3-(((3-hydroxy-2-(hydroxymethyl)propyl)(hydroxymethyl)amino)methyl)-1H-pyrazolo[4,3-d]pyrimidin-7(6H)-one;
7-((1,3-dihydroxy-2-(methylthiomethyl)propan-2-ylamino)methyl)-3H-pyrrolo[3,2-d]pyrimidin-4(5H)-one;
2-amino-7-((1,3-dihydroxy-2-(methylthiomethyl)propan-2-ylamino)methyl)-3H-pyrrolo[3,2-d]pyrimidin-4(5H)-one;
5-amino-3-((1,3-dihydroxy-2-(methylthiomethyl)propan-2-ylamino)methyl)-1H-pyrazolo[4,3-d]pyrimidin-7(6H)-one;
7-(((2R,3R)-2,3,4-trihydroxybutylamino)methyl)-3H-pyrrolo[3,2-d]pyrimidin-4(5H)-one;
7-(((2S,3S)-2,3,4-trihydroxybutylamino)methyl)-3H-pyrrolo[3,2-d]pyrimidin-4(5H)-one;
7-(((2R,3S)-2,3,4-trihydroxybutylamino)methyl)-3H-pyrrolo[3,2-d]pyrimidin-4(5H)-one;
7-(((2S,3R)-2,3,4-trihydroxybutylamino)methyl)-3H-pyrrolo[3,2-d]pyrimidin-4(5H)-one;
2-amino-7-(((2R,3R)-2,3,4-trihydroxybutylamino)methyl)-3H-pyrrolo[3,2-d]pyrimidin-4(5H)-one;
2-amino-7-(((2S,3S)-2,3,4-trihydroxybutylamino)methyl)-3H-pyrrolo[3,2-d]pyrimidin-4(5H)-one;
2-amino-7-(((2R,3S)-2,3,4-trihydroxybutylamino)methyl)-3H-pyrrolo[3,2-d]pyrimidin-4(5H)-one;
2-amino-7-(((2S,3R)-2,3,4-trihydroxybutylamino)methyl)-3H-pyrrolo[3,2-d]pyrimidin-4(5H)-one;
5-amino-3-(((2R,3R)-2,3,4-trihydroxybutylamino)methyl)-1H-pyrazolo[4,3-d]pyrimidin-7(6H)-one;
5-amino-3-(((2S,3S)-2,3,4-trihydroxybutylamino)methyl)-1H-pyrazolo[4,3-d]pyrimidin-7(6H)-one;
5-amino-3-(((2R,3S)-2,3,4-trihydroxybutylamino)methyl)-1H-pyrazolo[4,3-d]pyrimidin-7(6H)-one;
5-amino-3-(((2S,3R)-2,3,4-trihydroxybutylamino)methyl)-1H-pyrazolo[4,3-d]pyrimidin-7(6H)-one;
7-((benzyl((2R,3R)-3,4-dihydroxy-2-(methylthiomethyl)butyl)amino)methyl)-3H-pyrrolo[3,2-d]pyrimidin-4(5H)-one;
7-((benzyl((2S,3S)-3,4-dihydroxy-2-(methylthiomethyl)butyl)amino)methyl)-3H-pyrrolo[3,2-d]pyrimidin-4(5H)-one;
7-((benzyl((2R,3S)-3,4-dihydroxy-2-(methylthiomethyl)butyl)amino)methyl)-3H-pyrrolo[3,2-d]pyrimidin-4(5H)-one;
7-((benzyl((2S,3R)-3,4-dihydroxy-2-(methylthiomethyl)butyl)amino)methyl)-3H-pyrrolo[3,2-d]pyrimidin-4(5H)-one;
2-amino-7-((benzyl((2R,3R)-3,4-dihydroxy-2-(methylthiomethyl)butyl)amino)methyl)-3H-pyrrolo[3,2-d]pyrimidin-4(5H)-one;

2-amino-7-((benzyl((2S,3S)-3,4-dihydroxy-2-(methylthi-omethyl)butyl)amino)methyl)-3H-pyrrolo[3,2-d]pyrimidin-4(5H)-one;
2-amino-7-((benzyl((2R,3S)-3,4-dihydroxy-2-(methylthi-omethyl)butyl)amino)methyl)-3H-pyrrolo[3,2-d]pyrimidin-4(5H)-one;
2-amino-7-((benzyl((2S,3R)-3,4-dihydroxy-2-(methylthi-omethyl)butyl)amino)methyl)-3H-pyrrolo[3,2-d]pyrimidin-4(5H)-one;
(S)-7-(1-(1,3-dihydroxypropan-2-ylamino)-2-hydroxy-ethyl)-3H-pyrrolo[3,2-d]pyrimidin-4(5H)-one;
(R)-7-(1-(1,3-dihydroxypropan-2-ylamino)-2-hydroxy-ethyl)-3H-pyrrolo[3,2-d]pyrimidin-4(5H)-one;
(S)-2-amino-7-(1-(1,3-dihydroxypropan-2-ylamino)-2-hydroxyethyl)-3H-pyrrolo[3,2-d]pyrimidin-4(5H)-one;
(R)-2-amino-7-(1-(1,3-dihydroxypropan-2-ylamino)-2-hydroxyethyl)-3H-pyrrolo[3,2-d]pyrimidin-4(5H)-one;
(S)-3-(1-(1,3-dihydroxypropan-2-ylamino)-2-hydroxy-ethyl)-1H-pyrazolo[4,3-d]pyrimidin-7(6H)-one;
(R)-3-(1-(1,3-dihydroxypropan-2-ylamino)-2-hydroxy-ethyl)-1H-pyrazolo[4,3-d]pyrimidin-7(6H)-one;
7-(((2R,3R)-2,3-dihydroxy-4-(methylthio)butylamino)methyl)-3H-pyrrolo[3,2-d]pyrimidin-4(5H)-one;
7-(((2S,3S)-2,3-dihydroxy-4-(methylthio)butylamino)methyl)-3H-pyrrolo[3,2-d]pyrimidin-4(5H)-one;
7-(((2R,3S)-2,3-dihydroxy-4-(methylthio)butylamino)methyl)-3H-pyrrolo[3,2-d]pyrimidin-4(5H)-one;
7-(((2S,3R)-2,3-dihydroxy-4-(methylthio)butylamino)methyl)-3H-pyrrolo[3,2-d]pyrimidin-4(5H)-one;
2-amino-7-(((2R,3R)-2,3-dihydroxy-4-(methylthio)buty-lamino)methyl)-3H-pyrrolo[3,2-d]pyrimidin-4(5H)-one;
2-amino-7-(((2S,3S)-2,3-dihydroxy-4-(methylthio)buty-lamino)methyl)-3H-pyrrolo[3,2-d]pyrimidin-4(5H)-one;
2-amino-7-(((2R,3S)-2,3-dihydroxy-4-(methylthio)buty-lamino)methyl)-3H-pyrrolo[3,2-d]pyrimidin-4(5H)-one;
2-amino-7-(((2S,3R)-2,3-dihydroxy-4-(methylthio)buty-lamino)methyl)-3H-pyrrolo[3,2-d]pyrimidin-4(5H)-one;
(R)-7-((benzyl(2,3-dihydroxypropyl)amino)methyl)-3H-pyrrolo[3,2-d]pyrimidin-4(5H)-one;
(S)-7-((benzyl (2,3-dihydroxypropyl)amino)methyl)-3H-pyrrolo[3,2-d]pyrimidin-4(5H)-one;
(R)-2-amino-7-((benzyl (2,3-dihydroxypropyl)amino)me-thyl)-3H-pyrrolo[3,2-d]pyrimidin-4(5H)-one;
(S)-2-amino-7-((benzyl (2,3-dihydroxypropyl)amino)me-thyl)-3H-pyrrolo[3,2-d]pyrimidin-4(5H)-one;
(R)-3-((2,3-dihydroxypropylamino)methyl)-1H-pyrazolo[4,3-d]pyrimidin-7(6H)-one;
(S)-3-((2,3-dihydroxypropylamino)methyl)-1H-pyrazolo[4,3-d]pyrimidin-7(6H)-one;
(R)-7-(((2,3-dihydroxypropyl)(2-hydroxyethyl)amino)methyl)-3H-pyrrolo[3,2-d]pyrimidin-4(5H)-one;
(S)-7-(((2,3-dihydroxypropyl)(2-hydroxyethyl)amino)methyl)-3H-pyrrolo[3,2-d]pyrimidin-4(5H)-one;
(R)-2-amino-7-(((2,3-dihydroxypropyl)(2-hydroxyethyl)amino)methyl)-3H-pyrrolo[3,2-d]pyrimidin-4(5H)-one;
(S)-2-amino-7-(((2,3-dihydroxypropyl)(2-hydroxyethyl)amino)methyl)-3H-pyrrolo[3,2-d]pyrimidin-4(5H)-one;
(R)-3-(((2,3-dihydroxypropyl)(2-hydroxyethyl)amino)methyl)-1H-pyrazolo[4,3-d]pyrimidin-7(6H)-one;
(S)-3-(((2,3-dihydroxypropyl)(2-hydroxyethyl)amino)methyl)-1H-pyrazolo[4,3-d]pyrimidin-7(6H)-one;
(2R,3R)-7-((3,4-dihydroxy-2-(hydroxymethyl)buty-lamino)methyl)-3H-pyrrolo[3,2-d]pyrimidin-4(5H)-one;
(2S,3S)-7-((3,4-dihydroxy-2-(hydroxymethyl)buty-lamino)methyl)-3H-pyrrolo[3,2-d]pyrimidin-4(5H)-one; (2R,3S)-7-((3,4-dihydroxy-2-(hydroxymethyl)bu-tylamino)methyl)-3H-pyrrolo[3,2-d]pyrimidin-4(5H)-one; (2S,3R)-7-((3,4-dihydroxy-2-(hydroxymethyl)butylamino)methyl)-3H-pyrrolo[3,2-d]pyrimidin-4(5H)-one;
(2R,3R)-2-amino-7-((3,4-dihydroxy-2-(hydroxymethyl)butylamino)methyl)-3H-pyrrolo[3,2-d]pyrimidin-4(5H)-one;
(2S,3S)-2-amino-7-((3,4-dihydroxy-2-(hydroxymethyl)butylamino)methyl)-3H-pyrrolo[3,2-d]pyrimidin-4(5H)-one;
(2R,3S)-2-amino-7-((3,4-dihydroxy-2-(hydroxymethyl)butylamino)methyl)-3H-pyrrolo[3,2-d]pyrimidin-4(5H)-one;
(2S,3R)-2-amino-7-((3,4-dihydroxy-2-(hydroxymethyl)butylamino) methyl)-3H-pyrrolo[3,2-d]pyrimidin-4(5H)-one;
(2R,3R)-5-amino-3-((3,4-dihydroxy-2-(hydroxymethyl)butylamino)methyl)-1H-pyrazolo[4,3-d]pyrimidin-7(6H)-one;
(2S,3S)-5-amino-3-((3,4-dihydroxy-2-(hydroxymethyl)butylamino)methyl)-1H-pyrazolo[4,3-d]pyrimidin-7(6H)-one;
(2R,3S)-5-amino-3-((3,4-dihydroxy-2-(hydroxymethyl)butylamino)methyl)-1H-pyrazolo[4,3-d]pyrimidin-7(6H)-one;
(2S,3R)-5-amino-3-((3,4-dihydroxy-2-(hydroxymethyl)butylamino)methyl)-1H-pyrazolo[4,3-d]pyrimidin-7(6H)-one;
7-(((2R,3R)-3,4-dihydroxy-1-(methylthio)butan-2-ylamino)methyl)-3H-pyrrolo[3,2-d]pyrimidin-4(5H)-one;
7-(((2S,3S)-3,4-dihydroxy-1-(methylthio)butan-2-ylamino)methyl)-3H-pyrrolo[3,2-d]pyrimidin-4(5H)-one;
7-(((2R,3S)-3,4-dihydroxy-1-(methylthio)butan-2-ylamino)methyl)-3H-pyrrolo[3,2-d]pyrimidin-4(5H)-one;
7-(((2S,3R)-3,4-dihydroxy-1-(methylthio)butan-2-ylamino)methyl)-3H-pyrrolo[3,2-d]pyrimidin-4(5H)-one;
2-amino-7-(((2R,3R)-3,4-dihydroxy-1-(methylthio)bu-tan-2-ylamino)methyl)-3H-pyrrolo[3,2-d]pyrimidin-4(5H)-one;
2-amino-7-(((2S,3S)-3,4-dihydroxy-1-(methylthio)butan-2-ylamino)methyl)-3H-pyrrolo[3,2-d]pyrimidin-4(5H)-one;
2-amino-7-(((2R,3S)-3,4-dihydroxy-1-(methylthio)bu-tan-2-ylamino)methyl)-3H-pyrrolo[3,2-d]pyrimidin-4(5H)-one;
2-amino-7-(((2S,3R)-3,4-dihydroxy-1-(methylthio)bu-tan-2-ylamino)methyl)-3H-pyrrolo[3,2-d]pyrimidin-4(5H)-one;
3-(((2R,3R)-3,4-dihydroxy-1-(methylthio)butan-2-ylamino)methyl)-1H-pyrazolo[4,3-d]pyrimidin-7(6H)-one;
3-(((2S,3S)-3,4-dihydroxy-1-(methylthio)butan-2-ylamino)methyl)-1H-pyrazolo[4,3-d]pyrimidin-7(6H)-one;
3-(((2R,3S)-3,4-dihydroxy-1-(methylthio)butan-2-ylamino)methyl)-1H-pyrazolo[4,3-d]pyrimidin-7(6H)-one;

3-(((2S,3R)-3,4-dihydroxy-1-(methylthio)butan-2-ylamino)methyl)-1H-pyrazolo[4,3-d]pyrimidin-7(6H)-one;

3-(((2R,3R)-3,4-dihydroxy-2-(methylthiomethyl)butylamino)methyl)-1H-pyrazolo[4,3-d]pyrimidin-7(6H)-one;

3-(((2S,3S)-3,4-dihydroxy-2-(methylthiomethyl)butylamino)methyl)-1H-pyrazolo[4,3-d]pyrimidin-7(6H)-one;

3-(((2R,3S)-3,4-dihydroxy-2-(methylthiomethyl)butylamino)methyl)-1H-pyrazolo[4,3-d]pyrimidin-7(6H)-one;

3-(((2S,3R)-3,4-dihydroxy-2-(methylthiomethyl)butylamino)methyl)-1H-pyrazolo[4,3-d]pyrimidin-7(6H)-one;

2-amino-7-(((2R,3R)-3,4-dihydroxy-2-(methylthiomethyl)butylamino)methyl)-3H-pyrrolo[3,2-d]pyrimidin-4(5H)-one;

2-amino-7-(((2S,3S)-3,4-dihydroxy-2-(methylthiomethyl)butylamino)methyl)-3H-pyrrolo[3,2-d]pyrimidin-4(5H)-one;

2-amino-7-(((2R,3S)-3,4-dihydroxy-2-(methylthiomethyl)butylamino)methyl)-3H-pyrrolo[3,2-d]pyrimidin-4(5H)-one;

2-amino-7-(((2S,3R)-3,4-dihydroxy-2-(methylthiomethyl)butylamino)methyl)-3H-pyrrolo[3,2-d]pyrimidin-4(5H)-one;

7-(((2R,3R)-3,4-dihydroxy-2-(methylthiomethyl)butylamino)methyl)-3H-pyrrolo[3,2-d]pyrimidin-4(5H)-one;

7-(((2S,3S)-3,4-dihydroxy-2-(methylthiomethyl)butylamino)methyl)-3H-pyrrolo[3,2-d]pyrimidin-4(5H)-one;

7-(((2R,3S)-3,4-dihydroxy-2-(methylthiomethyl)butylamino)methyl)-3H-pyrrolo[3,2-d]pyrimidin-4(5H)-one; and 7-(((2S,3R)-3,4-dihydroxy-2-(methylthiomethyl)butylamino)methyl)-3H-pyrrolo[3,2-d]pyrimidin-4(5H)-one;

7-((1,3-dihydroxypropan-2-ylamino)methyl)-3H-pyrrolo[3,2-d]pyrimidin-4(5H)-one;

or a tautomer thereof, or a pharmaceutically acceptable salt thereof, or an ester prodrug form thereof.

8. A compound of the formula:

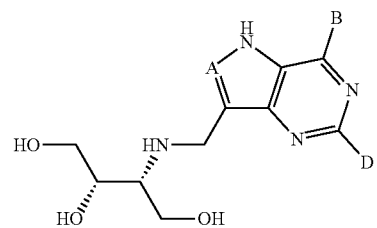

where A is N or CH; B is OH or alkoxy; and D is H, OH, $NH_2$, or $SCH_3$.

9. The compound (2S,3R)-3-((4-hydroxy-5H-pyrrolo[3,2-d]pyrimidin-7-yl)-methylamino)butane-1,2,4-triol having the formula:

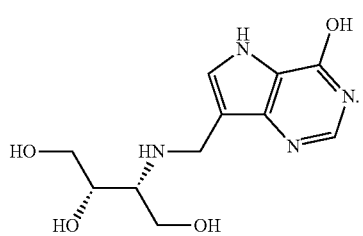 [SMILES: OC[C@@H](O)[C@@H](CO)NCc1c[nH]c2c(O)ncnc12]

10. A pharmaceutical composition comprising a pharmaceutically effective amount of a compound of claim 1.

11. The compound of claim 1 having the structure

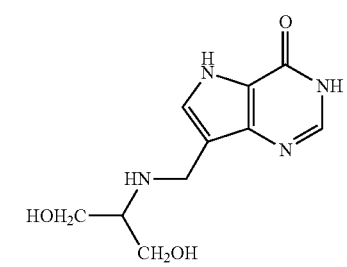 [SMILES: O=c1[nH]cnc2c(CNC(CO)CO)c[nH]c12]

or a tautomer thereof, or a pharmaceutically acceptable salt thereof, or an ester prodrug form thereof.

12. A pharmaceutical composition comprising a pharmaceutically effective amount of a compound of claim 7.

* * * * *

UNITED STATES PATENT AND TRADEMARK OFFICE
CERTIFICATE OF CORRECTION

PATENT NO. : 8,853,224 B2
APPLICATION NO. : 12/310708
DATED : October 7, 2014
INVENTOR(S) : Keith Clinch et al.

It is certified that error appears in the above-identified patent and that said Letters Patent is hereby corrected as shown below:

Column 1, lines 15-21, should read:

-- STATEMENT OF GOVERNMENT SUPPORT

This invention was made with government support under grant number GM41916 awarded by the National Institutes of Health. The government has certain rights in the invention. --

Signed and Sealed this
Third Day of November, 2015

Michelle K. Lee
*Director of the United States Patent and Trademark Office*